(12) United States Patent
Ji et al.

(10) Patent No.: US 11,168,080 B2
(45) Date of Patent: Nov. 9, 2021

(54) DYNAMIN-1-LIKE PROTEIN INHIBITORS

(71) Applicant: Mitobridge, Inc., Cambridge, MA (US)

(72) Inventors: Nan Ji, Arlington, MA (US);
Jeyaprakash Narayanan Seenisamy, Bangalore (IN)

(73) Assignee: Mitobridge, Inc., Cambridge, MA (US)

(*) Notice: Subject to any disclaimer, the term of this patent is extended or adjusted under 35 U.S.C. 154(b) by 0 days.

(21) Appl. No.: 16/605,801

(22) PCT Filed: Apr. 25, 2018

(86) PCT No.: PCT/US2018/029363
§ 371 (c)(1),
(2) Date: Oct. 17, 2019

(87) PCT Pub. No.: WO2018/200674
PCT Pub. Date: Nov. 1, 2018

(65) Prior Publication Data
US 2020/0131172 A1     Apr. 30, 2020

Related U.S. Application Data

(60) Provisional application No. 62/490,149, filed on Apr. 26, 2017.

(51) Int. Cl.
C07D 417/14     (2006.01)
C07D 401/14     (2006.01)
C07D 417/06     (2006.01)

(52) U.S. Cl.
CPC ......... *C07D 417/14* (2013.01); *C07D 401/14* (2013.01); *C07D 417/06* (2013.01)

(58) Field of Classification Search
CPC .................. C07D 417/14; C07D 401/14
See application file for complete search history.

(56) References Cited

U.S. PATENT DOCUMENTS 9,290,485 B2 * 3/2016 Brandl .................. A61P 31/00
2012/0035168 A1   2/2012 Brandl et al.

FOREIGN PATENT DOCUMENTS

| EP | 0411507 B1 | 2/1991 |
| EP | 2277858 A1 | 1/2011 |
| WO | 2014/108679 A1 | 7/2014 |
| WO | 2016/083816 A1 | 6/2016 |
| WO | 2016/083820 A1 | 6/2016 |

OTHER PUBLICATIONS

STN Registration No. 1347554-23-7, [1,1'-Biphenyl]-2-carboxylic acid, 4'-[[2-[(phenylamino)carbonyl]-5-propyl-1-yl]methyl]. 3 pages, Dec. 2, 2011.
STN Registration No. 1348029-82-2, [1,1'-Biphenyl]-2-carboxylic acid, 4'-[[2-[(phenylmethyl)amino]carbonyl]-5-propyl-1H-pyrrol-1-yl]methyl]. 3 pages, Dec. 4, 2011.
International Search Report and Written Opinion for Application No. PCT/US2018/029363, dated Jul. 11, 2018, 18 pages.

* cited by examiner

*Primary Examiner* — Kamal A Saeed
(74) *Attorney, Agent, or Firm* — McCarter & English, LLP; Steven G. Davis; Wei Song

(57) ABSTRACT

This application is directed to inhibitors of dynamin-1-like protein (Drp1) represented by the following structural formula (I): and methods for their use, such as to treat one or more DRP1-related diseases.

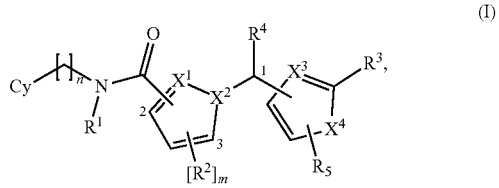

(I)

23 Claims, No Drawings

DYNAMIN-1-LIKE PROTEIN INHIBITORS

CROSS-REFERENCES TO RELATED APPLICATIONS

This application is a U.S. national stage filing, under 35 U.S.C. § 371(c), of International Application No. PCT/US2018/029363, filed on Apr. 25, 2018, which claims the benefit of U.S. Provisional Application No. 62/490,149, filed on Apr. 26, 2017. The entire teachings of the aforementioned applications are incorporated herein by reference.

FIELD OF THE INVENTION

This application is directed to inhibitors of dynamin-1-like protein (Drp1), and methods for their use, such as to treat one or more DRP1-related diseases.

BACKGROUND OF THE INVENTION

In healthy cells, fusion and fission events participate in regulating mitochondrial morphology. Drp1, a dynamin-related protein, mediates outer mitochondrial membrane fission. Upon induction of apoptosis, Drp1 translocates from the cytosol to mitochondria, where it preferentially localizes to potential sites of organelle division. Inhibition of Drp1 prevents the loss of the mitochondrial membrane potential and the release of cytochrome c, and reveals a reproducible swelling of the organelles. Remarkably, inhibition of Drp1 blocks cell death, implicating mitochondrial fission as an important step in cellular apoptosis. Thus, modulation Drp1 activity is effective in the treatment of a variety of conditions, such as, for example, cardiovascular disease, kidney disease, ophthalmic conditions, cancer, and cognitive disease. Indeed, Drp1 is an important biological target for compounds used to help treat and prevent diseases such as cardiovascular disease, kidney disease, ophthalmic conditions, cancer, cognitive disease, and other related conditions.

Accordingly, there remains a need in the art for novel compounds capable of effectively and reliably inhibiting Drp1 in vitro and in vivo. The present invention addresses these and other such needs.

SUMMARY OF THE INVENTION

Provided herein, inter alia, are compounds and compositions comprising such compounds that are useful for inhibiting Drp1 activity (see, e.g., Example 1). In particular, disclosed herein are methods for modulating the activity of Drp1 for the treatment of diseases, developmental delays, and symptoms related to mitochondrial dysfunction. For example, the disclosed compounds and compositions are useful in the treatment of mitochondrial diseases, such as Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, retinitis pigmentosa, and Pearson Syndrome. Alternatively, the disclosed compounds and compositions are useful in the treatment of other Drp1-related diseases, such as cardiovascular disease, kidney disease, ophthalmic conditions, cancer, cognitive disease, and other related conditions.

In one embodiment, provided herein is a compound represented by the following structural Formula (I):

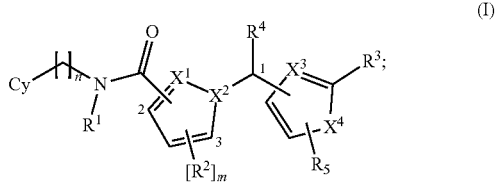

or a pharmaceutically acceptable salt thereof, wherein:

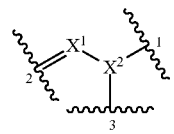

is

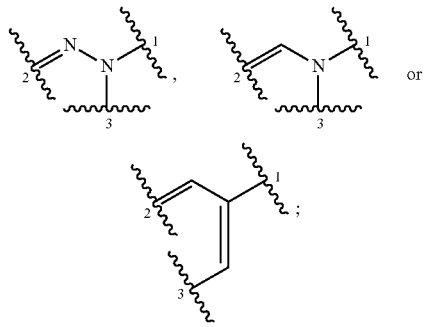

$X_3$ is N or $CR^5$;

$X_4$ is O, S, or —CH=CH—;

$R^1$, $R^4$, and $R^5$ are independently —H or —$CH_3$;

$R^2$ is —H, ($C_1$-$C_5$)alkyl, —$NO_2$, —$NH_2$, ($C_2$-$C_5$)acyl, ($C_1$-$C_5$)hydroxyalkyl, ($C_1$-$C_5$)methoxyalkyl, halo, cyano or phenyl wherein the phenyl represented by $R^2$ is optionally substituted by methyl, halo, methoxy, or halomethoxy;

$R^3$ is —$NR^6R^7$, optionally substituted phenyl, optionally substituted monocyclic nitrogen-containing heteroaryl group, or optionally substituted ($C_3$-$C_7$)cycloaliphatic group;

$R^6$ and $R^7$ are each independently ($C_1$-$C_5$)alkyl or —$NR^6R^7$ taken together is a 5-7 membered optionally substituted monocyclic non-aromatic heterocyclic group;

Cy is an optionally substituted ($C_6$-$C_{10}$) carbocylic aromatic group, optionally substituted ($C_3$-$C_{10}$)cycloaliphatic group, optionally substituted 5-10 membered non-aromatic heterocyclic group, or an optionally substituted 5-10 membered heteroaryl group;

n is 0 or 1; and m is 1 or 2.

Pharmaceutical compositions of compounds of the invention also are disclosed herein. Particular embodiments comprise a pharmaceutically acceptable carrier or excipient and one or more of the disclosed compounds, or a pharmaceutically acceptable salt thereof. The pharmaceutical compositions of the invention can be used in therapy, e.g., for treating a Drp1-related disease or condition in a subject.

Another embodiment comprises treating a Drp1-related disease or condition in a subject by administering to the subject a effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, in the manufacture of a medicament for treating a subject with a disease that can be ameliorated by inhibition of Dynamin-1-like protein (Drp1).

Also provided herein is the use of one or more of the disclosed compounds, or a pharmaceutically acceptable salt thereof, or a pharmaceutical composition comprising one or more of the disclosed compounds, in the manufacture of a medicament for treating a subject with acute kidney injury or cancer.

In another embodiment, provided herein the disclosed compounds, or a pharmaceutically acceptable salt thereof, or a pharmaceutical composition comprising one or more of the disclosed compounds are for use in treating a subject with a disease that can be ameliorated by inhibition of Dynamin-1-like protein (Drp1).

In another embodiment, provided herein the disclosed compounds, or a pharmaceutically acceptable salt thereof, or a pharmaceutical composition comprising one or more of the disclosed compounds are for use in treating a subject with acute kidney injury or cancer.

DETAILED DESCRIPTION

Dynamin-1-like protein is a GTPase that regulates mitochondrial fission. In humans, dynamin-1-like protein, which is typically referred to as dynamin-related protein 1 (Drp1), is encoded by the DNM1L gene. Inhibitors of Drp1 blocks cell death, implicating mitochondrial fission as an important step in apoptosis. Drp1 sequences (OMIM 603850) are publically available, for example, from GenBank® sequence database (e.g., BAA22193 (human, protein, AB006965 (human, nucleic acid))

Herein, the phrase "Drp-1 inhibitor" refers to substances that effectively deactivate the activity of Drp-1. Substances can be tested for their Drp-1 activity by contacting the substance with cells expressing Drp-1, detecting their binding with Drp-1 and then detecting signals that serve as the indicator of the deactivation of Drp-1 (see, e.g., Example 1).

Definitions

The term "acyl" means the radical C(O)R, wherein R is selected from alkyl.

The term "alkyl" used alone or as part of a larger moiety, such as "alkoxy", "haloalkyl", "haloalkoxy", and the like, means saturated aliphatic straight-chain or branched monovalent hydrocarbon radical. Unless otherwise specified, an alkyl group typically has 1 to 5 carbon atoms, i.e., $C_1$-$C_5$-alkyl. As used herein, a "$C_1$-$C_5$-alkyl" group means a radical having from 1 to 5 carbon atoms in a linear or branched arrangement, and includes methyl, ethyl, propyl, isopropyl, butyl, isobutyl, sec-butyl, tert-butyl, pentyl, isopentyl, sec-pentyl, 3-pentyl, neopentyl, and tert-pentyl.

"Carbocyclic group" refers to a 3-10 membered cyclic group in which the ring atoms are all carbon atoms. A carbocyclic group may be saturated (e.g., cycloalkyl), unsaturated, aromatic (e.g., phenyl, naphthyl or tetrahydronapthyl), or non-aromatic (e.g., cycloaliphatic). A carbocyclic group can be monocyclic or bicyclic.

"Cycloaliphatic" means a non-aromatic 3-10 membered saturated or unsaturated aliphatic cyclic hydrocarbon radical. It can be monocyclic or bicyclic (e.g., a bridged or fused bicyclic ring). Cyclopentenyl and cyclohexenyl are non-limiting examples of a cycloaliphatic group. Cycloalkyl means a saturated cycloaliphatic group, and includes, but is not limited to, cyclopropyl, cyclobutyl, cyclopentyl, cyclohexyl, cycloheptyl, and cyclooctyl.

"Cycloalkenyl" means a non-aromatic monocyclic or multicyclic ring system containing a carbon-carbon double bond and having about 3 to about 10 carbon atoms.

The term "non-aromatic heterocyclyl" or "non-aromatic heterocyclic group" refers to a monocyclic, fused bicyclic or bridged bicyclic non-aromatic ring radical containing from 5-10 ring atoms (i.e., "5-10 membered") selected from carbon and 1, 2 or 3 heteroatoms. Each heteroatom is independently selected from nitrogen, quaternary nitrogen, oxidized nitrogen (e.g., NO); oxygen; and sulfur, including sulfoxide and sulfone. Exemplary monocyclic non-aromatic heterocyles include, but are not limited to, morpholinyl, thiomorpholinyl, pyrrolidinonyl, pyrrolidinyl, piperidinyl, piperazinyl, hydantoinyl, valerolactamyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. Bicyclic non-aromatic heterocycles include monocyclic a non-aromatic heterocylic group fused to a phenyl group, a heteroaryl group or another non-aromatic heterocyclic group. Examples of bicyclic non-aromatic heterocycles include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to monocyclic or bicyclic aromatic ring groups having from five to ten ring atoms (i.e., "5-10 membered") selected from carbon and at least one (typically 1 to 4, more typically 1 or 2) heteroatoms (e.g., oxygen, nitrogen or sulfur).

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of bicyclic heteroaryl groups include benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl.

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art.

Suitable substituents are those which do not significantly decrease Drp-1 inhibitory activity. Unless otherwise indicated, exemplary substituents for a carbocylic aromatic group, a heteroaryl group, a cycloaliphatic group, an alkyl group and a non-aromatic heterocycle include but are not limited to halo, —CN, —NO$_2$, —OR$^a$, —NR$^b$R$^c$, —S(O)$_i$R$^a$, —C(=NR$^a$)NR$^b$R$^c$, —NR$^a$S(O)$_2$R$^b$, —S(O)$_2$NR$^b$R$^c$, —S(O)$_2$(NR$^a$)C(=O)R$^b$, —C(=O)OR$^a$, —OC(=O)OR$^a$, —C(=S)OR$^a$, —O(C=S)R$^a$, —C(=O)NR$^b$R$^c$, —NR$^a$C(=O)R$^b$, —C(=S)NR$^b$R$^c$, —NR$^a$C(=S)R$^b$, —NR$^a$(C=O)OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR(C=S)NR$^b$R$^c$, —C(=S)R$^a$, —C(=O)R$^a$, (C$_1$-C$_5$)alkyl, (C$_1$-C$_5$)hydroxyalkyl, (C$_1$-C$_5$)methoxyalkyl, phenyl, —CH$_2$=CH (phenyl), monocyclic heteroaryl group or monocyclic non-aromatic heterocycle and =O (for a cycloaliphatic, non-aromatic heterocycle and alkyl). i is 0, 1, or 2; and R$^{a-c}$ are each independently selected from —H or (C$_1$-C$_5$)alkyl. Additional substituents for a carbocyclic aromatic group include —OCH$_2$CH$_2$—, —OCH$_2$CH$_2$CH$_2$—, —NHCH$_2$CH$_2$—, —NHCH$_2$CH$_2$CH$_2$— or —NHC(O)CH$_2$— bonded to two adjacent ring carbon atoms of carbocyclic aromatic group.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds which have basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.,* 1977, 66:1-19.

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "effective amount" means an amount when administered to the subject which results in beneficial or desired results, including clinical results, e.g., inhibits, suppresses or reduces the symptoms of the condition being treated in the subject as compared to a control. For example, a effective amount can be given in unit dosage form (e.g., from 1 mg to about 50 g per day, e.g., from 1 mg to about 5 grams per day).

The particular mode of administration and the dosage regimen will be selected by the attending clinician, taking into account the particulars of the case (e.g., the subject, the disease, the disease state involved and the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a Drp1-related disease using the disclosed Drp1 inhibitors for guidance.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

Compounds of the Invention

Disclosed herein are embodiments of a compound having the general structure of Formula (I).

In a $1^{st}$ embodiment, the compound has the structure of Formula (I), wherein the optionally substituted phenyl, the optionally substituted monocyclic nitrogen-containing heteroaryl group and the optionally substituted cycloaliphatic group represented by $R^3$ and the optionally substituted 5-7 membered monocyclic non-aromatic heterocyclic group represented by $-NR^6R^7$ are each optionally and independently substituted with one or more groups represented by $R^8$, wherein: i) $R^8$ is selected from -halo, $-CN$, $-NO_2$, $-OR^a$, $-NR^bR^c$, $-S(O)_iR^a$, $-C(=NR^a)NR^bR^c$, $-NR^aS(O)_2R^b$, $-S(O)_2NR^bR^c$, $-C(=O)OR^a$, $-OC(=O)OR^a$, $-C(=S)OR^a$, $-O(C=S)R^a$, $-C(=O)NR^bR^c$, $-NR^aC(=O)R^b$, $-C(=S)NR^bR^c$, $-NR^aC(=S)R^b$, $-NR^a(C=O)OR^b$, $-O(C=O)NR^bR^c$, $-NR^a(C=S)OR^b$, $-O(C=S)NR^bR^c$, $-NR^a(C=O)NR^bR^c$, $-NR^a(C=S)NR^bR^c$, $-C(=S)R^a$, $-C(=O)R^a$, halo($C_1$-$C_5$)alkyl and ($C_1$-$C_5$)alkyl; and ii) two $R^8$ groups bonded to adjacent ring carbon atoms of the phenyl group represented by $R^3$ form $-OCH_2CH_2-$, $-OCH_2CH_2CH_2-$, $-NHCH_2CH_2-$, $-NHCH_2CH_2CH_2-$ or $-NHC(O)CH_2-$; the optionally substituted ($C_6$-$C_{10}$) carbocyclic aromatic group, the optionally substituted ($C_3$-$C_{10}$)cycloaliphatic group, the optionally substituted 5-10 membered non-aromatic heterocyclic group or the optionally substituted 5-10 membered heteroaryl group represented by Cy are each optionally and independently substituted with one or more groups represented by $R^9$, wherein: i) $R^9$ is selected from halo, $-CN$, $-NO_2$, $-OR^a$, $-NR^bR^c$, $-S(O)_iR^a$, $-C(=NR^a)NR^bR^c$, $-NR^aS(O)_2R^b$, $-S(O)_2NR^bR^c$, $-S(O)_2(NR^a)C(=O)R^b$, $-C(=O)OR^a$, $-OC(=O)OR^a$, $-C(=S)OR^a$, $-O(C=S)R^a$, $-C(=O)NR^bR^c$, $-NR^aC(=O)R^b$, $-C(=S)NR^bR^c$, $-NR^aC(=S)R^b$, $-NR^a(C=O)OR^b$, $-O(C=O)NR^bR^c$, $-NR^a(C=S)OR^b$, $-O(C=S)NR^bR^c$, $-NR^a(C=O)NR^bR^c$, $-NR^a(C=S)NR^bR^c$, $-C(=S)R^a$, $-C(=O)R^a$, ($C_1$-$C_5$)alkyl, ($C_1$-$C_5$)hydroxyalkyl, ($C_1$-$C_5$) methoxyalkyl, phenyl, $-CH_2=CH(phenyl)$, monocyclic heteroaryl group or monocyclic non-aromatic heterocyclic group; and ii) two $R^9$ groups bonded to adjacent ring carbon atoms of the carbocyclic aromatic group represented by Cy form $-OCH_2CH_2-$, $-OCH_2CH_2CH_2-$, $-NHCH_2CH_2-$, $-NHCH_2CH_2CH_2-$ or $-NHC(O)CH_2-$; and wherein the ($C_1$-$C_5$)alkyl, phenyl, monocyclic heteroaryl group and monocyclic non-aromatic heterocyclic groups in the substituents represented by Cy are optionally and independently substituted with one or more groups selected from halo, methoxy, —COOH, halomethoxy, methyl and =O (for a non-aromatic heterocyclic group); i is 0, 1, or 2; and $R^{a-c}$ are each independently selected from —H or $(C_1-C_5)$alkyl; and the remaining variable are the same as defined for Formula (I).

In a $2^{nd}$ embodiment, the compound of Formula (I) is represented by the following structural formula (II):

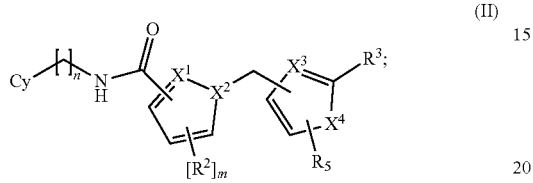
(II)

or a pharmaceutically acceptable salt thereof, wherein the variables are as defined for Formula (I) or in the $1^{st}$ embodiment.

In a $3^{rd}$ embodiment, the compound is represented by structural formula (III):

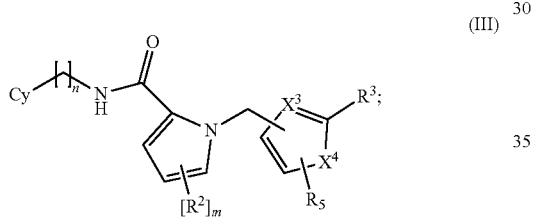
(III)

or a pharmaceutically acceptable salt thereof, wherein the variables are as defined for Formula (I) or in the $1^{st}$ embodiment.

In a $4^{th}$ embodiment, the compound is represented by structural Formula (IV):

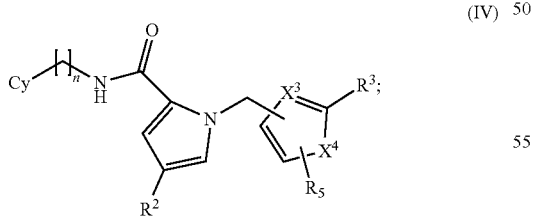
(IV)

or a pharmaceutically acceptable salt thereof, wherein the variables are as defined for Formula (I) or in the $1^{st}$ embodiment.

In a $5^{th}$ embodiment, the compound is represented by a structural formula selected from structural Formulae (V), (VI), (VII), and (VIII):

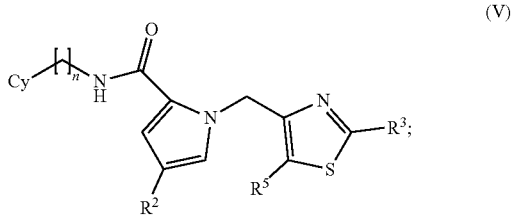
(V)

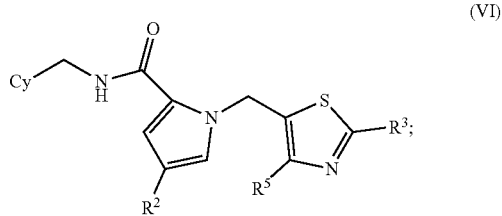
(VI)

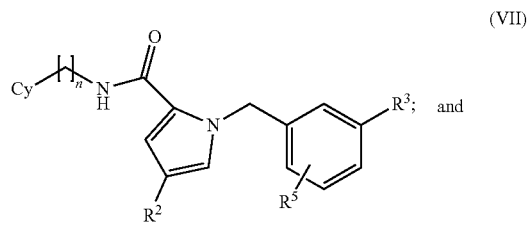
(VII) and

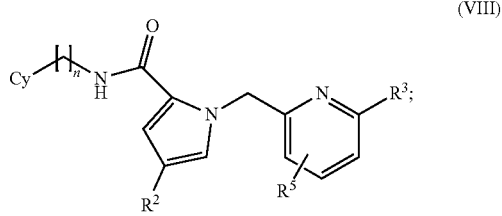
(VIII)

or a pharmaceutically acceptable salt thereof, wherein the variables are as defined for structural Formula (I) or in the $1^{st}$ embodiment.

In a $6^{th}$ embodiment, the compound is represented by a structural formula selected from Formulas (IX), (X), and (XI):

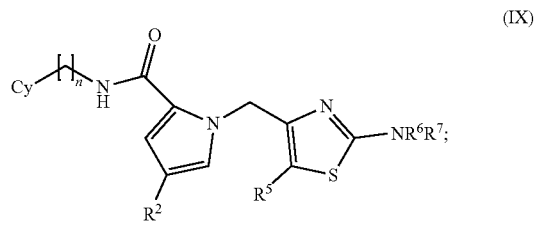
(IX)

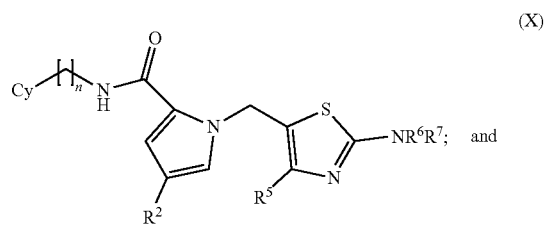
(X) and

-continued

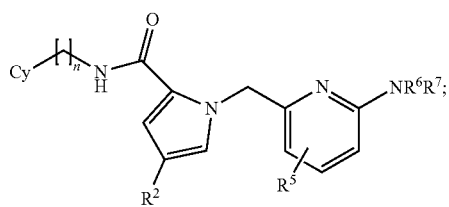

(XI)

or a pharmaceutically acceptable salt thereof, wherein the variables are as defined for Formula (I) or in the 1st embodiment.

In a 7th embodiment, the compound is represented by structural Formula (XII):

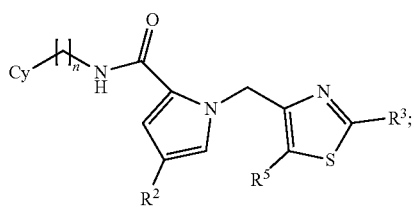

(XII)

or a pharmaceutically acceptable salt thereof, wherein the variables are as defined for Formula (I) or in the 1st embodiment.

In an 8th embodiment, the compound is represented by structural Formula (XIII):

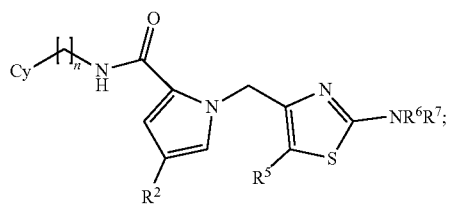

(XIII)

or a pharmaceutically acceptable salt thereof, wherein the variables are as defined for Formula (I) or in the 1st embodiment.

In a 9th embodiment, the compound of any one of the 1st, 2nd, 3rd, 4th, 5th, 6th, 7th, or 8th embodiments, Cy is

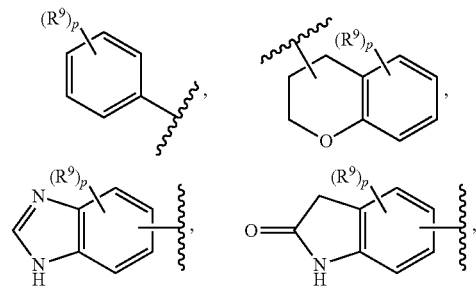

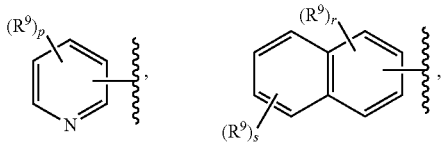

$(C_3-C_8)$cycloalkyl or tetrahydropyranyl;

$R^9$ is selected from halo, —CN, —NO$_2$, —OR$^a$, —NR$^b$R$^c$, —S(O)$_i$R$^a$, —C(=NR$^a$)NR$^b$R$^c$, —NR$^a$S(O)$_2$R$^b$, —S(O)$_2$NR$^b$R$^c$, —S(O)$_2$(NR$^a$)C(=O)R$^b$, —C(=O)OR$^a$, —OC(=O)OR$^a$, —C(=S)OR$^a$, —O(C=S)R$^a$, —C(=O)NR$^b$R$^c$, —NR$^a$C(=O)R$^b$, —C(=S)NR$^b$R$^c$, —NR$^a$C(=S)R$^b$, —NR$^a$(C=O)OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR$^a$(C=S)NR$^b$R$^c$, —C(=S)R$^a$, —C(=O)R$^a$, $(C_1-C_5)$alkyl, $(C_1-C_5)$hydroxyalkyl, $(C_1-C_5)$methoxyalkyl, phenyl, —CH$_2$=CH(phenyl), monocyclic heteroaryl group or monocyclic non-aromatic heterocyclic group; and wherein the $(C_1-C_5)$alkyl, phenyl, monocyclic heteroaryl group and monocyclic non-aromatic heterocyclic groups in the substituents represented by Cy are optionally and independently substituted with one or more groups selected from halo, methoxy, halomethoxy, methyl, —COOH and =O (for a non-aromatic heterocyclic group); the $(C_3-C_8)$cycloalkyl and tetrahydropyranyl are optionally and independently substituted with methyl or —COOH;

p is 0, 1, 2 or 3;

s and r are 0, 1, 2 or 3 and s+r are <3; and the remaining variables are as defined for Formula (I) or in the 1st, 2nd, 3rd, 4th, 5th, 6th,7th, or 8th embodiments.

In a 10th embodiment, the compound of Formula (I) or any one of the 1st, 2nd, 3rd, 4th,5th, 6th, 7th, 8th, or 9th embodiments, or a pharmaceutically acceptable salt thereof, n is 0, and the remaining variables are as defined for Formula (I) or in the 1st, 2nd, 3rd, 4th, 5th, 6th, 7th, 8th or 9th embodiments.

In an 11th embodiment, the compound of Formula (I) or any one of the 1st, 2nd, 3rd, 4th, 5th, 6th, 7th, 8th, or 9th embodiments, or a pharmaceutically acceptable salt thereof, wherein n is 1, and the remaining variables are as defined for Formula (I) or in the 1st, 2nd, 3rd, 4th, 5th, 6th,7th, 8th, or 9th embodiments.

In a 12th embodiment, the compound of Formula (I) or any one of the 1st, 2nd, 3rd, 4th,5th, 6th, 7th,h 8th, 9th, 10th, or 11th embodiments, or a pharmaceutically acceptable salt thereof, wherein —NR$^6$R$^7$ is

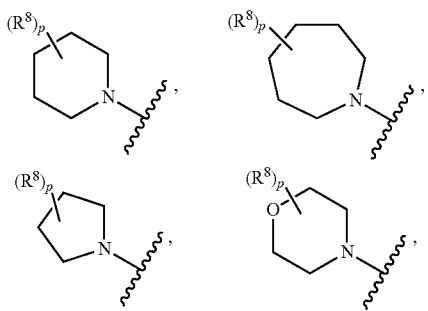

and p is 0, 1, 2 or 3, or wherein $R^6$ and $R^7$ are independently hydrogen or $C_1-C_3$ alkyl, and the remaining variables are as defined for Formula (I) or in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, or 11$^{th}$ embodiments.

In a 13$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$9$^{th}$, 10$^{th}$, 11$^{th}$, or 12$^{th}$ embodiments, or a pharmaceutically acceptable salt thereof, wherein each R$^8$ is independently methyl or flouro, and the remaining variables are as defined for Formula (I) or in the 1$^{st}$, 2$^{nd}$, 3$^{rd}$, 4th, 5$^{th}$, 6$^{th}$, 7$^{th}$, 8$^{th}$, 9$^{th}$, 10$^{th}$, 11$^{th}$, or 12$^{th}$ embodiments.

In a 14$^{th}$ embodiment, the compound of any one of the 1$^{st}$, 2$^{nd}$, 3$^{rd}$, 4$^{th}$, 5$^{th}$, 7$^{th}$, 9$^{th}$, 10$^{th}$, or 11$^{th}$ embodiments, or a pharmaceutically acceptable salt thereof, wherein:

R$^3$ is

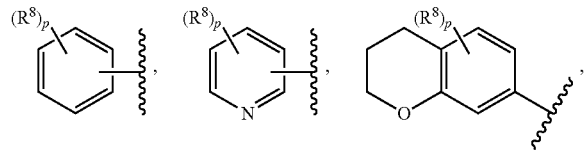

pyrazolyl, or (C$_3$-C$_5$)cycloaliphatic;

each R$^8$ is independently selected from -halo, —CN, —NO$_2$, —OR$^a$, —NR$^b$R$^c$, —S(O)$_i$R$^a$, —C(=NR$^a$)NR$^b$R$^c$, —NR$^a$S(O)$_2$R$^b$, —S(O)$_2$NR$^b$R$^c$, —C(=O)OR$^a$, —OC(=O)OR$^a$, —C(=S)OR$^a$, —O(C=S)R$^a$, —C(=O)NR$^b$R$^c$, NR$^a$C(=O)R$^b$, —C(=S)NR$^b$R$^c$, —NR$^a$C(=S)R$^b$, —NR$^a$(C=O)OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR$^a$(C=S)NR$^b$R$^c$, —C(=S)R$^a$, —C(=O)R$^a$, halo(C$_1$-C$_5$)alkyl and (C$_1$-C$_5$)alkyl;

the pyrazolyl, the (C$_3$-C$_8$)cycloaliphatic are each optionally and independently substituted with methyl; and p is 0, 1, 2 or 3; and the remaining variables are as defined for Formula (I) or in the 1$^{st}$, 2$^{nd}$, 3$^{rd}$, 4$^{th}$, 5$^{th}$, 6$^{th}$7$^{th}$, 8$^{th}$, 9$^{th}$, 10$^{th}$, or 11$^{th}$ embodiments.

In a 15$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$9$^{th}$, 10$^{th}$, 11$^{th}$, or 14$^{th}$ embodiments, or a pharmaceutically acceptable salt thereof, wherein each R$^8$ is independently (C$_1$-C$_5$)alkyl, —OR$^a$, —S(O)$_2$NR$^b$R$^c$, —NR$^a$S(O)$_2$R$^b$, —C(=O)NR$^b$R$^c$, NR$^a$C(=O)R$^b$, —C(=O)OR$^a$, —C(=S)OR$^a$, —C(=S)NR$^b$R$^c$ or —NR$^a$C(=S)R$^b$, and the remaining variables are as defined for Formula (I) or in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, or 14$^{th}$ embodiments.

In a 16$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$9$^{th}$, 10$^{th}$, 11$^{th}$, or 14$^{th}$ embodiments, or a pharmaceutically acceptable salt thereof, wherein each R$^8$ is independently methyl, —NH$_2$SO$_2$CH$_3$, —OCH$_3$, or —C(=O)NH$_2$, and the remaining variables are as defined for Formula (I) or in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, or 14$^{th}$ embodiments.

In a 17$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$9$^{th}$, 10$^{th}$, 11$^{th}$, 12$^{th}$, 13$^{th}$, 14$^{th}$, 15$^{th}$, or 16$^{th}$ embodiments, or a pharmaceutically acceptable salt thereof, wherein each R$^9$ is independently halo, (C$_1$-C$_3$) alkyl, —OR$^a$, (C$_1$-C$_3$)hydroxyalkyl, —S(O)$_2$NR$^b$R$^c$, —NR$^a$S(O)$_2$R$^b$, —C(=O)NR$^b$R$^c$, —NR$^a$C(=O)R$^b$, —C(=S)NR$^b$R$^c$ or —NR$^a$C(=S)R$^b$, —S(O)$_2$(NR$^a$)C(=O)R$^b$, —C(=O)OH, —C(=S)OH, —CH$_2$=CH(phenyl), phenyl optionally substituted with -methyl or succinimidyl or 5-6 membered monocyclic heteroaryl group optionally substituted with one or more methyl groups, and the remaining variables are as defined for Formula (I) or in the 1st, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$, 15$^{th}$, or 16$^{th}$ embodiments.

In a 18$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$, 15$^{th}$, or 16$^{th}$ embodiments, or a pharmaceutically acceptable salt thereof, wherein R$^2$ is —H, —CH$_3$, —CH$_2$CH$_3$, —NO$_2$, —NH$_2$, Cl, Br, —CN, —CH(CH$_3$)OH, —C(=O)CH$_3$, —CH(CH$_3$)OCH$_3$, or phenyl; and each R$^9$ is independently F, I, —CH$_3$, —OH, —C(=O)OH, —C(O)NHCH$_3$, —CH$_2$OH, —S(O)$_2$NH$_2$, —S(O)$_2$(NH)C(=O)CH$_3$, isoxazolyl optionally substituted with one or two methyl groups, pyridyl, pyrazolyl, furanyl, tetrazolyl, —CH$_2$=CH(phenyl) or phenyl optionally substituted with methyl or —COOH; and the remaining variables are as defined for Formula (I) or in the 1$^{st}$, 2$^{nd}$, 3$^{rd}$, 4$^{th}$, 5, 6$^{th}$, 7$^{th}$, 8$^{th}$, 9$^{th}$, 10$^{th}$, 11$^{th}$, 12$^{th}$, 13$^{th}$, 14$^{th}$, 15$^d$, or 16$^{th}$ embodiments.

In a 19$^{th}$ embodiment, the compound of any one of the 1$^{st}$, 2$^{nd}$, 3$^{rd}$, 4$^{th}$, 5$^{th}$, 6$^{th}$, 7$^{th}$, 8$^{th}$9$^{th}$, 10$^{th}$, 11$^{th}$, 12$^{th}$, 13$^{th}$, 14$^{th}$, 15$^{th}$, or 16$^{th}$ embodiments, or a pharmaceutically acceptable salt thereof, wherein R$^2$ is Br, Cl, —CH$_3$, —CH$_2$CH$_3$, or phenyl; and each R$^9$ is independently F, methyl, —C(=O) OH, —C(O)NHCH$_3$, isoxazolyl optionally substituted with one or two methyl groups, pyrazolyl, furanyl, tetrazolyl, or S(O)$_2$(NH)C(=O)CH$_3$; and the remaining variables are as defined for Formula (I) or in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$, 15$^{th}$, or 16$^{th}$ embodiments.

Methods of Treatment

Methods of treating a Drp1-related disease or condition in a subject are disclosed. The methods can include administering to the subject a effective amount of one or more compounds or compositions provided herein.

In one embodiment, the Drp1-related disease is a mitochondrial disease. Examples of mitochondrial diseases include, but are not limited to, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the Drp1-related disease is a vascular disease (such as a cardiovascular disease or any disease that would benefit from increasing vascularization in tissues exhibiting impaired or inadequate blood flow). In other embodiments, the Drp1-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the Drp1-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the Drp1-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the Drp1-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the Drp1-related disease is a neuronal activation disorder, Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the Drp1-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the Drp1-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the Drp1-related disease is a beta oxidation disease. Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In some embodiments, the Drp1-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the Drp1-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the Drp1-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the Drp1-related disease is a metabolic disease. Examples of metabolic disorders include, but are not limited to, hyperlipidemia, dyslipidemia, hyperchlosterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer's disease, neurodegenerative disease including Parkison's disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the Drp1-related disease is cancer. Examples of cancer include, but are not limited to, cancers of the colon, large intestine, skin, breast, prostate, ovary, and/or lung.

In other embodiments, the Drp1-related disease is an ischemic injury. Examples of ischemic injuries include, but are not limited to, cardiac ischemia, such as myocardial infarction; brain ischemia (e.g., acute ischemic stroke; chronic ischemic of the brain, such as vascular dementia; and transient ischemic attack (TIA); bowel ischemia, such as ischemic colitis; limb ischemia, such as acute arm or leg ischemia; subcutaneous ischemia, such as cyanosis or gangrene; and ischemic organ injury, such as ischemic renal injury (IRI).

In still other embodiments, the Drp1-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury (also known as acute renal failure), chronic renal failure, diabetic nephropathy, or Bartter's syndrome.

Pharmaceutical Compositions and Administration Thereof
Additional Therapeutic Agents Pharmaceutical compositions are disclosed that include one or more compounds provided herein (such as 1, 2, 3, 4, or 5 of such compounds), and typically at least one additional substance, such as an excipient, a known therapeutic other than those of the present disclosure, and combinations thereof. In some embodiments, the disclosed Drp1 inhibitors can be used in combination with other agents known to have beneficial activity with the disclosed Drp1 inhibitors. For example, disclosed compounds can be administered alone or in combination with one or more other mitodondrial-modulating compounds, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (−)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

EXEMPLIFICATION

Example 1: Drp1 Activity Screen

The GTPase activity of Drp1 was assayed using a colorimetric assay similar to as described previously by Leonard M. et al. "Robust colorimetric assays for dynamin's basal and stimulated GTPase activities." Methods Enzymol. 2005, Vol. 404, pp. 490-503. Briefly, for GTPase assays of purified Drp1 inhibitor samples, 0.6 µM Drp1 preincubated with 0.1 mg/mL liposomes (consisting of 80% soybean lipids/20% cardiolipin) and inhibitor was added to 1 mM GTP in a microtiter plate for 20 min at 37° C. in 4 mM $MgCl_2$, 10 mM Hepes (pH 7.0), 100 mM KCl, 1 mM DTT. Reactions were stopped by diluting with 0.5 mM EDTA. Samples were then incubated with malachite green reagent (1 mM malachite green and 50 mM ammonium molybdate in 1 N HCl), and the absorbance at 650 nm was measured. The reaction rates, $IC_{50}$ values, and max % inhibition were determined using Excel/GraphPad Prism software.

TABLE 1

DRP1 Activity Screen

| Compound No. | Structure | $IC_{50}$ (µM) | max % inh |
|---|---|---|---|
| A-1 | 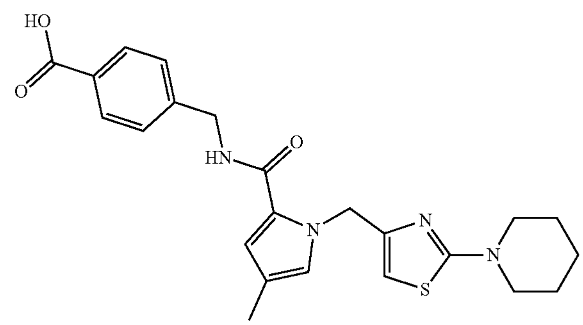 [SMILES: Cc1cc(C(=O)NCc2ccc(C(=O)O)cc2)n(Cc2csc(N3CCCCC3)n2)c1] | 6.4 | 89 |
| A-2 | 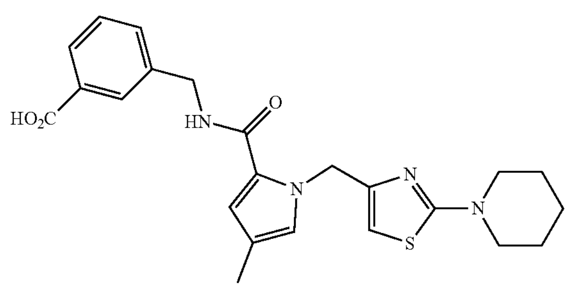 [SMILES: Cc1cc(C(=O)NCc2cccc(C(=O)O)c2)n(Cc2csc(N3CCCCC3)n2)c1] | 3.2 | 93 |
| A-3 | 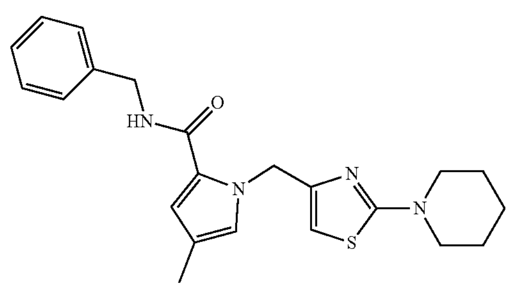 [SMILES: Cc1cc(C(=O)NCc2ccccc2)n(Cc2csc(N3CCCCC3)n2)c1] | 4.8 | 70 |

TABLE 1-continued

DRP1 Activity Screen

| Compound No. | Structure | IC$_{50}$ (μM) | max % inh |
|---|---|---|---|
| A-4 | 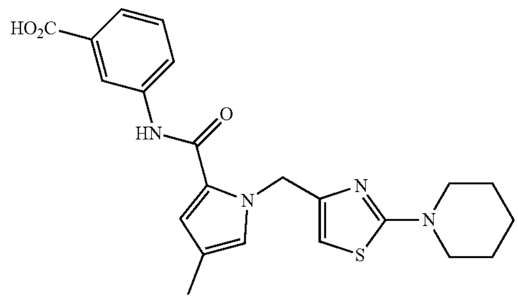 [SMILES: Cc1cc(C(=O)Nc2cccc(C(=O)O)c2)n(Cc2csc(N3CCCCC3)n2)c1] | 7.0 | 74 |
| A-5 | 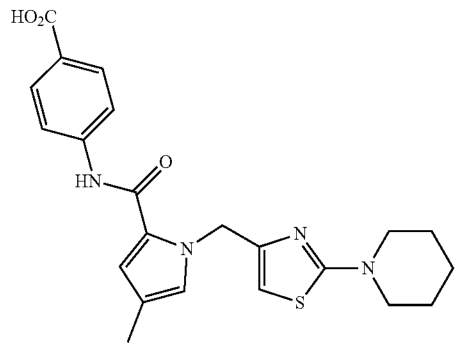 [SMILES: Cc1cc(C(=O)Nc2ccc(C(=O)O)cc2)n(Cc2csc(N3CCCCC3)n2)c1] | 1.9 | 84 |
| A-6 | 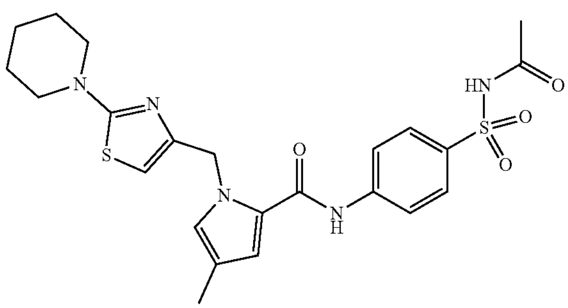 [SMILES: CC(=O)NS(=O)(=O)c1ccc(NC(=O)c2cc(C)cn2Cc2csc(N3CCCCC3)n2)cc1] | 5.0 | 71 |
| A-7 | 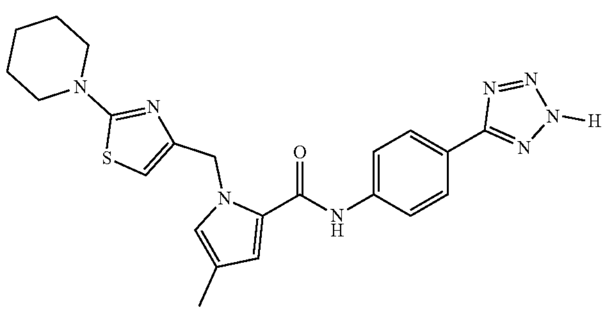 [SMILES: Cc1cc(C(=O)Nc2ccc(-c3nn[nH]n3)cc2)n(Cc2csc(N3CCCCC3)n2)c1] | 0.91 | 91 |
| A-8 | 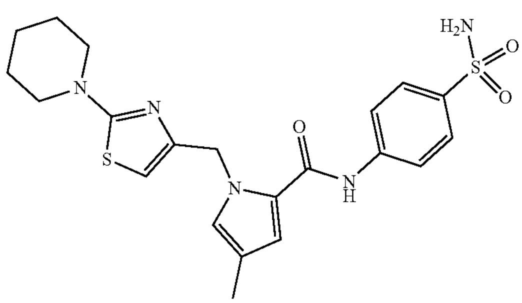 [SMILES: Cc1cc(C(=O)Nc2ccc(S(N)(=O)=O)cc2)n(Cc2csc(N3CCCCC3)n2)c1] | 2.5 | 78 |

TABLE 1-continued
DRP1 Activity Screen
| Compound No. | Structure | IC$_{50}$ (µM) | max % inh |
|---|---|---|---|
| A-9 | 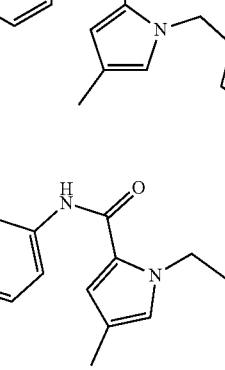 | 51 | 64 |
| A-10 | 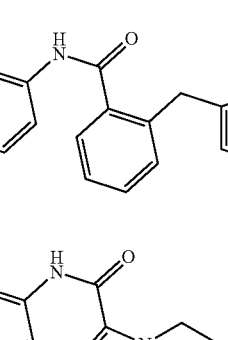 | 78 | 56 |
| A-11 | 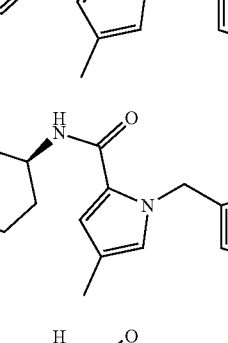 | >100 | 13 |
| A-12 | 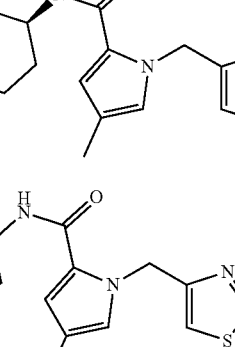 | 25 | 47 |
| A-13 | 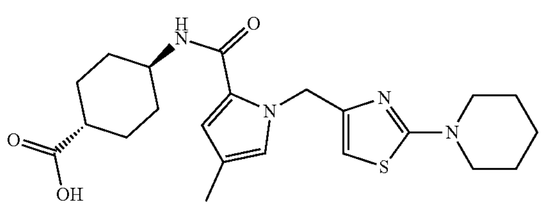 [SMILES: Cc1cc(C(=O)N[C@H]2CC[C@H](C(=O)O)CC2)n(Cc2csc(N3CCCCC3)n2)c1] | 5.5 | 75 |
| A-14 | 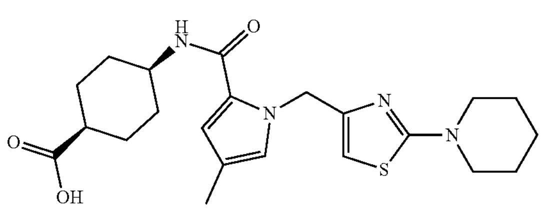 [SMILES: Cc1cc(C(=O)N[C@H]2CC[C@@H](C(=O)O)CC2)n(Cc2csc(N3CCCCC3)n2)c1] | 39 | 64 |
| A-15 | 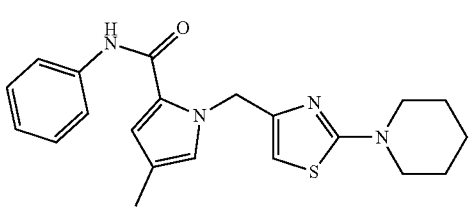 [SMILES: Cc1cc(C(=O)Nc2ccccc2)n(Cc2csc(N3CCCCC3)n2)c1] | 2.2 | 68 |

TABLE 1-continued

DRP1 Activity Screen

| Compound No. | Structure | IC$_{50}$ (μM) | max % inh |
|---|---|---|---|
| A-16 | 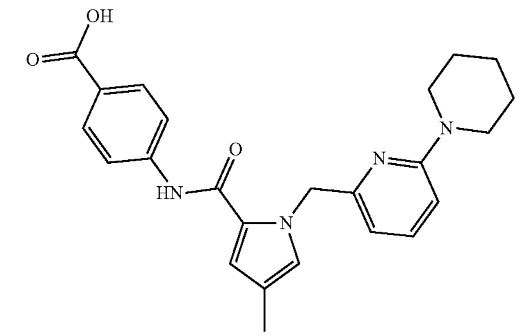 [SMILES: Cc1cc(C(=O)Nc2ccc(C(=O)O)cc2)n(Cc2cccc(N3CCCCC3)n2)c1] | 1.7 | 86 |
| A-17 | 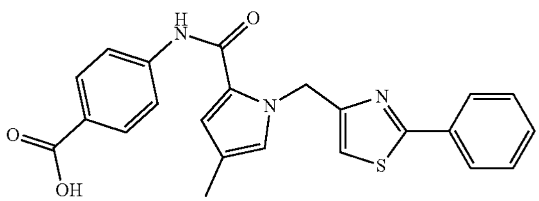 [SMILES: Cc1cc(C(=O)Nc2ccc(C(=O)O)cc2)n(Cc2csc(-c3ccccc3)n2)c1] | 3.8 | 55 |
| A-18 | 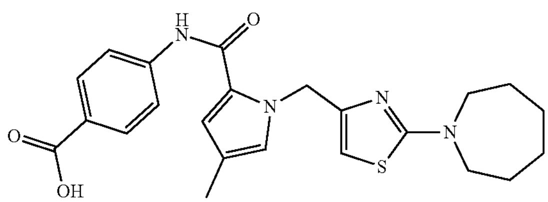 [SMILES: Cc1cc(C(=O)Nc2ccc(C(=O)O)cc2)n(Cc2csc(N3CCCCCC3)n2)c1] | 3.4 | 70 |
| A-19 | 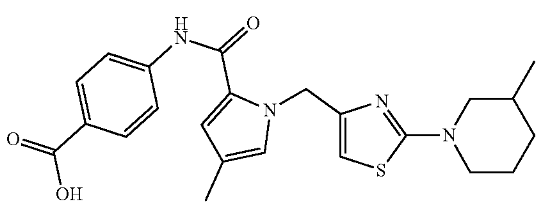 [SMILES: Cc1cc(C(=O)Nc2ccc(C(=O)O)cc2)n(Cc2csc(N3CCCC(C)C3)n2)c1] | 2.7 | 72 |
| A-20 | 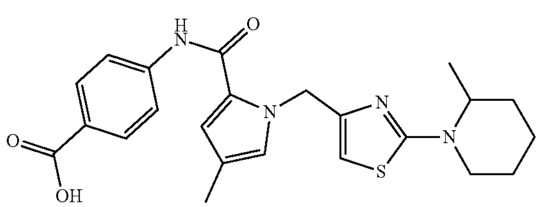 [SMILES: Cc1cc(C(=O)Nc2ccc(C(=O)O)cc2)n(Cc2csc(N3CCCCC3C)n2)c1] | 3.9 | 79 |
| A-21 | 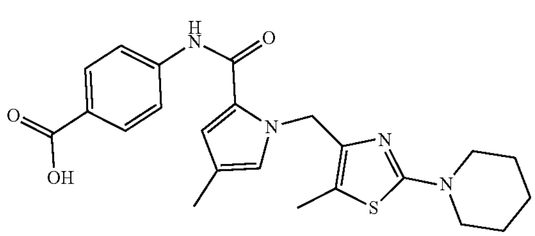 [SMILES: Cc1cc(C(=O)Nc2ccc(C(=O)O)cc2)n(Cc2nc(N3CCCCC3)sc2C)c1] | 11.9 | 70 |

TABLE 1-continued

DRP1 Activity Screen

| Compound No. | Structure | IC$_{50}$ (μM) | max % inh |
|---|---|---|---|
| A-22 | 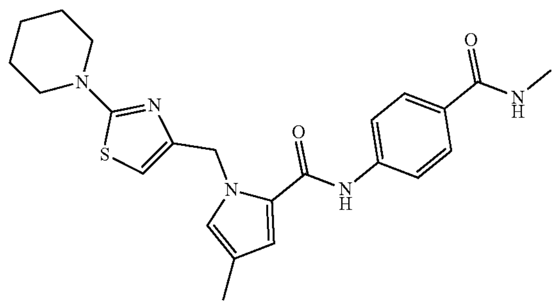 [SMILES: CNC(=O)c1ccc(NC(=O)c2cc(C)cn2Cc2csc(N3CCCCC3)n2)cc1] | 1.8 | 64 |
| A-23 | 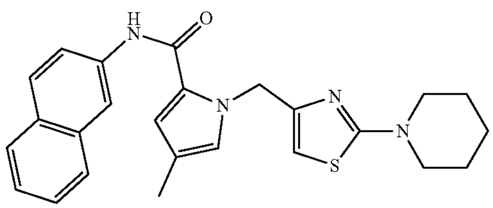 [SMILES: Cc1cc(C(=O)Nc2ccc3ccccc3c2)n(Cc2csc(N3CCCCC3)n2)c1] | 1.6 | 37 |
| A-24 | 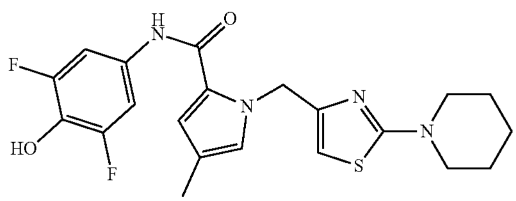 [SMILES: Cc1cc(C(=O)Nc2cc(F)c(O)c(F)c2)n(Cc2csc(N3CCCCC3)n2)c1] | 21.8 | 29 |
| A-25 | 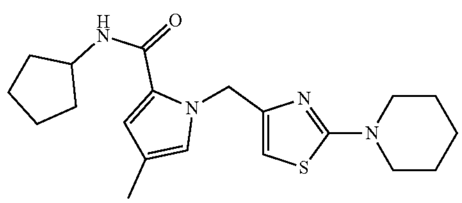 [SMILES: Cc1cc(C(=O)NC2CCCC2)n(Cc2csc(N3CCCCC3)n2)c1] | 5.7 | 66 |
| A-26 | 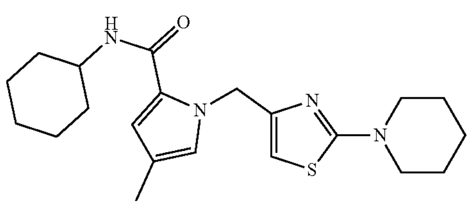 [SMILES: Cc1cc(C(=O)NC2CCCCC2)n(Cc2csc(N3CCCCC3)n2)c1] | 1.7 | 40 |
| A-27 | 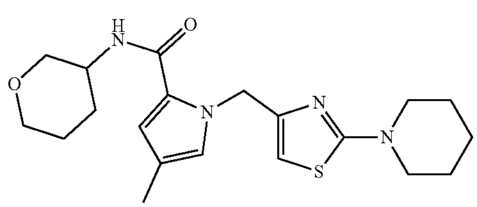 [SMILES: Cc1cc(C(=O)NC2CCCOC2)n(Cc2csc(N3CCCCC3)n2)c1] | 9.6 | 71 |

TABLE 1-continued
DRP1 Activity Screen
| Compound No. | Structure | IC$_{50}$ (μM) | max % inh |
|---|---|---|---|
| A-28 | 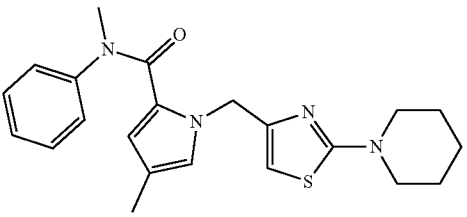 [SMILES: Cc1cc(C(=O)N(C)c2ccccc2)n(Cc2csc(N3CCCCC3)n2)c1] | >100 | 15 |
| A-29 | 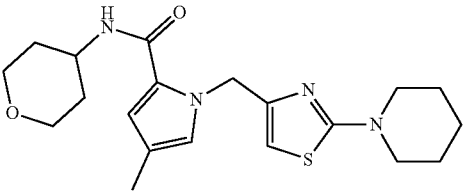 [SMILES: Cc1cc(C(=O)NC2CCOCC2)n(Cc2csc(N3CCCCC3)n2)c1] | 14.4 | 62 |
| A-30 | 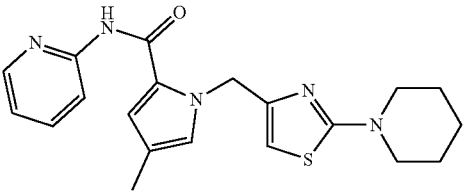 [SMILES: Cc1cc(C(=O)Nc2ccccn2)n(Cc2csc(N3CCCCC3)n2)c1] | 8.7 | 63 |
| A-31 | 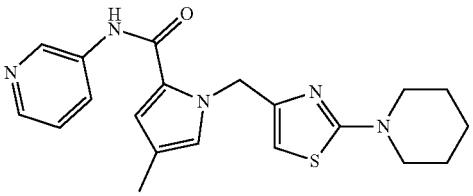 [SMILES: Cc1cc(C(=O)Nc2cccnc2)n(Cc2csc(N3CCCCC3)n2)c1] | 7.6 | 59 |
| A-32 | 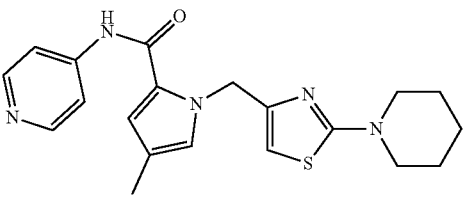 [SMILES: Cc1cc(C(=O)Nc2ccncc2)n(Cc2csc(N3CCCCC3)n2)c1] | 10.3 | 55 |
| A-33 | 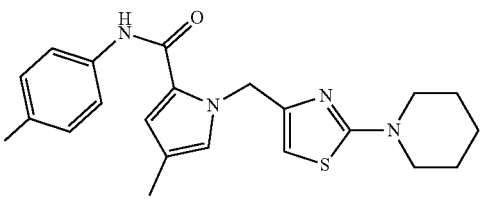 | 4.5 | 34 |
| A-34 | 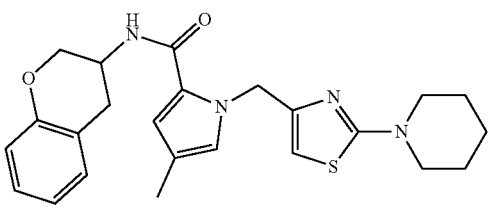 [SMILES: Cc1cc(C(=O)NC2COc3ccccc3C2)n(Cc2csc(N3CCCCC3)n2)c1] | 9.0 | 35 |

TABLE 1-continued
DRP1 Activity Screen
| Compound No. | Structure | IC$_{50}$ (μM) | max % inh |
|---|---|---|---|
| A-35 | 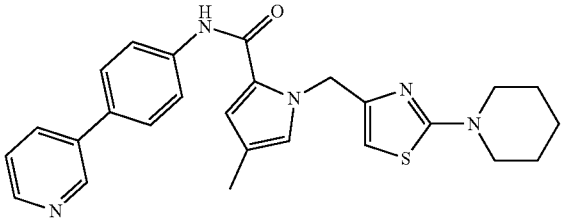 [SMILES: Cc1cc(C(=O)Nc2ccc(-c3cccnc3)cc2)n(Cc2csc(N3CCCCC3)n2)c1] | 1.2 | 67 |
| A-36 | 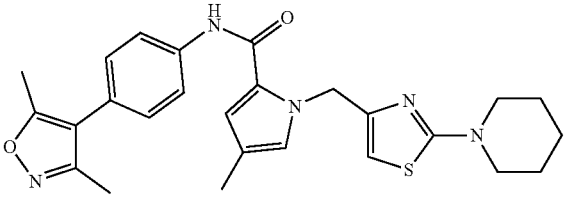 [SMILES: Cc1cc(C(=O)Nc2ccc(-c3c(C)noc3C)cc2)n(Cc2csc(N3CCCCC3)n2)c1] | 1.4 | 44 |
| A-37 | 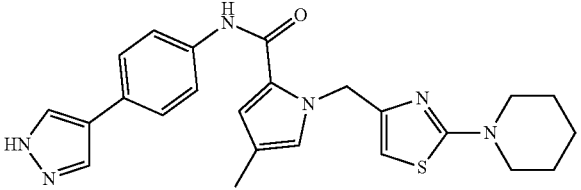 [SMILES: Cc1cc(C(=O)Nc2ccc(-c3cn[nH]c3)cc2)n(Cc2csc(N3CCCCC3)n2)c1] | 1.2 | 71 |
| A-38 | 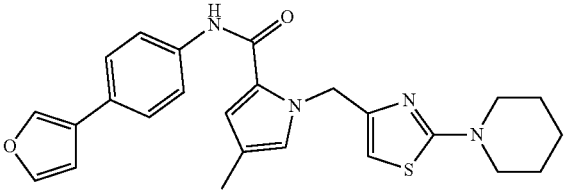 [SMILES: Cc1cc(C(=O)Nc2ccc(-c3ccoc3)cc2)n(Cc2csc(N3CCCCC3)n2)c1] | 1.2 | 47 |
| A-39 | 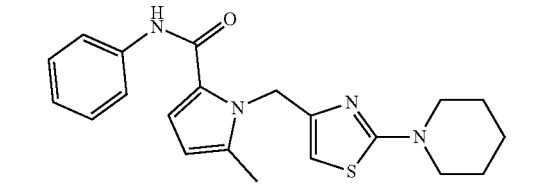 [SMILES: Cc1ccc(C(=O)Nc2ccccc2)n1Cc1csc(N2CCCCC2)n1] | 36 | 26 |
| A-40 | 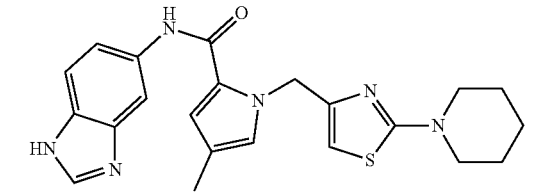 [SMILES: Cc1cc(C(=O)Nc2ccc3[nH]cnc3c2)n(Cc2csc(N3CCCCC3)n2)c1] | 2.9 | 72 |
| A-41 | 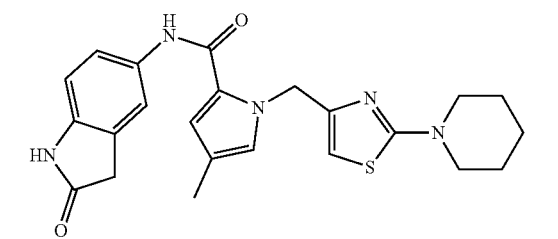 [SMILES: Cc1cc(C(=O)Nc2ccc3c(c2)CC(=O)N3)n(Cc2csc(N3CCCCC3)n2)c1] | 4.2 | 74 |

TABLE 1-continued

DRP1 Activity Screen

| Compound No. | Structure | IC$_{50}$ (μM) | max % inh |
|---|---|---|---|
| A-42 | 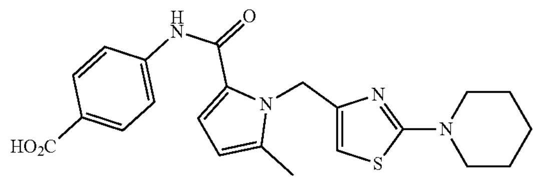 [SMILES: Cc1ccc(C(=O)Nc2ccc(C(=O)O)cc2)n1Cc1csc(N2CCCCC2)n1] | 26 | 58 |
| A-43 | 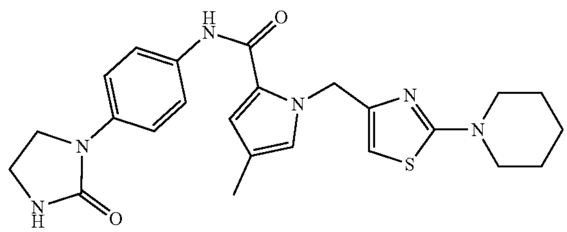 [SMILES: Cc1cc(C(=O)Nc2ccc(N3CCNC3=O)cc2)n(Cc2csc(N3CCCCC3)n2)c1] | 4.3 | 66 |
| A-44 | 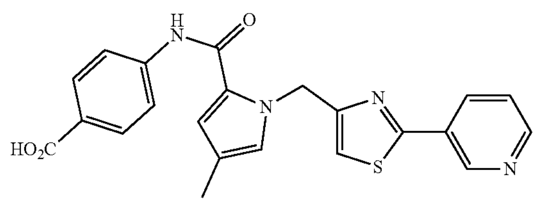 [SMILES: Cc1cc(C(=O)Nc2ccc(C(=O)O)cc2)n(Cc2csc(-c3cccnc3)n2)c1] | 69 | 27 |
| A-45 | 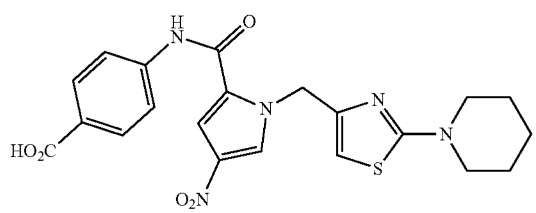 | 22 | 49 |
| A-46 | 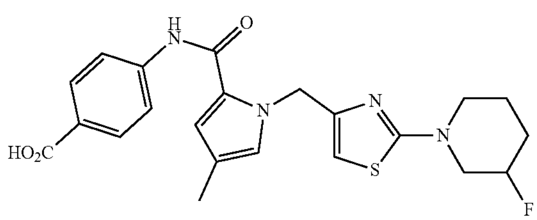 [SMILES: Cc1cc(C(=O)Nc2ccc(C(=O)O)cc2)n(Cc2csc(N3CCCC(F)C3)n2)c1] | 12.7 | 64 |
| A-47 | 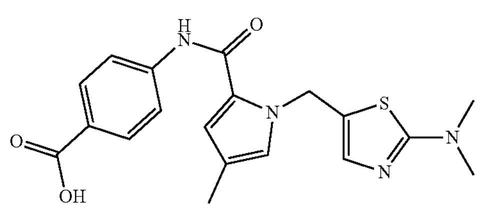 [SMILES: Cc1cc(C(=O)Nc2ccc(C(=O)O)cc2)n(Cc2cnc(N(C)C)s2)c1] | 16.3 | 59 |
| A-48 | 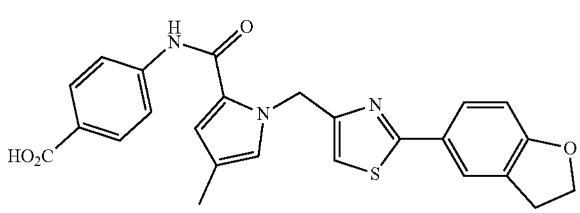 [SMILES: Cc1cc(C(=O)Nc2ccc(C(=O)O)cc2)n(Cc2csc(-c3ccc4c(c3)CCO4)n2)c1] | 39.5 | 58 |

TABLE 1-continued
DRP1 Activity Screen
| Compound No. | Structure | IC$_{50}$ (μM) | max % inh |
|---|---|---|---|
| A-49 | 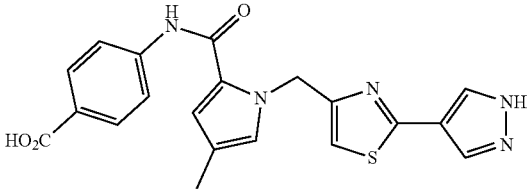 [SMILES: Cc1cc(C(=O)Nc2ccc(C(=O)O)cc2)n(Cc2csc(-c3cn[nH]c3)n2)c1] | 5.6 | 79 |
| A-50 | 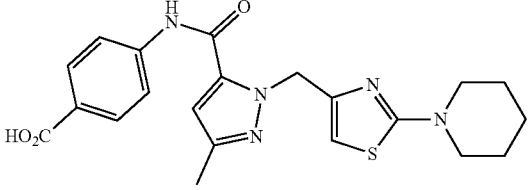 [SMILES: Cc1cc(C(=O)Nc2ccc(C(=O)O)cc2)n(Cc2csc(N3CCCCC3)n2)n1] | 30.5 | 41 |
| A-51 | 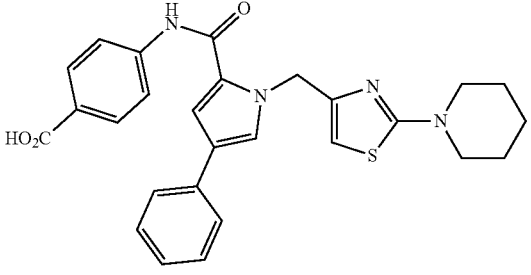 [SMILES: O=C(O)c1ccc(NC(=O)c2cc(-c3ccccc3)cn2Cc2csc(N3CCCCC3)n2)cc1] | 1.8 | 78 |
| A-52 | 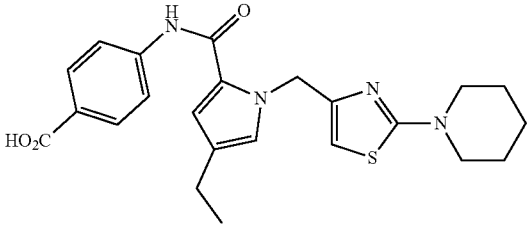 [SMILES: CCc1cc(C(=O)Nc2ccc(C(=O)O)cc2)n(Cc2csc(N3CCCCC3)n2)c1] | 2.1 | 81 |
| A-53 | 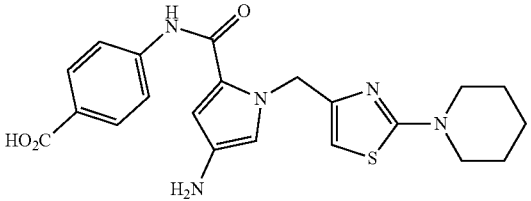 | >100 | 32 |
| A-54 | 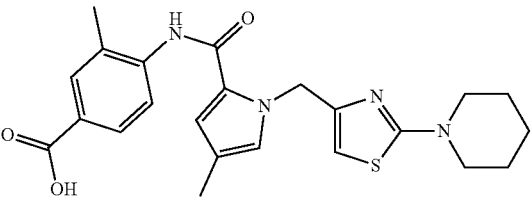 [SMILES: Cc1cc(C(=O)Nc2ccc(C(=O)O)cc2C)n(Cc2csc(N3CCCCC3)n2)c1] | >100 | 44 |

TABLE 1-continued

DRP1 Activity Screen

| Compound No. | Structure | IC$_{50}$ (µM) | max % inh |
|---|---|---|---|
| A-55 | 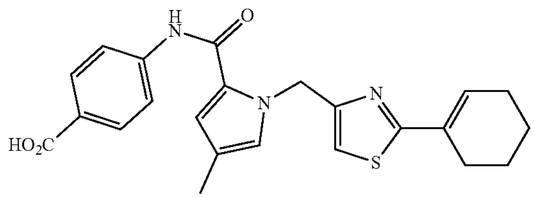 [SMILES: Cc1cc(C(=O)Nc2ccc(C(=O)O)cc2)n(Cc2csc(C3=CCCCC3)n2)c1] | 11.6 | 80 |
| A-56 | 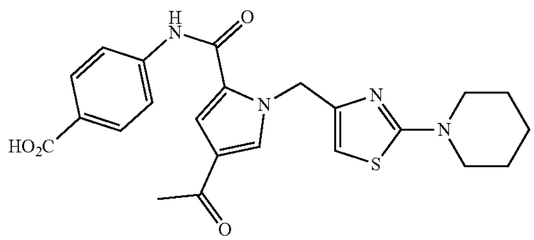 [SMILES: CC(=O)c1cc(C(=O)Nc2ccc(C(=O)O)cc2)n(Cc2csc(N3CCCCC3)n2)c1] | >100 | 46 |
| A-57 | 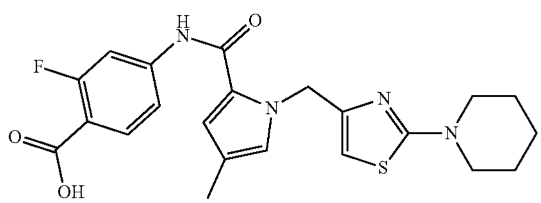 [SMILES: Cc1cc(C(=O)Nc2ccc(C(=O)O)c(F)c2)n(Cc2csc(N3CCCCC3)n2)c1] | 2.8 | 80 |
| A-58 | 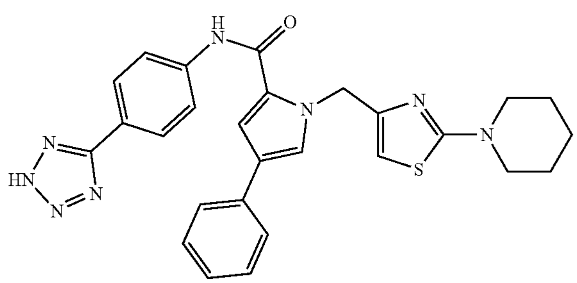 [SMILES: O=C(Nc1ccc(-c2nn[nH]n2)cc1)c1cc(-c2ccccc2)cn1Cc1csc(N2CCCCC2)n1] | 2.2 | 98 |
| A-59 | 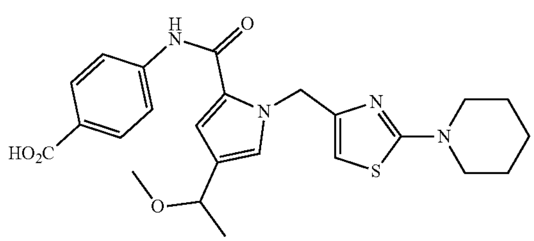 [SMILES: COC(C)c1cc(C(=O)Nc2ccc(C(=O)O)cc2)n(Cc2csc(N3CCCCC3)n2)c1] | 17.2 | 59 |
| A-60 | 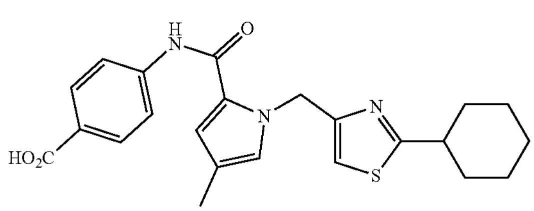 [SMILES: Cc1cc(C(=O)Nc2ccc(C(=O)O)cc2)n(Cc2csc(C3CCCCC3)n2)c1] | 8.9 | 70 |

TABLE 1-continued

DRP1 Activity Screen

| Compound No. | Structure | IC$_{50}$ (μM) | max % inh |
|---|---|---|---|
| A-61 | 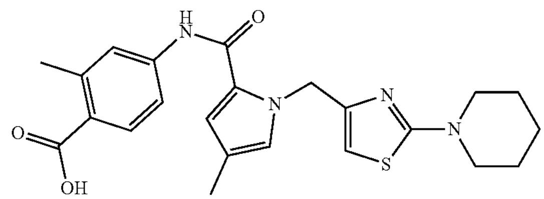 | 2.5 | 85 |
| A-62 | 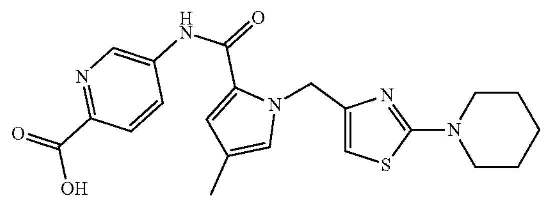 [SMILES: Cc1cc(C(=O)Nc2ccc(C(=O)O)nc2)n(Cc2csc(N3CCCCC3)n2)c1] | 17 | 70 |
| A-63 | 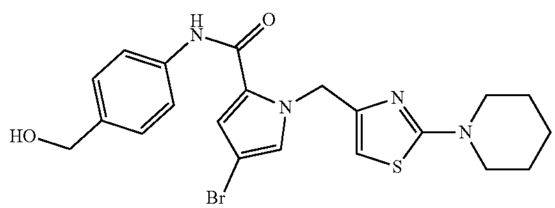 [SMILES: O=C(Nc1ccc(CO)cc1)c1cc(Br)cn1Cc1csc(N2CCCCC2)n1] | 3.4 | 68 |
| A-64 | 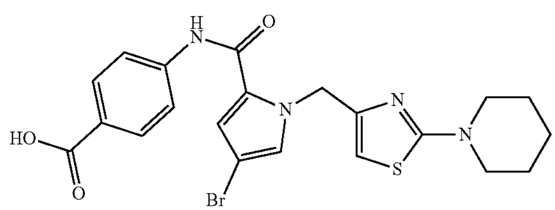 [SMILES: O=C(O)c1ccc(NC(=O)c2cc(Br)cn2Cc2csc(N3CCCCC3)n2)cc1] | >100 | 6 |
| A-65 | 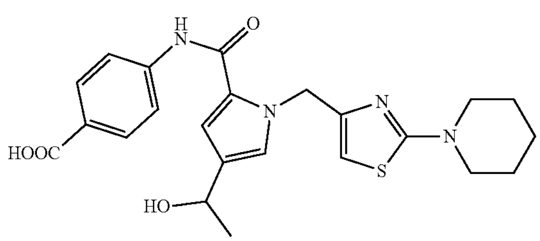 [SMILES: CC(O)c1cc(C(=O)Nc2ccc(C(=O)O)cc2)n(Cc2csc(N3CCCCC3)n2)c1] | 43.7 | 48 |
| A-66 | 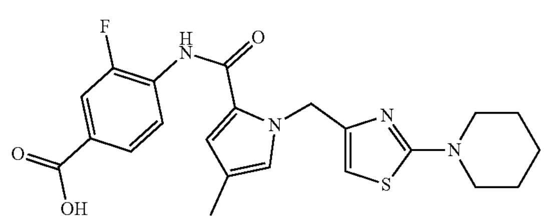 [SMILES: Cc1cc(C(=O)Nc2ccc(C(=O)O)cc2F)n(Cc2csc(N3CCCCC3)n2)c1] | 7.8 | 67 |

TABLE 1-continued

DRP1 Activity Screen

| Compound No. | Structure | IC$_{50}$ (μM) | max % inh |
|---|---|---|---|
| A-67 | 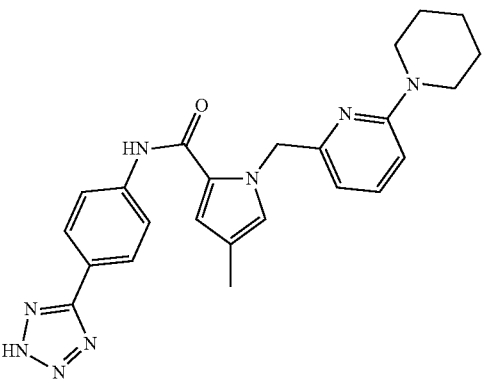 [SMILES: Cc1cc(C(=O)Nc2ccc(-c3nn[nH]n3)cc2)n(Cc2cccc(N3CCCCC3)n2)c1] | 2.1 | 78 |
| A-68 | 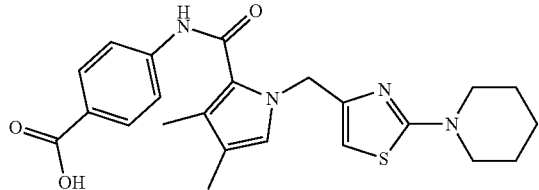 [SMILES: Cc1cn(Cc2csc(N3CCCCC3)n2)c(C(=O)Nc2ccc(C(=O)O)cc2)c1C] | 30.5 | 65 |
| A-69 | 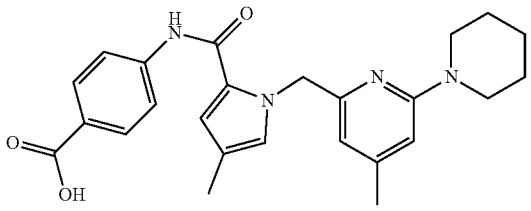 [SMILES: Cc1cc(Cn2cc(C)cc2C(=O)Nc2ccc(C(=O)O)cc2)nc(N2CCCCC2)c1] | 11.7 | 67 |
| A-70 | 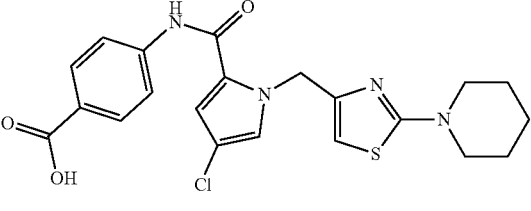 [SMILES: O=C(O)c1ccc(NC(=O)c2cc(Cl)cn2Cc2csc(N3CCCCC3)n2)cc1] | 2.3 | 77 |
| A-71 | 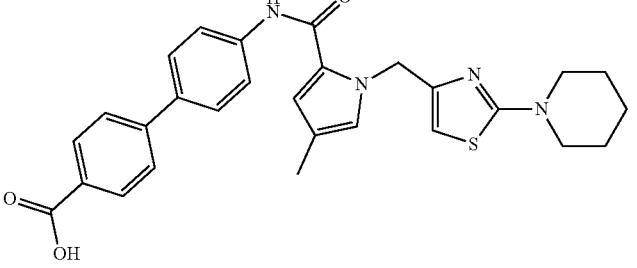 | 0.72 | 83 |

Example 2: Synthetic Protocol for Compound Embodiments

Abbreviations

Me methyl
Et ethyl
nPr n-propyl
iPr isopropyl
cPr cyclopropyl
nBu n-butyl
iBu isobutyl
Boc tert-butyloxycarbonyl
Ac acetyl
Ph phenyl
Tf trifluoromethanesulfonyl
Ts 4-methylphenylsulfonyl
EDCI 3-(3-dimethylaminopropyl)-1-ethylcarbodiimide HOBt 1-hydroxybenzotriazole
HATU 1-[bis(dimethylamino)methylene]-1H-1,2,3-triazolo[4,5-b]pyridinium 3-oxide hexafluorophosphate
HBTU N,N,N,N',N'-Tetramethyl-O-(1H-benzotriazol-1-yl)uronium hexafluorophosphate
DIPEA diisopropylethylamine
Togni's reagent 3,3-dimethyl-1-(trifluoromethyl)-1,2-benziodoxole
DCM dichloromethane
DME dimethoxyethane
DMF N,N-dimethylformamide
DMF.DMA N,N-dimethylformamide dimethyl acetal
DMSO dimethylsulfoxide
TFA trifluoroacetic acid
THF tetrahydrofuran
MW microwave irradiation
CMTP (cyanomethylene)tributylphosphorane
DIBAL-H diisobutylaluminium hydride
TEA triethylamine
aq aqueous
M concencetration expressed in mol/L
RT room temperature
TLC thin lay chromatography
HPLC high-performance liquid chromatography
MPLC medium pressure liquid chromatography
LCMS liquid chromatography-mass spectrometry
ESI+ m/z values in mass spectroscopy (Ionization ESI)
ESI− m/z values in mass spectroscopy (Ionization ESI)
$^1$H NMR (DMSO-$d_6$) δ (ppm) of peak in $^1$H NMR in DMSO-$d_6$
s singlet (spectrum)
d doublet (spectrum)
t triplet (spectrum)
q quartet (spectrum)
dd double doublet (spectrum)
br broad line (spectrum)
m multiplet (spectrum)

Example 2a: Left Region Compound Embodiments

General Scheme

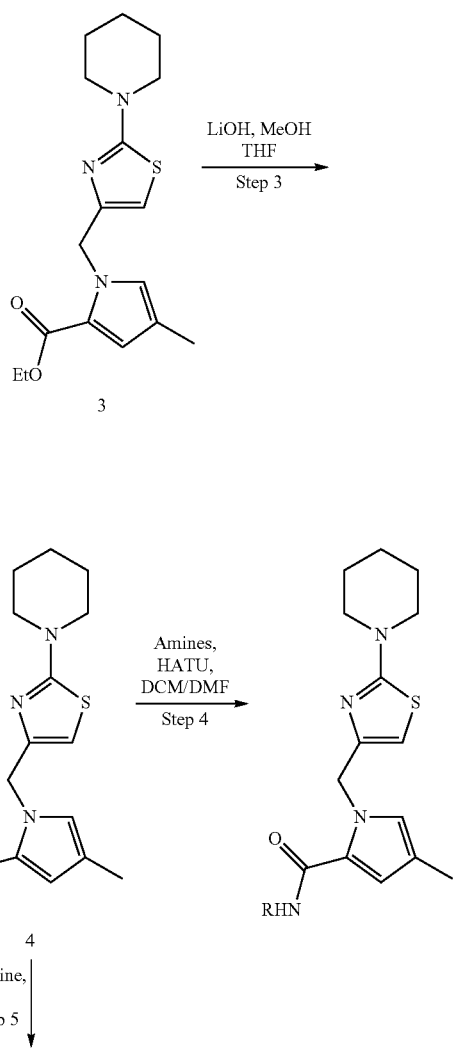

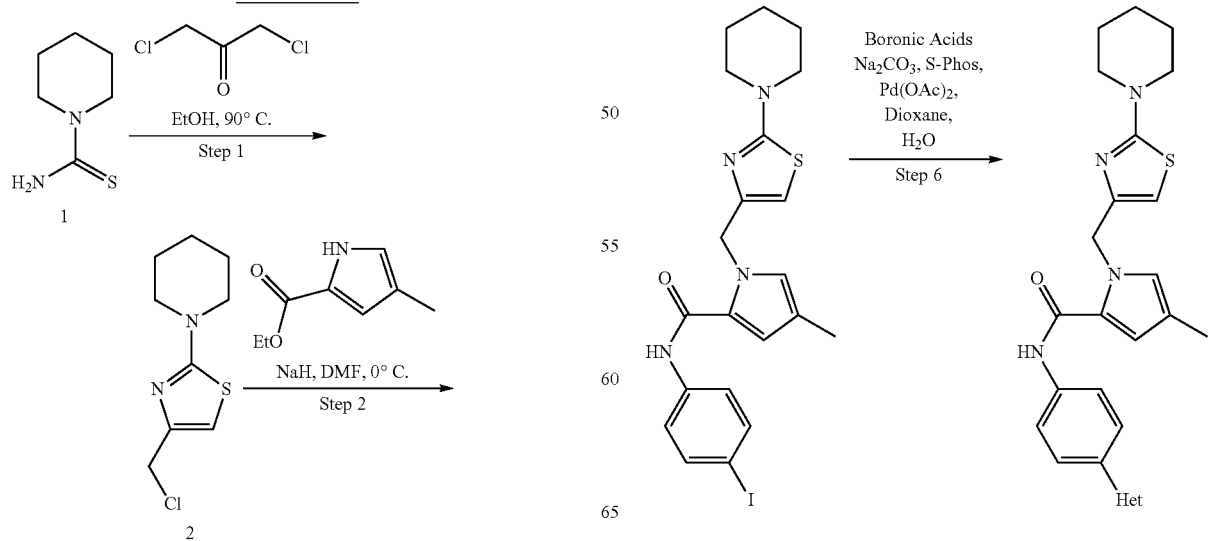

Preparation of 4-(chloromethyl)-2-(piperidin-1-yl)thiazole

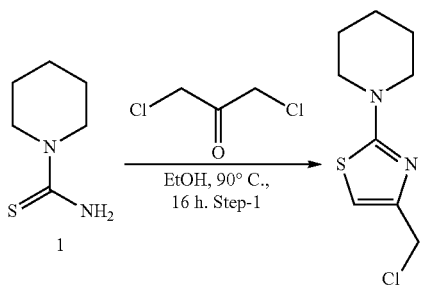

1,3-Dichloroacetone (17.5 g, 0.139 mol, 1 equiv) was added to a stirred solution of piperidine-1-carbothioamide (1) (20.0 g, 0.139 mol, 1 equiv) in EtOH (400 mL) at ambient temperature. The reaction mixture was stirred at 90° C. for 16 h, and then cooled to ambient temperature. The resultant mixture was concentrated under vacuum. The residue was basified with 10% NaHCO$_3$ aqueous solution and extracted with DCM (2×200 mL). The combined organic layer was washed with water (200 mL), brine (200 mL), dried over Na$_2$SO$_4$, filtered and concentrated under vacuum. The crude product was purified by silica gel column chromatography (10% ethyl acetate-hexanes) to provide compound 2 as a colorless liquid (15.0 g, 50%).

LC-MS (ESI$^+$): m/z 217.3 (M+H)$^+$

1H-NMR (400 MHz, DMSO-d6): δ 6.84 (s, 1H), 4.55 (s, 2H), 3.39-3.35 (m, 4H), 1.59-1.53 (m, 6H).

Preparation of Ethyl 4-methyl-1-((2-(piperidin-1-yl)thiazol-4-yl)methyl)-1H-pyrrole-2-carboxylate

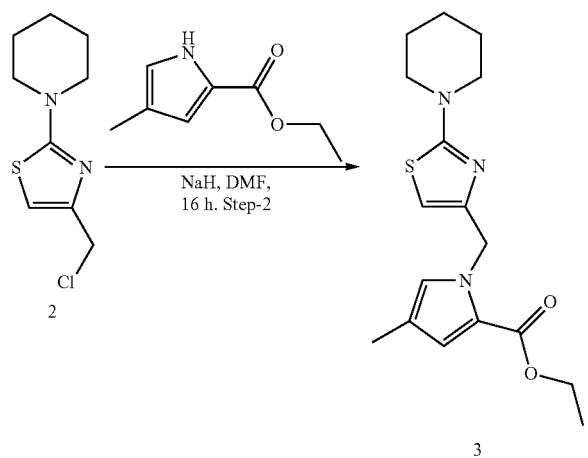

NaH (1.01 g, 42.1 mmol, 3 equiv) was added to a stirred solution of ethyl 4-methyl-1H-pyrrole-2-carboxylate (2.29 g, 14.9 mmol, 1 equiv) in DMF (30 mL) at 0° C. After the reaction mixture was stirred at 0° C. for 30 min, 4-(chloromethyl)-2-(piperidin-1-yl)thiazole (2) (3.23 g, 14.9 mmol, 1 equiv) was added at 0° C. The reaction mixture was allowed to warm to ambient temperature and stirred for 16 h. The reaction mixture was quenched with ice and extracted with ethyl acetate (2×100 mL). The combined organic layers were washed with water (2×100 mL), brine (100 mL), dried over Na$_2$SO$_4$, filtered and concentrated under vacuum. The crude product was purified by silica gel column chromatography (20% ethyl acetate-hexanes) to provide compound 3 as a pale brown solid (2.50 g, 45%).

LC-MS (ESI$^+$): m/z 334.0 (M+H)$^+$

1H-NMR (400 MHz, DMSO-d6): δ 6.93 (s, 1H), 6.69 (s, 1H), 6.10 (s, 1H), 5.29 (s, 2H), 4.15 (q, J=7.2 Hz, 2H), 3.35-3.33 (m, 4H), 2.01 (s, 3H), 1.57-1.56 (m, 6H), 1.22 (t, J=7.2 Hz, 3H).

Preparation of 4-methyl-1-((2-(piperidin-1-yl)thiazol-4-yl)methyl)-1H-pyrrole-2-carboxylic Acid

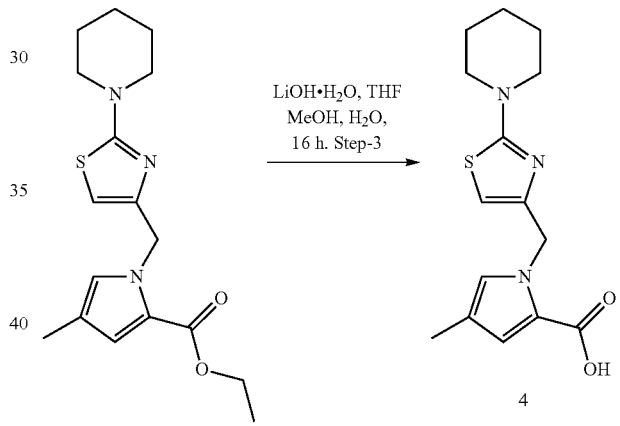

LiOH.H$_2$O (0.971 g, 23.1 mmol, 3 equiv) was added to a stirred solution of ethyl 4-methyl-1-((2-(piperidin-1-yl)thiazol-4-yl)methyl)-1H-pyrrole-2-carboxylate (3) (2.69 g, 8.09 mmol, 1 equiv) in THF (20 mL), MeOH (20 mL) and H$_2$O (20 mL) at ambient temperature. The reaction mixture was stirred for 16 h, then concentrated under vacuum. The residue was acidified with 1.5 M hydrochloric acid and the resulting mixture was extracted with DCM (2×75 mL). The combined organic layers were washed with water (100 mL), brine (100 mL), dried over Na$_2$SO$_4$, filtered and concentrated under vacuum to provide compound 4 as a pale brown solid (2.20 g, 89%) without further purification.

LC-MS (ESI$^+$): m/z 306.0 (M+H)$^+$

1H-NMR (300 MHz, DMSO-d6): δ 6.89 (s, 1H), 6.65 (s, 1H), 6.08 (s, 1H), 5.31 (s, 2H), 3.34-3.33 (m, 4H), 2.68 (s, 3H), 1.59-1.56 (m, 6H).

Synthesis of Compound A-13

Preparation of Methyl trans-4-(4-methyl-1-((2-(piperidin-1-yl)thiazol-4-yl)methyl)-1H-pyrrole-2-carboxamido)cyclohexane-1-carboxylate

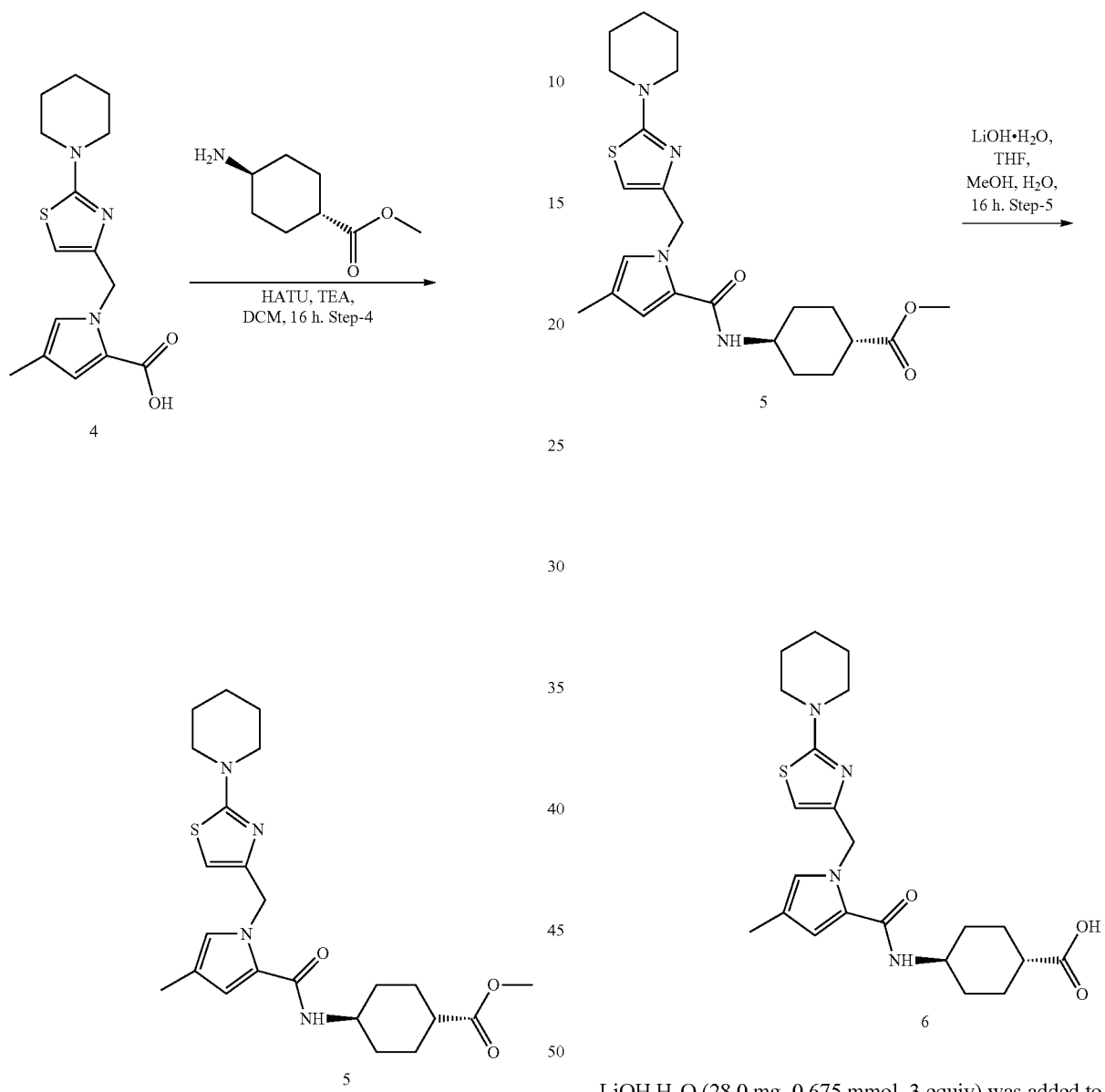

TEA (198 mg, 1.97 mmol, 3 equiv), HATU (497 mg, 1.31 mmol, 2 equiv) and methyl trans-4-aminocyclohexane-1-carboxylate (152 mg, 0.786 mmol, 1.2 equiv) were added to a stirred solution of 4-methyl-1-((2-(piperidin-1-yl)thiazol-4-yl)methyl)-1H-pyrrole-2-carboxylic acid (4) (200 mg, 0.655 mmol, 1 equiv) in DCM (20 mL) at ambient temperature. The reaction mixture was stirred for 16 h. The reaction mixture was diluted with DCM (30 mL) washed with water (30 mL), brine (30 mL), dried over $Na_2SO_4$, filtered and concentrated. The crude product was purified by silica gel column chromatography (50% ethyl acetate-hexanes) to provide compound 5 as a white solid (100 mg, 34%).

LC-MS (ESI$^+$): m/z 445.0 (M+H)$^+$

Preparation of trans-4-(4-methyl-1-((2-(piperidin-1-yl)thiazol-4-yl)methyl)-1H-pyrrole-2-carboxamido)cyclohexane-1-carboxylic Acid

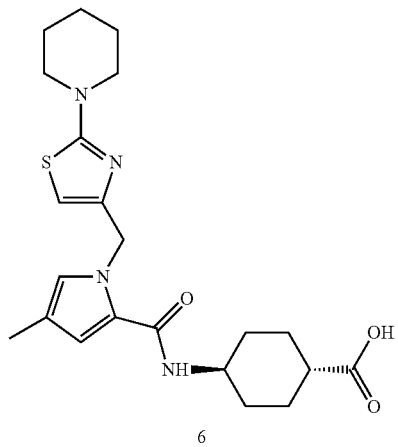

$LiOH \cdot H_2O$ (28.0 mg, 0.675 mmol, 3 equiv) was added to a stirred solution of methyl trans-4-(4-methyl-1-((2-(piperidin-1-yl)thiazol-4-yl)methyl)-1H-pyrrole-2-carboxamido)cyclohexane-1-carboxylate (5) (100 mg, 0.225 mmol, 1 equiv) in THF (2 mL), MeOH (2 mL) and $H_2O$ (2 mL) at ambient temperature. The reaction mixture was stirred for 16 h, then concentrated under vacuum. The residue was acidified with 1.5 M hydrochloric acid and the obtained solid was filtered dried under vacuum to provide compound 6 (A-13) as a white solid (40.0 mg, 41%).

LC-MS (ESI$^+$): m/z 431.3 (M+H)$^+$

1H-NMR (400 MHz, Methanol-$d_4$): δ 6.69 (s, 1H), 6.55 (s, 1H), 6.06 (s, 1H), 5.31 (s, 2H), 3.79-3.68 (m, 1H), 3.46-3.37 (m, 4H), 2.28-2.19 (m, 1H), 2.08-1.91 (m, 7H), 1.70-1.61 (m, 6H), 1.59-1.46 (m, 2H), 1.41-1.27 (m, 3H).

Synthesis of Compound A-14

Preparation of Methyl cis-4-(4-methyl-1-((2-(piperidin-1-yl)thiazol-4-yl)methyl)-1H-pyrrole-2-carboxamido)cyclohexane-1-carboxylate

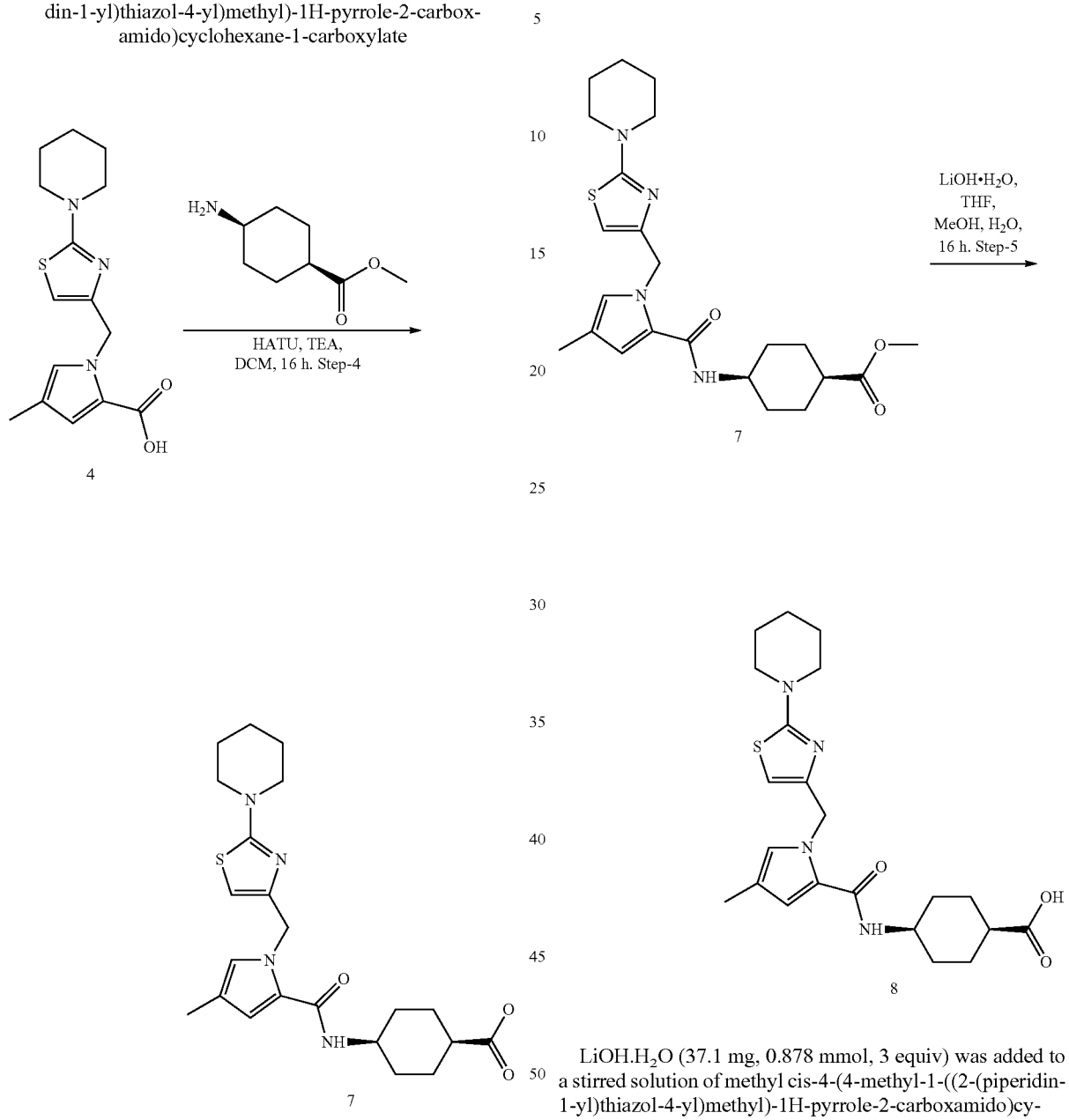

Preparation of cis-4-(4-methyl-1-((2-(piperidin-1-yl)thiazol-4-yl)methyl)-1H-pyrrole-2-carboxamido)cyclohexane-1-carboxylic Acid TEA (198 mg, 1.97 mmol, 3 equiv), HATU (497 mg, 1.31 mmol, 2 equiv) and methyl cis-4-aminocyclohexane-1-carboxylate (152 mg, 0.786 mmol, 1.2 equiv) were added to a stirred solution of 4-methyl-1-((2-(piperidin-1-yl)thiazol-4-yl)methyl)-1H-pyrrole-2-carboxylic acid (4) (200 mg, 0.655 mmol, 1 equiv) in DCM (20 mL) at ambient temperature. The reaction mixture was stirred for 16 h. The reaction mixture was diluted with DCM (30 mL) washed with water (30 mL), brine (30 mL), dried over Na$_2$SO$_4$, filtered and concentrated. The crude product was purified by silica gel column chromatography (50% ethyl acetate-hexanes) to provide compound 7 as a pale brown solid (130 mg, 45%).

LC-MS (ESI$^+$): m/z 445.1 (M+H)$^+$

LiOH.H$_2$O (37.1 mg, 0.878 mmol, 3 equiv) was added to a stirred solution of methyl cis-4-(4-methyl-1-((2-(piperidin-1-yl)thiazol-4-yl)methyl)-1H-pyrrole-2-carboxamido)cyclohexane-1-carboxylate (7) (130 mg, 0.292 mmol, 1 equiv) in THF (5 mL), MeOH (5 mL) and H$_2$O (5 mL) at ambient temperature. The reaction mixture was stirred for 16 h, then concentrated under vacuum. The residue was acidified with 1.5 M hydrochloric acid and extracted with DCM (2×30 mL). The combined organic layers were washed with water (30 mL), brine (30 mL), dried over Na$_2$SO$_4$, filtered and concentrated under vacuum. The crude product was purified by Prep HPLC (0-40% CH$_3$CN—H$_2$O) to provide compound 8 (A-14) as a pale brown solid (50.0 mg, 50%).

LC-MS (ESI$^+$): m/z 431.3 (M+H)$^+$

1H-NMR (400 MHz, DMSO-d6): δ 12.12 (s, 1H), 7.66 (d, J=8.0 Hz, 1H), 6.68 (s, 1H), 6.56 (s, 1H), 6.13 (s, 1H), 5.30 (s, 2H), 3.78-3.67 (m, 1H), 3.39-3.27 (m, 4H), 2.49-2.41 (m, 1H), 2.02-1.88 (m, 5H), 1.63-1.42 (m, 12H).

Synthesis of Compound A-15

Preparation of 4-methyl-N-phenyl-1-((2-(piperidin-1-yl)thiazol-4-yl)methyl)-1H-pyrrole-2-carboxamide

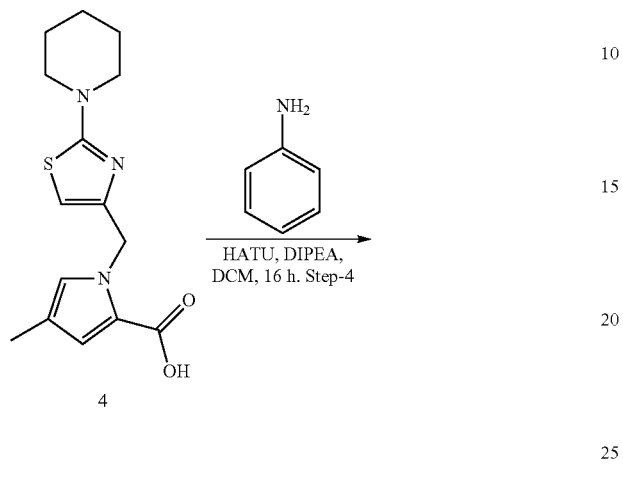

Synthesis of Compound A-22

Preparation of 4-methyl-N-(4-(methylcarbamoyl)phenyl)-1-((2-(piperidin-1-yl)thiazol-4-yl)methyl)-1H-pyrrole-2-carboxamide

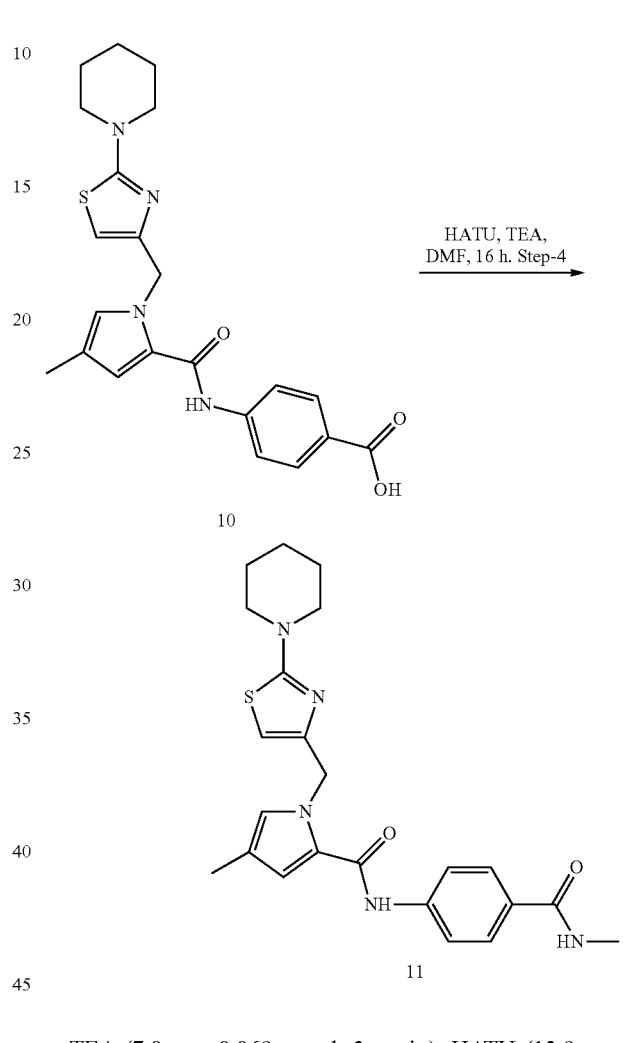

DIPEA (63.1 mg, 0.489 mmol, 3 equiv), HATU (92.9 mg, 0.244 mmol, 1.5 equiv) and aniline (18.2 mg, 0.195 mmol, 1.2 equiv) were added to a stirred solution of 4-methyl-1-((2-(piperidin-1-yl)thiazol-4-yl)methyl)-1H-pyrrole-2-carboxylic acid (4) (50.0 mg, 0.163 mmol, 1 equiv) in DCM (3 mL) at ambient temperature. The reaction mixture was stirred for 16 h. The reaction mixture was diluted with DCM (30 mL) washed with water (30 mL), brine (30 mL), dried over $Na_2SO_4$, filtered and concentrated. The crude product was purified by Prep HPLC (0-60% $CH_3CN-H_2O$) to provide compound 9 (A-15) as a pale brown gummy solid (20.0 mg, 32%).

LC-MS (ESI$^+$): m/z 380.9 (M+H)$^+$

1H-NMR (400 MHz, DMSO-d6): δ 9.74 (s, 1H), 7.69 (d, J=7.6 Hz, 2H), 7.34-7.25 (m, 2H), 7.03 (t, J=7.2 Hz, 1H), 6.88-6.81 (m, 2H), 6.16 (s, 1H), 5.35 (s, 2H), 3.38-3.28 (m, 4H), 2.05 (s, 3H), 1.60-1.49 (m, 6H).

TEA (7.0 mg, 0.069 mmol, 3 equiv), HATU (12.9 mg, 0.034 mmol, 1.5 equiv) and methyl amine (2 M solution in THF) (5.89 mL, 0.115 mmol, 5 equiv) were added to a stirred solution of 4-(4-methyl-1-((2-(piperidin-1-yl)thiazol-4-yl)methyl)-1H-pyrrole-2-carboxamido)benzoic acid (10) (10.0 mg, 0.023 mmol, 1 equiv) in DMF (1 mL) at ambient temperature. The reaction mixture was stirred for 16 h. The reaction mixture was concentrated under vacuum, residue was diluted with water and extracted with ethyl acetate (2×20 mL). The combined organic layers were washed with water (20 mL), brine (20 mL), dried over $Na_2SO_4$, filtered and concentrated. The crude product was purified by silica gel column chromatography (50% ethyl acetate-hexanes) to provide compound 11 (A-22) as a white solid (3.0 mg, 30%).

LC-MS (ESI$^+$): m/z 437.9 (M+H)$^+$

1H-NMR (400 MHz, Methanol-d$_4$): δ 7.81-7.76 (m, 2H), 7.75-7.71 (m, 2H), 6.82 (s, 2H), 6.17 (s, 1H), 5.39 (s, 2H), 3.45-3.38 (m, 4H), 2.93 (s, 3H), 2.11 (s, 3H), 1.70-1.58 (m, 6H).

Synthesis of Compound A-23

Preparation of 4-methyl-N-(naphthalen-2-yl)-1-((2-(piperidin-1-yl)thiazol-4-yl)methyl)-1H-pyrrole-2-carboxamide

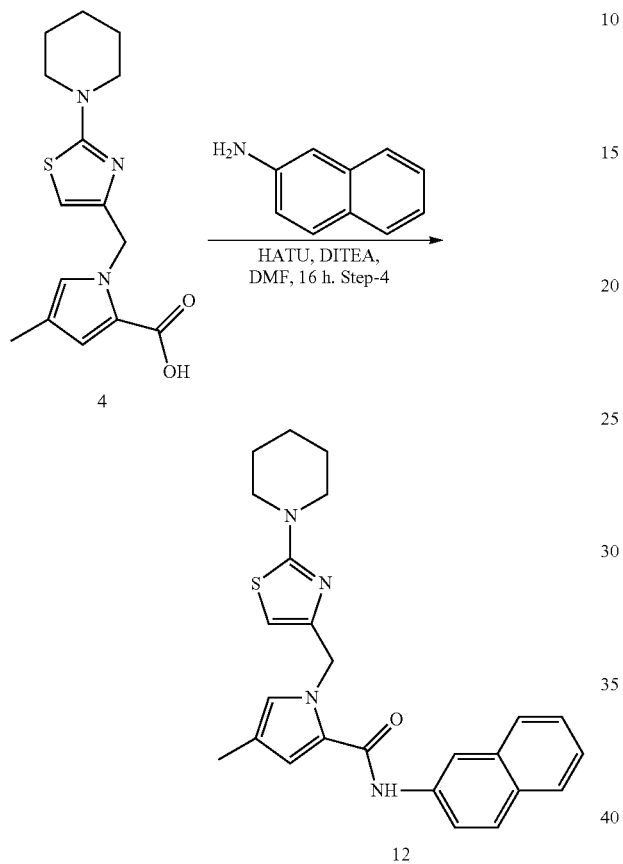

DIPEA (634 mg, 4.91 mmol, 3 equiv), HATU (934 mg, 2.46 mmol, 1.5 equiv) and naphthalen-2-amine (257 mg, 1.81 mmol, 1.1 equiv) were added to a stirred solution of 4-(4-methyl-1-((2-(piperidin-1-yl)thiazol-4-yl)methyl)-1H-pyrrole-2-carboxamido)benzoic acid (4) (500 mg, 1.64 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over $Na_2SO_4$, filtered and concentrated. The crude product was purified by silica gel column chromatography (50% ethyl acetate-hexanes) to provide compound 12 (A-23) as a white solid (140 mg, 20%).

LC-MS (ESI$^+$): m/z 431.3 (M+H)$^+$

1H-NMR (400 MHz, DMSO-d6): δ 9.95 (s, 1H), 8.39 (s, 1H), 7.89-7.79 (m, 3H), 7.78-7.72 (m, 1H), 7.50-7.43 (m, 1H), 7.41-7.36 (m, 1H), 6.93-6.86 (m, 2H), 6.18 (s, 1H), 5.39 (s, 2H), 3.39-3.29 (m, 4H), 2.07 (s, 3H), 1.58-1.48 (m, 6H).

Synthesis of Compound A-24

Preparation of N-(3,5-difluoro-4-hydroxyphenyl)-4-methyl-1-((2-(piperidin-1-yl)thiazol-4-yl)methyl)-1H-pyrrole-2-carboxamide

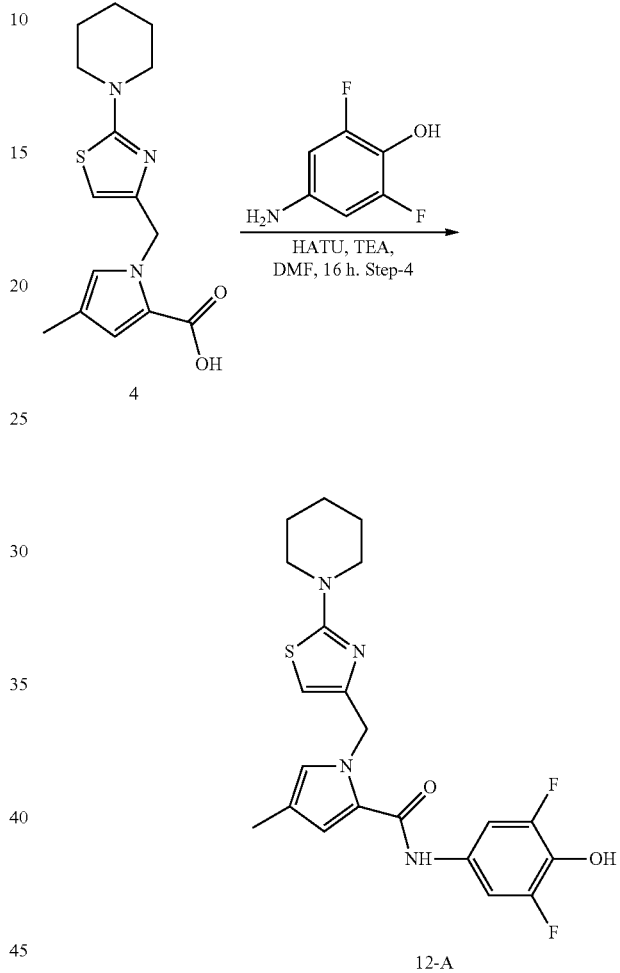

TEA (298 mg, 2.95 mmol, 3 equiv), HATU (561 mg, 1.48 mmol, 1.5 equiv) and 4-amino-2,6-difluorophenol (214 mg, 1.48 mmol, 1.5 equiv) were added to a stirred solution of 4-methyl-1-((2-(piperidin-1-yl)thiazol-4-yl)methyl)-1H-pyrrole-2-carboxylic acid (4) (300 mg, 0.982 mmol, 1 equiv) in DMF (10 mL) at ambient temperature. The reaction mixture was stirred at 70° C. for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by Prep HPLC (0-60% $CH_3CN$—$H_2O$) to provide compound 12-A (A-24) as a pale brown solid (15.0 mg, 4%).

LC-MS (ESI$^+$): m/z 433.3 (M+H)$^+$

1H-NMR (400 MHz, DMSO-d6): δ 7.13 (s, 1H), 6.99 (s, 1H), 6.35-6.27 (m, 2H), 6.19 (s, 1H), 5.29 (s, 2H), 3.39-3.31 (m, 4H), 2.06 (s, 3H), 1.61-1.52 (m, 6H).

Synthesis of Compound A-25

Preparation of N-cyclopentyl-4-methyl-1-((2-(piperidin-1-yl)thiazol-4-yl)methyl)-1H-pyrrole-2-carboxamide

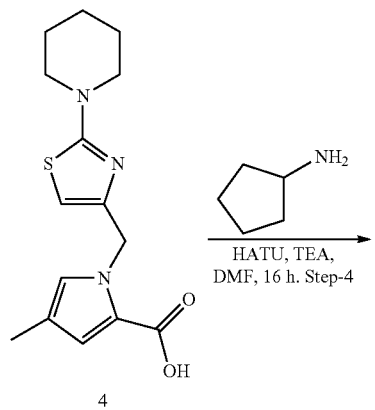

Synthesis of Compound A-26

Preparation of N-cyclohexyl-4-methyl-1-((2-(piperidin-1-yl)thiazol-4-yl)methyl)-1H-pyrrole-2-carboxamide

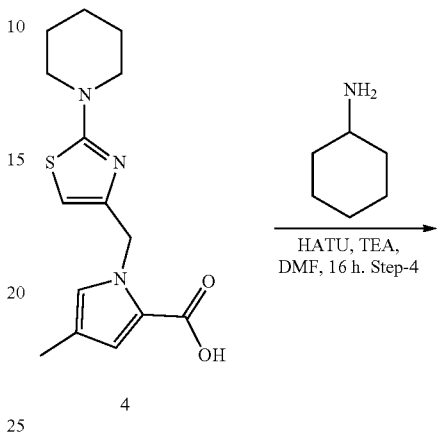

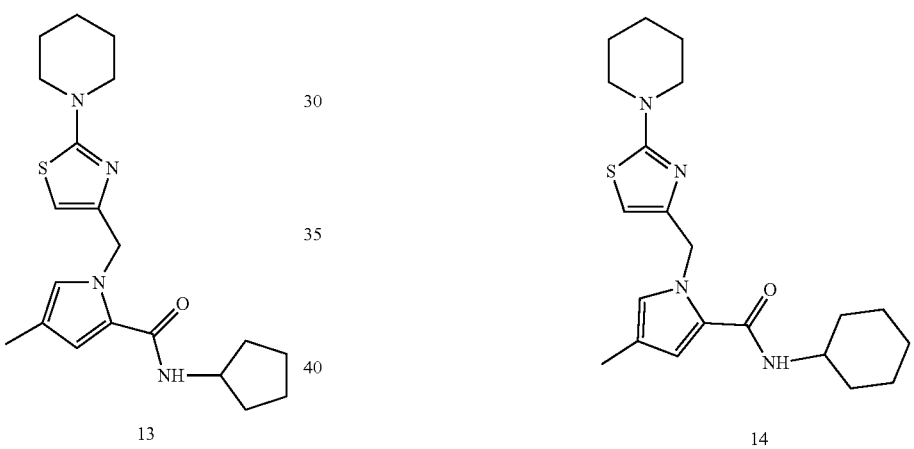

TEA (99.1 mg, 0.979 mmol, 3 equiv), HATU (249 mg, 0.654 mmol, 2 equiv) and cyclopentylamine (41.7 mg, 0.489 mmol, 1.5 equiv) were added to a stirred solution of 4-methyl-1-((2-(piperidin-1-yl)thiazol-4-yl)methyl)-1H-pyrrole-2-carboxylic acid (4) (100 mg, 0.327 mmol, 1 equiv) in DMF (5 mL) at ambient temperature. The reaction mixture was stirred for 16 h. then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by silica gel column chromatography (50% ethyl acetate-hexanes) to provide compound 13 (A-25) as a white solid (71.0 mg, 58%).

LC-MS (ESI$^+$): m/z 373.3 (M+H)$^+$

1H-NMR (400 MHz, DMSO-d6): δ 7.74 (d, J=7.6 Hz, 1H), 6.70 (s, 1H), 6.59 (s, 1H), 6.13 (s, 1H), 5.31 (s, 2H), 4.15-4.05 (m, 1H), 3.39-3.30 (m, 4H), 1.99 (s, 3H), 1.89-1.73 (m, 2H), 1.70-1.61 (m, 2H), 1.60-1.53 (m, 6H), 1.52-1.39 (m, 4H).

TEA (99.1 mg, 0.979 mmol, 3 equiv), HATU (249 mg, 0.654 mmol, 2 equiv) and cyclohexylamine (48.6 mg, 0.489 mmol, 1.5 equiv) were added to a stirred solution of 4-methyl-1-((2-(piperidin-1-yl)thiazol-4-yl)methyl)-1H-pyrrole-2-carboxylic acid (4) (100 mg, 0.327 mmol, 1 equiv) in DMF (5 mL) at ambient temperature. The reaction mixture was stirred for 16 h. then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by silica gel column chromatography (50% ethyl acetate-hexanes) to provide compound 14 (A-26) as a white solid (76.0 mg, 60%).

LC-MS (ESI$^+$): m/z 387.2 (M+H)$^+$

1H-NMR (400 MHz, DMSO-d6): δ 7.66 (d, J=8.4 Hz, 1H), 6.70 (s, 1H), 6.58 (s, 1H), 6.13 (s, 1H), 5.30 (s, 2H), 3.68-3.58 (m, 1H), 3.39-3.29 (m, 4H), 1.99 (s, 3H), 1.77-1.67 (m, 4H), 1.62-1.52 (m, 7H), 1.31-1.18 (m, 4H), 1.17-1.11 (m, 1H).

Synthesis of Compound A-27

Preparation of 4-methyl-1-((2-(piperidin-1-yl)thiazol-4-yl)methyl)-N-(tetrahydro-2H-pyran-3-yl)-1H-pyrrole-2-carboxamide

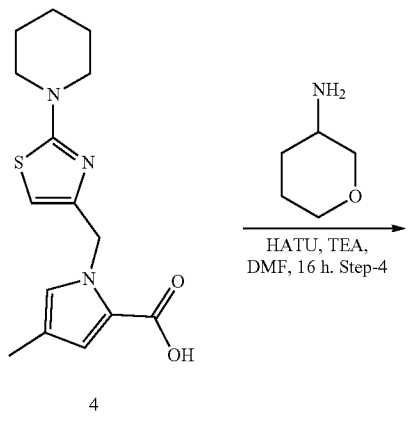

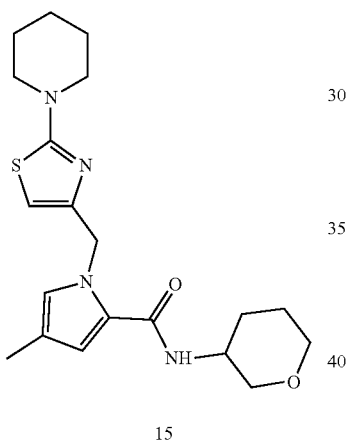

TEA (99.1 mg, 0.979 mmol, 3 equiv), HATU (249 mg, 0.654 mmol, 2 equiv) and tetrahydro-2H-pyran-3-amine (49.5 mg, 0.489 mmol, 1.5 equiv) were added to a stirred solution of 4-methyl-1-((2-(piperidin-1-yl)thiazol-4-yl)methyl)-1H-pyrrole-2-carboxylic acid (4) (100 mg, 0.327 mmol, 1 equiv) in DMF (5 mL) at ambient temperature. The reaction mixture was stirred for 16 h. then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by silica gel column chromatography (50% ethyl acetate-hexanes) to provide compound 15 (A-27) as a white solid. (85.0 mg, 66%).

LC-MS (ESI$^+$): m/z 389.2 (M+H)$^+$

1H-NMR (400 MHz, DMSO-d6): δ 7.66 (d, J=7.6 Hz, 1H), 6.72 (s, 1H), 6.61 (s, 1H), 6.13 (s, 1H), 5.30 (s, 2H), 3.85-3.68 (m, 3H), 3.39-3.30 (m, 4H), 3.28-3.19 (m, 1H), 3.13-3.03 (m, 1H), 1.99 (s, 3H), 1.89-1.79 (m, 1H), 1.71-1.62 (m, 1H), 1.61-1.46 (m, 8H).

Synthesis of Compound A-28

Preparation of N,4-dimethyl-N-phenyl-1-((2-(piperidin-1-yl)thiazol-4-yl)methyl)-1H-pyrrole-2-carboxamide

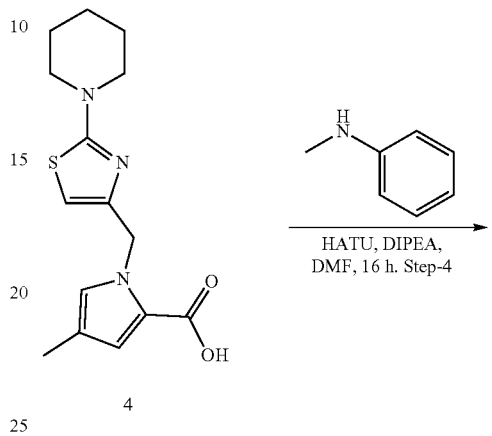

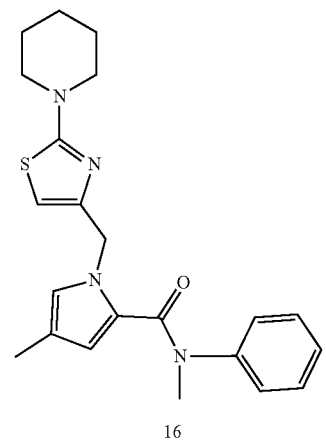

DIPEA (190 mg, 1.47 mmol, 3 equiv), HATU (280 mg, 0.736 mmol, 1.5 equiv) and N-methylaniline (61.3 mg, 0.589 mmol, 1.2 equiv) were added to a stirred solution of 4-(4-methyl-1-((2-(piperidin-1-yl)thiazol-4-yl)methyl)-1H-pyrrole-2-carboxamido) benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-60% CH$_3$CN—H$_2$O) to provide compound 16 (A-28) as a pale brown gum (44.0 mg, 23%).

LC-MS (ESI$^+$): m/z 395.2 (M+H)$^+$

1H-NMR (400 MHz, DMSO-d6): δ 7.35-7.26 (m, 2H), 7.24-7.17 (m, 1H), 7.16-7.10 (m, 2H), 6.64 (s, 1H), 6.34 (s, 1H), 5.34 (s, 1H), 5.22 (s, 2H), 3.44-3.39 (m, 4H), 3.28 (s, 3H), 1.72 (s, 3H), 1.62-1.51 (m, 6H).

57
Synthesis of Compound A-29

Preparation of 4-methyl-1-((2-(piperidin-1-yl)thiazol-4-yl)methyl)-N-(tetrahydro-2H-pyran-4-yl)-1H-pyrrole-2-carboxamide

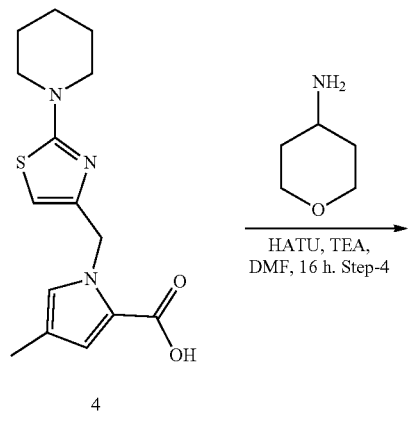

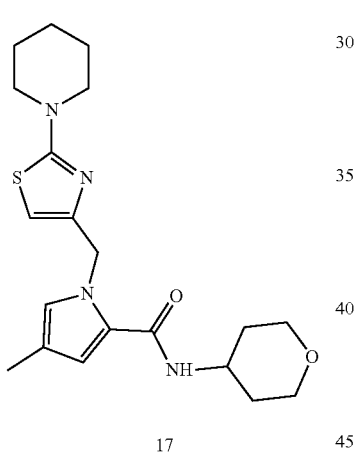

TEA (99.1 mg, 0.979 mmol, 3 equiv), HATU (248 mg, 0.654 mmol, 2 equiv) and tetrahydro-2H-pyran-4-amine (49.5 mg, 0.489 mmol, 1.5 equiv) were added to a stirred solution of 4-methyl-1-((2-(piperidin-1-yl)thiazol-4-yl)methyl)-1H-pyrrole-2-carboxylic acid (4) (100 mg, 0.327 mmol, 1 equiv) in DMF (5 mL) at ambient temperature. The reaction mixture was stirred for 16 h. then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by Prep HPLC (0-40% $CH_3CN$—$H_2O$) to provide compound 17 (A-29) as an off-white solid (25.0 mg, 20%).

LC-MS (ESI$^+$): m/z 389.2 (M+H)$^+$

1H-NMR (400 MHz, DMSO-d6): δ 7.77 (d, J=7.9 Hz, 1H), 6.72 (s, 1H), 6.60 (s, 1H), 6.13 (s, 1H), 5.31 (s, 2H), 3.93-3.81 (m, 3H), 3.40-3.31 (m, 4H), 2.00 (s, 3H), 1.71-1.63 (m, 2H), 1.60-1.45 (m, 8H).

58
Synthesis of Compound A-30

Preparation of 4-methyl-1-((2-(piperidin-1-yl)thiazol-4-yl)methyl)-N-(pyridin-2-yl)-1H-pyrrole-2-carboxamide

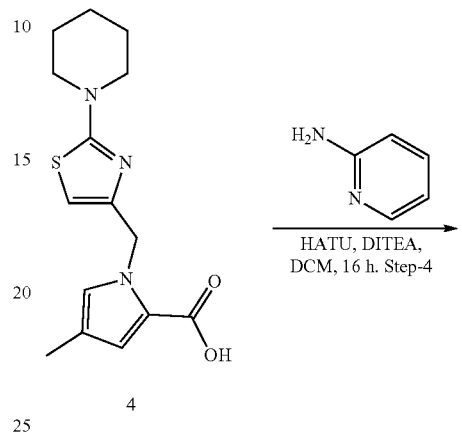

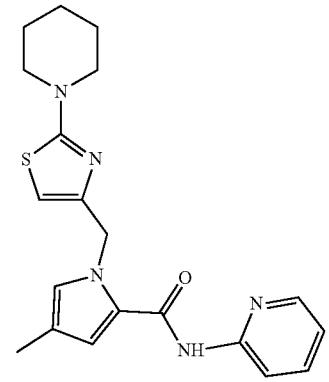

DIPEA (190 mg, 1.47 mmol, 3 equiv), HATU (280 mg, 0.736 mmol, 1.5 equiv) and pyridin-2-amine (46.2 mg, 0.589 mmol, 1.2 equiv) were added to a stirred solution of 4-(4-methyl-1-((2-(piperidin-1-yl)thiazol-4-yl)methyl)-1H-pyrrole-2-carboxamido) benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by Prep HPLC (0-30% $CH_3CN$—$H_2O$) to provide compound 18 (A-30) as a pale brown gum (59.0 mg, 32%).

LC-MS (ESI$^+$): m/z 382.3 (M+H)$^+$

1H-NMR (400 MHz, DMSO-d6): δ 10.59 (s, 1H), 8.35-8.34 (m, 1H), 7.97-7.93 (m, 2H), 7.23-7.21 (m, 1H), 7.07 (s, 1H), 6.96 (s, 1H), 6.18 (s, 1H), 5.37 (s, 2H), 3.34-3.31 (m, 4H), 2.04 (s, 3H), 1.59-1.48 (m, 6H).

Synthesis of Compound A-32

Preparation of 4-methyl-1-((2-(piperidin-1-yl)thiazol-4-yl)methyl)-N-(pyridin-4-yl)-1H-pyrrole-2-carboxamide

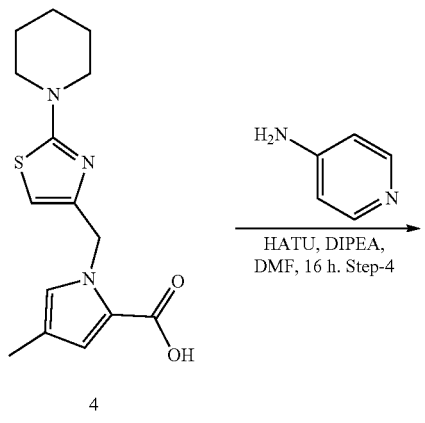

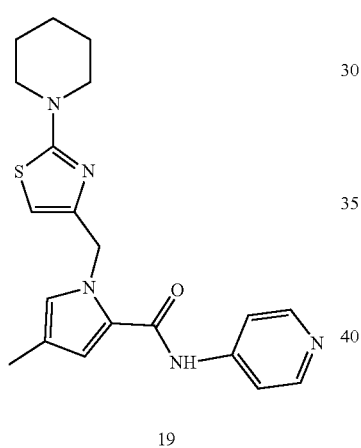

DIPEA (190 mg, 1.47 mmol, 3 equiv), HATU (280 mg, 0.736 mmol, 1.5 equiv) and pyridin-4-amine (46.2 mg, 0.589 mmol, 1.2 equiv) were added to a stirred solution of 4-(4-methyl-1-((2-(piperidin-1-yl)thiazol-4-yl)methyl)-1H-pyrrole-2-carboxamido) benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The reside was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-30% CH$_3$CN—H$_2$O) to provide compound 19 (A-32) as a pale brown gum (56.0 mg, 30%).

LC-MS (ESI$^+$): m/z 382.3 (M+H)$^+$

1H-NMR (400 MHz, DMSO-d6): δ 11.01 (s, 1H), 8.68 (d, J=7.1 Hz, 2H), 8.21 (d, J=7.2 Hz, 2H), 7.08 (s, 2H), 6.22 (s, 1H), 5.36 (s, 2H), 3.38-3.29 (m, 4H), 2.08 (s, 3H), 1.60-1.49 (m, 6H).

Synthesis of Compound A-33

Preparation of N-(4-iodophenyl)-4-methyl-1-((2-(piperidin-1-yl)thiazol-4-yl)methyl)-1H-pyrrole-2-carboxamide

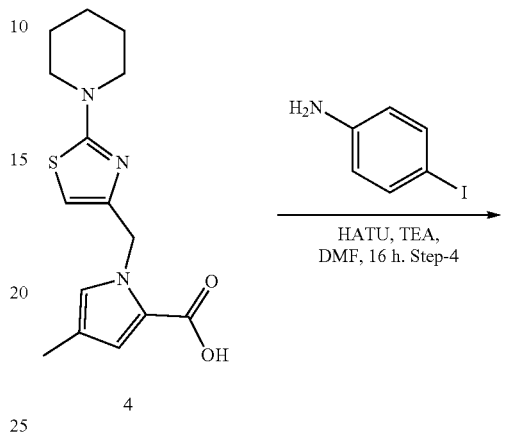

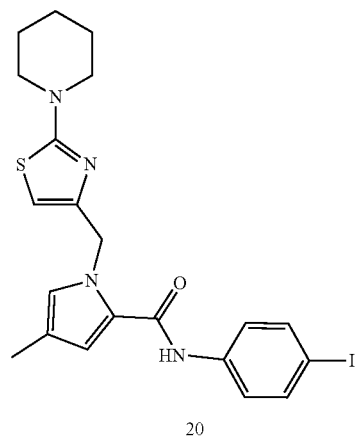

TEA (1.94 g, 19.2 mmol, 3 equiv), HATU (4.96 g, 13.1 mmol, 2 equiv) and 4-iodoaniline (1.72 g, 7.85 mmol, 1.2 equiv) were added to a stirred solution of 4-methyl-1-((2-(piperidin-1-yl)thiazol-4-yl)methyl)-1H-pyrrole-2-carboxylic acid (4) (2.0 g, 5.99 mmol, 1 equiv) in DMF (30 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×70 mL). The combined organic layers were washed with water (2×100 mL), brine (100 mL), dried over Na$_2$SO$_4$, filtered and concentrated. The crude product was purified by silica gel column chromatography (20% ethyl acetate-hexanes) to provide compound 20 (A-33) as a pale brown solid (1.20 g, 36%).

LC-MS (ESI$^+$): m/z 507.0 (M+H)$^+$

1H-NMR (400 MHz, DMSO-d6): δ 9.83 (s, 1H), 7.64-7.59 (m, 2H), 7.57-7.52 (m, 2H), 6.87-6.81 (m, 2H), 6.16 (s, 1H), 5.33 (s, 2H), 3.35-3.29 (m, 4H), 2.04 (s, 3H), 1.58-1.50 (m, 6H).

61
Synthesis of Compound A-34

Preparation of N-(chroman-3-yl)-4-methyl-1-((2-(piperidin-1-yl)thiazol-4-yl)methyl)-1H-pyrrole-2-carboxamide

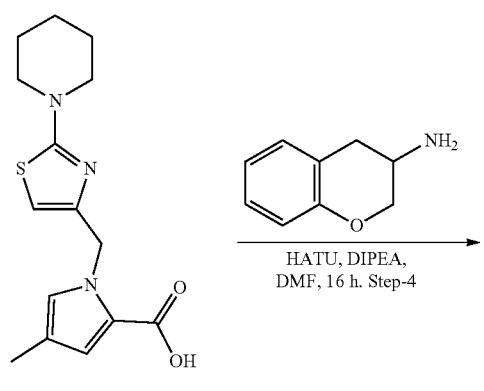

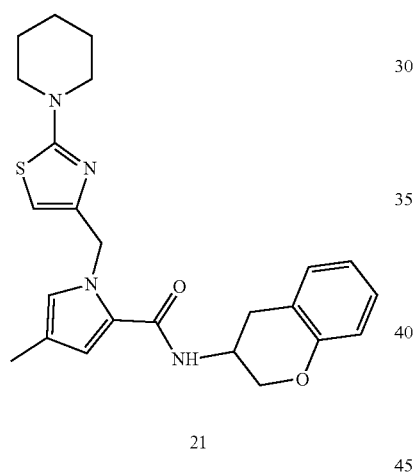

DIPEA (152 mg, 1.18 mmol, 3 equiv), HATU (224 mg, 0.589 mmol, 1.5 equiv) and chroman-3-amine (70.3 mg, 0.471 mmol, 1.2 equiv) were added to a stirred solution of 4-methyl-1-((2-(piperidin-1-yl)thiazol-4-yl)methyl)-1H-pyrrole-2-carboxylic acid (4) (120 mg, 0.393 mmol, 1 equiv) in DMF (5 mL) at ambient temperature. The reaction mixture was stirred for 16 h, then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-60% CH$_3$CN—H$_2$O) to provide compound 21 (A-34) as a white solid (60.0 mg, 35%).

LC-MS (ESI$^+$): m/z 437.3 (M+H)$^+$

1H-NMR (400 MHz, DMSO-d6): δ 7.88 (d, J=7.2 Hz, 1H), 7.14-7.05 (m, 2H), 6.89-6.83 (m, 1H), 6.80-6.73 (m, 2H), 6.64 (s, 1H), 6.16 (s, 1H), 5.33 (s, 2H), 4.28-4.11 (m, 2H), 3.79 (t, J=9.6 Hz, 1H), 3.40-3.33 (m, 4H), 2.99-2.83 (m, 2H), 2.00 (s, 3H), 1.61-1.52 (m, 6H).

62
Synthesis of Compound A-35

Preparation of 4-methyl-1-((2-(piperidin-1-yl)thiazol-4-yl)methyl)-N-(4-(pyridin-3-yl)phenyl)-1H-pyrrole-2-carboxamide

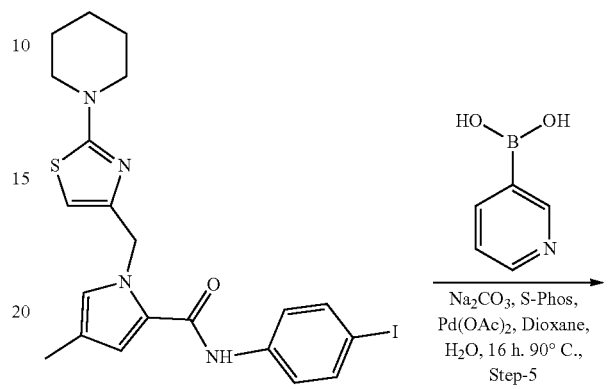

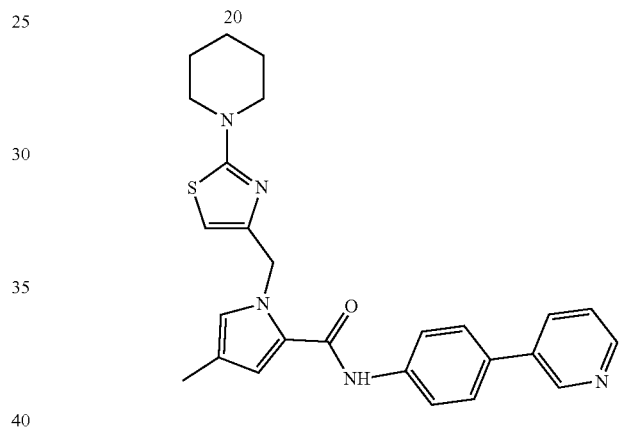

Pyridin-3-ylboronic acid (54.6 mg, 0.444 mmol, 1.5 equiv), Na$_2$CO$_3$ (93.2 mg, 0.889 mmol, 3 equiv), SPhos (11.9 mg, 0.029 mmol, 0.1 equiv) and Pd(OAc)$_2$ (3.3 mg, 0.014 mmol, 0.05 equiv) were added to a stirred solution N-(4-iodophenyl)-4-methyl-1-((2-(piperidin-1-yl)thiazol-4-yl)methyl)-1H-pyrrole-2-carboxamide (20) (150 mg, 0.296 mmol, 1 equiv) in dioxane (7 mL) and H$_2$O (3 mL) at ambient temperature. The reaction mixture was degassed for 5 min with N$_2$ gas, heated to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over Na$_2$SO$_4$, filtered through celite bed and concentrated. The crude product was purified by Prep HPLC (0-30% CH$_3$CN—H$_2$O) to provide compound 22 (A-35) as an off-white solid (87.0 mg, 63%).

LC-MS (ESI$^+$): m/z 458.3 (M+H)$^+$

1H-NMR (400 MHz, DMSO-d6): δ 9.90 (s, 1H), 8.90 (s, 1H), 8.54 (d, J=4.6 Hz, 1H), 8.10-8.0 (m, 1H), 7.89-7.82 (m, 2H), 7.75-7.67 (m, 2H), 7.49-7.43 (m, 1H), 6.90-6.85 (m, 2H), 6.19 (s, 1H), 5.37 (s, 2H), 3.38-3.30 (m, 4H), 2.06 (s, 3H), 1.59-1.51 (m, 6H).

63
Synthesis of Compound A-36

Preparation of N-(4-(3,5-dimethylisoxazol-4-yl)phenyl)-4-methyl-1-((2-(piperidin-1-yl)thiazol-4-yl)methyl)-1H-pyrrole-2-carboxamide

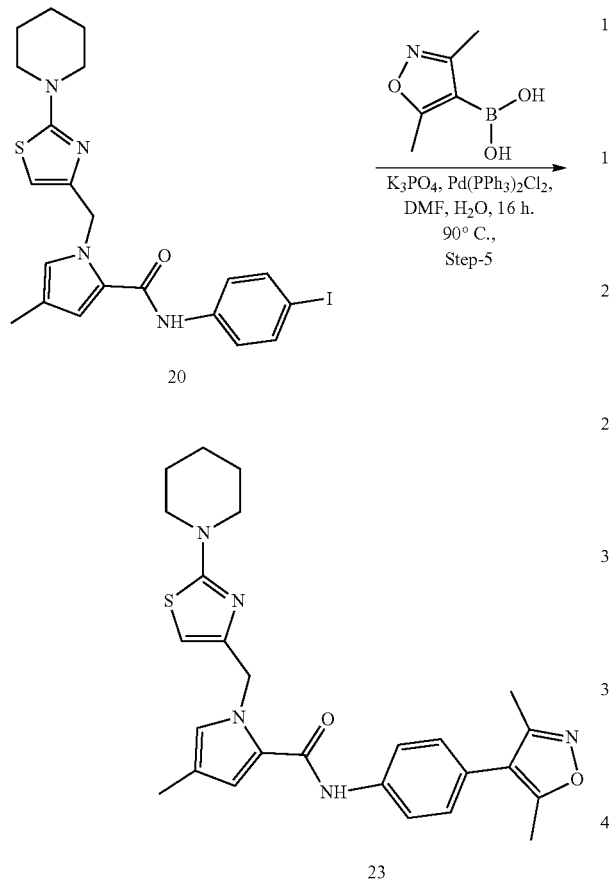

(3,5-Dimethylisoxazol-4-yl)boronic acid (62.6 mg, 0.444 mmol, 1.5 equiv), $K_3PO_4$ (188 mg, 0.889 mmol, 3 equiv) and $Pd(PPh_3)_3Cl_2$ (9.8 mg, 0.014 mmol, 0.05 equiv) were added to a stirred solution N-(4-iodophenyl)-4-methyl-1-((2-(piperidin-1-yl)thiazol-4-yl)methyl)-1H-pyrrole-2-carboxamide (20) (150 mg, 0.296 mmol, 1 equiv) in DMF (7 mL) and $H_2O$ (3 mL) at ambient temperature. The reaction mixture was degassed for 5 min with $N_2$ gas, heated to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over $Na_2SO_4$, filtered through celite bed and concentrated. The crude product was purified by Prep HPLC (0-60% $CH_3CN—H_2O$) to provide compound 23 (A-36) as a pale brown solid (30.0 mg, 21%).

LC-MS (ESI$^+$): m/z 476.2 (M+H)$^+$

1H-NMR (400 MHz, DMSO-d6): δ 9.86 (s, 1H), 7.79 (d, J=8.4 Hz, 2H), 7.31 (d, J=8.8 Hz, 2H), 6.88-6.81 (m, 2H), 6.18 (s, 1H), 5.35 (s, 2H), 3.35-3.29 (m, 4H), 2.39 (s, 3H), 2.22 (s, 3H), 2.05 (s, 3H), 1.59-1.50 (m, 6H).

64
Synthesis of Compound A-37

Preparation of N-(4-(1H-pyrazol-4-yl)phenyl)-4-methyl-1-((2-(piperidin-1-yl)thiazol-4-yl)methyl)-1H-pyrrole-2-carboxamide

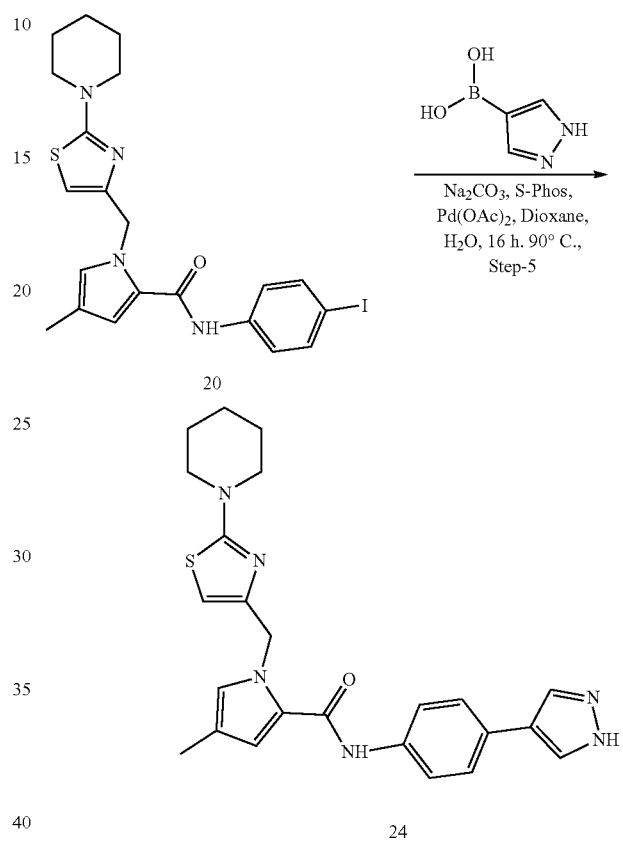

(1H-Pyrazol-4-yl)boronic acid (49.2 mg, 0.444 mmol, 1.5 equiv), $Na_2CO_3$ (93.2 mg, 0.889 mmol, 3 equiv), SPhos (11.9 mg, 0.029 mmol, 0.1 equiv) and $Pd(OAc)_2$ (3.3 mg, 0.014 mmol, 0.05 equiv) were added to a stirred solution N-(4-iodophenyl)-4-methyl-1-((2-(piperidin-1-yl)thiazol-4-yl)methyl)-1H-pyrrole-2-carboxamide (20) (150 mg, 0.296 mmol, 1 equiv) in dioxane (7 mL) and $H_2O$ (3 mL) at ambient temperature. The reaction mixture was degassed for 5 min with $N_2$ gas, heated to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over $Na_2SO_4$, filtered through celite bed and concentrated. The crude product was purified by Prep HPLC (0-40% $CH_3CN—H_2O$) to provide compound 24 (A-37) as a pale brown solid (39.0 mg, 29%).

LC-MS (ESI$^+$): m/z 447.3 (M+H)$^+$

1H-NMR (400 MHz, DMSO-d6): δ 9.74 (s, 1H), 8.01 (s, 2H), 7.68 (d, J=8.5 Hz, 2H), 7.53 (d, J=8.5 Hz, 2H), 6.87-6.82 (m, 2H), 6.17 (s, 1H), 5.36 (s, 2H), 3.35-3.29 (m, 4H), 2.05 (s, 3H), 1.59-1.50 (m, 6H).

Synthesis of Compound A-38

Preparation of N-(4-(furan-3-yl)phenyl)-4-methyl-1-((2-(piperidin-1-yl)thiazol-4-yl)methyl)-1H-pyrrole-2-carboxamide

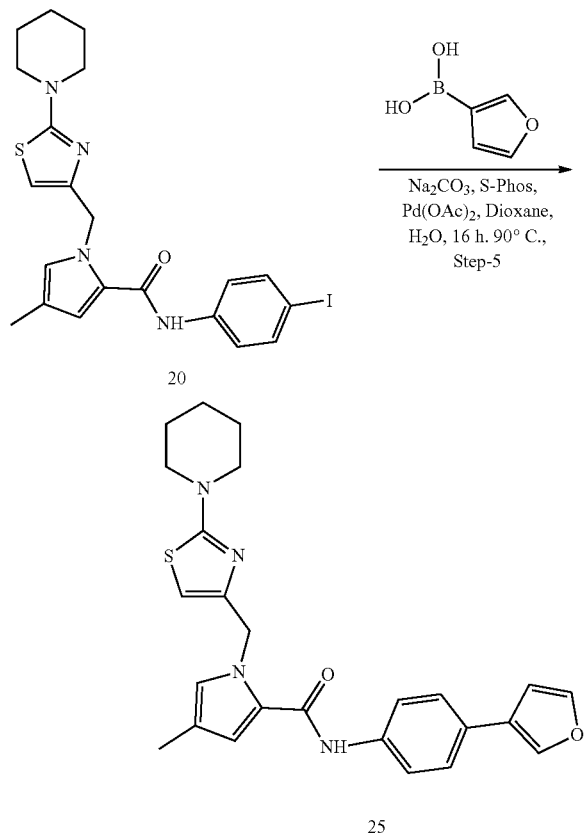

Furan-3-ylboronic acid (49.2 mg, 0.444 mmol, 1.5 equiv), $Na_2CO_3$ (93.2 mg, 0.889 mmol, 3 equiv), SPhos (11.9 mg, 0.029 mmol, 0.1 equiv) and $Pd(OAc)_2$ (3.3 mg, 0.014 mmol, 0.05 equiv) were added to a stirred solution N-(4-iodophenyl)-4-methyl-1-((2-(piperidin-1-yl)thiazol-4-yl)methyl)-1H-pyrrole-2-carboxamide (20) (150 mg, 0.296 mmol, 1 equiv) in dioxane (7 mL) and $H_2O$ (3 mL) at ambient temperature. The reaction mixture was degassed for 5 min with $N_2$ gas, heated to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over $Na_2SO_4$, filtered through celite bed and concentrated. The crude product was purified by Prep HPLC (0-60% $CH_3CN$—$H_2O$) to provide compound 25 (A-38) as an off-white solid (30.0 mg, 22%).

LC-MS (ESI+): m/z 447.3 (M+H)+

1H-NMR (400 MHz, DMSO-d6): δ 9.79 (s, 1H), 8.12 (s, 1H), 7.72 (d, J=8.3 Hz, 3H), 7.55 (d, J=8.6 Hz, 2H), 6.94 (s, 1H), 6.88-6.82 (m, 2H), 6.17 (s, 1H), 5.36 (s, 2H), 3.34-3.30 (m, 4H), 2.05 (s, 3H), 1.58-1.51 (m, 6H).

Synthesis of Compound A-43

Preparation of 4-methyl-N-(4-(2-oxoimidazolidin-1-yl)phenyl)-1-((2-(piperidin-1-yl)thiazol-4-yl)methyl)-1H-pyrrole-2-carboxamide

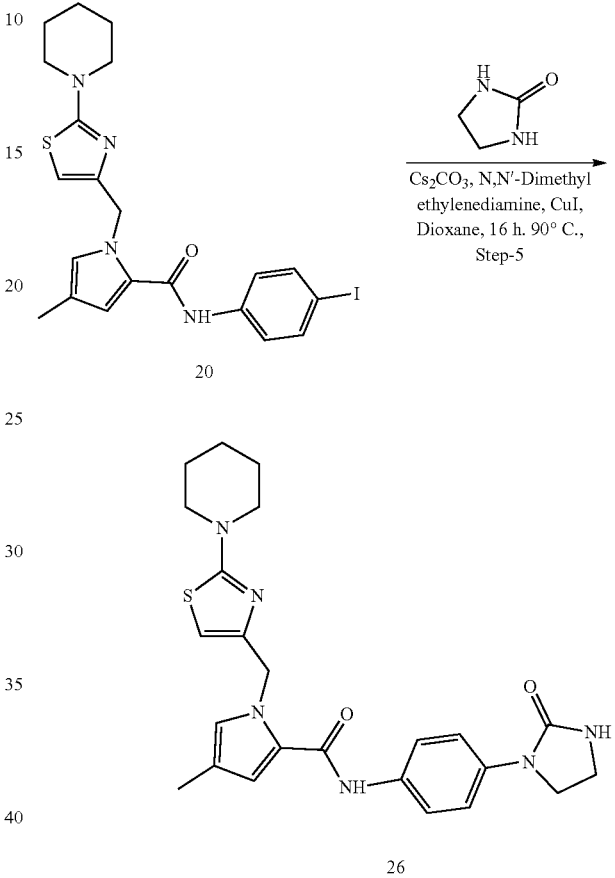

Imidazolidin-2-one (38.2 mg, 0.444 mmol, 1.5 equiv), $Cs_2CO_3$ (290 mg, 0.888 mmol, 3 equiv), N,N'-dimethylethylenediamine (2.6 mg, 0.029 mmol, 0.1 equiv) and CuI (5.6 mg, 0.029 mmol, 0.1 equiv) were added to a stirred solution N-(4-iodophenyl)-4-methyl-1-((2-(piperidin-1-yl)thiazol-4-yl)methyl)-1H-pyrrole-2-carboxamide (20) (150 mg, 0.296 mmol, 1 equiv) in dioxane (7 mL) and $H_2O$ (3 mL) at ambient temperature. The reaction mixture was heated to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over $Na_2SO_4$, filtered through celite bed and concentrated. The crude product was purified by Prep HPLC (0-40% $CH_3CN$—$H_2O$) to provide compound 26 (A-43) as a pale brown solid (27.0 mg, 20%).

LC-MS (ESI+): m/z 465.2 (M+H)+

1H-NMR (400 MHz, DMSO-d6): δ 9.68 (s, 1H), 7.60 (d, J=7.6 Hz, 2H), 7.47 (d, J=8.8 Hz, 2H), 6.85-6.81 (m, 3H), 6.18 (s, 1H), 5.36 (s, 2H), 3.82 (t, J=8.0 Hz, 2H), 3.36-3.29 (m, 6H), 2.04 (s, 3H), 1.58-1.51 (m, 6H).

Synthesis of Compound A-56

Preparation of Methyl 4-acetyl-1-((2-(piperidin-1-yl)thiazol-4-yl)methyl)-1H-pyrrole-2-carboxylate

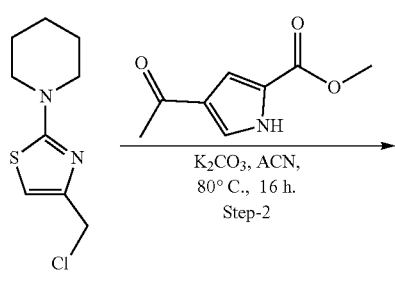

Preparation of 4-acetyl-1-((2-(piperidin-1-yl)thiazol-4-yl)methyl)-1H-pyrrole-2-carboxylic Acid

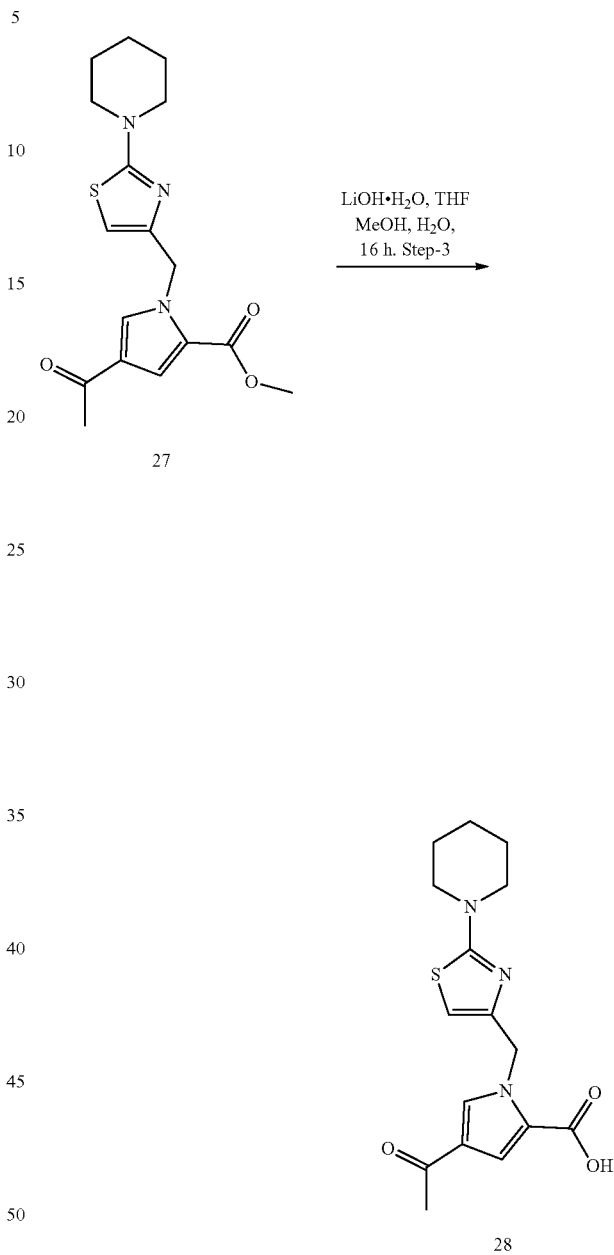

4-(Chloromethyl)-2-(piperidin-1-yl)thiazole (2) (5.43 g, 0.025 mol, 1.2 equiv) and $K_2CO_3$ (8.65 g, 0.062 mol, 3 equiv) were added to a stirred solution of methyl 4-acetyl-1H-pyrrole-2-carboxylate (3.49 g, 0.019 mol, 1 equiv) in $CH_3CN$ (50 mL) at ambient temperature. The reaction mixture was heated to 80° C. and stirred for 16 h. The reaction mixture was filtered and concentrated under vacuum. The crude product was purified by silica gel column chromatography (20% ethyl acetate-hexanes) to provide compound 27 as a white solid (5.0 g, 69%).

LC-MS (ESI$^+$): m/z 348.1 (M+H)$^+$

1H-NMR (400 MHz, DMSO-d6): δ 7.89 (s, 1H), 7.24 (s, 1H), 6.27 (s, 1H), 5.40 (s, 2H), 3.75 (s, 3H), 3.34-3.30 (m, 4H), 2.35 (s, 3H), 1.58-1.52 (m, 6H).

LiOH.H$_2$O (1.81 g, 43.1 mmol, 3 equiv) was added to a stirred solution of methyl 4-acetyl-1-((2-(piperidin-1-yl)thiazol-4-yl)methyl)-1H-pyrrole-2-carboxylate (27) (5.0 g, 14.4 mmol, 1 equiv) in THF (30 mL), MeOH (30 mL) and H$_2$O (30 mL) at ambient temperature. The reaction mixture was stirred for 16 h, then concentrated under vacuum. The residue was acidified with 1.5 M hydrochloric acid and the resulting mixture was extracted with DCM (2×100 mL). The combined organic layers were washed with water (100 mL), brine (100 mL), dried over Na$_2$SO$_4$, filtered and concentrated under vacuum to provide compound 28 as a white solid (4.0 g, 84%) without further purification.

LC-MS (ESI$^+$): m/z 334.1 (M+H)$^+$

Preparation of 4-acetyl-N-(4-iodophenyl)-1-((2-(piperidin-1-yl)thiazol-4-yl)methyl)-1H-pyrrole-2-carboxamide

Preparation of 4-(4-acetyl-1-((2-(piperidin-1-yl)thiazol-4-yl)methyl)-1H-pyrrole-2-carboxamido) benzoic Acid

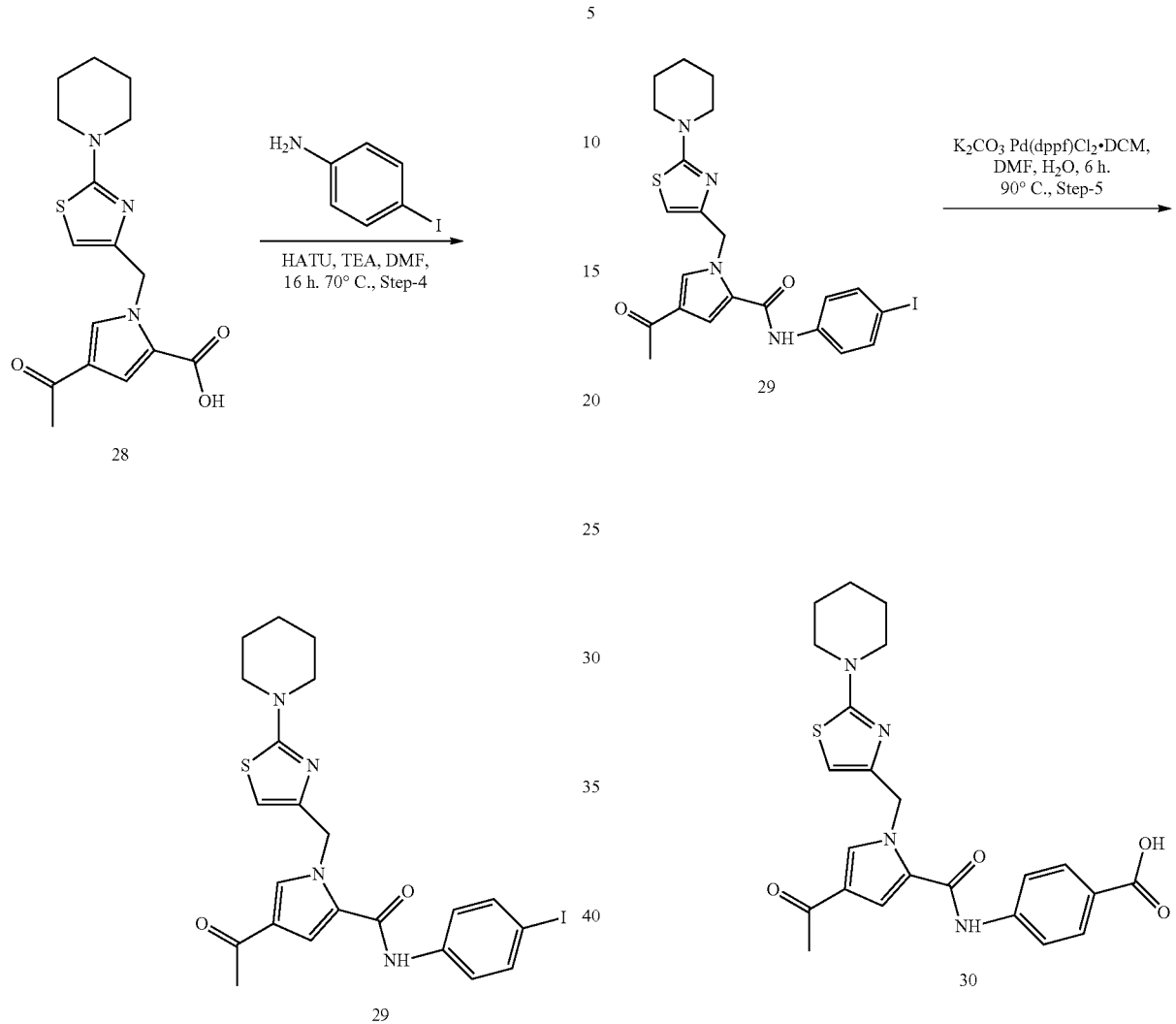

TEA (1.71 g, 16.9 mmol, 3 equiv), HATU (4.48 g, 11.8 mmol, 2 equiv) and 4-iodoaniline (1.97 g, 9.01 mmol, 1.5 equiv) were added to a stirred solution of 4-acetyl-1-((2-(piperidin-1-yl)thiazol-4-yl)methyl)-1H-pyrrole-2-carboxylic acid (28) (2.0 g, 6.01 mmol, 1 equiv) in DMF (30 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×100 mL). The combined organic layers were washed with water (2×100 mL), brine (100 mL), dried over $Na_2SO_4$, filtered and concentrated. The crude product was purified by silica gel column chromatography (30% ethyl acetate-hexanes) to provide compound 29 as a white solid (1.50 g, 47%).

LC-MS (ESI⁺): m/z 535.0 (M+H)⁺

1H-NMR (400 MHz, DMSO-d6): δ 10.16 (s, 1H), 7.88 (s, 1H), 7.66 (d, J=8.8 Hz, 2H), 7.56 (d, J=8.8 Hz, 2H), 7.39 (s, 1H), 6.31 (s, 1H), 5.45 (s, 2H), 3.34-3.30 (m, 4H), 2.36 (s, 3H), 1.58-1.50 (m, 6H).

$K_2CO_3$ (1.16 g, 8.39 mmol, 3 equiv) and Pd(dppf)Cl₂—CH₂Cl₂ (0.219 g, 0.269 mmol, 0.1 equiv) were added to a stirred solution 4-acetyl-N-(4-iodophenyl)-1-((2-(piperidin-1-yl)thiazol-4-yl)methyl)-1H-pyrrole-2-carboxamide (29) (1.49 g, 2.81 mmol, 1 equiv) in DMF (20 mL) and H₂O (6 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×100 mL). The combined organic layers were washed with water (100 mL), brine (100 mL), dried over Na₂SO₄, filtered through celite bed and concentrated. The crude product was purified by Prep HPLC (0-30% CH₃CN—H₂O) to provide compound 30 (A-56) as a white solid (600 mg, 44%).

LC-MS (ESI⁺): m/z 453.3 (M+H)⁺

1H-NMR (400 MHz, DMSO-d6): δ 10.35 (s, 1H), 7.93-7.89 (m, 3H), 7.88-7.82 (m, 2H), 7.45 (s, 1H), 6.33 (s, 1H), 5.46 (s, 2H), 3.34-3.30 (m, 4H), 2.38 (s, 3H), 1.56-1.50 (m, 6H).

Synthesis of Compound A-59

Preparation of 4-(4-(1-methoxyethyl)-1-((2-(piperidin-1-yl)thiazol-4-yl)methyl)-1H-pyrrole-2-carboxamido)benzoic Acid

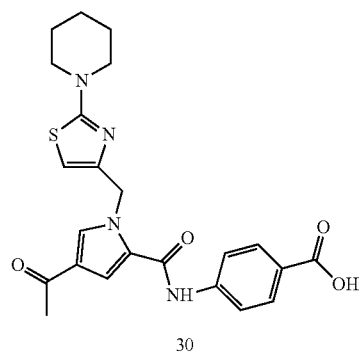

30

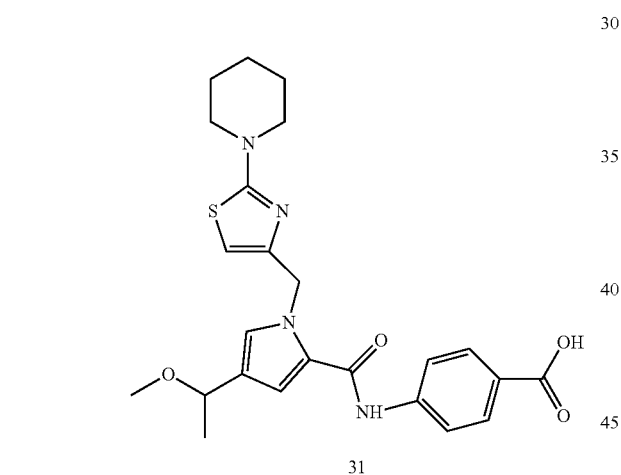

31

NaBH₄ (50.2 mg, 1.33 mmol, 2 equiv) was added to a stirred solution 4-(4-acetyl-1-((2-(piperidin-1-yl)thiazol-4-yl)methyl)-1H-pyrrole-2-carboxamido)benzoic acid (30) (300 mg, 0.663 mmol, 1 equiv) in THF (5 mL) and MeOH (95 mL) at 0° C. The reaction mixture was stirred at ambient temperature for 16 h. The reaction mixture was quenched with ice, resulting mixture was extracted with ethyl acetate (2×50 mL). The combined organic layers were washed with water (50 mL), brine (50 mL), dried over Na₂SO₄, filtered and concentrated. The crude product was purified by Prep HPLC (0-40% CH₃CN—H₂O) to provide compound 31 (A-59) as a white solid (20.0 mg, 6%).

LC-MS (ESI⁺): m/z 468.8 (M+H)⁺

1H-NMR (400 MHz, DMSO-d6): δ 12.68 (s, 1H), 10.10 (s, 1H), 7.92-7.82 (m, 4H), 7.10-7.04 (m, 2H), 6.17 (s, 1H), 5.40 (s, 2H), 4.28-4.26 (m, 1H), 3.39-3.30 (m, 4H), 3.14 (s, 3H), 1.58-1.51 (m, 6H), 1.38 (d, J=6.40 Hz, 3H).

Synthesis of Compound A-65

Preparation of 4-(4-(1-hydroxyethyl)-1-((2-(piperidin-1-yl)thiazol-4-yl)methyl)-1H-pyrrole-2-carboxamido)benzoic Acid

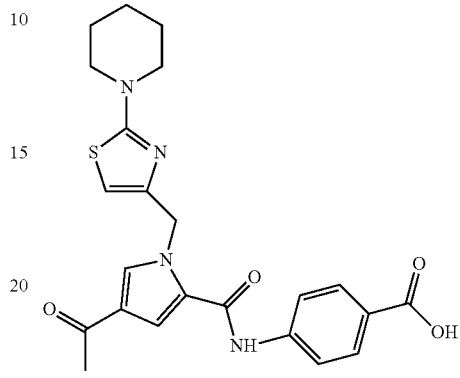

30

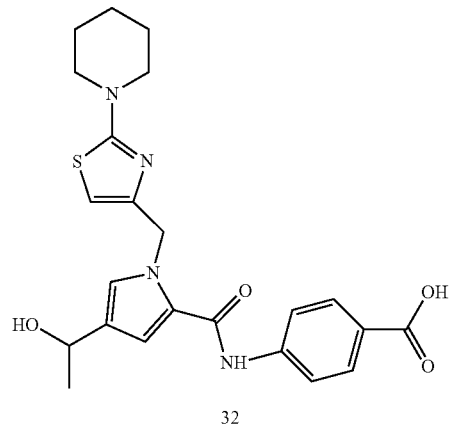

32

NaBH₄ (50.2 mg, 0.663 mmol, 2 equiv) was added to a stirred solution 4-(4-acetyl-1-((2-(piperidin-1-yl)thiazol-4-yl)methyl)-1H-pyrrole-2-carboxamido)benzoic acid (30) (300 mg, 0.663 mmol, 1 equiv) in THF (10 mL) at 0° C. The reaction mixture was stirred at ambient temperature for 16 h. The reaction mixture was quenched with ice, resulting mixture was extracted with ethyl acetate (2×30 mL). The combined organic layers were washed with water (30 mL), brine (30 mL), dried over Na₂SO₄, filtered and concentrated. The crude product was purified by silica gel column chromatography (50% ethyl acetate-hexanes) to provide compound 32 (A-65) as a white solid (20.0 mg, 7%).

LC-MS (ESI⁺): m/z 454.8 (M+H)⁺

1H-NMR (400 MHz, DMSO-d6): δ 9.86 (s, 1H), 7.81-7.76 (m, 2H), 7.72-7.63 (m, 2H), 7.02-6.91 (m, 2H), 6.21 (s, 1H), 5.37 (s, 2H), 4.85 (d, J=4.4 Hz, 1H), 4.69-4.61 (m, 1H), 3.39-3.30 (m, 4H), 1.59-1.50 (m, 6H), 1.34 (d, J=6.4 Hz, 3H).

Synthesis of Compound A-9

Preparation of 4-(chloromethyl)-N,N-diethylthiazol-2-amine

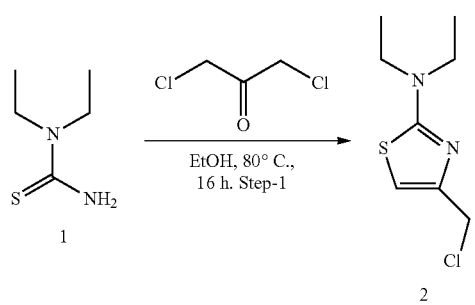

1,3-Dichloroacetone (0.959 g, 7.55 mmol, 1 equiv) was added to a stirred solution of 1,1-diethylthiourea (1) (1.0 g, 7.56 mmol, 1 equiv) in EtOH (15 mL) at ambient temperature. The reaction mixture was stirred at 80° C. for 16 h, and then cooled to ambient temperature. The resultant mixture was concentrated under vacuum. The residue was basified with 10% NaHCO$_3$ aqueous solution and extracted with DCM (2×50 mL). The combined organic layers were washed with water (75 mL), brine (75 mL), dried over Na$_2$SO$_4$, filtered and concentrated under vacuum. The crude product was purified by silica gel column chromatography (10% ethyl acetate-hexanes) to provide compound 2 as colorless liquid (750 mg, 53%).

LC-MS (ESI$^+$): m/z 205.0 (M+H)$^+$

1H-NMR (300 MHz, DMSO-d6): δ 7.04 (s, 1H), 4.71 (s, 2H), 3.55 (q, J=6.6 Hz, 4H), 1.19 (t, J=6.9 Hz, 6H).

Preparation of Ethyl 1-((2-(diethylamino)thiazol-4-yl)methyl)-4-methyl-1H-pyrrole-2-carboxylate

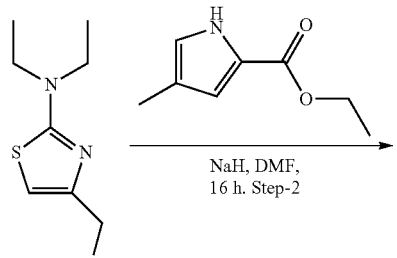

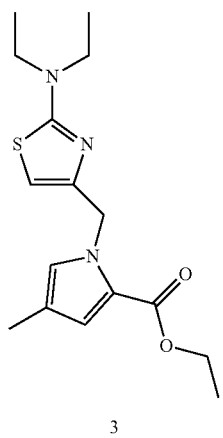

NaH (265 mg, 60% w/w in mineral oil, 5.51 mmol, 1.5 equiv) was added to a stirred solution of ethyl 4-methyl-1H-pyrrole-2-carboxylate (563 mg, 3.68 mmol, 1 equiv) in DMF (15 mL) at 0° C. After the reaction mixture was stirred at 0° C. for 30 min, 4-(chloromethyl)-N,N-diethylthiazol-2-amine (2) (750 mg, 3.68 mmol, 1 equiv) was added at 0° C. The reaction mixture was allowed to warm to ambient temperature and stirred for 16 h. The reaction mixture was quenched with ice and extracted with ethyl acetate (2×50 mL). The combined organic layers were washed with water (2×50 mL), brine (50 mL), dried over Na$_2$SO$_4$, filtered and concentrated under vacuum. The crude product was purified by silica gel column chromatography (20% ethyl acetate-hexanes) to provide compound 3 as a pale brown solid (590 mg, 50%).

LC-MS (ESI$^+$): m/z 321.9 (M+H)$^+$

1H-NMR (300 MHz, DMSO-d6): δ 11.52 (s, 1H), 6.94 (s, 1H), 6.68 (s, 1H), 5.98 (s, 1H), 5.28 (s, 2H), 4.21-4.11 (m, 2H), 3.43-3.33 (m, 4H), 2.00 (s, 3H), 1.28-1.22 (m, 3H), 1.17-1.10 (m, 6H).

Preparation of 1-((2-(diethylamino)thiazol-4-yl)methyl)-4-methyl-1H-pyrrole-2-carboxylic Acid

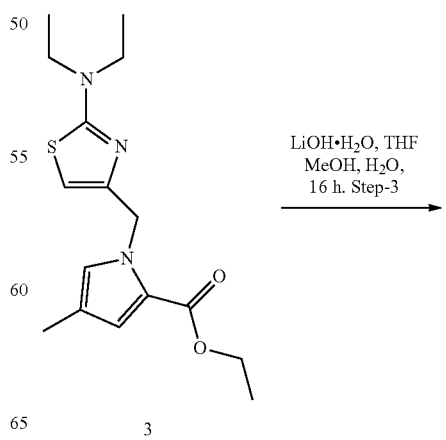

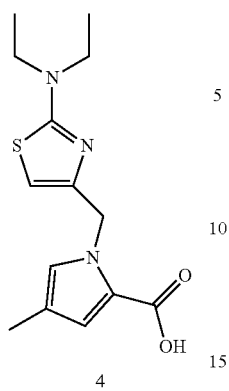

LiOH.H$_2$O (232 mg, 5.53 mmol, 3 equiv) was added to a stirred solution of ethyl 1-((2-(diethylamino)thiazol-4-yl)methyl)-4-methyl-1H-pyrrole-2-carboxylate (3) (590 mg, 1.84 mmol, 1 equiv) in THF (2 mL), MeOH (2 mL) and H$_2$O (2 mL) at ambient temperature. The reaction mixture was stirred for 16 h, and then concentrated under vacuum. The residue was acidified with 1.5 M hydrochloric acid and the resulting mixture was extracted with DCM (2×30 mL). The combined organic layers were washed with water (30 mL), brine (30 mL), dried over Na$_2$SO$_4$, filtered and concentrated under vacuum to provide compound 4 as a pale brown solid (431 mg, 80%) without further purification.

LC-MS (ESI$^+$): m/z 294.0 (M+H)$^+$

Preparation of Methyl 4-(1-((2-(diethylamino)thiazol-4-yl)methyl)-4-methyl-1H-pyrrole-2-carboxamido)benzoate

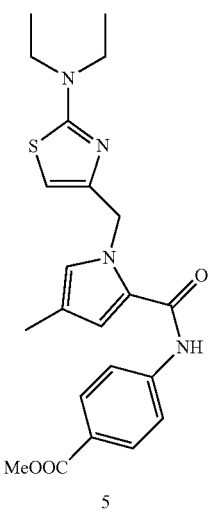

DIPEA (568 mg, 4.40 mmol, 3 equiv), HATU (1.11 g, 2.92 mmol, 2 equiv) and methyl 4-aminobenzoate (332 mg, 2.20 mmol, 1.5 equiv) were added to a stirred solution of 1-((2-(diethylamino)thiazol-4-yl)methyl)-4-methyl-1H-pyrrole-2-carboxylic acid (4) (0.429 g, 1.46 mmol, 1 equiv) in DMF (10 mL) at ambient temperature. The reaction mixture was stirred at 70° C. for 16 h, and then cooled to ambient temperature, concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by Prep HPLC (0-60% CH$_3$CN—H$_2$O) to provide compound 5 as a pale brown solid (31.0 mg, 5%).

LC-MS (ESI$^+$): m/z 427.1 (M+H)$^+$

Preparation of 4-(1-((2-(diethylamino)thiazol-4-yl)methyl)-4-methyl-1H-pyrrole-2-carboxamido)benzoic Acid

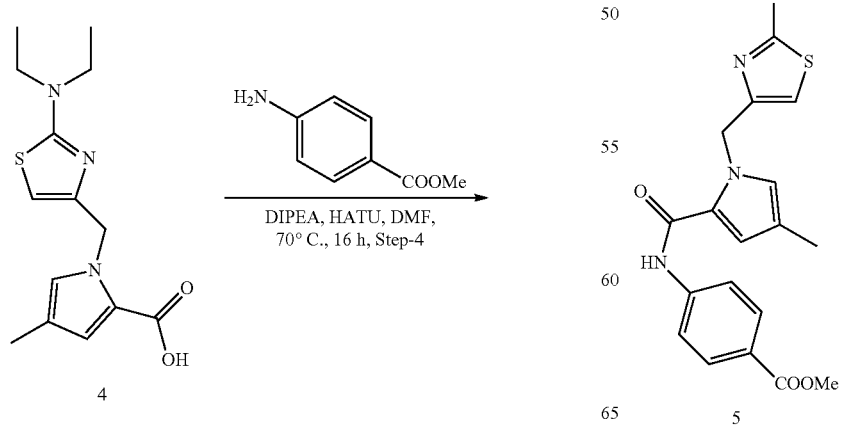

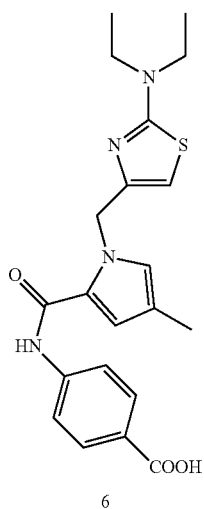

LiOH.H$_2$O (8.82 mg, 0.211 mmol, 3 equiv) was added to a stirred solution of methyl 4-(1-((2-(diethylamino)thiazol-4-yl)methyl)-4-methyl-1H-pyrrole-2 carboxamido) benzoate (5) (30.0 mg, 0.069 mmol, 1 equiv) in THF (1 mL), MeOH (1 mL) and H$_2$O (1 mL) at ambient temperature. The reaction mixture was stirred for 16 h, and then concentrated under vacuum. The residue was acidified with 1.5 M hydrochloric acid and the resulting mixture was extracted with DCM (2×20 mL). The combined organic layers were washed with water (20 mL), brine (20 mL), dried over Na$_2$SO$_4$, filtered and concentrated. The crude product was purified by Prep HPLC (0-50% CH$_3$CN—H$_2$O) to provide compound 6 (A-9) as a pale brown gum (5.0 mg, 16%).

LC-MS (ESI$^+$): m/z 412.9 (M+H)$^+$

1H-NMR (400 MHz, DMSO-d6): δ 10.01 (s, 1H), 7.84 (d, J=8.0 Hz, 2H), 7.82 (d, J=8.0 Hz, 2H), 6.88 (s, 2H), 6.04 (s, 1H), 5.33 (s, 2H), 3.45 (q, J=7.2 Hz, 4H), 2.04 (s, 3H), 1.08 (t, J=7.2 Hz, 6H).

Synthesis of Compound A-10

Preparation of 4-(chloromethyl)-2-(pyrrolidin-1-yl)thiazole

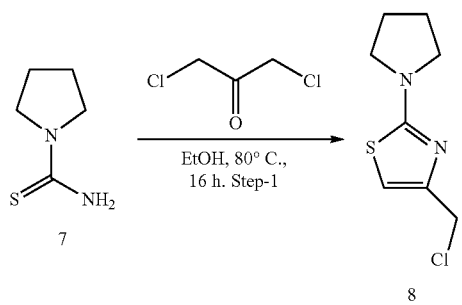 [SMILES: NC(=S)N1CCCC1 ; O=C(CCl)CCl ; ClCc1csc(N2CCCC2)n1]

1,3-Dichloroacetone (1.95 g, 15.5 mmol, 1 equiv) was added to a stirred solution of pyrrolidine-1-carbothioamide (7) (2.0 g, 15.5 mmol, 1 equiv) in EtOH (30 mL) at ambient temperature. The reaction mixture was stirred at 80° C. for 16 h, and then cooled to ambient temperature. The resultant mixture was concentrated under vacuum. The residue was basified with 10% NaHCO$_3$ aqueous solution and extracted with DCM (2×75 mL). The combined organic layers were washed with water (75 mL), brine (75 mL), dried over Na$_2$SO$_4$, filtered and concentrated under vacuum. The crude product was purified by silica gel column chromatography (10% ethyl acetate-hexanes) to provide compound 8 as an off-white solid (1.40 g, 46%).

LC-MS (ESI$^+$): m/z 203.2 (M+H)$^+$

1H-NMR (300 MHz, DMSO-d6): δ 6.77 (s, 1H), 4.56 (s, 2H), 3.37-3.33 (m, 4H), 1.96 (s, 4H).

Preparation of Ethyl 4-methyl-1-((2-(pyrrolidin-1-yl)thiazol-4-yl)methyl)-1H-pyrrole-2-carboxylate

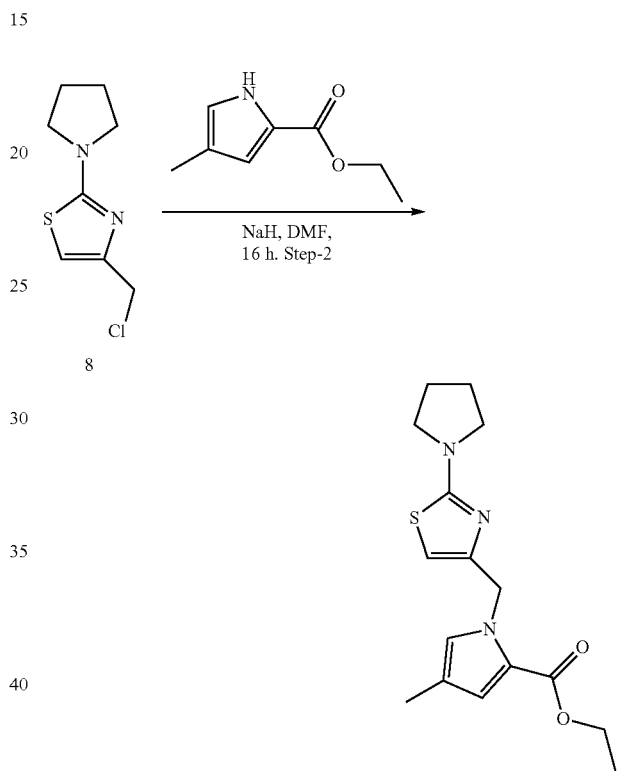

NaH (0.468 g, 60% w/w in mineral oil, 9.80 mmol, 1.5 equiv) was added to a stirred solution of ethyl 4-methyl-1H-pyrrole-2-carboxylate (1.00 g, 6.53 mmol, 1 equiv) in DMF (30 mL) at 0° C. After the reaction mixture was stirred at 0° C. for 30 min, 4-(chloromethyl)-2-(pyrrolidin-1-yl)thiazole (8) (1.37 g, 6.75 mmol, 1.05 equiv) was added at 0° C. The reaction mixture was allowed to warm to ambient temperature and stirred for 16 h. The reaction mixture was quenched with ice and extracted with ethyl acetate (2×50 mL). The combined organic layers were washed with water (2×50 mL), brine (50 mL), dried over Na$_2$SO$_4$, filtered and concentrated under vacuum. The crude product was purified by silica gel column chromatography (20% ethyl acetate-hexanes) to provide compound 9 as a pale brown solid (0.65 g, 30%).

LC-MS (ESI$^+$): m/z 320.0 (M+H)$^+$

1H-NMR (400 MHz, DMSO-d6): δ 6.92 (s, 1H), 6.69 (s, 1H), 6.01 (s, 1H), 5.30 (s, 2H), 4.15 (q, J=7.2 Hz, 2H), 3.33-3.30 (m, 4H), 2.00 (s, 3H), 1.97-1.94 (m, 4H), 1.23 (t, J=7.2 Hz, 3H).

Preparation of 4-methyl-1-((2-(pyrrolidin-1-yl)thiazol-4-yl)methyl)-1H-pyrrole-2-carboxylic Acid

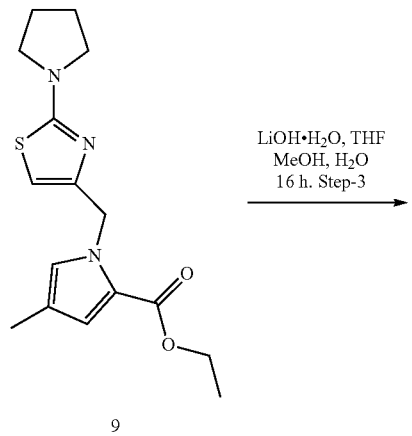

Preparation of Methyl 4-(4-methyl-1-((2-(pyrrolidin-1-yl)thiazol-4-yl)methyl)-1H-pyrrole-2-carboxamido)benzoate

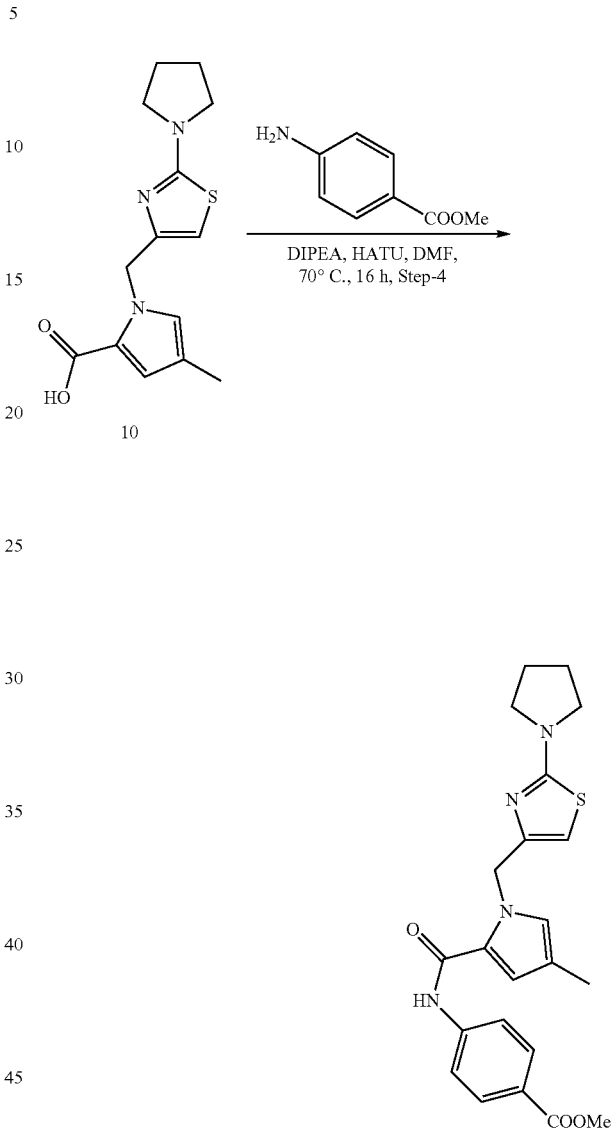

LiOH.H$_2$O (257 mg, 6.11 mmol, 3 equiv) was added to a stirred solution of ethyl 4-methyl-1-((2-(pyrrolidin-1-yl)thiazol-4-yl)methyl)-1H-pyrrole-2-carboxylate (9) (650 mg, 2.04 mmol, 1 equiv) in THF (5 mL), MeOH (5 mL) and H$_2$O (5 mL) at ambient temperature. The reaction mixture was stirred for 16 h, and then concentrated under vacuum. The residue was acidified with 1.5 M hydrochloric acid and the resulting mixture was extracted with DCM (2×30 mL). The combined organic layers were washed with water (30 mL), brine (30 mL), dried over Na$_2$SO$_4$, filtered and concentrated under vacuum to provide compound 10 as a pale brown solid (474 mg, 80%) without further purification.

LC-MS (ESI$^+$): m/z 292.0 (M+H)$^+$

1H-NMR (400 MHz, DMSO-d6): δ 12.02 (s, 1H), 6.86 (s, 1H), 6.63 (s, 1H), 5.98 (s, 1H), 5.32 (s, 2H), 3.33-3.30 (m, 4H), 2.00 (s, 3H), 1.97-1.94 (m, 4H).

DIPEA (798 mg, 6.18 mmol, 4 equiv), HATU (1.2 mg, 3.09 mmol, 2 equiv) and methyl 4-aminobenzoate (471 mg, 2.15 mmol, 1.1 equiv) were added to a stirred solution of 4-methyl-1-((2-(pyrrolidin-1-yl)thiazol-4-yl)methyl)-1H-pyrrole-2-carboxylic acid (10) (450 mg, 1.55 mmol, 1 equiv) in DMF (10 mL) at ambient temperature. The reaction mixture was stirred at 70° C. for 16 h, and then cooled to ambient temperature, concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (30% ethyl acetate-hexanes) to provide compound 11 as a pale brown solid (32.0 mg, 5%).

LC-MS (ESI$^+$): m/z 425.2 (M+H)$^+$

Preparation of 4-(4-methyl-1-((2-(pyrrolidin-1-yl)thiazol-4-yl)methyl)-1H-pyrrole-2-carboxamido)benzoic Acid

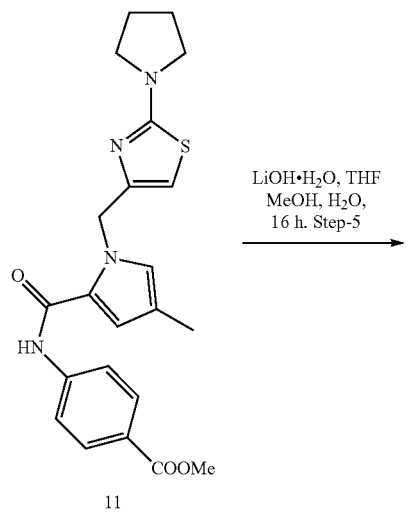

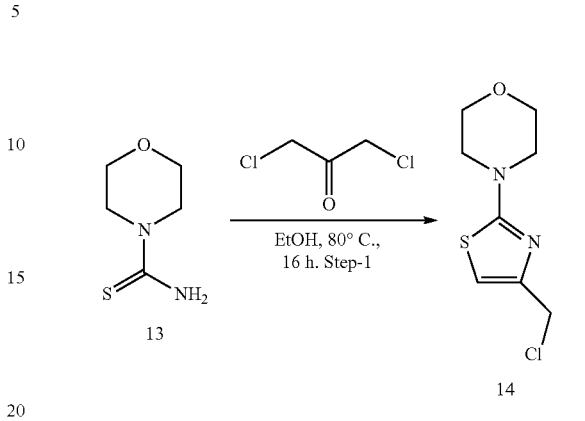

Synthesis of Compound A-12

Preparation of 4-(4-(chloromethyl)thiazol-2-yl)morpholine 1,3-Dichloroacetone (3.34 g, 0.020 mol, 1 equiv) was added to a stirred solution of morpholine-4-carbothioamide (13) (3.0 g, 0.020 mol, 1 equiv) in EtOH (30 mL) at ambient temperature. The reaction mixture was stirred at 80° C. for 16 h, and then cooled to ambient temperature. The resultant mixture was concentrated under vacuum. The residue was basified with 10% NaHCO$_3$ aqueous solution and extracted with DCM (2×100 mL). The combined organic layers were washed with water (100 mL), brine (100 mL), dried over Na$_2$SO$_4$, filtered and concentrated under vacuum. The crude product was purified by silica gel column chromatography (10% ethyl acetate-hexanes) to provide compound 14 as a colorless liquid (1.55 g, 35%).

LC-MS (ESI$^+$): m/z 218.9 (M+H)$^+$

Preparation of 4-methyl-1-((2-morpholinothiazol-4-yl)methyl)-1H-pyrrole-2-carboxylic Acid

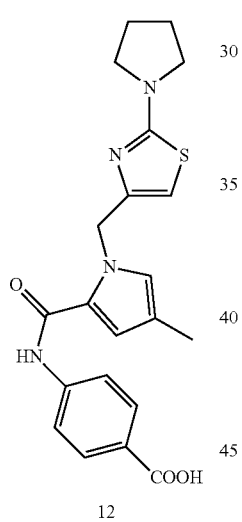

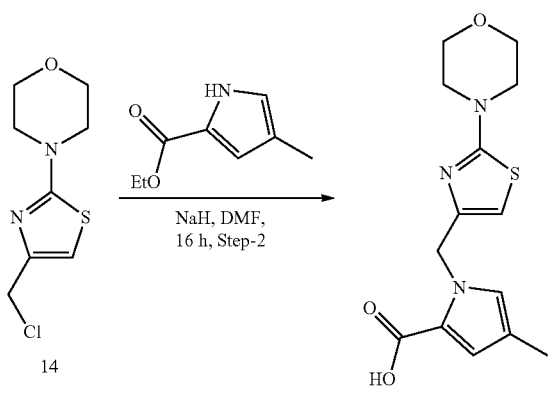

LiOH.H$_2$O (7.21 mg, 0.171 mmol, 3 equiv) was added to a stirred solution of methyl 4-(4-methyl-1-((2-(pyrrolidin-1-yl)thiazol-4-yl)methyl)-1H-pyrrole-2-carboxamido)benzoate (11) (30.0 mg, 0.057 mmol, 1 equiv) in THF (1.0 mL), MeOH (1 mL) and H$_2$O (1 mL) at ambient temperature. The reaction mixture was stirred for 16 h, and then concentrated under vacuum. The residue was acidified with 1.5 M hydrochloric acid and the resulting mixture was extracted with DCM (2×20 mL). The combined organic layers were washed with water (20 mL), brine (20 mL), dried over Na$_2$SO$_4$, filtered and concentrated. The crude product was purified by Prep HPLC (0-40% CH$_3$CN—H$_2$O) to provide compound 12 (A-10) as a pale brown gum (7.0 mg, 30%).

LC-MS (ESI$^+$): m/z 410.9 (M+H)$^+$

1H-NMR (400 MHz, DMSO-d6): δ 10.03 (s, 1H), 7.89-7.79 (m, 4H), 6.92 (s, 2H), 6.09 (s, 1H), 5.37 (s, 2H), 3.39-3.30 (m, 4H), 2.04 (s, 3H), 1.99-1.92 (m, 4H).

NaH (0.930 g, 60% w/w in mineral oil, 0.019 mol, 3 equiv) was added to a stirred solution of ethyl 4-methyl-1H-pyrrole-2-carboxylate (1.0 g, 6.52 mmol, 1 equiv) in DMF (20 mL) at 0° C. After the reaction mixture was stirred at 0° C. for 30 min, 4-(4-(chloromethyl)thiazol-2-yl)morpholine (14) (1.55 g, 7.08 mmol, 1.1 equiv) was added at 0° C. The reaction mixture was allowed to warm to ambient temperature and stirred for 16 h. The reaction mixture was quenched with ice, acidified with 1.5 M hydrochloric acid and extracted with ethyl acetate (2×50 mL). The combined organic layers were washed with water (2×50 mL), brine (50 mL), dried over Na$_2$SO$_4$, filtered and concentrated under vacuum. The crude product was purified by silica gel column chromatography (40% ethyl acetate-hexanes) to provide compound 15 as a pale brown solid (600 mg, 30%).

LC-MS (ESI$^+$): m/z 307.9 (M+H)$^+$

Preparation of Methyl 4-(4-methyl-1-((2-morpholinothiazol-4-yl)methyl)-1H-pyrrole-2-carboxamido) benzoate

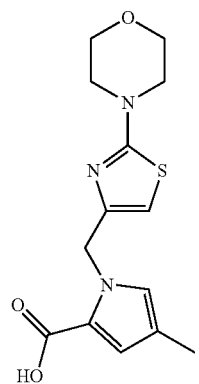

Preparation of 4-(4-methyl-1-((2-morpholinothiazol-4-yl)methyl)-1H-pyrrole-2-carboxamido)benzoic Acid

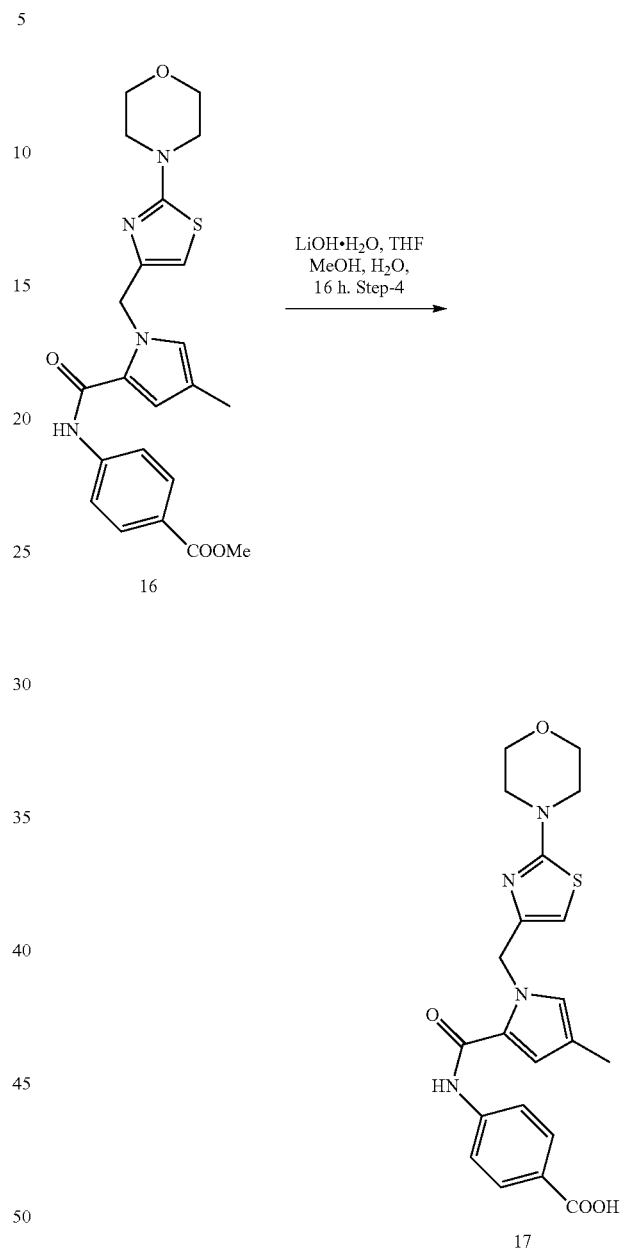

DIPEA (757 mg, 5.86 mmol, 3 equiv), HATU (1.11 g, 2.93 mmol, 1.5 equiv) and methyl 4-aminobenzoate (471 mg, 2.15 mmol, 1.1 equiv) were added to a stirred solution of 4-methyl-1-((2-morpholinothiazol-4-yl)methyl)-1H-pyrrole-2-carboxylic acid (15) (600 mg, 1.95 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 16 as a pale brown solid (150 mg, 15%).

LC-MS (ESI$^+$): m/z 440.9 (M+H)$^+$

LiOH.H$_2$O (42.8 mg, 1.02 mmol, 3 equiv) was added to a stirred solution of methyl 4-(4-methyl-1-((2-morpholinothiazol-4-yl)methyl)-1H-pyrrole-2-carboxamido)benzoate (16) (150 mg, 0.340 mmol, 1 equiv) in THF (1 mL), MeOH (1 mL) and H$_2$O (1 mL) at ambient temperature. The reaction mixture was stirred for 16 h, and then concentrated under vacuum. The residue was acidified with 1.5 M hydrochloric acid and the resulting mixture was extracted with DCM (2×30 mL). The combined organic layers were washed with water (30 mL), brine (30 mL), dried over Na$_2$SO$_4$, filtered and concentrated. The crude product was purified by Prep HPLC (0-30% CH$_3$CN—H$_2$O) to provide compound 17 (A-12) as a pale brown solid (21.0 mg, 15%).

LC-MS (ESI$^+$): m/z 427.2 (M+H)$^+$

1H-NMR (400 MHz, DMSO-d6): δ 9.85 (s, 1H), 7.82 (d, J=8.4 Hz, 2H), 7.67 (d, J=8.8 Hz, 2H), 6.85 (s, 2H), 6.25 (s, 1H), 5.36 (s, 2H), 3.64 (t, J=4.8 Hz, 4H), 3.38-3.29 (m, 4H), 2.04 (s, 3H).

Synthesis of Compound A-1

Preparation of Methyl 4-((4-methyl-1-((2-(piperidin-1-yl)thiazol-4-yl)methyl)-1H-pyrrole-2-carboxamido)methyl)benzoate

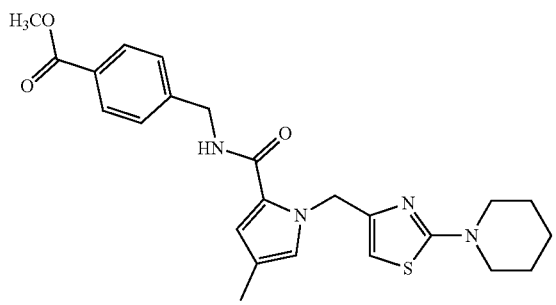

5b5

To a solution of 4-methyl-1-((2-(piperidin-1-yl)thiazol-4-yl)methyl)-1H-pyrrole-2-carboxylic acid (4) (200 mg, 0.66 mmol), methyl 4-(aminomethyl) benzoate hydrochloride (160 mg, 0.79 mmol) and HOBt (97.2 mg, 0.72 mmol) in DMF (4 mL) were added EDCI (188 mg, 0.98 mmol) and DIPEA (422 mg, 3.3 mmol) under $N_2$. The reaction mixture was stirred at room temperature overnight and then poured into water. The resulting mixture was extracted with EtOAc. The combined organic layers were dried over anhydrous $Na_2SO_4$ and concentrated under reduced pressure. The residue was purified by silica gel column chromatography to give compound 5b5 (218 mg, 73.5% yield) as a pale yellow oil.

Preparation of 4-((4-methyl-1-((2-(piperidin-1-yl)thiazol-4-yl)methyl)-1H-pyrrole-2-carboxamido)methyl)benzoic Acid

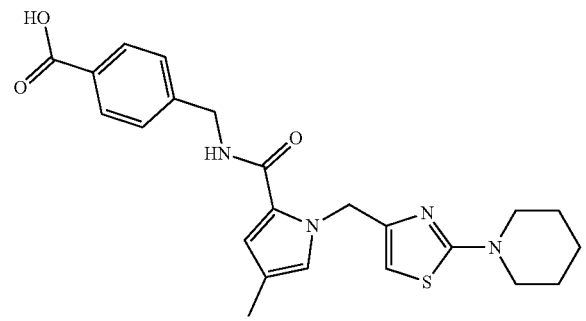

A-1

To a solution of compound 5b5 (218 mg, 0.481 mmol) in MeOH (4 mL) was added $LiOH \cdot H_2O$ (32 mg, 0.8 mmol) at room temperature. The reaction mixture was stirred overnight and then adjusted to pH=5-6 with aqueous HCl (4 N). All solvents were removed under reduced pressure and the residue was purified by silica gel column chromatography to give A-1 (56 mg, 26% yield).

LC-MS (ESI+): m/z 439.5 (M+H)+

$^1$H NMR (400 MHz, DMSO-d$_6$): δ 12.90 (brs, 1H), 8.59 (t, J=6.4 Hz, 1H), 7.87 (d, J=8.0 Hz, 2H), 7.33 (d, J=8.0 Hz, 2H), 6.77 (s, 1H), 6.66 (s, 1H), 6.06 (s, 1H), 5.33 (s, 2H), 4.41 (d, J=6.0 Hz, 2H), 2.00 (s, 3H), 1.56 (brs, 6H), 1.23 (brs, 4H).

Synthesis of Compound A-2

Preparation of Methyl 3-((4-methyl-1-((2-(piperidin-1-yl)thiazol-4-yl)methyl)-1H-pyrrole-2-carboxamido)methyl)benzoate

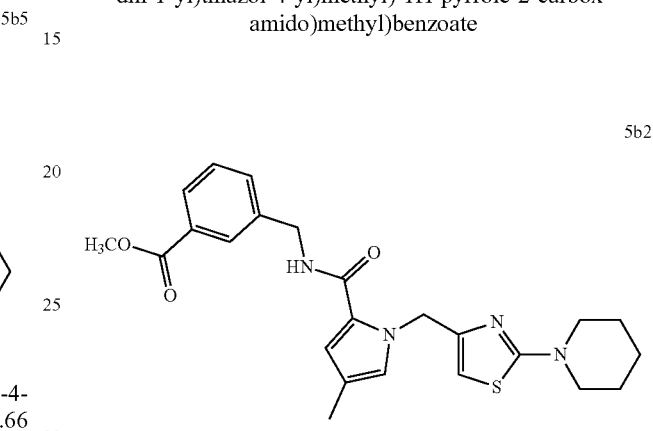

5b2

To a solution of 4-methyl-1-((2-(piperidin-1-yl)thiazol-4-yl)methyl)-1H-pyrrole-2-carboxylic acid (4) (100 mg, 0.33 mmol), methyl 3-(aminomethyl)benzoate hydrochloride (65.7 mg, 0.33 mmol) and HOBt (48.6 mg, 0.36 mmol) in DMF (2 mL) were added EDCI (69 mg, 0.36 mmol) and DIPEA (85.3 mg, 0.66 mmol) under $N_2$. The reaction mixture was stirred at room temperature overnight and then poured into water. The resulting mixture was extracted with EtOAc. The combined organic layers were dried over anhydrous $Na_2SO_4$ and concentrated under reduced pressure. The residue was purified by silica gel column chromatography to give compound 5b2 (90 mg, 61% yield) as a pale yellow oil.

Preparation of 3-((4-methyl-1-((2-(piperidin-1-yl)thiazol-4-yl)methyl)-1H-pyrrole-2-carboxamido)methyl)benzoic Acid

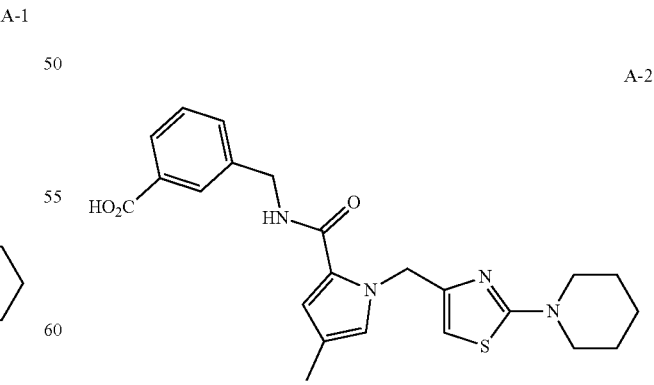

A-2

To a solution of compound 5b2 (120 mg, 0.265 mmol) in MeOH (4 mL) was added $LiOH \cdot H_2O$ (32 mg, 0.8 mmol) at room temperature. The reaction mixture was stirred overnight and then adjusted to pH=5-6 with aqueous HCl (4 N).

All solvents were removed under reduced pressure and the residue was purified by silica gel column chromatography to give compound A-2 (73 mg, 63.1% yield).

LC-MS (ESI+): m/z 439.3 (M+H)+

1H NMR (400 MHz, CDCl3): δ 8.03 (s, 1H), 7.99 (d, J=8.0 Hz, 1H), 7.58 (d, J=7.6 Hz, 1H), 7.42 (t, J=8.0 Hz, 1H), 6.70 (brs, 1H), 6.50 (d, J=1.6 Hz, 1H), 6.27 (br, s, 1H), 5.30 (s, 2H), 4.65 (d, J=6.0 Hz, 1H), 3.33 (brs, 4H), 2.05 (s, 3H), 1.57 (br, s, 6H).

Synthesis of Compound A-3

Preparation of N-benzyl-4-methyl-1-((2-(piperidin-1-yl)thiazol-4-yl)methyl)-1H-pyrrole-2-carboxamide

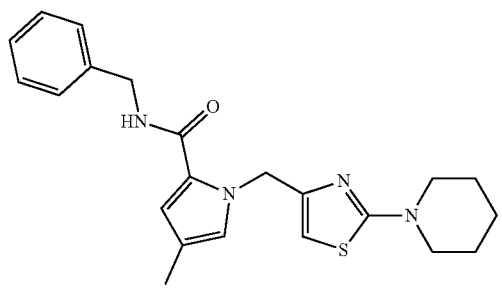

A-3

To a solution of 4-methyl-1-((2-(piperidin-1-yl)thiazol-4-yl)methyl)-1H-pyrrole-2-carboxylic acid (4) (100 mg, 0.33 mmol), benzylamine (70.0 mg, 0.65 mmol) and HOBt (54.0 mg, 0.4 mmol) in DMF (2 mL) were added EDCI (75 mg, 0.4 mmol) and DIPEA (211 mg, 1.6 mmol) under N2. The reaction mixture was stirred at room temperature overnight and then poured into water. The resulting mixture was extracted with EtOAc. The combined organic layers were dried over anhydrous Na2SO4 and concentrated under reduced pressure. The residue was purified by silica gel column chromatography to give A-3 (60 mg, 23% yield) as a pale yellow oil.

LC-MS (ESI+): m/z 395.6 (M+H)+

1H NMR (400 MHz, DMSO-d6): δ 8.52 (t, J=6.0 Hz, 1H), 7.19-7.38 (m, 5H), 6.75 (s, 1H), 6.64 (s, 1H), 6.08 (s, 1H), 5.33 (s, 2H), 4.36 (d, J=6.0 Hz, 2H), 2.00 (s, 3H), 1.56 (brs, 6H), 1.23 (br, s, 4H).

Synthesis of Compound A-4

Preparation of Methyl 3-(4-methyl-1-((2-(piperidin-1-yl)thiazol-4-yl)methyl)-1H-pyrrole-2-carboxamido)benzoate

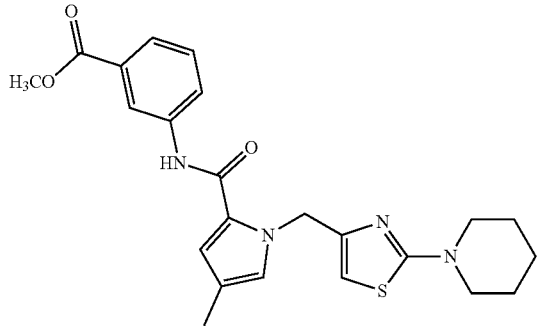

5b4

To a solution of 4-methyl-1-((2-(piperidin-1-yl)thiazol-4-yl)methyl)-1H-pyrrole-2-carboxylic acid (4) (500 mg, 1.64 mmol), methyl 3-aminobenzoate (250 mg, 1.65 mmol) and HOBt (265 mg, 1.96 mmol) in DMF (20 mL) were added HATU (740 mg, 1.96 mmol) and DIPEA (1.05 g, 8.12 mmol) under N2. The reaction mixture was stirred at 80° C. overnight and then poured into water. The resulting mixture was extracted with EtOAc. The combined organic layers were dried over anhydrous Na2SO4 and concentrated under reduced pressure. The residue was purified by prep-HPLC to give compound 5b4 (100 mg, 14% yield) as a pale yellow oil.

Preparation of 3-(4-methyl-1-((2-(piperidin-1-yl)thiazol-4-yl)methyl)-1H-pyrrole-2-carboxamido)benzoic Acid

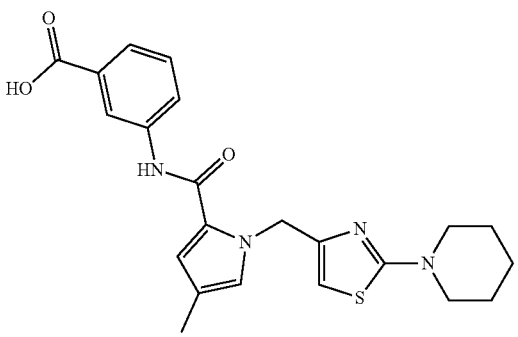

A-4

To a solution of compound 5b4 (100 mg, 0.23 mmol) in MeOH (4 mL) was added LiOH.H2O (29 mg, 0.69 mmol) at room temperature. The reaction mixture was stirred overnight and then adjusted to pH=5-6 with aqueous HCl (4 N). All solvents were removed under reduced pressure and the residue was purified by silica gel column chromatography to give compound A-4 (40 mg, 41% yield).

LC-MS (ESI+): m/z 423.5 (M−H)−

Synthesis of Compound A-5

Preparation of 4-(4-methyl-1-((2-(piperidin-1-yl)thiazol-4-yl)methyl)-1H-pyrrole-2-carboxamido)benzoic Acid

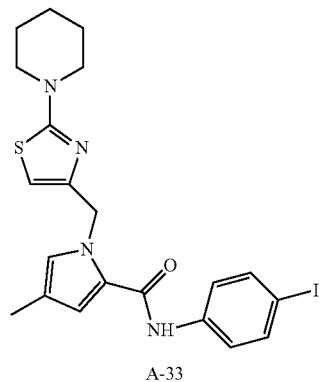

Synthesis of Compound A-71

Preparation of 4'-(4-methyl-1-((2-(piperidin-1-yl)thiazol-4-yl)methyl)-1H-pyrrole-2-carboxamido)-[1,1'-biphenyl]-4-carboxylic Acid

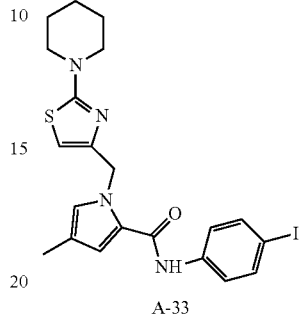

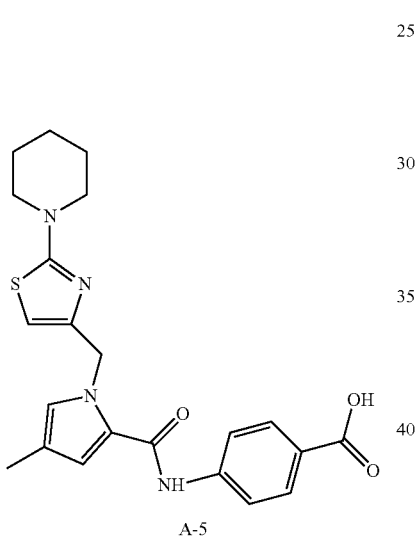

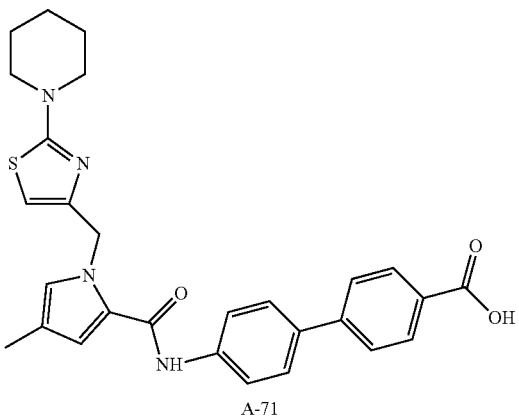

K$_2$CO$_3$ (409 mg, 2.96 mmol, 3 equiv) and Pd(dppf)Cl$_2$·DCM (80 mg, 0.09 mmol, 0.1 equiv) were added to a stirred solution N-(4-iodophenyl)-4-methyl-1-((2-(piperidin-1-yl)thiazol-4-yl)methyl)-1H-pyrrole-2-carboxamide (A-33) (500 mg, 0.988 mmol, 1 equiv) in DMF (20 mL) and H$_2$O (10 mL) at ambient temperature. The reaction mixture was heated to 90° C. and stirred for 8 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (75 mL), brine (75 mL), dried over (Na$_2$SO$_4$), filtered through Celite® bed and concentrated. The crude product was purified by Prep HPLC (0-40% CH$_3$CN—H$_2$O) to provide A-5 as a pale brown solid (100 mg, 23%).

LC-MS (ESI$^+$): m/z 425.0 (M+H)$^+$

1H-NMR (400 MHz, DMSO-d6): δ 10.04 (s, 1H), 7.93-7.77 (m, 4H), 6.91 (s, 2H), 6.19 (s, 1H), 5.36 (s, 2H), 3.36 (brs, 4H), 2.06 (s, 3H), 1.56 (brs, 6H).

Methyl 4-(4,4,5,5-tetramethyl-1,3,2-dioxaborolan-2-yl)benzoate (388.28 mg, 1.48 mmol, 1.5 equiv), K$_2$CO$_3$ (409 mg, 2.96 mmol, 3 equiv) and Pd(dppf)Cl$_2$·DCM (80 mg, 0.09 mmol, 0.1 equiv) were added to a stirred solution N-(4-iodophenyl)-4-methyl-1-((2-(piperidin-1-yl)thiazol-4-yl)methyl)-1H-pyrrole-2-carboxamide (A-33) (500 mg, 0.988 mmol, 1 equiv) in dioxane (20 mL) and H$_2$O (10 mL) at ambient temperature. The reaction mixture was degassed for 5 min with N$_2$ gas, heated to 80° C. and stirred for 16 h. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered through celite bed and concentrated. The crude product was purified by Prep HPLC (0-30% CH$_3$CN—H$_2$O) to provide compound A-71 as an pale brown solid (100 mg, 20%).

LC-MS (ESI$^+$): m/z 501.0 (M+H)$^+$

1H-NMR (400 MHz, DMSO-d6): δ 12.94 (s, 1H), 9.89 (s, 1H), 8.00 (d, J=7.60 Hz, 2H), 7.93-7.62 (m, 6H), 6.87 (s, 2H), 6.19 (s, 1H), 5.37 (s, 2H), 3.33 (brs, 4H), 2.06 (s, 3H), 1.55 (brs, 6H).

Synthesis of Compound A-69

Preparation of Ethyl 6-(piperidin-1-yl)picolinate

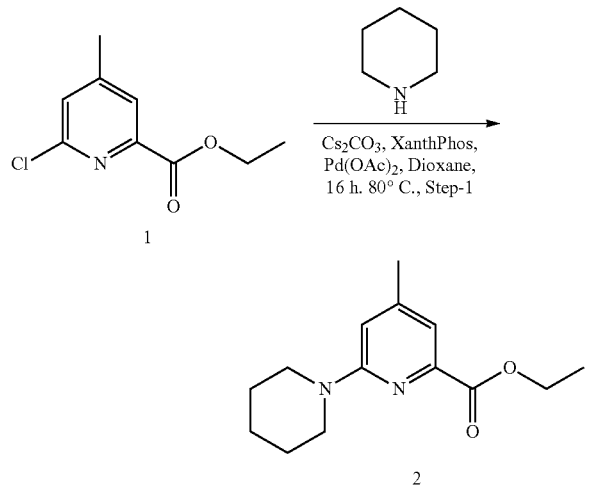

Piperidine (1.18 g, 13.95 mmol, 1.5 equiv), Cs$_2$CO$_3$ (9.13 g, 28.02 mmol, 3 equiv), XanthPhos (0.53 g, 0.93 mmol, 0.1 equiv) and Pd(OAc)$_2$ (0.10 g, 0.467 mmol, 0.05 equiv) were added to a stirred ethyl 6-chloro-4-methylpicolinate (1) (2.0 g, 9.34 mmol, 1 equiv) in dioxane (30 mL) at ambient temperature. The reaction mixture was degassed for 5 min. with N$_2$ gas and warmed to 80° C. and stirred for 16 h. The reaction mixture was cooled to ambient temperature and then concentrated under vacuum. The residue was diluted with water and the resulting mixture was extracted with ethyl acetate (2×75 mL). The combined organic layers were washed with water (75 mL), brine (75 mL), dried over Na$_2$SO$_4$, filtered through Celite® bed and concentrated. The crude product was purified by silica gel column chromatography (20% ethyl acetate-hexanes) to provide compound 2 as a white solid (2 g, 87%).

LC-MS (ESI$^+$): m/z 249.3 (M+H)$^+$

1H-NMR (300 MHz, DMSO-d6): δ 7.10 (s, 1H), 6.88 (s, 1H), 4.41-4.23 (m, 2H), 3.62-3.43 (m, 4H), 2.27 (s, 3H), 1.68-1.42 (m, 6H), 1.37-1.21 (m, 3H).

Preparation of (4-methyl-6-(piperidin-1-yl)pyridin-2-yl)methanol

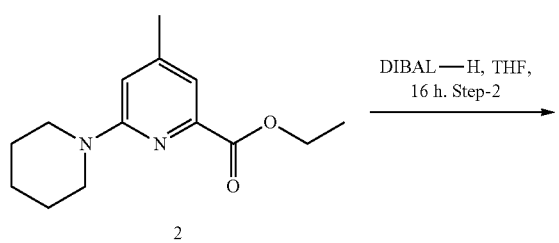

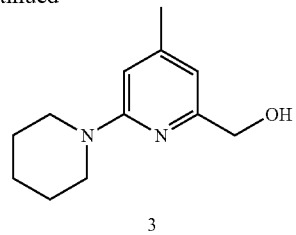

DIBAL-H (1.0 M in THF) (24.15 mL, 24.15 mmol, 3 equiv) was added to a stirred solution of ethyl 4-methyl-6-(piperidin-1-yl)picolinate (2) (2.0 g, 8.05 mmol, 1 equiv) in THF (10 mL) at −78° C. The reaction mixture was allowed to warm to ambient temperature and stirred for 16 h. The reaction mixture was quenched with MeOH (24 mL) and 1.5 M hydrochloric acid (24 mL) at 0° C., resultant mixture was concentrated under vacuum. The residue was diluted with water, the resultant mixture was extracted with ethyl acetate (2×75 mL). The combined organic layers were washed with water (2×100 mL), brine (100 mL), dried over Na$_2$SO$_4$, filtered and concentrated under vacuum to provide compound 3 as a colorless liquid (1.3 g, 78%) without further purification.

LC-MS (ESI$^+$): m/z 207.2 (M+H)$^+$

1H-NMR (300 MHz, DMSO-d6): δ 6.53 (s, 1H), 6.50 (s, 1H), 5.10 (t, J=6.00 Hz, 1H), 4.33 (d, J=5.70 Hz, 2H), 3.52-3.41 (m, 4H), 2.20 (s, 3H), 1.63-1.42 (m, 6H).

Preparation of 2-(chloromethyl)-4-methyl-6-(piperidin-1-yl)pyridine

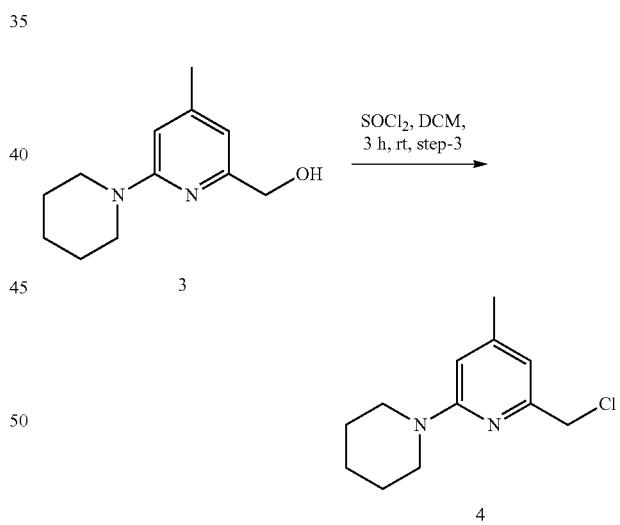

SOCl$_2$ (1.0 mL) was added to a stirred solution of (4-methyl-6-(piperidin-1-yl)pyridin-2-yl)methanol (3) (1.3 g, 6.31 mmol, 1 equiv) in DCM (20 mL) at 0° C. The reaction mixture was allowed to warm to ambient temperature and stirred for 3 h. The reaction mixture was concentrated under vacuum and azeotroped with toluene. The residue was basified with 10% NaHCO$_3$ aqueous solution and the resulting mixture was extracted with DCM (2×50 mL). The combined organic layers were washed with water (50 mL), brine (50 mL), dried over Na$_2$SO$_4$, filtered and concentrated under vacuum to provide compound 4 as a pale brown liquid (1.1 g, 78%) without further purification.

LC-MS (ESI⁺): m/z 225.3 (M+H)⁺

Preparation of Ethyl 4-methyl-1-((4-methyl-6-(piperidin-1-yl)pyridin-2-yl)methyl)-1H-pyrrole-2-carboxylate Preparation of 4-methyl-1-((4-methyl-6-(piperidin-1-yl)pyridin-2-yl)methyl)-1H-pyrrole-2-carboxylic Acid

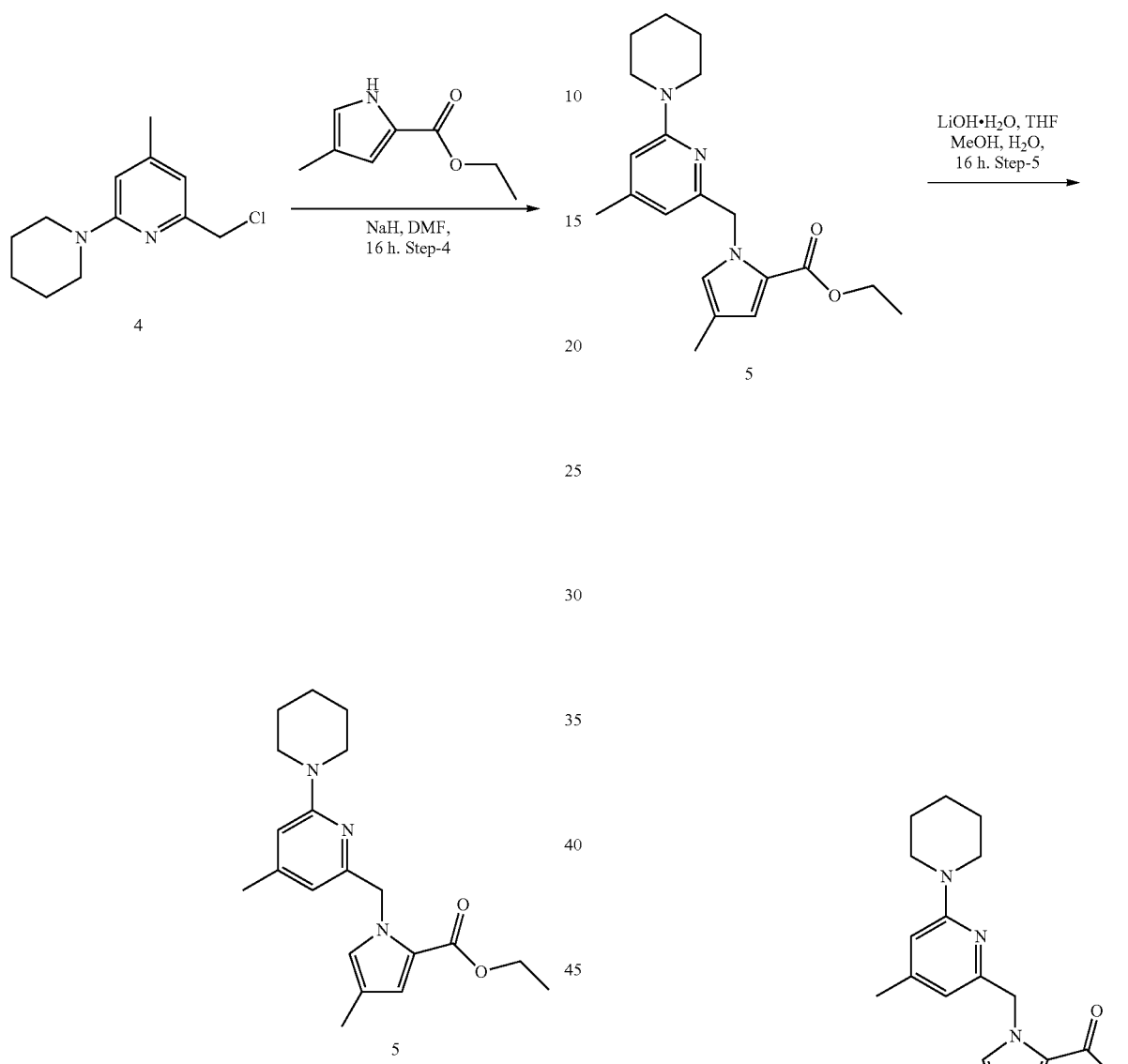

NaH (0.29 g, 60% w/w in mineral oil, 7.36 mmol, 1.5 equiv) was added to a stirred solution of ethyl 4-methyl-1H-pyrrole-2-carboxylate (0.67 g, 4.41 mmol, 0.9 equiv) in DMF (10 mL) at 0° C. After the reaction mixture was stirred at 0° C. for 30 min, 2-(chloromethyl)-4-methyl-6-(piperidin-1-yl)pyridine (4) (1.1 g, 4.91 mmol, 1 equiv) was added at 0° C. The reaction mixture was allowed to warm to ambient temperature and stirred for 16 h. The reaction mixture was quenched with ice and extracted with ethyl acetate (2×50 mL). The combined organic layers were washed with water (2×50 mL), brine (50 mL), dried over Na₂SO₄, filtered and concentrated under vacuum. The crude product was purified by silica gel column chromatography (20% ethyl acetate-hexanes) to provide compound 5 as a pale brown liquid (1.3 g, 77%).

LC-MS (ESI⁺): m/z 342.0 (M+H)⁺

LiOH.H₂O (480.06 mg, 11.43 mmol, 3 equiv) was added to a stirred solution of ethyl-4-methyl-1-((4-methyl-6-(piperidin-1-yl)pyridin-2-yl)methyl)-1H-pyrrole-2-carboxylate (5) (1.3 g, 3.81 mmol, 1 equiv) in THF (10 mL), MeOH (10 mL) and H₂O (10 mL) at ambient temperature. The reaction mixture was stirred for 16 h, and then concentrated under vacuum. The residue was acidified with 1.5 M hydrochloric acid and the obtained solid was filtered, washed water and dried under vacuum to get the required compound 6 as pale brown solid (1.0 g, 84%) without further purification.

LC-MS (ESI⁺): m/z 314.0 (M+H)⁺

95

Preparation of N-(4-iodophenyl)-4-methyl-1-((4-methyl-6-(piperidin-1-yl)pyridin-2-yl)methyl)-1H-pyrrole-2-carboxamide

96

Preparation of 4-(4-methyl-1-((4-methyl-6-(piperidin-1-yl)pyridin-2-yl)methyl)-1H-pyrrole-2-carboxamido)benzoic Acid

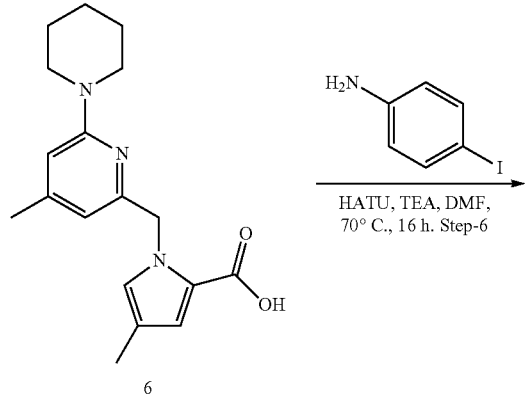

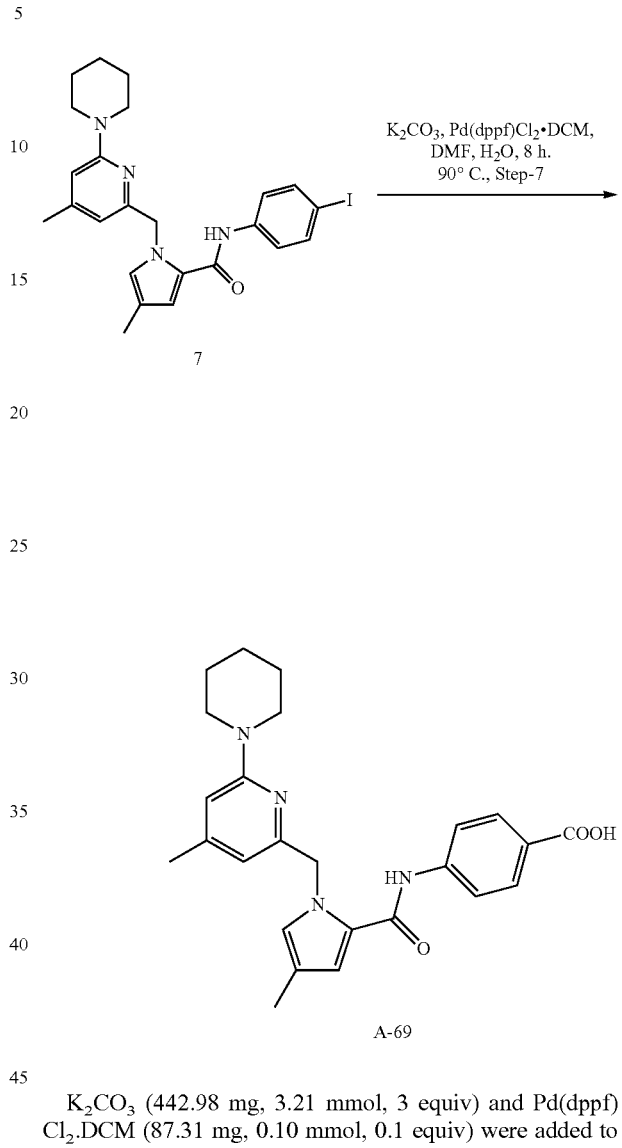

TEA (821.13 mg, 8.13 mmol, 3 equiv), HATU (2.05 g, 5.42 mmol, 2 equiv) and 4-iodoaniline (890.23 mg, 4.06 mmol, 1.5 equiv) were added to a stirred solution of 4-methyl-1-((4-methyl-6-(piperidin-1-yl)pyridin-2-yl)methyl)-1H-pyrrole-2-carboxylic acid (6) (850 mg, 2.71 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×40 mL). The combined organic layers were washed with water (2×40 mL), brine (40 mL), dried over $Na_2SO_4$, filtered and concentrated. The crude product was purified by silica gel column chromatography (20% ethyl acetate-hexanes) to provide compound 7 as a pale brown solid (0.55 g, 39%).

LC-MS (ESI$^+$): m/z 514.8 (M+H)$^+$ $K_2CO_3$ (442.98 mg, 3.21 mmol, 3 equiv) and Pd(dppf)Cl$_2$.DCM (87.31 mg, 0.10 mmol, 0.1 equiv) were added to a stirred solution N-(4-iodophenyl)-4-methyl-1-((4-methyl-6-(piperidin-1-yl)pyridin-2-yl)methyl)-1H-pyrrole-2-carboxamide (7) (550 mg, 1.07 mmol, 1 equiv) in DMF (10 mL) and H$_2$O (5 mL) at ambient temperature. The reaction mixture was heated to 90° C. and stirred for 8 h under 3 atm CO. The reaction mixture was cooled to ambient temperature and then concentrated under vacuum. The residue was acidified with 1.5 M hydrochloric acid and the resulting mixture was extracted with DCM (2×40 mL). The combined organic layers were washed with water (40 mL), brine (40 mL), dried over Na$_2$SO$_4$, filtered through celite bed and concentrated. The crude product was purified by Prep HPLC (0-30% CH$_3$CN—H$_2$O) to provide compound A-69 as a white solid (25 mg, 6%).

LC-MS (ESI$^+$): m/z 433.0 (M+H)$^+$

1H-NMR (400 MHz, DMSO-d6): δ 12.54 (s, 1H), 10.02 (s, 1H), 7.91-7.78 (m, 4H), 6.93 (s, 2H), 6.46 (s, 1H), 5.87 (s, 1H), 5.39 (s, 2H), 3.48-3.40 (m, 4H), 2.15-2.06 (m, 6H), 1.62-1.52 (m, 6H).

Synthesis of Compound A-70

Preparation of (2-bromothiazol-4-yl)methanol

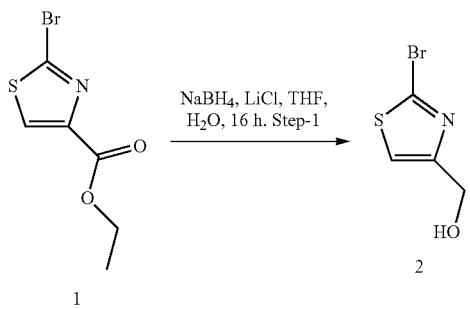

NaBH$_4$ (2.49 g, 0.066 mol, 3 equiv), LiCl (2.79 g, 0.066 mol, 3 equiv) and H$_2$O (30 mL) were added to a stirred solution ethyl 2-bromothiazole-4-carboxylate (1) (5.0 g, 0.022 mol, 1 equiv) in THF (50 mL) at 0° C. The reaction mixture was allowed to warm to ambient temperature and stirred for 16 h. The reaction mixture was quenched with 1.5 M hydrochloric acid and the resulting mixture was extracted with ethyl acetate (2×150 mL). The combined organic layers were washed with water (150 mL), brine (150 mL), dried over Na$_2$SO$_4$, filtered through celite bed and concentrated to provide compound 2 as a pale brown liquid (3.0 g, 68%).

LC-MS (ESI$^+$): m/z 195.9 (M+H)$^+$

1H-NMR (300 MHz, DMSO-d6): δ 7.48 (s, 1H), 5.43 (t, J=5.7 Hz, 1H), 4.52 (d, J=5.7 Hz, 2H).

Preparation of Methyl 4-(4-chloro-1H-pyrrole-2-carboxamido)benzoate

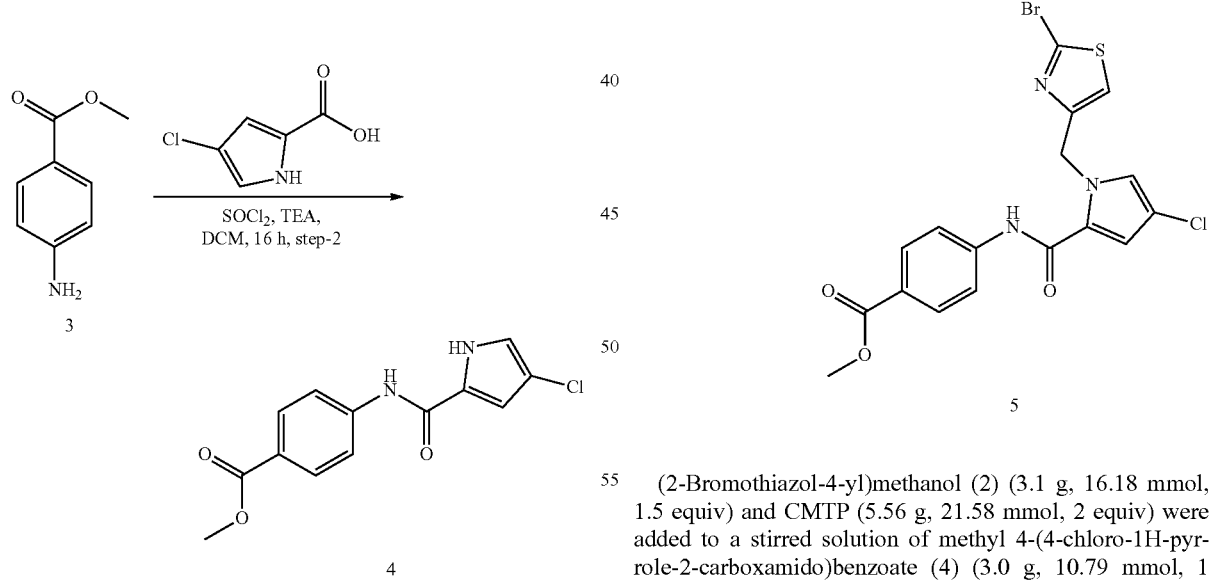

SOCl$_2$ (3 mL) was added to a stirred solution of 4-chloro-1H-pyrrole-2-carboxylic acid (2.0 g, 13.79 mmol, 1 equiv) in DCM (30 mL) at 0° C. After the reaction mixture was stirred at ambient temperature for 2 h, the resultant mixture was concentrated under vacuum and azeotroped with toluene. The residue was dissolved in DCM (30 mL) and added to a stirred solution of methyl 4-aminobenzoate (3) (2.29 g, 15.16 mmol, 1.1 equiv) and TEA (4.17 g, 41.37 mmol, 3 equiv) in DCM (20 mL) at 0° C. The reaction mixture was allowed to warm to ambient temperature and stirred for 16 h. The reaction mixture was diluted with DCM (50 mL) and washed with water (50 mL), brine (50 mL), dried over Na$_2$SO$_4$, filtered and concentrated under vacuum. The crude product was purified by silica gel column chromatography (20% ethyl acetate-hexanes) to provide compound 4 as a pale brown solid (3.0 g, 78%).

LC-MS (ESI$^+$): m/z 279.0 (M+H)$^+$

Preparation of Methyl 4-(1-((2-bromothiazol-4-yl)methyl)-4-chloro-1H-pyrrole-2-carboxamido)benzoate

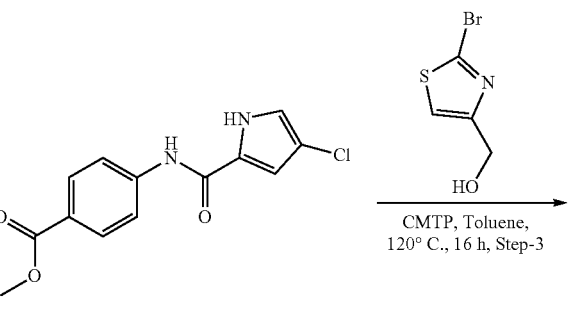

(2-Bromothiazol-4-yl)methanol (2) (3.1 g, 16.18 mmol, 1.5 equiv) and CMTP (5.56 g, 21.58 mmol, 2 equiv) were added to a stirred solution of methyl 4-(4-chloro-1H-pyrrole-2-carboxamido)benzoate (4) (3.0 g, 10.79 mmol, 1 equiv) in toluene (50 mL) at ambient temperature. The reaction mixture was warmed to 120° C. and stirred for 16 h, and then reaction mixture was cooled to ambient temperature, concentrated under vacuum. The crude product was purified by silica gel column chromatography (20% ethyl acetate-hexanes) to provide compound 5 as a pale brown solid (1 g, 20%).

LC-MS (ESI$^+$): m/z 456.0 (M+2H)$^+$

Preparation of Methyl 4-(4-chloro-1-((2-(piperidin-1-yl)thiazol-4-yl)methyl)-1H-pyrrole-2-carboxamido)benzoate

Preparation of 4-(4-chloro-1-((2-(piperidin-1-yl)thiazol-4-yl)methyl)-1H-pyrrole-2-carboxamido)benzoic Acid

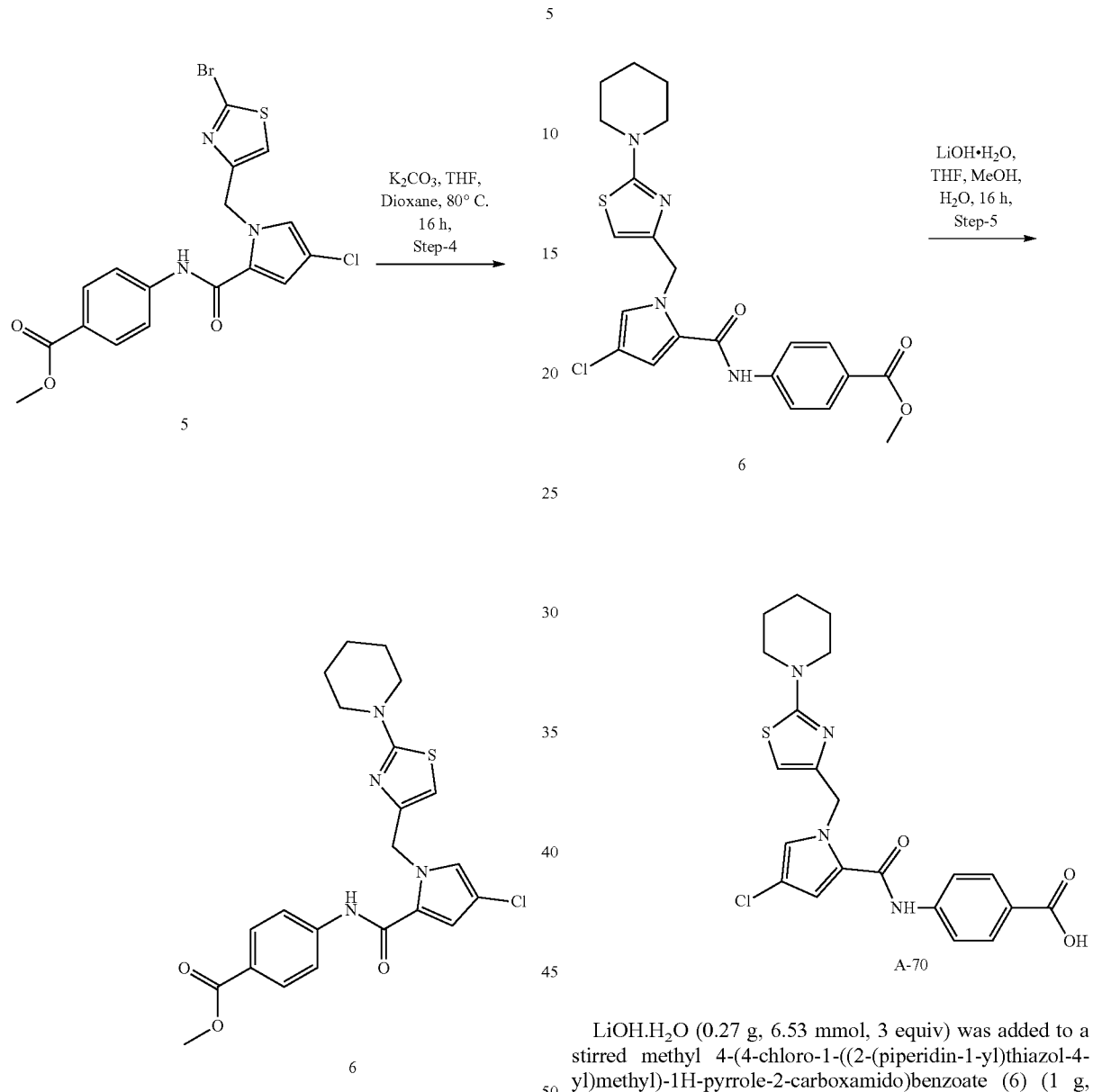

K$_2$CO$_3$ (0.90 g, 6.57 mmol, 3 equiv) and Piperidine (0.18 g, 2.19 mmol, 1 equiv) were added to a stirred solution of methyl 4-(1-((2-bromothiazol-4-yl)methyl)-4-chloro-1H-pyrrole-2-carboxamido)benzoate (5) (1.0 g, 2.19 mmol, 1 equiv) in THF (20 mL) and dioxane (20 mL) at ambient temperature. The reaction mixture was warmed to 80° C. and stirred for 16 h, and then reaction mixture was cooled to ambient temperature, concentrated under vacuum. The residue was diluted with water and the resulting mixture was extracted with ethyl acetate (2×40 mL). The combined organic layers were washed with water (50 mL), brine (50 mL), dried over Na$_2$SO$_4$, filtered and concentrated under vacuum to provide compound 6 as a pale brown solid (1 g, 99%) without further purification.

LC-MS (ESI$^+$): m/z 459.2 (M+H)$^+$

LiOH.H$_2$O (0.27 g, 6.53 mmol, 3 equiv) was added to a stirred methyl 4-(4-chloro-1-((2-(piperidin-1-yl)thiazol-4-yl)methyl)-1H-pyrrole-2-carboxamido)benzoate (6) (1 g, 2.17 mmol, 1 equiv) in THF (10 mL), MeOH (10 mL) and H$_2$O (10 mL) at ambient temperature. The reaction mixture was stirred for 16 h, and then reaction mixture was concentrated under vacuum. The residue was acidified with 1.5 M hydrochloric acid and the resulting mixture was extracted with DCM (2×40 mL). The combined organic layers were washed with water (50 mL), brine (50 mL), dried over Na$_2$SO$_4$, filtered and concentrated under vacuum. The crude product was purified by Prep HPLC (0-40% CH$_3$CN—H$_2$O) to provide compound A-70 as a white solid (100.0 mg, 10%).

LC-MS (ESI$^+$): m/z 444.8 (M+H)$^+$

1H-NMR (400 MHz, DMSO-d6): δ 10.14 (s, 1H), 7.88 (d, J=8.80 Hz, 2H), 7.77 (d, J=8.40 Hz, 2H), 7.25 (s, 1H), 7.04 (s, 1H), 6.30 (s, 1H), 5.38 (s, 2H), 3.31 (brs, 4H), 1.53 (m, 6H).

Synthesis of Compound A-7

Preparation of N-(4-(1H-tetrazol-5-yl)phenyl)-4-methyl-1-((2-(piperidin-1-yl)thiazol-4-yl)methyl)-1H-pyrrole-2-carboxamide

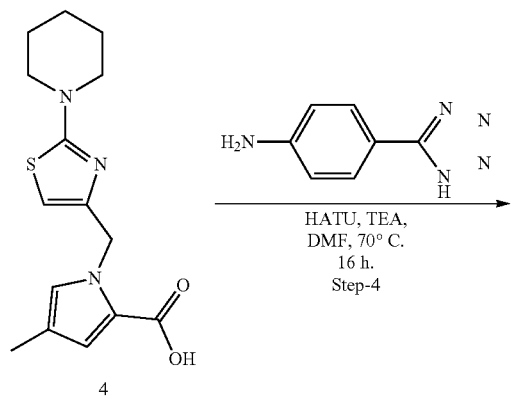

Synthesis of Compound A-6

Preparation of N-(4-(N-acetylsulfamoyl)phenyl)-4-methyl-1-((2-(piperidin-1-yl)thiazol-4-yl)methyl)-1H-pyrrole-2-carboxamide

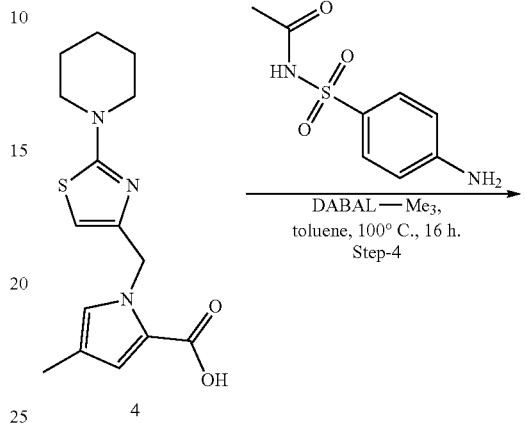

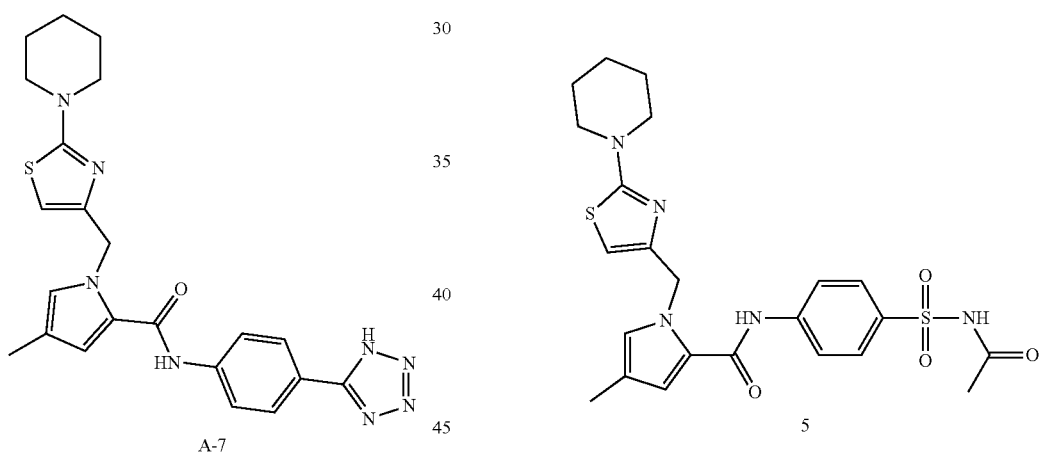

To a stirred solution of 4-methyl-1-((2-(piperidin-1-yl)thiazol-4-yl)methyl)-1H-pyrrole-2-carboxylic acid (4) (1.00 g, 3.20 mmol, 1 equiv) in DMF (20 mL), were added TEA (0.993 g, 9.8 mmol, 3 equiv), HATU (2.43 g, 6.40 mmol, 2 equiv) and 4-(1H-tetrazol-5-yl)aniline (0.772 g, 4.80 mol, 1.5 equiv] at ambient temperature. The reaction mixture was stirred at 70° C. for 16 h. The reaction mixture was concentrated under vacuum. The residue was diluted with water and extracted with ethyl acetate (2×50 mL). The combined organic layers were washed with water (2×50 mL), brine solution (50 mL), dried over $Na_2SO_4$, filtered and concentrated under vacuum. The crude product was purified by Prep HPLC to give compound A-7 as pale brown solid (A-7) (0.160 g, 11% yield).

LC-MS (ESI$^+$): m/z 449.2 (M+H)$^+$ $^1$H-NMR (400 MHz, DMSO-d$_6$): δ 10.05 (s, 1H), 7.99-7.92 (m, 4H), 6.91 (s, 2H), 6.20 (s, 1H), 5.37 (s, 2H), 3.36-3.35 (m, 4H), 2.06 (s, 3H), 1.56-1.55 (m, 6H).

N-((4-Aminophenyl)sulfonyl)acetamide (129 mg, 0.599 mmol, 1 equiv) and DABAL-Me$_3$ (154 mg, 0.599 mmol, 1 equiv) were added to a stirred solution of ethyl 4-methyl-1-((2-(piperidin-1-yl)thiazol-4-yl)methyl)-1H-pyrrole-2-carboxylate (4) (200 mg, 0.599 mmol, 1 equiv) in toluene (10 mL) at ambient temperature. The reaction mixture was heated to 100° C. and stirred for 16 h. The reaction mixture was cooled to ambient temperature and quenched with water and the resulting mixture was extracted with ethyl acetate (2×50 mL). The combined organic layers were washed with water (50 mL), brine (50 mL), dried over $Na_2SO_4$, filtered and concentrated. The crude product was purified by Prep HPLC (0-40% $CH_3CN-H_2O$) to provide compound 5 (A-6) as a pale brown solid (24.0 mg, 8%).

LC-MS (ESI$^+$): m/z 502.2 (M+H)$^+$

1H-NMR (400 MHz, DMSO-d6): δ 11.96 (s, 1H), 10.15 (s, 1H), 7.92 (d, J=8.8 Hz, 2H), 7.83 (d, J=8.8 Hz, 2H), 6.91 (s, 2H), 6.19 (s, 1H), 5.34 (s, 2H), 3.39-3.30 (m, 4H), 2.05 (s, 3H), 1.91 (s, 3H), 1.59-1.51 (m, 6H).

Synthesis of Compound A-8

Preparation of 4-methyl-1-((2-(piperidin-1-yl)thiazol-4-yl)methyl)-N-(4-sulfamoylphenyl)-1H-pyrrole-2-carboxamide

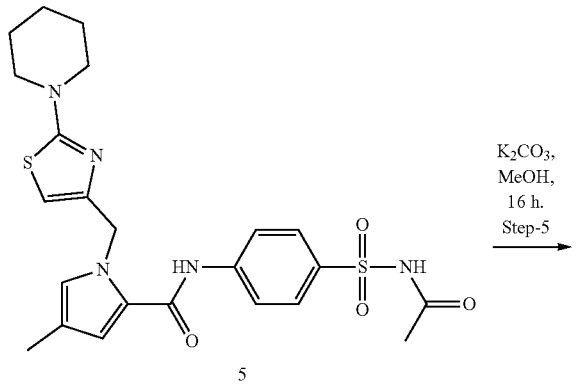

Synthesis of Compound A-31

Preparation of 4-methyl-1-((2-(piperidin-1-yl)thiazol-4-yl)methyl)-N-(pyridin-3-yl)-1H-pyrrole-2-carboxamide

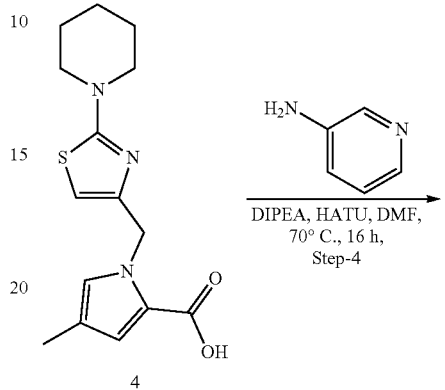

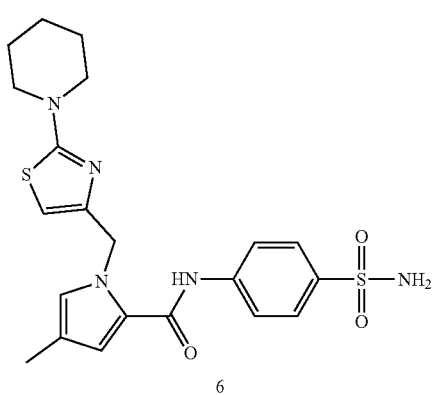

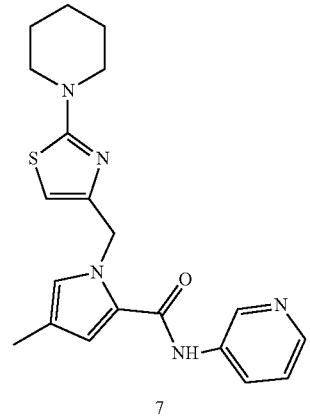

$K_2CO_3$ (82.4 mg, 0.597 mmol, 3 equiv) was added to a stirred solution of N-(4-(N-acetylsulfamoyl)phenyl)-4-methyl-1-((2-(piperidin-1-yl)thiazol-4-yl)methyl)-1H-pyrrole-2-carboxamide (5) (100 mg, 0.199 mmol, 1 equiv) in MeOH (5 mL) at ambient temperature and stirred for 16 h. The reaction mixture was concentrated under vacuum, residue was diluted with water and resultant mixture was extracted with ethyl acetate (2×30 mL). The combined organic layers were washed with water (30 mL), brine (30 mL), dried over $Na_2SO_4$, filtered and concentrated. The crude product was purified by Prep HPLC (0-40% $CH_3CN$—$H_2O$) to provide compound 6 (A-8) as a pale brown solid (9.0 mg, 10%).

LC-MS (ESI$^+$): m/z 459.8 (M+H)$^+$

1H-NMR (400 MHz, DMSO-d6): δ 10.04 (s, 1H), 7.86 (d, J=8.8 Hz, 2H), 7.74 (d, J=9.2 Hz, 2H), 7.23 (s, 2H), 6.89 (s, 2H), 6.17 (s, 1H), 5.35 (s, 2H), 3.39-3.31 (m, 4H), 2.05 (s, 3H), 1.59-1.51 (m, 6H).

DIPEA (190 mg, 1.48 mmol, 3 equiv), HATU (280 mg, 0.736 mmol, 1.5 equiv) and pyridin-3-amine (46.2 mg, 0.589 mmol, 1.2 equiv) were added to a stirred solution of 4-(4-methyl-1-((2-(piperidin-1-yl)thiazol-4-yl)methyl)-1H-pyrrole-2-carboxamido)benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over $Na_2SO_4$, filtered and concentrated. The crude product was purified by Prep HPLC (0-30% $CH_3CN$—$H_2O$) to provide compound 7 (A-31) as a pale brown gum (56.0 mg, 30%).

LC-MS (ESI$^+$): m/z 382.3 (M+H)$^+$

1H-NMR (400 MHz, DMSO-d6): δ 10.45 (s, 1H), 9.22 (s, 1H), 8.52 (d, J=5.8 Hz, 2H), 7.86 (t, J=7.3 Hz, 1H), 6.98 (s, 2H), 6.19 (s, 1H), 5.37 (s, 2H), 3.39-3.31 (m, 4H), 2.07 (s, 3H), 1.59-1.51 (m, 6H).

105
Synthesis of Compound A-40

Preparation of N-(1H-indazol-5-yl)-4-methyl-1-((2-(piperidin-1-yl)thiazol-4-yl)methyl)-1H-pyrrole-2-carboxamide

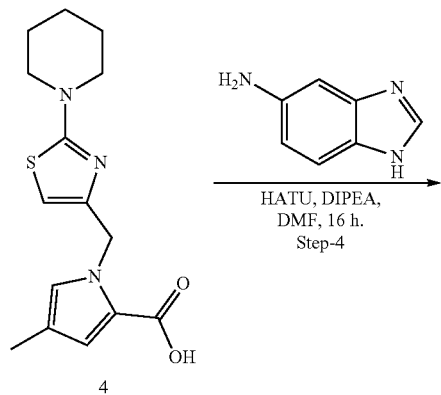

DIPEA (190 mg, 1.48 mmol, 3 equiv), HATU (280 mg, 0.736 mmol, 1.5 equiv) and 1H-indazol-5-amine (78.5 mg, 0.589 mmol, 1.2 equiv) were added to a stirred solution of 4-(4-methyl-1-((2-(piperidin-1-yl)thiazol-4-yl)methyl)-1H-pyrrole-2-carboxamido)benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-40% CH$_3$CN—H$_2$O) to provide compound 8 (A-40) as an off-white solid (110 mg, 55%).

LC-MS (ESI$^+$): m/z 421.3 (M+H)$^+$

1H-NMR (400 MHz, DMSO-d6): δ 12.94 (s, 1H), 9.76 (s, 1H), 8.14 (s, 1H), 8.00 (s, 1H), 7.59-7.52 (m, 1H), 7.49-7.44 (m, 1H), 6.82 (s, 2H), 6.17 (s, 1H), 5.36 (s, 2H), 3.39-3.31 (m, 4H), 2.05 (s, 3H), 1.59-1.51 (m, 6H).

106
Synthesis of Compound A-41

Preparation of 4-methyl-N-(2-oxoindolin-5-yl)-1-((2-(piperidin-1-yl)thiazol-4-yl)methyl)-1H-pyrrole-2-carboxamide

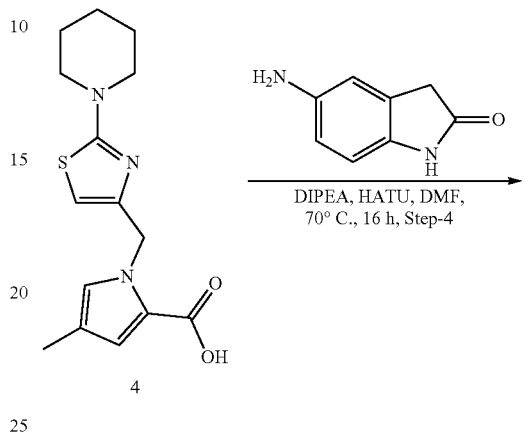

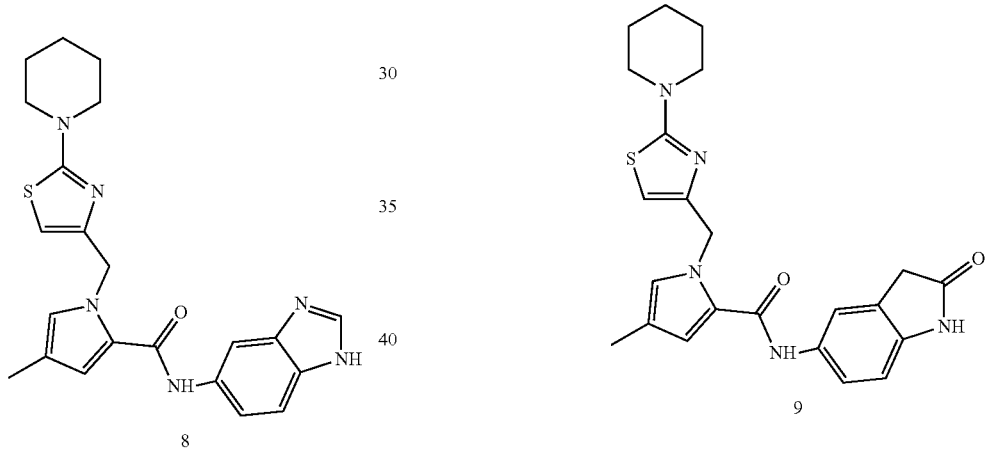

DIPEA (190 mg, 1.48 mmol, 3 equiv), HATU (280 mg, 0.736 mmol, 1.5 equiv) and 5-aminoindolin-2-one (87.2 mg, 0.589 mmol, 1.2 equiv) were added to a stirred solution of 4-(4-methyl-1-((2-(piperidin-1-yl)thiazol-4-yl)methyl)-1H-pyrrole-2-carboxamido)benzoic acid (4) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-40% CH$_3$CN—H$_2$O) to provide compound 9 (A-41) as an off-white solid (60.0 mg, 28%).

LC-MS (ESI$^+$): m/z 436.2 (M+H)$^+$

1H-NMR (400 MHz, DMSO-d6): δ 10.30 (s, 1H), 9.65 (s, 1H), 7.60 (s, 1H), 7.41 (d, J=8.3 Hz, 1H), 6.84 (s, 1H), 6.80 (s, 1H), 6.74 (d, J=8.3 Hz, 1H), 6.18 (s, 1H), 5.35 (s, 2H), 3.47 (s, 2H), 3.39-3.31 (m, 4H), 2.05 (s, 3H), 1.59-1.51 (m, 6H).

Synthesis of Compound A-57

Preparation of N-(3-fluoro-4-iodophenyl)-4-methyl-1-((2-(piperidin-1-yl)thiazol-4-yl)methyl)-1H-pyrrole-2-carboxamide

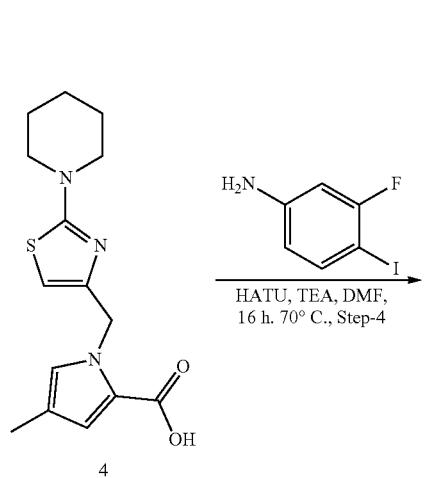

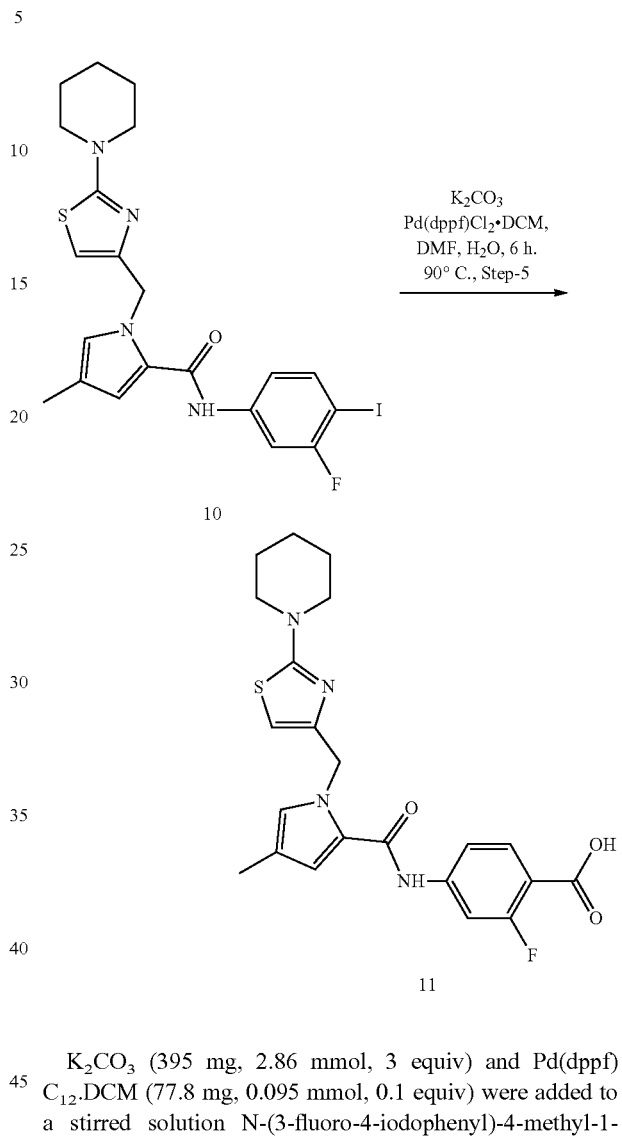

Preparation of 2-fluoro-4-(4-methyl-1-((2-(piperidin-1-yl)thiazol-4-yl)methyl)-1H-pyrrole-2-carboxamido)benzoic Acid TEA (0.695 g, 6.78 mmol, 3 equiv), HATU (1.74 g, 4.57 mmol, 2 equiv) and 3-fluoro-4-iodoaniline (0.816 mg, 0.003 mmol, 1.5 equiv) were added to a stirred solution of 4-methyl-1-((2-(piperidin-1-yl)thiazol-4-yl)methyl)-1H-pyrrole-2-carboxylic acid (4) (0.700 g, 0.002 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over $Na_2SO_4$, filtered and concentrated. The crude product was purified by silica gel column chromatography (30% ethyl acetate-hexanes) to provide compound 10 as a pale brown solid (500 mg, 41%).

LC-MS (ESI$^+$): m/z 525.1 (M+H)$^+$ $K_2CO_3$ (395 mg, 2.86 mmol, 3 equiv) and Pd(dppf)Cl$_2$·DCM (77.8 mg, 0.095 mmol, 0.1 equiv) were added to a stirred solution N-(3-fluoro-4-iodophenyl)-4-methyl-1-((2-(piperidin-1-yl)thiazol-4-yl)methyl)-1H-pyrrole-2-carboxamide (10) (500 mg, 0.954 mmol, 1 equiv) in DMF (10 mL) and H$_2$O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered through celite bed and concentrated. The crude product was purified by Prep HPLC (0-50% CH$_3$CN—H$_2$O) to provide compound 11 (A-57) as a pale brown solid (20.0 mg, 5%).

LC-MS (ESI$^+$): m/z 442.8 (M+H)$^+$

1H-NMR (400 MHz, DMSO-d6): δ 10.17 (s, 1H), 7.87-7.80 (m, 1H), 7.76 (dd, J=1.9, 13.9 Hz, 1H), 7.57 (dd, J=1.9, 8.7 Hz, 1H), 6.91 (d, J=9.8 Hz, 2H), 6.20 (s, 1H), 5.34 (s, 2H), 3.39-3.31 (m, 4H), 2.06 (s, 3H), 1.59-1.51 (m, 6H).

Synthesis of Compound A-61

Preparation of N-(4-iodo-3-methylphenyl)-4-methyl-1-((2-(piperidin-1-yl)thiazol-4-yl)methyl)-1H-pyrrole-2-carboxamide

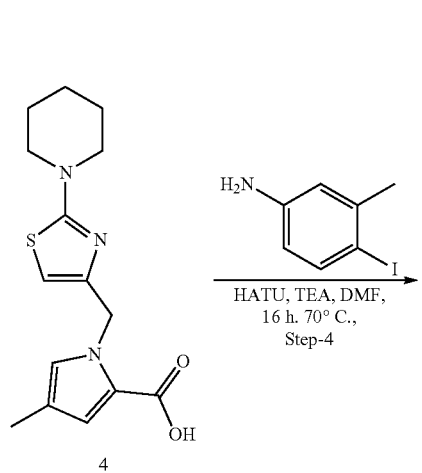

TEA (497 mg, 4.92 mmol, 3 equiv), HATU (1.24 g, 3.28 mmol, 2 equiv) and 4-iodo-3-methylaniline (573 mg, 2.46 mmol, 1.5 equiv) were added to a stirred solution of 4-methyl-1-((2-(piperidin-1-yl)thiazol-4-yl)methyl)-1H-pyrrole-2-carboxylic acid (4) (600 mg, 1.64 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over $Na_2SO_4$, filtered and concentrated. The crude product was purified by silica gel column chromatography (20% ethyl acetate-hexanes) to provide compound 12 as a pale brown solid (300 mg, 35%).

LC-MS (ESI⁺): m/z 521.0 (M+H)⁺

Preparation of 2-methyl-4-(4-methyl-1-((2-(piperidin-1-yl)thiazol-4-yl)methyl)-1H-pyrrole-2-carboxamido)benzoic Acid

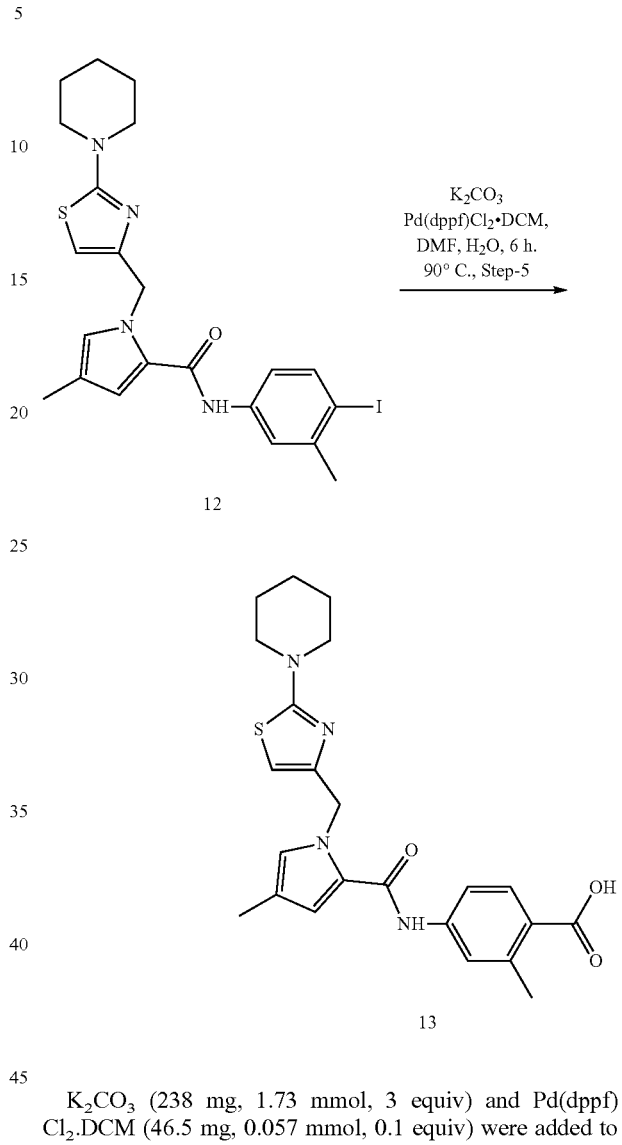

$K_2CO_3$ (238 mg, 1.73 mmol, 3 equiv) and Pd(dppf)Cl₂·DCM (46.5 mg, 0.057 mmol, 0.1 equiv) were added to a stirred solution N-(4-iodo-3-methylphenyl)-4-methyl-1-((2-(piperidin-1-yl)thiazol-4-yl)methyl)-1H-pyrrole-2-carboxamide (12) (300 mg, 0.576 mmol, 1 equiv) in DMF (10 mL) and $H_2O$ (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over $Na_2SO_4$, filtered through celite bed and concentrated. The crude product was purified by Prep HPLC (0-50% $CH_3CN$—$H_2O$) to provide compound 13 (A-61) as a pale brown solid (80.0 mg, 32%).

LC-MS (ESI⁺): m/z 438.8 (M+H)⁺

1H-NMR (400 MHz, DMSO-d6): δ 9.91 (s, 1H), 7.82 (d, J=8.2 Hz, 1H), 7.66-7.61 (m, 2H), 6.90 (s, 2H), 6.18 (s, 1H), 5.36 (s, 2H), 3.39-3.31 (m, 4H), 2.05 (s, 3H), 1.59-1.51 (m, 6H).

Synthesis of Compound A-62

Preparation of N-(6-iodopyridin-3-yl)-4-methyl-1-((2-(piperidin-1-yl)thiazol-4-yl)methyl)-1H-pyrrole-2-carboxamide

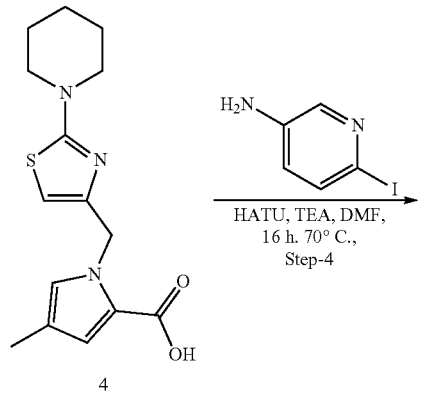

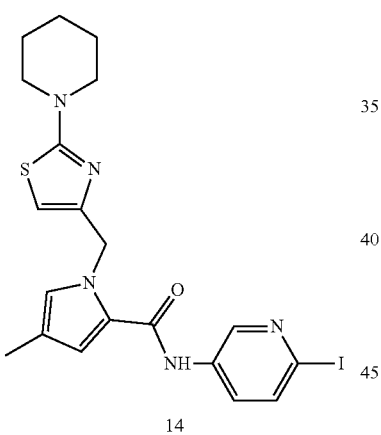

14

TEA (497 mg, 4.92 mmol, 3 equiv), HATU (1.24 g, 3.28 mmol, 2 equiv) and 6-iodopyridin-3-amine (541 mg, 2.46 mmol, 1.5 equiv) were added to a stirred solution of 4-methyl-1-((2-(piperidin-1-yl)thiazol-4-yl)methyl)-1H-pyrrole-2-carboxylic acid (4) (600 mg, 1.64 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 14 as a pale brown solid (300 mg, 36%).

LC-MS (ESI$^+$): m/z 508.0 (M+H)$^+$

Preparation of 5-(4-methyl-1-((2-(piperidin-1-yl)thiazol-4-yl)methyl)-1H-pyrrole-2-carboxamido)picolinic Acid

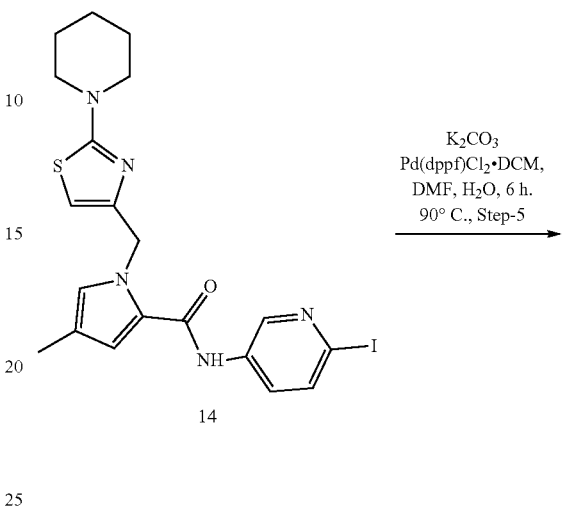

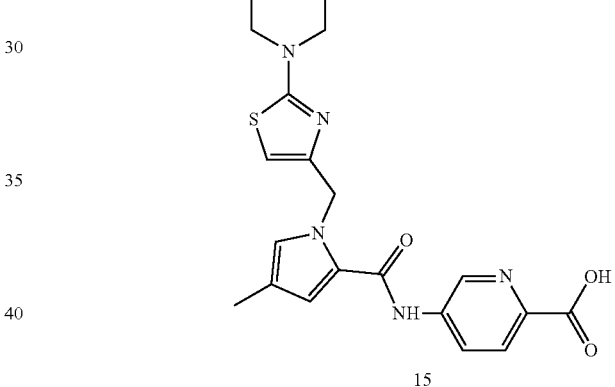

15

K$_2$CO$_3$ (245 mg, 1.78 mmol, 3 equiv) and Pd(dppf)Cl$_2$.DCM (48.2 mg, 0.059 mmol, 0.1 equiv) were added to a stirred solution N-(6-iodopyridin-3-yl)-4-methyl-1-((2-(piperidin-1-yl)thiazol-4-yl)methyl)-1H-pyrrole-2-carboxamide (14) (300 mg, 0.591 mmol, 1 equiv) in DMF (10 mL) and H$_2$O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered through celite bed and concentrated. The crude product was purified by Prep HPLC (0-30% CH$_3$CN—H$_2$O) to provide compound 15 (A-62) as a pale brown solid (30.0 mg, 12%).

LC-MS (ESI$^+$): m/z 425.8 (M+H)$^+$

1H-NMR (400 MHz, DMSO-d6): δ 10.23 (s, 1H), 8.96 (s, 1H), 8.33 (d, J=8.8 Hz, 1H), 8.02 (d, J=8.2 Hz, 1H), 6.93 (s, 2H), 6.19 (s, 1H), 5.36 (s, 2H), 3.39-3.31 (m, 4H), 2.06 (s, 3H), 1.59-1.51 (m, 6H).

Example 2b: Right Region Compound Embodiments

Synthesis of Compound A-17

General Scheme:

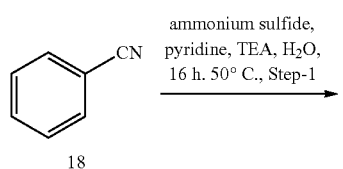

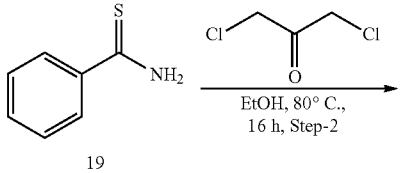

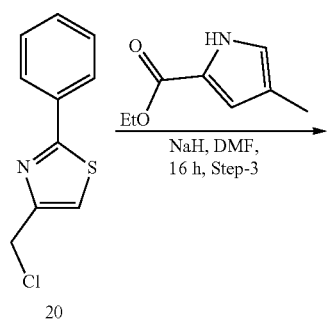

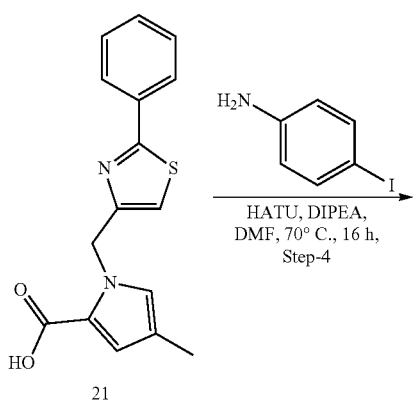

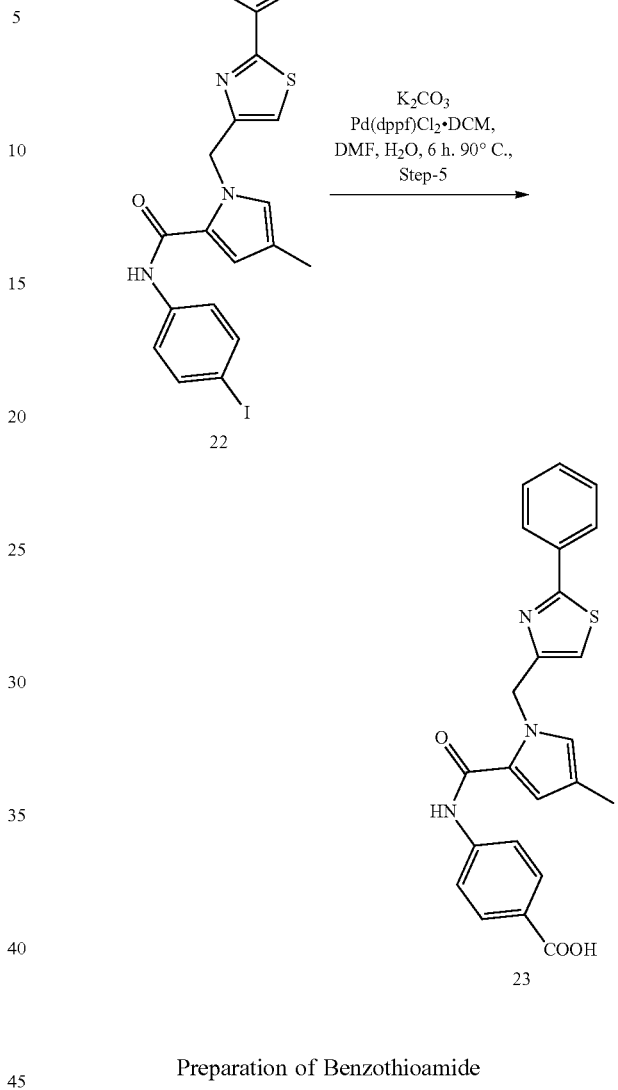

Preparation of Benzothioamide

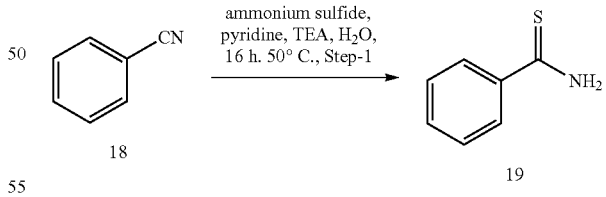

TEA (10.7 g, 0.106 mol, 1.1 equiv) and ammonium sulfide (7.22 g, 0.106 mol, 1.1 equiv) in water (37 mL) were added to a stirred solution benzonitrile (18) (10.0 g, 0.096 mol, 1 equiv) in pyridine (50 mL) at ambient temperature. The reaction mixture was heated to 50° C. and stirred for 16 h. The reaction mixture was cooled to ambient temperature and then concentrated under vacuum. The residue was acidified with 1.5 M hydrochloric acid and the resulting mixture was extracted with DCM (2×150 mL). The combined organic layers were washed with water (200 mL), brine (150 mL), dried over $Na_2SO_4$, filtered and concentrated under vacuum to provide compound 19 as a pale brown solid (8.0 g, 60%) without further purification.

LC-MS (ESI+): m/z 138.1 (M+H)+

Preparation of 4-(chloromethyl)-2-phenylthiazole

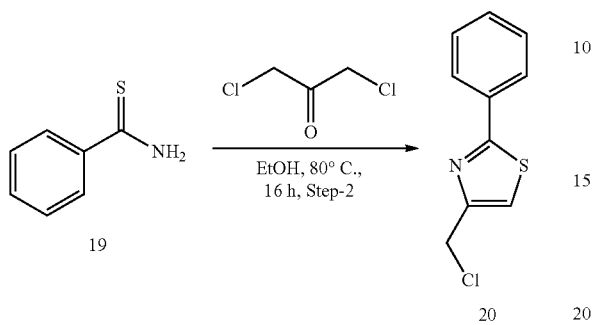

1,3-Dichloroacetone (2.64 g, 0.021 mol, 1 equiv) was added to a stirred solution of benzothioamide (19) (3.0 g, 0.021 mol, 1 equiv) in EtOH (50 mL) at ambient temperature. The reaction mixture was stirred at 90° C. for 16 h, and then cooled to ambient temperature. The resultant mixture was concentrated under vacuum. The residue was basified with 10% NaHCO$_3$ aqueous solution and extracted with DCM (2×75 mL). The combined organic layer was washed with water (100 mL), brine (100 mL), dried over Na$_2$SO$_4$, filtered and concentrated under vacuum. The crude product was purified by silica gel column chromatography (10% ethyl acetate-hexanes) to provide compound 20 as a pale brown solid (2.0 g, 45%).

LC-MS (ESI+): m/z 210.2 (M+H)+

Preparation of 4-methyl-1-((2-phenylthiazol-4-yl)methyl)-1H-pyrrole-2-carboxylic Acid

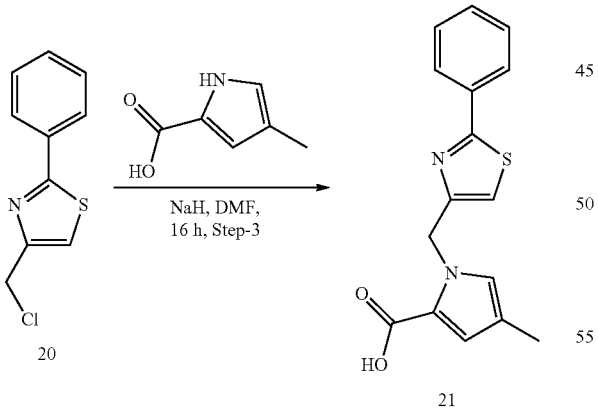

NaH (330 mg, 60% w/w in mineral oil, 8.14 mmol, 1.5 equiv) was added to a stirred solution of ethyl 4-methyl-1H-pyrrole-2-carboxylate (790 mg, 5.15 mmol, 1.1 equiv) in DMF (10 mL) at 0° C. After the reaction mixture was stirred at 0° C. for 30 min, 4-(chloromethyl)-2-phenylthiazole (20) (1.0 g, 5.15 mmol, 1 equiv) was added at 0° C. The reaction mixture was allowed to warm to ambient temperature and stirred for 16 h. The reaction mixture was quenched with ice, acidified with 1.5 M hydrochloric acid and extracted with ethyl acetate (2×50 mL). The combined organic layers were washed with water (2×50 mL), brine (50 mL), dried over Na$_2$SO$_4$, filtered and concentrated under vacuum. The crude product was purified by silica gel column chromatography (40% ethyl acetate-hexanes) to provide compound 21 as a pale brown solid (600 mg, 45%).

LC-MS (ESI+): m/z 299.0 (M+H)+

1H-NMR (300 MHz, DMSO-d6): δ 12.10 (s, 1H), 7.91-7.90 (m, 2H), 7.51-7.48 (m, 3H), 7.08-7.01 (m, 2H), 6.69 (s, 1H), 5.62 (s, 2H), 2.02 (s, 3H).

Preparation of N-(4-iodophenyl)-4-methyl-1-((2-phenylthiazol-4-yl)methyl)-1H-pyrrole-2-carboxamide

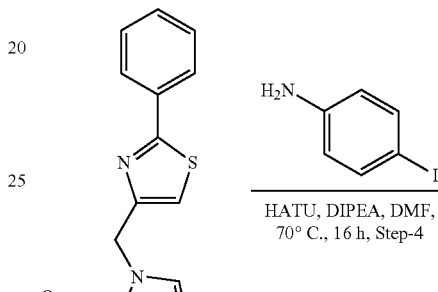

DIPEA (649 mg, 5.03 mmol, 3 equiv), HATU (956 mg, 2.52 mmol, 1.5 equiv) and 4-iodoaniline (441 mg, 2.01 mmol, 1.2 equiv) were added to a stirred solution of 4-methyl-1-((2-phenylthiazol-4-yl)methyl)-1H-pyrrole-2-carboxylic acid (21) (500 mg, 1.68 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 22 as a pale brown solid (300 mg, 35%).

LC-MS (ESI⁺): m/z 499.7 (M+H)⁺

Preparation of 4-(4-methyl-1-((2-phenylthiazol-4-yl)methyl)-1H-pyrrole-2-carboxamido)benzoic Acid

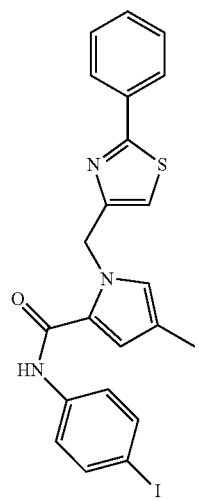

K₂CO₃ (249 mg, 1.80 mmol, 3 equiv) and Pd(dppf)Cl₂.DCM (49.8 mg, 0.060 mmol, 0.1 equiv) were added to a stirred solution N-(4-iodophenyl)-4-methyl-1-((2-phenylthiazol-4-yl)methyl)-1H-pyrrole-2-carboxamide (22) (300 mg, 0.601 mmol, 1 equiv) in DMF (10 mL) and H₂O (3.0 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered through celite bed and concentrated. The crude product was purified by Prep HPLC (0-60% CH₃CN—H₂O) to provide compound 23 (A-17) as an off-white solid (50.0 mg, 20%).

LC-MS (ESI⁺): m/z 418.2 (M+H)⁺

1H-NMR (400 MHz, DMSO-d6): δ 12.69 (s, 1H), 10.67 (s, 1H), 7.92-7.82 (m, 6H), 7.49-7.43 (m, 3H), 7.20 (s, 1H), 7.02 (s, 1H), 6.96 (s, 1H), 5.67 (s, 2H), 2.07 (s, 3H).

Synthesis of Compound A-18

Preparation of 2-(azepan-1-yl)-4-(chloromethyl)thiazole

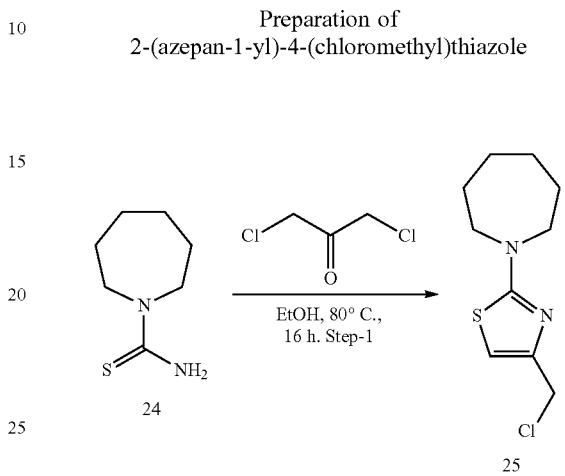

1,3-Dichloroacetone (3.93 g, 0.031 mol, 1 equiv) was added to a stirred solution of azepane-1-carbothioamide (24) (5.0 g, 0.031 mol, 1 equiv) in EtOH (100 mL) at ambient temperature. The reaction mixture was heated to 70° C. and stirred for 16 h, and then cooled to ambient temperature. The resultant mixture was concentrated under vacuum. The residue was basified with 10% NaHCO₃ aqueous solution and extracted with DCM (2×200 mL). The combined organic layers were washed with water (200 mL), brine (200 mL), dried over Na₂SO₄, filtered and concentrated under vacuum. The crude product was purified by silica gel column chromatography (20% ethyl acetate-hexanes) to provide compound 25 as a pale brown solid (4.0 g, 55%).

LC-MS (ESI⁺): m/z 230.9 (M+H)⁺

1H-NMR (400 MHz, DMSO-d6): δ 6.74 (s, 1H), 4.54 (s, 2H), 3.50-3.49 (m, 4H), 1.74-1.73 (m, 4H), 1.52-1.51 (m, 4H).

Preparation of Ethyl 1-((2-(azepan-1-yl)thiazol-4-yl)methyl)-4-methyl-1H-pyrrole-2-carboxylate

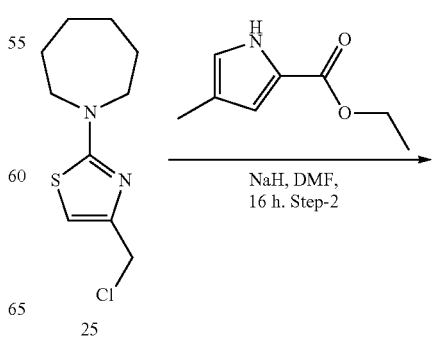

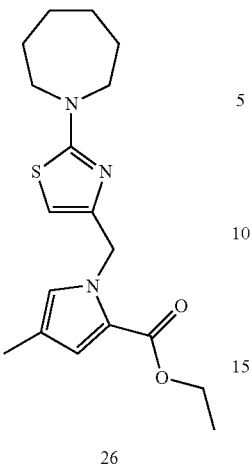

26

NaH (620 mg, 60% w/w in mineral oil, 0.026 mol, 1.5 equiv) was added to a stirred solution of ethyl 4-methyl-1H-pyrrole-2-carboxylate (2.39 g, 0.015 mol, 0.9 equiv) in DMF (50 mL) at 0° C. After the reaction mixture was stirred at 0° C. for 30 min, 2-(azepan-1-yl)-4-(chloromethyl)thiazole (25) (4.0 g, 0.017 mol, 1 equiv) was added at 0° C. The reaction mixture was allowed to warm to ambient temperature and stirred for 16 h. The reaction mixture was quenched with ice and extracted with ethyl acetate (2×100 mL). The combined organic layers were washed with water (2×100 mL), brine (100 mL), dried over Na$_2$SO$_4$, filtered and concentrated under vacuum. The crude product was purified by silica gel column chromatography (20% ethyl acetate-hexanes) to provide compound 26 as a pale brown solid (3.0 g, 50%).

LC-MS (ESI$^+$): m/z 348.1 (M+H)$^+$

1H-NMR (300 MHz, DMSO-d6): δ 6.94 (s, 1H), 6.69 (s, 1H), 5.94 (s, 1H), 5.28 (s, 2H), 4.15 (q, J=7.2 Hz, 2H), 3.52-3.44 (m, 4H), 2.00 (s, 3H), 1.76-1.69 (m, 4H), 1.57-1.48 (m, 4H), 1.22 (t, J=7.2 Hz, 3H).

Preparation of 1-((2-(azepan-1-yl)thiazol-4-yl)methyl)-4-methyl-1H-pyrrole-2-carboxylic Acid

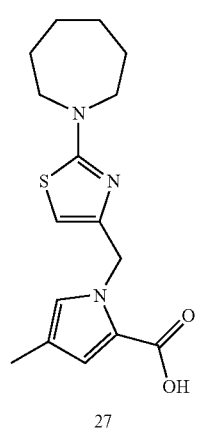

27

LiOH.H$_2$O (1.08 g, 0.025 mol, 3 equiv) was added to a stirred solution of ethyl 1-((2-(azepan-1-yl)thiazol-4-yl)methyl)-4-methyl-1H-pyrrole-2-carboxylate (26) (3.0 g, 8.64 mmol, 1 equiv) in THF (20 mL), MeOH (20 mL) and H$_2$O (20 mL) at ambient temperature. The reaction mixture was stirred for 16 h, and then concentrated under vacuum. The residue was acidified with 1.5 M hydrochloric acid and the resulting mixture was extracted with DCM (2×75 mL). The combined organic layers were washed with water (100 mL), brine (100 mL), dried over Na$_2$SO$_4$, filtered and concentrated under vacuum to provide compound 27 as a white solid (2.20 g, 80%) without further purification.

LC-MS (ESI$^+$): m/z 320.0 (M+H)$^+$

1H-NMR (400 MHz, DMSO-d6): δ 12.02 (s, 1H), 6.90 (s, 1H), 6.65 (s, 1H), 5.94 (s, 1H), 5.31 (s, 2H), 3.51-3.48 (m, 4H), 2.00 (s, 3H), 1.73-1.71 (m, 4H), 1.52-1.50 (m, 4H).

Preparation of 1-((2-(azepan-1-yl)thiazol-4-yl)methyl)-N-(4-iodophenyl)-4-methyl-1H-pyrrole-2-carboxamide

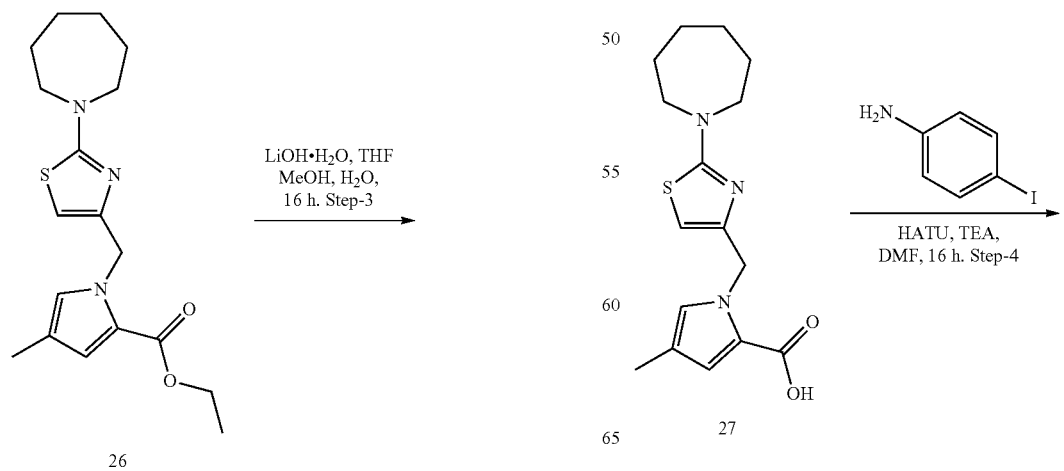

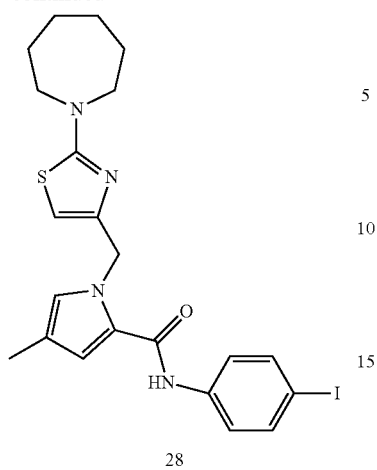

28

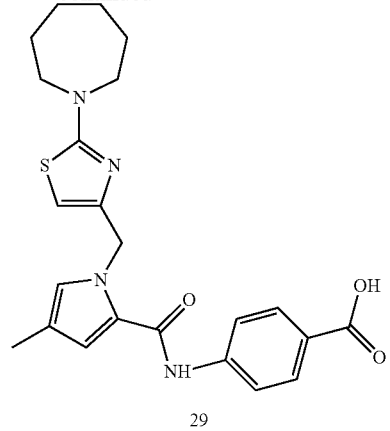

29

TEA (1.19 g, 9.08 mmol, 3 equiv), HATU (2.35 g, 6.18 mmol, 2 equiv) and 4-iodoaniline (0.820 g, 3.74 mmol, 1.2 equiv) were added to a stirred solution of 1-((2-(azepan-1-yl)thiazol-4-yl)methyl)-4-methyl-1H-pyrrole-2-carboxylic acid (27) (1.0 g, 3.13 mmol, 1 equiv) in DMF (20 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×70 mL). The combined organic layers were washed with water (2×100 mL), brine (100 mL), dried over Na₂SO₄, filtered and concentrated. The crude product was purified by silica gel column chromatography (20% ethyl acetate-hexanes) to provide compound 28 as a pale brown solid (900 mg, 56%).

LC-MS (ESI⁺): m/z 520.7 (M+H)⁺

1H-NMR (400 MHz, DMSO-d6): δ 9.81 (s, 1H), 7.62 (d, J=8.4 Hz, 2H), 7.54 (d, J=8.4 Hz, 2H), 6.86-6.83 (m, 2H), 6.00 (s, 1H), 5.33 (s, 2H), 3.46-3.43 (m, 4H), 2.03 (s, 3H), 1.68-1.66 (m, 4H), 1.49-1.46 (m, 4H).

K₂CO₃ (637 mg, 4.614 mmol, 3 equiv) and Pd(dppf)Cl₂·DCM (126 mg, 0.153 mmol, 0.1 equiv) were added to a stirred solution 1-((2-(azepan-1-yl)thiazol-4-yl)methyl)-N-(4-iodophenyl)-4-methyl-1H-pyrrole-2-carboxamide (28) (800 mg, 1.54 mmol, 1 equiv) in dioxane (20 mL) and H₂O (10 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×75 mL). The combined organic layers were washed with water (75 mL), brine (75 mL), dried over Na₂SO₄, filtered through celite bed and concentrated. The crude product was purified by Prep HPLC (0-30% CH₃CN—H₂O) to provide compound 29 (A-18) as a white solid (60.0 mg, 9%).

LC-MS (ESI⁺): m/z 439.0 (M+H)⁺

1H-NMR (400 MHz, DMSO-d6): δ 12.57 (brs, 1H), 10.04 (s, 1H), 7.90-7.81 (m, 4H), 6.93 (s, 2H), 6.08 (s, 1H), 5.38 (s, 2H), 3.52-3.45 (m, 4H), 2.06 (s, 3H), 1.75-1.68 (m, 4H), 1.55-1.49 (m, 4H).

Synthesis of Compound A-19

Preparation of 4-(1-((2-(azepan-1-yl)thiazol-4-yl)methyl)-4-methyl-1H-pyrrole-2-carboxamido)benzoic Acid Preparation of Ethyl (3-methylpiperidine-1-carbonothioyl)carbamate

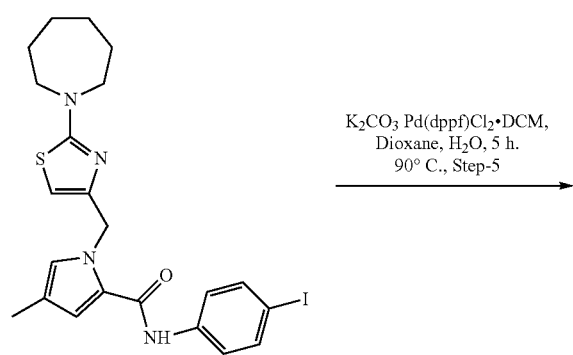

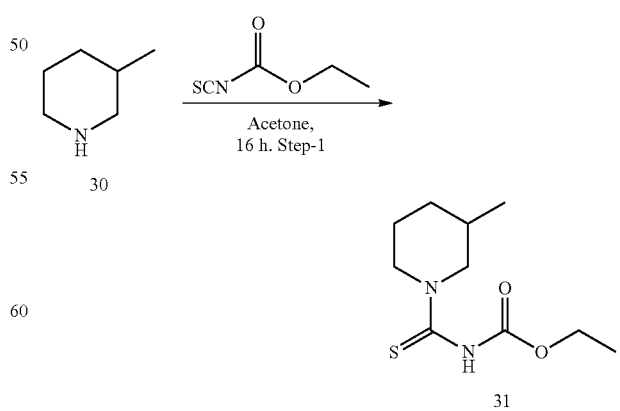

Ethoxycarbonyl isothiocyanate (6.55 g, 0.050 mol, 1 equiv) was added to a stirred solution of 3-methylpiperidine

(30) (5.0 g, 0.050 mol, 1 equiv) in acetone (70 mL) at 0° C. The reaction mixture was allowed to warm to ambient temperature and stirred for 16 h. The reaction mixture was concentrated under vacuum. The crude product was recrystallized with hexanes and ethyl acetate to provide compound 31 as a white solid (8.08 g, 70%).

LC-MS (ESI+): m/z 231.0 (M+H)+

1H-NMR (400 MHz, DMSO-d6): δ 9.95 (s, 1H), 4.80-4.74 (m, 1H), 4.08 (q, J=7.0 Hz, 2H), 3.85-3.82 (m, 1H), 3.15-3.09 (m, 1H), 2.94-2.85 (m, 1H), 1.77-1.67 (m, 3H), 1.51-1.42 (m, 1H), 1.25-1.14 (m, 4H), 0.91-0.81 (m, 3H).

Preparation of 3-methylpiperidine-1-carbothioamide

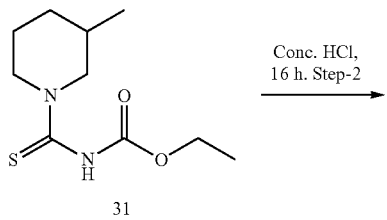

A solution of ethyl (3-methylpiperidine-1-carbonothioyl)carbamate (31) (8.0 g, 0.034 mol, 1 equiv) in conc. hydrochloric acid (70 mL) was heated to 100° C. and stirred for 16 h. The reaction mixture was concentrated under vacuum. The residue was basified with 10% NaHCO₃ aqueous solution and the resulting mixture was extracted with DCM (2×150 mL). The combined organic layers were washed with water (150 mL), brine (150 mL), dried over Na₂SO₄, filtered and concentrated under vacuum to provide compound 32 as a white solid (4.80 g, 89%) without further purification.

LC-MS (ESI+): m/z 159.1 (M+H)+

Preparation of 4-(chloromethyl)-2-(3-methylpiperidin-1-yl)thiazole

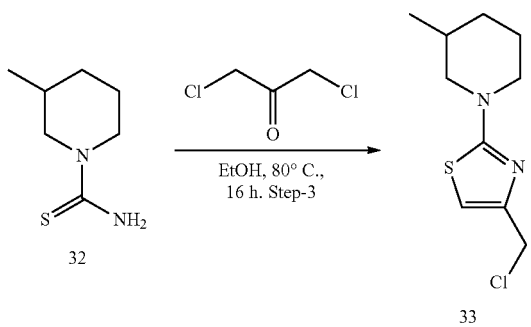

1,3-Dichloroacetone (3.85 g, 0.030 mol, 1 equiv) was added to a stirred solution of 3-methylpiperidine-1-carbothioamide (32) (4.80 g, 0.030 mol, 1 equiv) in EtOH (60 mL) at ambient temperature. The reaction mixture was heated to 80° C. and stirred for 6 h, and then cooled to ambient temperature. The resultant mixture was concentrated under vacuum. The residue was basified with 10% NaHCO₃ aqueous solution and extracted with DCM (2×150 mL). The combined organic layers were washed with water (200 mL), brine (200 mL), dried over Na₂SO₄, filtered and concen-trated under vacuum. The crude product was purified by silica gel column chromatography (20% ethyl acetate-hexanes) to provide compound 33 as a pale brown solid (4.30 g, 62%).

LC-MS (ESI+): m/z 231.0 (M+H)+

1H-NMR (300 MHz, DMSO-d6): δ 6.84 (s, 1H), 4.56 (s, 2H), 3.79-3.74 (m, 2H), 2.98-2.90 (m, 1H), 2.66-2.51 (m, 1H), 1.78-1.60 (m, 3H), 1.53-1.49 (m, 1H), 1.13-1.09 (m, 1H), 0.91 (d, J=6.6 Hz, 3H).

Preparation of Ethyl 4-methyl-1-((2-(3-methylpiperidin-1-yl)thiazol-4-yl)methyl)-1H-pyrrole-2-carboxylate

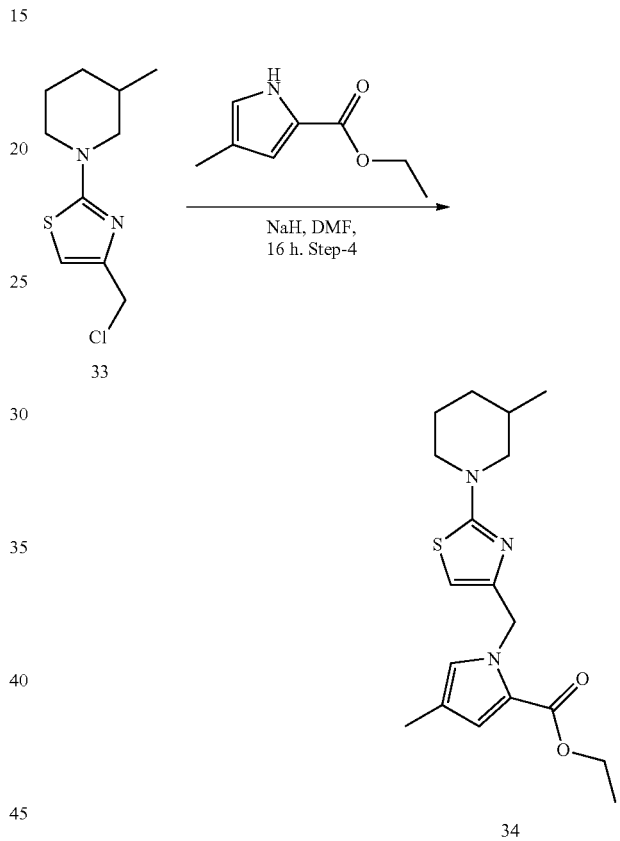

NaH (669 mg, 60% w/w in mineral oil, 0.028 mol, 1.5 equiv) was added to a stirred solution of ethyl 4-methyl-1H-pyrrole-2-carboxylate (2.57 g, 0.016 mol, 0.9 equiv) in DMF (40 mL) at 0° C. After the reaction mixture was stirred at 0° C. for 30 min, 4-(chloromethyl)-2-(3-methylpiperidin-1-yl)thiazole (33) (4.30 g, 0.018 mol, 1 equiv) was added at 0° C. The reaction mixture was allowed to warm to ambient temperature and stirred for 16 h. The reaction mixture was quenched with ice and extracted with ethyl acetate (2×100 mL). The combined organic layers were washed with water (2×100 mL), brine (100 mL), dried over Na₂SO₄, filtered and concentrated under vacuum. The crude product was purified by silica gel column chromatography (20% ethyl acetate-hexanes) to provide compound 34 as a pale brown solid (3.0 g, 46%).

LC-MS (ESI+): m/z 348.0 (M+H)+

1H-NMR (400 MHz, DMSO-d6): δ 6.93 (s, 1H), 6.69 (s, 1H), 6.07 (s, 1H), 5.29 (s, 2H), 4.15 (q, J=7.1 Hz, 2H), 3.75-3.72 (m, 2H), 2.94-2.88 (m, 1H), 2.62-2.51 (m, 1H), 2.01 (s, 3H), 1.77-1.62 (m, 3H), 1.51-1.48 (m, 1H), 1.24 (t, J=7.01 Hz, 3H), 1.15-1.08 (m, 1H), 0.90 (d, J=6.6 Hz, 3H).

Preparation of 4-methyl-1-((2-(3-methylpiperidin-1-yl)thiazol-4-yl)methyl)-1H-pyrrole-2-carboxylic Acid

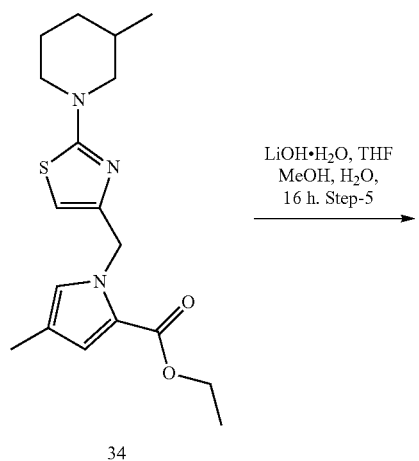

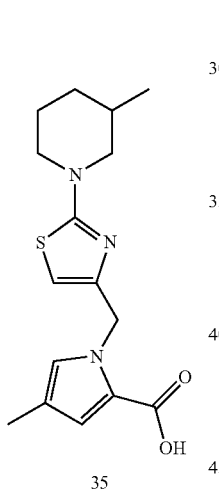

LiOH·H₂O (1.09 g, 0.025 mol, 3 equiv) was added to a stirred solution of ethyl 4-methyl-1-((2-(3-methylpiperidin-1-yl)thiazol-4-yl)methyl)-1H-pyrrole-2-carboxylate (34) (3.0 g, 8.63 mol, 1 equiv) in THF (20 mL), MeOH (20 mL) and H₂O (20 mL) at ambient temperature. The reaction mixture was stirred for 16 h, and then concentrated under vacuum. The residue was acidified with 1.5 M hydrochloric acid and the resulting mixture was extracted with DCM (2×75 mL). The combined organic layers were washed with water (100 mL), brine (100 mL), dried over Na₂SO₄, filtered and concentrated under vacuum to provide compound 35 as a white solid (2.20 g, 80%) without further purification.

LC-MS (ESI⁺): m/z 319.9 (M+H)⁺

1H-NMR (400 MHz, DMSO-d6): δ 12.01 (brs, 1H), 6.86 (s, 1H), 6.63 (s, 1H), 6.04 (s, 1H), 5.31 (s, 2H), 3.76-3.73 (m, 2H), 2.94-2.87 (m, 1H), 2.62-2.56 (m, 1H), 2.00 (s, 3H), 1.77-1.62 (m, 3H), 1.60-1.48 (m, 1H), 1.15-1.08 (m, 1H), 0.90 (d, J=6.4 Hz, 3H).

Preparation of N-(4-iodophenyl)-4-methyl-1-((2-(3-methylpiperidin-1-yl)thiazol-4-yl)methyl)-1H-pyrrole-2-carboxamide

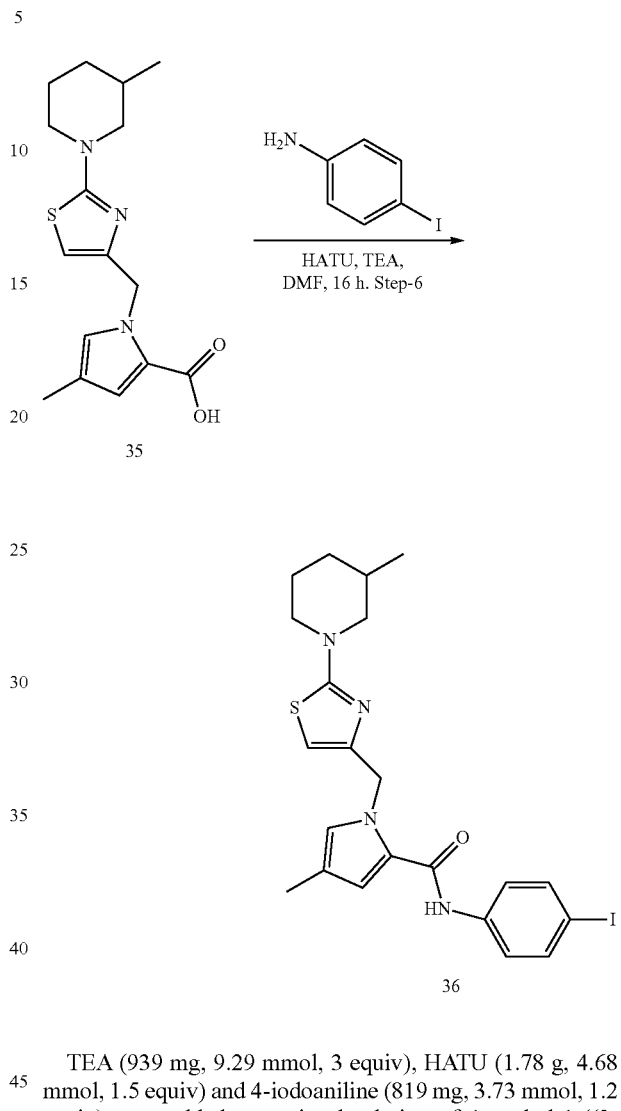

TEA (939 mg, 9.29 mmol, 3 equiv), HATU (1.78 g, 4.68 mmol, 1.5 equiv) and 4-iodoaniline (819 mg, 3.73 mmol, 1.2 equiv) were added to a stirred solution of 4-methyl-1-((2-(3-methylpiperidin-1-yl)thiazol-4-yl)methyl)-1H-pyrrole-2-carboxylic acid (35) (1.0 g, 3.13 mmol, 1 equiv) in DMF (20 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×70 mL). The combined organic layers were washed with water (2×100 mL), brine (100 mL), dried over Na₂SO₄, filtered and concentrated. The crude product was purified by silica gel column chromatography (20% ethyl acetate-hexanes) to provide compound 36 as a pale brown solid (800 mg, 49%).

LC-MS (ESI⁺): m/z 521.0 (M+H)⁺

1H-NMR (400 MHz, DMSO-d6): δ 9.83 (s, 1H), 7.62 (d, J=8.8 Hz, 2H), 7.54 (d, J=8.4 Hz, 2H), 6.85-6.82 (m, 2H), 6.13 (s, 1H), 5.33 (s, 2H), 3.72-3.69 (m, 2H), 2.89-2.83 (m, 1H), 2.58-2.55 (m, 1H), 2.03 (s, 3H), 1.74-1.71 (m, 1H), 1.66-1.58 (m, 2H), 1.50-1.44 (m, 1H), 1.12-1.03 (m, 1H), 0.85 (d, J=6.8 Hz, 3H).

Preparation of 4-(4-methyl-1-((2-(3-methylpiperidin-1-yl)thiazol-4-yl)methyl)-1H-pyrrole-2-carboxamido)benzoic Acid

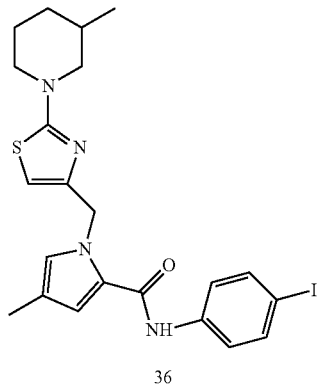
36

Synthesis of Compound A-20

Preparation of Ethyl 2-(2-methylpiperidin-1-yl)thiazole-4-carboxylate

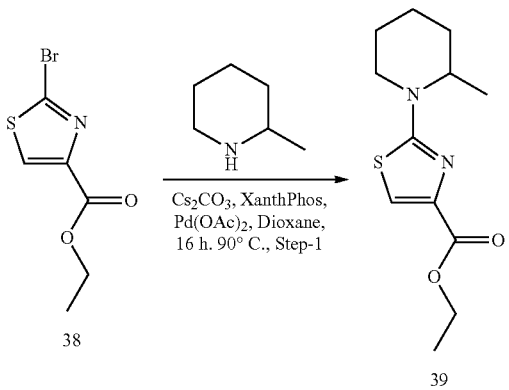

2-Methylpiperidine (2.67 g, 0.027 mol, 1.2 equiv), $Cs_2CO_3$ (22.2 g, 0.068 mol, 3 equiv), XanthPhos (1.31 g, 2.11 mmol, 0.1 equiv) and $Pd(OAc)_2$ (0.250 g, 1.11 mmol, 0.05 equiv) were added to a stirred ethyl 2-bromothiazole-4-carboxylate (38) (5.0 g, 0.022 mol, 1 equiv) in dioxane (100 mL) at ambient temperature. The reaction mixture was degassed for 5 min. with $N_2$ gas and warmed to 90° C. and stirred for 16 h. The reaction mixture was cooled to ambient temperature and then concentrated under vacuum. The residue was diluted with water and the resulting mixture was extracted with ethyl acetate (2×150 mL). The combined organic layers were washed with water (150 mL), brine (150 mL), dried over $Na_2SO_4$, filtered through celite bed and concentrated. The crude product was purified by silica gel column chromatography (20% ethyl acetate-hexanes) to provide compound 39 pale brown solid (2.20 g, 32%).

LC-MS (ESI⁺): m/z 255.2 (M+H)⁺

1H-NMR (400 MHz, DMSO-d6): δ 7.61 (s, 1H), 4.24-4.19 (m, 2H), 3.73-3.69 (m, 1H), 3.17-3.08 (m, 1H), 1.72-1.57 (m, 4H), 1.46-1.43 (m, 1H), 1.26 (t, J=6.8 Hz, 3H), 1.16 (d, J=6.8 Hz, 3H).

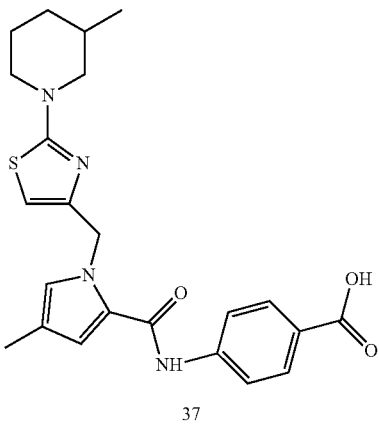
37

$K_2CO_3$ (557 mg, 4.04 mmol, 3 equiv) and Pd(dppf)Cl₂.DCM (54.9 mg, 0.067 mmol, 0.05 equiv) were added to a stirred solution N-(4-iodophenyl)-4-methyl-1-((2-(3-methylpiperidin-1-yl)thiazol-4-yl)methyl)-1H-pyrrole-2-carboxamide (36) (700 mg, 1.35 mmol, 1 equiv) in dioxane (20 mL) and H₂O (10 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×75 mL). The combined organic layers were washed with water (75 mL), brine (75 mL), dried over Na₂SO₄, filtered through celite bed and concentrated. The crude product was purified by Prep HPLC (0-50% CH₃CN—H₂O) to provide compound 37 (A-19) as a white solid (60.0 mg, 9%).

LC-MS (ESI⁺): m/z 439.3 (M+H)⁺

1H-NMR (400 MHz, DMSO-d6): δ 12.46 (s, 1H), 10.04 (s, 1H), 7.91-7.81 (m, 4H), 6.90 (s, 2H), 6.17 (s, 1H), 5.35 (s, 2H), 3.76-3.69 (m, 2H), 2.96-2.86 (m, 1H), 2.54-2.48 (m, 2H), 2.05 (s, 3H), 1.78-1.62 (m, 3H), 1.51-1.44 (m, 1H), 1.26-1.05 (m, 1H), 0.89-0.82 (m, 3H).

Preparation of (2-(2-methylpiperidin-1-yl)thiazol-4-yl)methanol

DIBAL-H (1M in THF) (25.9 mL, 25.9 mmol, 3 equiv) was added to a stirred solution of ethyl 2-(2-methylpiperidin-1-yl)thiazole-4-carboxylate (39) (2.20 g, 8.65 mmol, 1 equiv) in THF (20 mL) at −78.0° C. The reaction mixture was allowed to warm to ambient temperature and stirred for 16 h. The reaction mixture was quenched with MeOH (26 mL) and 1.5 M hydrochloric acid (26 mL). The resultant mixture was concentrated under vacuum. The residue was diluted with water and the resultant mixture was extracted with ethyl acetate (2×50 mL). The combined organic layers were washed with water (2×50 mL), brine (50 mL), dried ($Na_2SO_4$), filtered and concentrated under vacuum to provide compound 40 as a white solid (1.50 g, 82%).

LC-MS (ESI$^+$): m/z 213.1 (M+H)$^+$

Preparation of Ethyl 4-methyl-1-((2-(2-methylpiperidin-1-yl)thiazol-4-yl)methyl)-1H-pyrrole-2-carboxylate

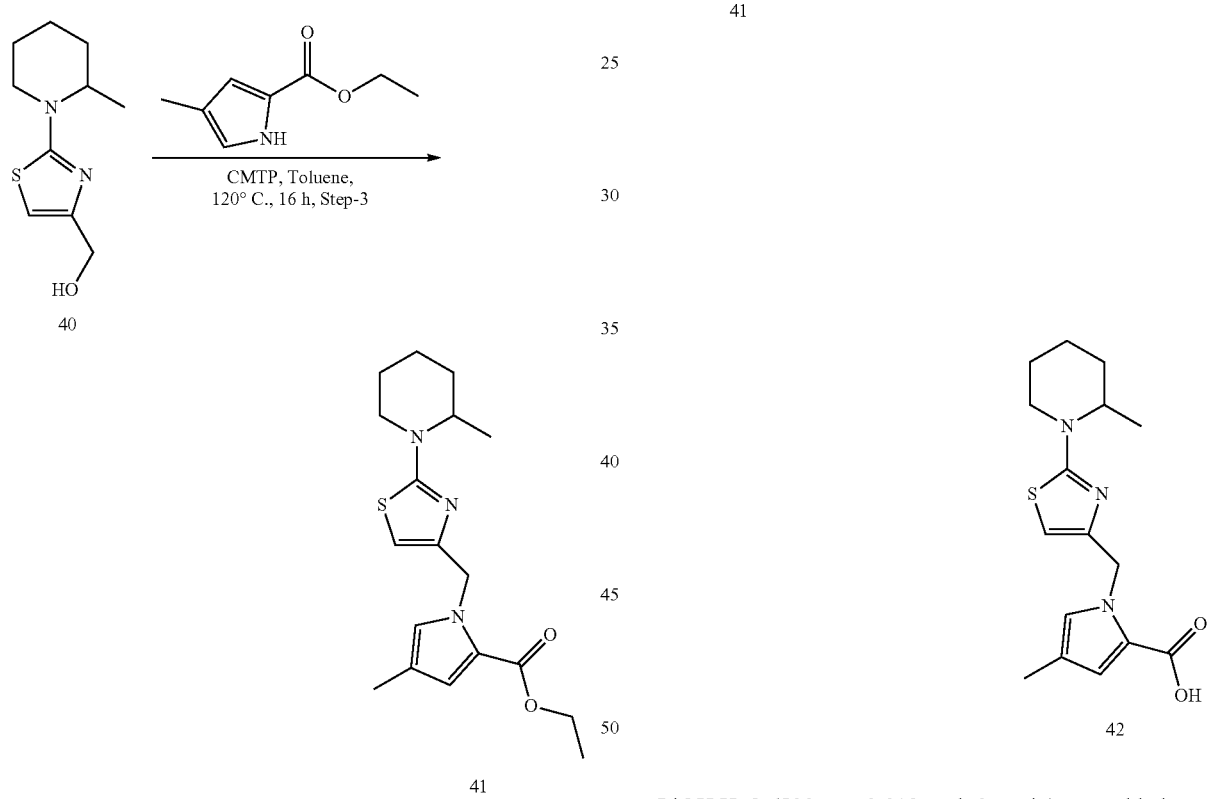

(2-(2-Methylpiperidin-1-yl)thiazol-4-yl)methanol (40) (1.50 g, 7.06 mmol, 1 equiv) and CMTP (3.38 g, 0.014 mol, 2 equiv) were added to a stirred solution of ethyl 4-methyl-1H-pyrrole-2-carboxylate (1.16 g, 7.57 mmol, 1 equiv) in toluene (30 mL) at ambient temperature. The reaction mixture was warmed to 120° C. and stirred for 16 h, and then reaction mixture was cooled to ambient temperature, concentrated under vacuum. The crude product was purified by silica gel column chromatography (20% ethyl acetate-hexanes) to provide compound 41 as a pale brown solid (1.45 g, 60%).

LC-MS (ESI$^+$): m/z 348.1 (M+H)$^+$

Preparation of 4-methyl-1-((2-(2-methylpiperidin-1-yl)thiazol-4-yl)methyl)-1H-pyrrole-2-carboxylic Acid LiOH.$H_2O$ (500 mg, 0.012 mol, 3 equiv) was added to a stirred solution of ethyl 4-methyl-1-((2-(2-methylpiperidin-1-yl)thiazol-4-yl)methyl)-1H-pyrrole-2-carboxylate (41) (1.45 g, 4.17 mmol, 1 equiv) in THF (15 mL), MeOH (15 mL) and $H_2O$ (15 mL) at ambient temperature. The reaction mixture was stirred for 16 h, and then concentrated under vacuum. The residue was acidified with 1.5 M hydrochloric acid and the resulting mixture was extracted with DCM (2×50 mL). The combined organic layers were washed with water (50 mL), brine (50 mL), dried over $Na_2SO_4$, filtered and concentrated under vacuum to provide compound 42 as a pale brown solid (1.14 g, 90%) without further purification.

LC-MS (ESI$^+$): m/z 320.0 (M+H)$^+$

131

Preparation of N-(4-iodophenyl)-4-methyl-1-((2-(2-methylpiperidin-1-yl)thiazol-4-yl)methyl)-1H-pyrrole-2-carboxamide

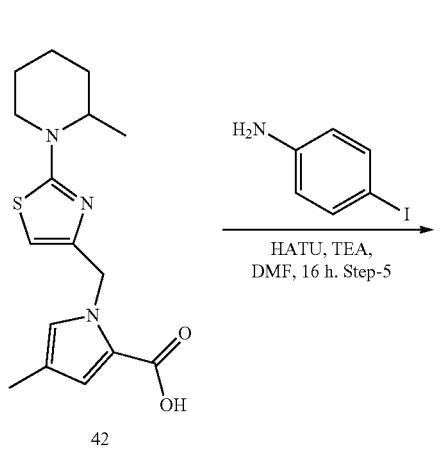

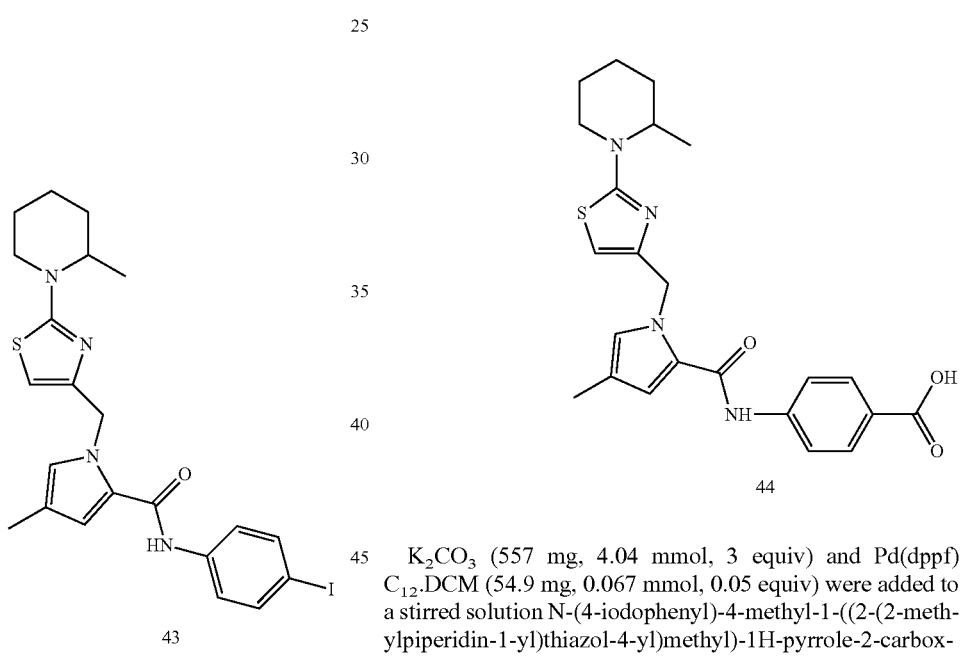

TEA (940 mg, 9.29 mmol, 3 equiv), HATU (1.78 g, 4.68 mmol, 1.5 equiv) and 4-iodoaniline (0.820 g, 3.74 mmol, 1.2 equiv) were added to a stirred solution of 4-methyl-1-((2-(2-methylpiperidin-1-yl)thiazol-4-yl)methyl)-1H-pyrrole-2-carboxylic acid (42) (1.0 g, 3.13 mmol, 1 equiv) in DMF (20 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×70 mL). The combined organic layers were washed with water (2×100 mL), brine (100 mL), dried over Na$_2$SO$_4$, filtered and concentrated. The crude product was purified by silica gel column chromatography (20% ethyl acetate-hexanes) to provide compound 43 as a pale brown solid (800 mg, 49%).

LC-MS (ESI$^+$): m/z 520.8 (M+H)$^+$

132

Preparation of 4-(4-methyl-1-((2-(2-methylpiperidin-1-yl)thiazol-4-yl)methyl)-1H-pyrrole-2-carboxamido)benzoic Acid

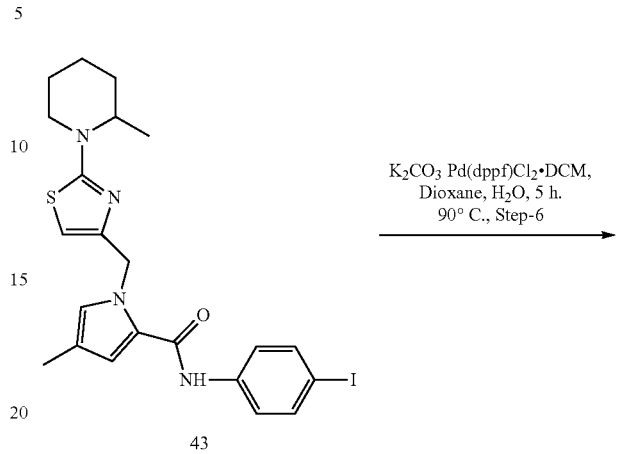

K$_2$CO$_3$ (557 mg, 4.04 mmol, 3 equiv) and Pd(dppf)C$_{12}$·DCM (54.9 mg, 0.067 mmol, 0.05 equiv) were added to a stirred solution N-(4-iodophenyl)-4-methyl-1-((2-(2-methylpiperidin-1-yl)thiazol-4-yl)methyl)-1H-pyrrole-2-carboxamide (43) (700 mg, 1.35 mmol, 1 equiv) in dioxane (20 mL) and H$_2$O (10 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×75 mL). The combined organic layers were washed with water (75 mL), brine (75 mL), dried over Na$_2$SO$_4$, filtered through celite bed and concentrated. The crude product was purified by Prep HPLC (0-50% CH$_3$CN—H$_2$O) to provide compound 44 (A-20) as a white solid (55.0 mg, 10%).

LC-MS (ESI$^+$): m/z 439.3 (M+H)$^+$

1H-NMR (400 MHz, DMSO-d6): δ 10.04 (s, 1H), 7.90-7.81 (m, 4H), 6.91 (s, 2H), 6.16 (s, 1H), 5.36 (s, 2H), 4.15-4.11 (m, 1H), 3.67-3.63 (m, 1H), 3.09-3.03 (m, 1H), 2.06 (s, 3H), 1.67-1.54 (m, 5H), 1.51-1.40 (m, 1H), 1.12 (d, J=6.7 Hz, 3H).

133

Synthesis of Compound A-44

Preparation of Methyl 4-(4-methyl-1-((2-(pyridin-3-yl)thiazol-4-yl)methyl)-1H-pyrrole-2-carboxamido)benzoate

134

Preparation of 4-(4-methyl-1-((2-(pyridin-3-yl)thiazol-4-yl)methyl)-1H-pyrrole-2-carboxamido)benzoic Acid

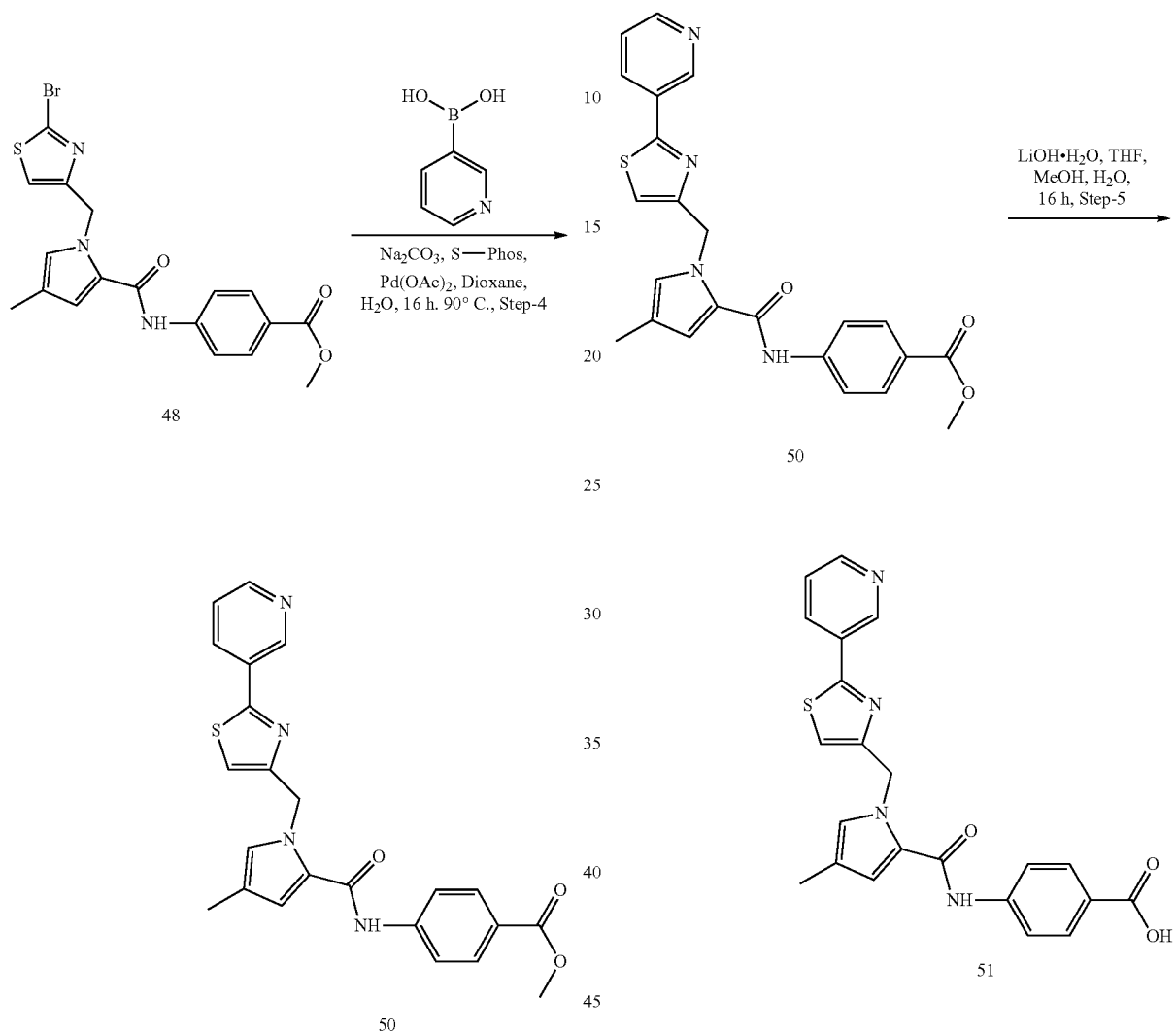

Pyridin-3-ylboronic acid (63.8 mg, 0.519 mmol, 1.5 equiv), Na$_2$CO$_3$ (109 mg, 1.04 mmol, 3 equiv), SPhos (14.2 mg, 0.034 mmol, 0.1 equiv) and Pd(OAc)$_2$ (3.9 mg, 0.017 mmol, 0.05 equiv) were added to a stirred methyl 4-(1-((2-bromothiazol-4-yl) methyl)-4-methyl-1H-pyrrole-2-carboxamido) benzoate (48) (150 mg, 0.346 mmol, 1 equiv) in dioxane (10 mL) and H$_2$O (3 mL) at ambient temperature. The reaction mixture was degassed for 5 min. with N$_2$ gas and warmed to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×30 mL). The combined organic layers were washed with water (30 mL), brine (30 mL), dried over Na$_2$SO$_4$, filtered through celite bed and concentrated under vacuum to provide compound 50 as a pale brown solid (150 mg, crude) without further purification.

LC-MS (ESI$^+$): m/z 433.0 (M+H)$^+$

LiOH.H$_2$O (43.7 mg, 1.041 mmol, 3 equiv) was added to a stirred 4-(4-methyl-1-((2-(pyridin-3-yl)thiazol-4-yl)methyl)-1H-pyrrole-2-carboxamido)benzoic acid (50) (150 mg, 0.347 mmol, 1 equiv) in THF (5 mL), MeOH (5 mL) and H$_2$O (5 mL) at ambient temperature. The reaction mixture was stirred for 16 h, and then reaction mixture was concentrated under vacuum. The residue was acidified with 1.5 M hydrochloric acid and the resulting mixture was extracted with DCM (2×30 mL). The combined organic layers were washed with water (30 mL), brine (30 mL), dried over Na$_2$SO$_4$, filtered and concentrated under vacuum. The crude product was purified by Prep HPLC (0-40% CH$_3$CN—H$_2$O) to provide compound 51 (A-44) as a pale brown solid (50.0 mg, 34%).

LC-MS (ESI$^+$): m/z 419.2 (M+H)$^+$

1H-NMR (400 MHz, DMSO-d6): δ 10.00 (s, 1H), 9.08 (s, 1H), 8.65 (d, J=4.4 Hz, 1H), 8.25 (d, J=8.0 Hz, 1H), 7.87 (d, J=8.4 Hz, 2H), 7.79 (d, J=8.4 Hz, 2H), 7.53-7.51 (m, 1H), 7.28 (s, 1H), 7.02 (s, 1H), 6.96 (s, 1H), 5.70 (s, 2H), 2.07 (s, 3H).

135
Synthesis of Compound A-46

Preparation of Methyl 4-(1-((2-(3-fluoropiperidin-1-yl)thiazol-4-yl)methyl)-4-methyl-1H-pyrrole-2-carboxamido)benzoate

136
Preparation of 4-(1-((2-(3-fluoropiperidin-1-yl)thiazol-4-yl)methyl)-4-methyl-1H-pyrrole-2-carboxamido)benzoic Acid

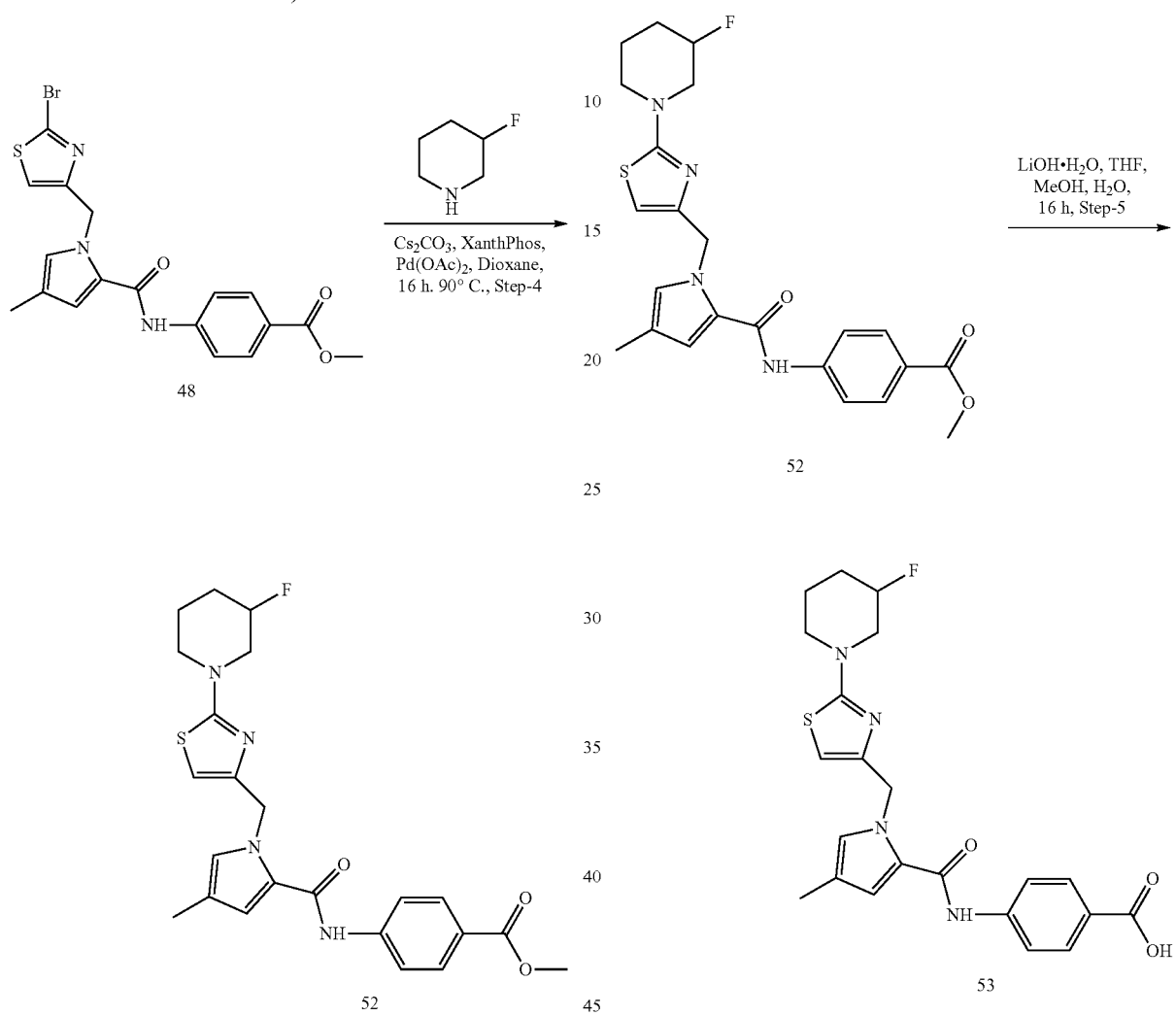

3-Fluoropiperidine (53.5 mg, 0.519 mmol, 1.5 equiv), Cs₂CO₃ (338 mg, 1.04 mmol, 3 equiv), XanthPhos (19.9 mg, 0.034 mmol, 0.1 equiv) and Pd(OAc)₂ (3.87 mg, 0.017 mmol, 0.05 equiv) were added to a stirred methyl 4-(1-((2-bromothiazol-4-yl) methyl)-4-methyl-1H-pyrrole-2-carboxamido) benzoate (48) (150 mg, 0.346 mmol, 1 equiv) in dioxane (10 mL) at ambient temperature. The reaction mixture was degassed for 5 min. with N₂ gas and warmed to 90° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (30 mL), brine (30 mL), dried over Na₂SO₄, filtered through celite bed and concentrated. The crude product was purified by silica gel column chromatography (20% ethyl acetate-hexanes) to provide compound 52 as a pale brown solid (40.0 mg, 25%).

LC-MS (ESI⁺): m/z 457.1 (M+H)⁺

LiOH.H₂O (10.9 mg, 0.263 mmol, 3 equiv) was added to a stirred methyl 4-(1-((2-(3-fluoropiperidin-1-yl)thiazol-4-yl)methyl)-4-methyl-1H-pyrrole-2-carboxamido) benzoate (52) (40.0 mg, 0.087 mmol, 1 equiv) in THF (2 mL), MeOH (2 mL) and H₂O (2 mL) at ambient temperature. The reaction mixture was stirred for 16 h. Then reaction mixture was concentrated under vacuum. The residue was acidified with 1.5 M hydrochloric acid and the resulting mixture was extracted with DCM (2×30 mL). The combined organic layers were washed with water (30 mL), brine (30 mL), dried over Na₂SO₄, filtered and concentrated under vacuum. The crude product was purified by Prep HPLC (0-40% CH₃CN—H₂O) to provide compound 53 (A-46) as a pale brown solid (10.0 mg, 26%).

LC-MS (ESI⁺): m/z 443.2 (M+H)⁺

1H-NMR (400 MHz, DMSO-d6): δ 12.78 (s, 1H), 10.03 (s, 1H), 7.89-7.81 (m, 4H), 6.90 (s, 2H), 6.21 (s, 1H), 5.38-5.33 (m, 2H), 4.87-4.74 (m, 1H), 3.69-3.52 (m, 1H), 3.71-3.36 (m, 2H), 3.21-3.16 (m, 1H), 2.06 (s, 3H), 1.88-1.76 (m, 3H), 1.55-1.52 (m, 1H).

137

Synthesis of Compound A-47

Preparation of Methyl 4-(1-((2-(dimethylamino)thiazol-4-yl)methyl)-4-methyl-1H-pyrrole-2-carboxamido)benzoate

138

Preparation of 4-(1-((2-(dimethylamino)thiazol-4-yl)methyl)-4-methyl-1H-pyrrole-2-carboxamido)benzoic Acid

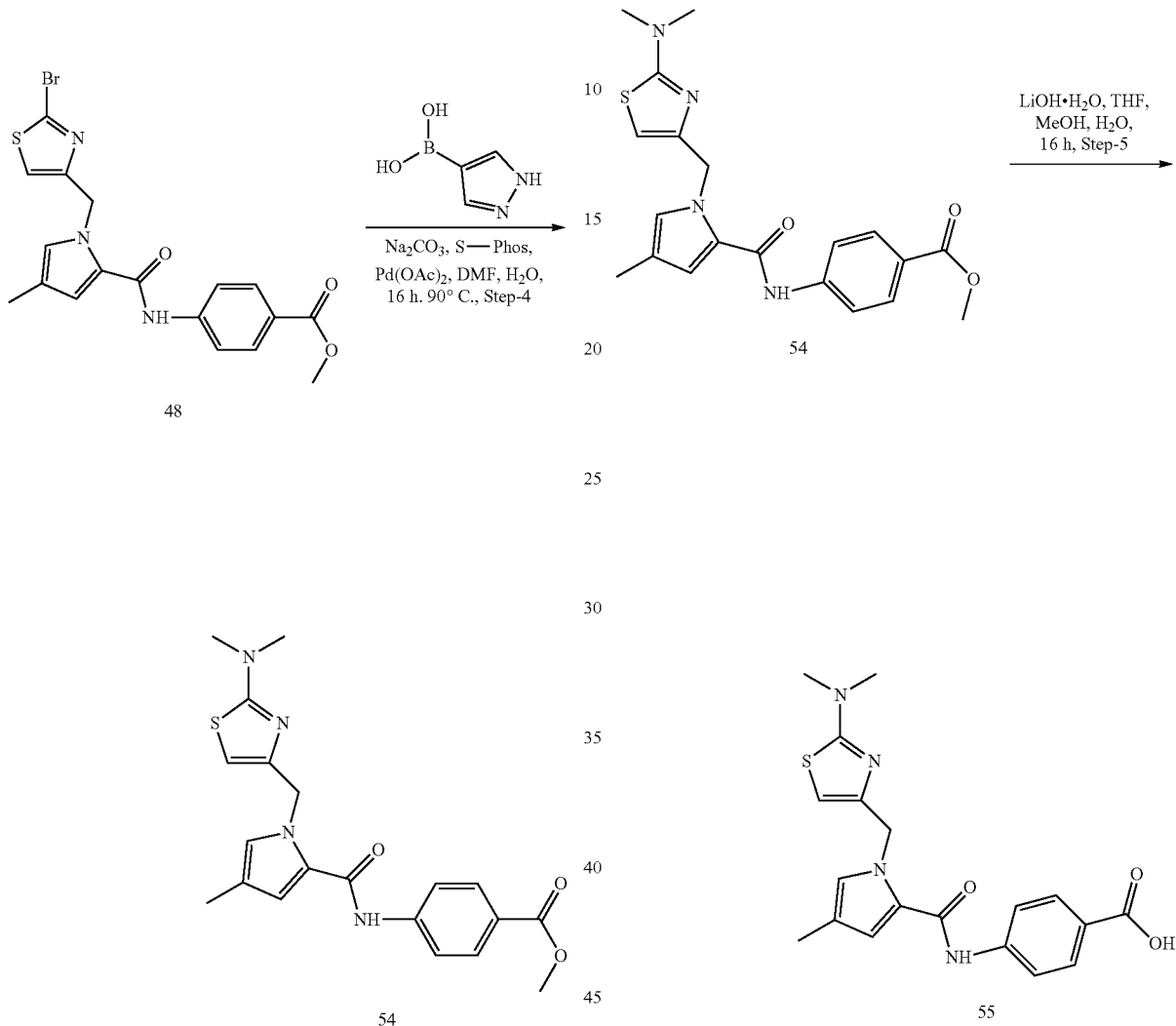

(1H-Pyrazol-4-yl)boronic acid (58.1 mg, 0.519 mmol, 1.5 equiv), $Na_2CO_3$ (109 mg, 1.04 mmol, 3 equiv), SPhos (14.2 mg, 0.034 mmol, 0.1 equiv) and $Pd(OAc)_2$ (3.9 mg, 0.017 mmol, 0.05 equiv) were added to a stirred methyl 4-(1-((2-bromothiazol-4-yl) methyl)-4-methyl-1H-pyrrole-2-carboxamido) benzoate (48) (150 mg, 0.346 mmol, 1 equiv) in DMF (10 mL) and $H_2O$ (3 mL) at ambient temperature. The reaction mixture was degassed for 5 min. with $N_2$ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×30 mL). The combined organic layers were washed with water (30 mL), brine (30 mL), dried over $Na_2SO_4$, filtered through celite bed and concentrated under vacuum to provide compound 54 as a pale brown solid (150 mg, crude) without further purification.

LC-MS (ESI$^+$): m/z 399.1 (M+H)$^+$ $LiOH.H_2O$ (47.5 mg, 1.13 mmol, 3 equiv) was added to a methyl 4-(1-((2-(dimethylamino)thiazol-4-yl)methyl)-4-methyl-1H-pyrrole-2-carboxamido)benzoate (54) (150 mg, 0.376 mmol, 1 equiv) in THF (3 mL), MeOH (3 mL) and $H_2O$ (3 mL) at ambient temperature. The reaction mixture was stirred for 16 h, and then reaction mixture was concentrated under vacuum. The residue was acidified with 1.5 M hydrochloric acid and the resulting mixture was extracted with ethyl acetate (2×30 mL). The combined organic layers were washed with water (30 mL), brine (30 mL), dried over $Na_2SO_4$, filtered and concentrated under vacuum. The crude product was purified by Prep HPLC (0-30% $CH_3CN$—$H_2O$) to provide compound 55 (A-47) as a pale brown solid (20.0 mg, 14%).

LC-MS (ESI$^+$): m/z 385.2 (M+H)$^+$

1H-NMR (400 MHz, DMSO-d6): δ 12.78 (brs, 1H), 10.02 (s, 1H), 7.90-7.81 (m, 4H), 6.91 (s, 2H), 6.14 (s, 1H), 5.37 (s, 2H), 2.99 (s, 6H), 2.06 (s, 3H).

Synthesis of Compound A-48

Preparation of Methyl 4-(1-((2-(2,3-dihydrobenzofuran-5-yl)thiazol-4-yl)methyl)-4-methyl-1H-pyrrole-2-carboxamido)benzoate

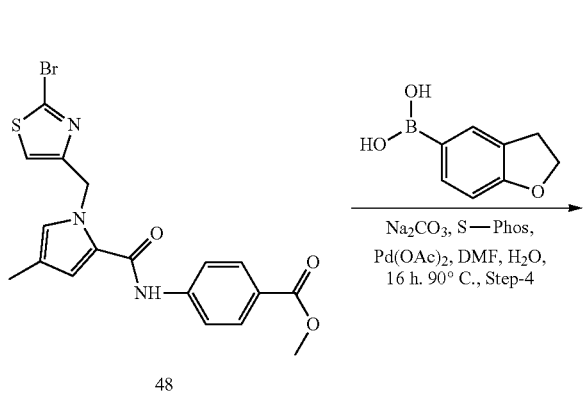

Preparation of 4-(1-((2-(2,3-dihydrobenzofuran-5-yl)thiazol-4-yl)methyl)-4-methyl-1H-pyrrole-2-carboxamido)benzoic Acid

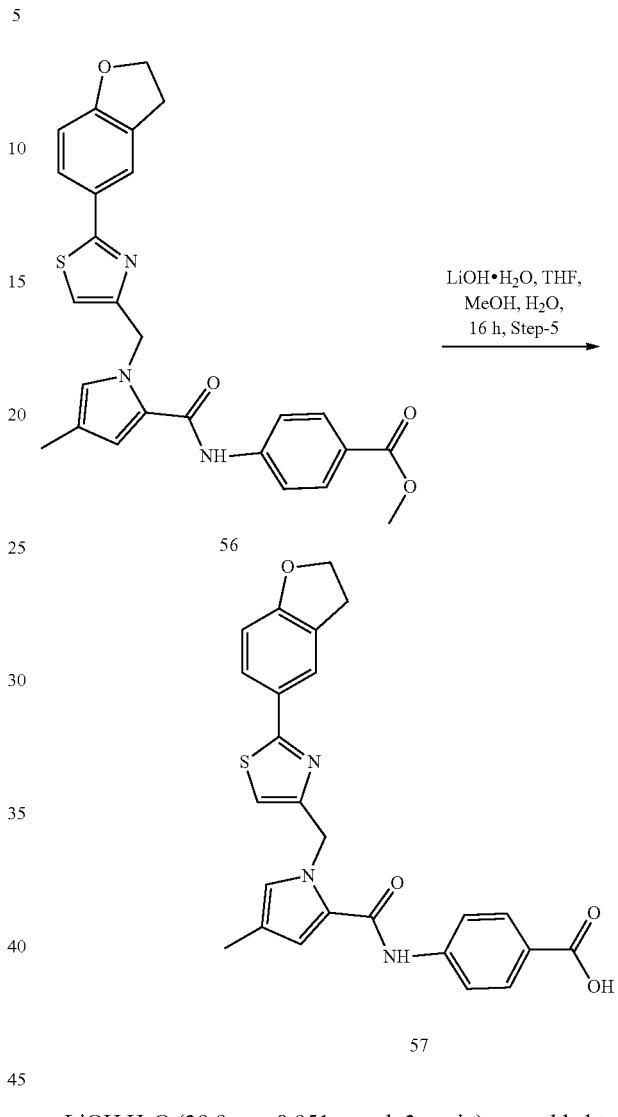

(2,3-Dihydrobenzofuran-5-yl)boronic acid (85.1 mg, 0.519 mmol, 1.5 equiv), Na$_2$CO$_3$ (109 mg, 1.04 mmol, 3 equiv), SPhos (14.2 mg, 0.034 mmol, 0.1 equiv) and Pd(OAc)$_2$ (3.9 mg, 0.017 mmol, 0.05 equiv) were added to a stirred methyl 4-(1-((2-bromothiazol-4-yl) methyl)-4-methyl-1H-pyrrole-2-carboxamido) benzoate (48) (150 mg, 0.346 mmol, 1 equiv) in DMF (10 mL) and H$_2$O (3 mL) at ambient temperature. The reaction mixture was degassed for 5 min. with N$_2$ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×30 mL). The combined organic layers were washed with water (30 mL), brine (30 mL), dried over Na$_2$SO$_4$, filtered through celite bed and concentrated under vacuum to provide compound 56 as a pale brown solid (150 mg, crude) without further purification.

LC-MS (ESI$^+$): m/z 474.0 (M+H)$^+$

LiOH.H$_2$O (39.9 mg, 0.951 mmol, 3 equiv) was added to methyl 4-(1-((2-(2,3-dihydrobenzofuran-5-yl)thiazol-4-yl) methyl)-4-methyl-1H-pyrrole-2-carboxamido)benz-oate (56) (150 mg, 0.317 mmol, 1 equiv) in THF (5 mL), MeOH (5 mL) and H$_2$O (5 mL) at ambient temperature. The reaction mixture was stirred for 16 h, and then reaction mixture was concentrated under vacuum. The residue was acidified with 1.5 M hydrochloric acid and the resulting mixture was extracted with ethyl acetate (2×30 mL). The combined organic layers were washed with water (30 mL), brine (30 mL), dried over Na$_2$SO$_4$, filtered and concentrated under vacuum. The crude product was purified by Prep HPLC (0-30% CH$_3$CN—H$_2$O) to provide compound 57 (A-48) as a pale brown solid (40.0 mg, 27%).

LC-MS (ESI$^+$): m/z 460.2 (M+H)$^+$

1H-NMR (400 MHz, DMSO-d6): δ 12.67 (s, 1H), 10.06 (s, 1H), 7.92-7.81 (m, 4H), 7.76 (s, 1H), 7.67-7.62 (m, 1H), 7.10-7.07 (m, 1H), 6.99 (s, 1H), 6.93 (s, 1H), 6.86-6.78 (m, 1H), 5.62 (s, 2H), 4.59 (t, J=8.4 Hz, 2H), 3.19 (t, J=7.6 Hz, 2H), 2.06 (s, 3H).

Synthesis of Compound A-49

Preparation of Methyl 4-(1-((2-(1H-pyrazol-4-yl)thiazol-4-yl)methyl)-4-methyl-1H-pyrrole-2-carboxamido)benzoate

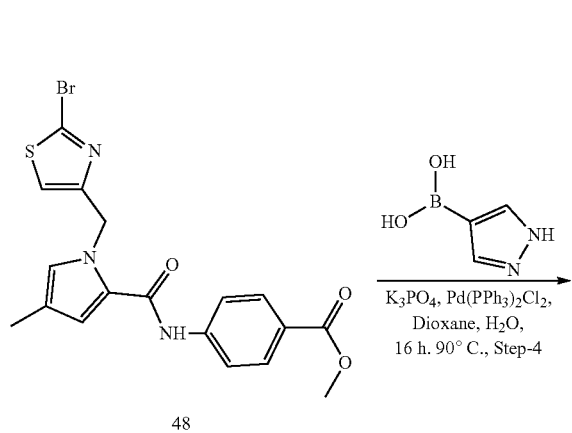

Preparation of 4-(1-((2-(1H-pyrazol-4-yl)thiazol-4-yl)methyl)-4-methyl-1H-pyrrole-2-carboxamido)benzoic Acid

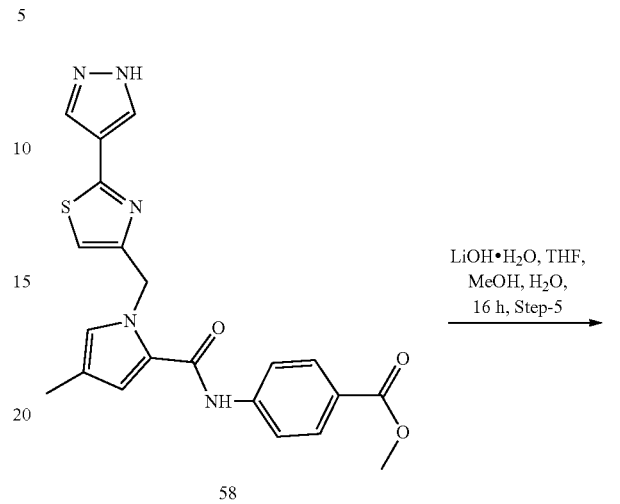

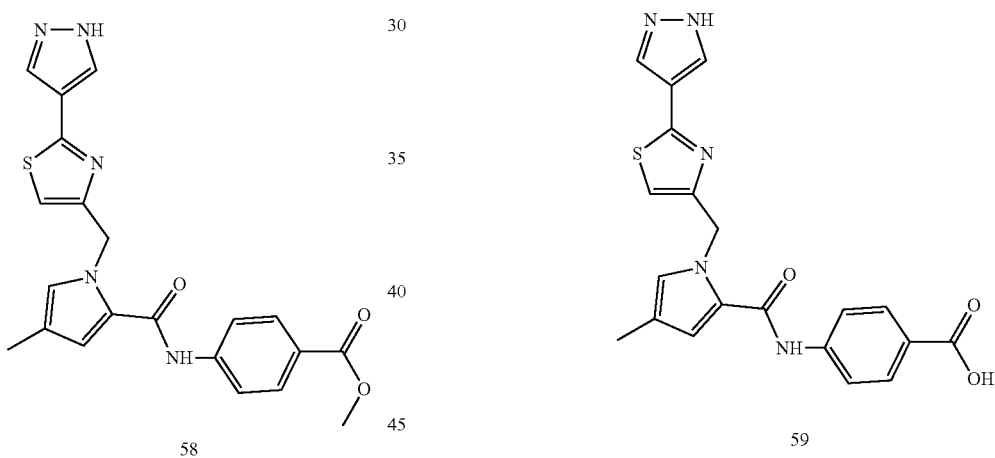

(1H-Pyrazol-4-yl)boronic acid (58.1 mg, 0.519 mmol, 1.5 equiv), $K_3PO_4$ (220 mg, 1.04 mmol, 3 equiv) and Pd(PPh$_3$)$_2$Cl$_2$ (24.3 mg, 0.034 mmol, 0.1 equiv) were added to a stirred methyl 4-(1-((2-bromothiazol-4-yl) methyl)-4-methyl-1H-pyrrole-2-carboxamido) benzoate (48) (150 mg, 0.346 mmol, 1 equiv) in dioxane (10 mL) and H$_2$O (3 mL) at ambient temperature. The reaction mixture was degassed for 5 min. with N$_2$ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×30 mL). The combined organic layers were washed with water (30 mL), brine (30 mL), dried over Na$_2$SO$_4$, filtered through celite bed and concentrated under vacuum to provide compound 58 as a pale brown solid (150 mg, crude) without further purification.

LC-MS (ESI$^+$): m/z 422.0 (M+H)$^+$

LiOH.H$_2$O (44.9 mg, 1.07 mmol, 3 equiv) was added to a methyl 4-(1-((2-(1H-pyrazol-4-yl)thiazol-4-yl)methyl)-4-methyl-1H-pyrrole-2-carboxamido)benzoate (58) (150 mg, 0.356 mmol, 1 equiv) in THF (5 mL), MeOH (5 mL) and H$_2$O (5 mL) at ambient temperature. The reaction mixture was stirred for 16 h and then reaction mixture was concentrated under vacuum. The residue was acidified with 1.5 M hydrochloric acid and the resulting mixture was extracted with ethyl acetate (2×30 mL). The combined organic layers were washed with water (30 mL), brine (30 mL), dried (Na$_2$SO$_4$), filtered and concentrated under vacuum. The crude product was purified by Prep HPLC (0-40% CH$_3$CN—H$_2$O) to provide compound 59 (A-49) as a pale brown solid (70.0 mg, 48%).

LC-MS (ESI$^+$): m/z 408.0 (M+H)$^+$

1H-NMR (400 MHz, DMSO-d6): δ 10.02 (s, 1H), 8.11 (brs, 2H), 7.90-7.79 (m, 4H), 6.99-6.92 (m, 3H), 5.60 (s, 2H), 2.06 (s, 3H).

Synthesis of Compound A-55

Preparation of Methyl 4-(1-((2-(cyclohex-1-en-1-yl) thiazol-4-yl)methyl)-4-methyl-1H-pyrrole-2-carboxamido)benzoate

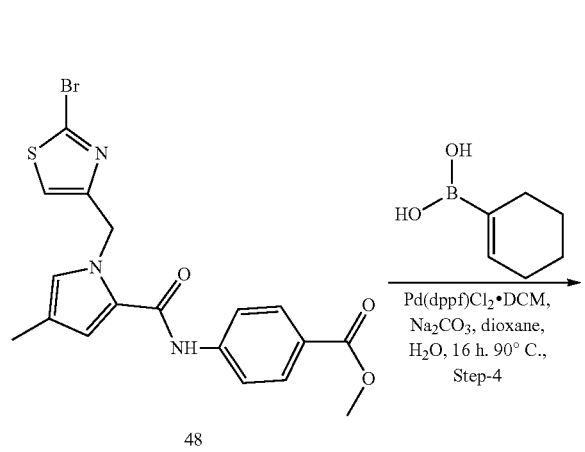

Preparation of 4-(1-((2-(cyclohex-1-en-1-yl) thiazol-4-yl)methyl)-4-methyl-1H-pyrrole-2-carboxamido) benzoic Acid

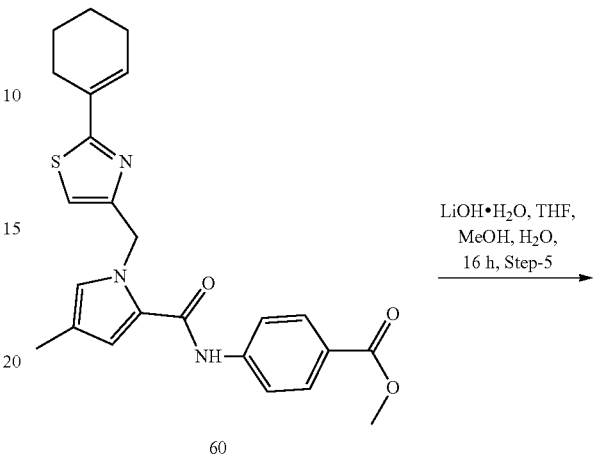

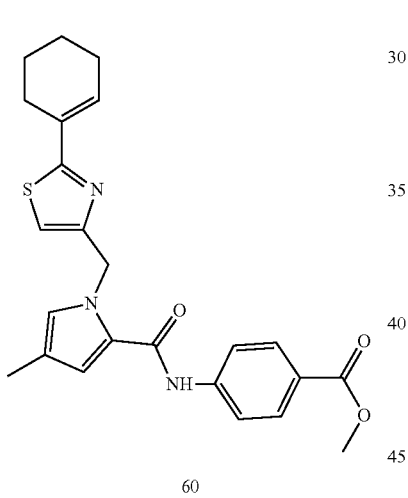

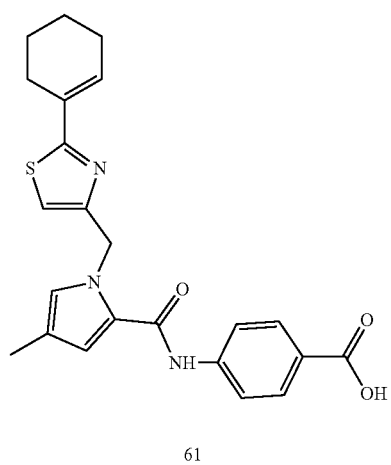

Cyclohexenylboronic acid (131 mg, 1.04 mmol, 1.5 equiv), $Na_2CO_3$ (220 mg, 1.04 mmol, 3 equiv) and Pd(dppf)$Cl_2$.DCM (3.9 mg, 0.017 mmol, 0.05 equiv) were added to a stirred methyl 4-(1-((2-bromothiazol-4-yl) methyl)-4-methyl-1H-pyrrole-2-carboxamido) benzoate (48) (300 mg, 0.692 mmol, 1 equiv) in dioxane (10 mL) and $H_2O$ (3 mL) at ambient temperature. The reaction mixture was degassed for 5 min. with $N_2$ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×30 mL). The combined organic layers were washed with water (30 mL), brine (30 mL), dried over $Na_2SO_4$, filtered through celite bed and concentrated under vacuum to provide compound 60 as a pale brown solid (300 mg, crude) without further purification.

LC-MS (ESI⁺): m/z 436.2 (M+H)⁺

LiOH.$H_2O$ (145 mg, 3.444 mmol, 5 equiv) was added to a stirred solution of methyl 4-(1-((2-(cyclohex-1-en-1-yl) thiazol-4-yl)methyl)-4-methyl-1H-pyrrole-2-carboxamido) benzoate (60) (300 mg, 0.688 mmol, 1 equiv) in THF (5 mL), MeOH (5 mL) and $H_2O$ (5 mL) at ambient temperature. The reaction mixture stirred for 16 h, and then reaction mixture was concentrated under vacuum. The residue was acidified with 1.5 M hydrochloric acid and the resulting mixture was extracted with ethyl acetate (2×30 mL). The combined organic layers were washed with water (50 mL), brine (50 mL), dried over $Na_2SO_4$, filtered and concentrated under vacuum. The crude product was purified by Prep HPLC (0-40% $CH_3CN$—$H_2O$) to provide compound 61 (A-55) as a pale brown solid (90.0 mg, 30%).

LC-MS (ESI⁺): m/z 422.2 (M+H)⁺

1H-NMR (400 MHz, DMSO-d6): δ 12.66 (s, 1H), 10.01 (s, 1H), 7.90-7.78 (m, 4H), 6.97-6.89 (m, 3H), 6.58 (s, 1H), 5.56 (s, 2H), 2.43-2.33 (m, 2H), 2.36-2.32 (m, 2H), 2.05 (s, 3H), 1.67-1.56 (m, 4H).

145
Synthesis of Compound A-60

Preparation of 4-(1-((2-cyclohexylthiazol-4-yl)methyl)-4-methyl-1H-pyrrole-2-carboxamido)benzoic Acid

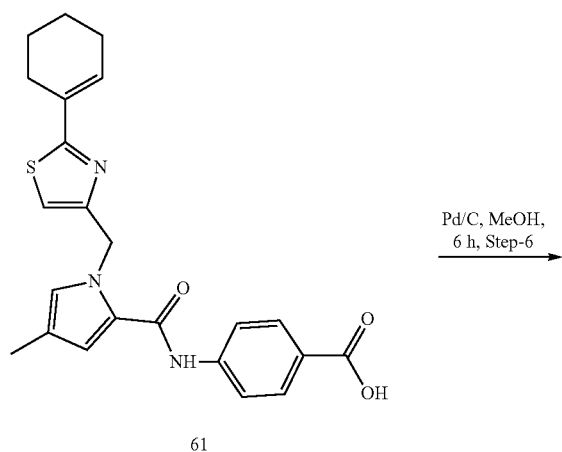

61

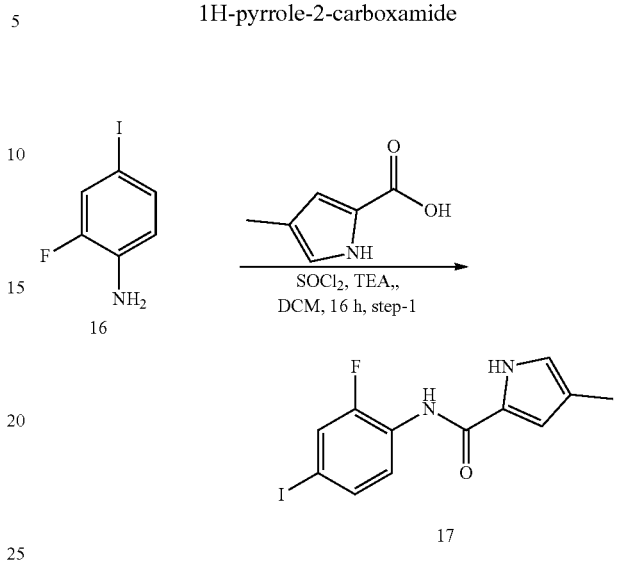

62

10% Pd/C (10.0 mg) was added to a stirred solution of 4-(1-((2-(cyclohex-1-en-1-yl)thiazol-4-yl)methyl)-4-methyl-1H-pyrrole-2-carboxamido)benzoic acid (61) (60.0 mg, 0.142 mmol, 1 equiv) in MeOH (10 mL) at ambient temperature. The reaction mixture stirred for 6 h under hydrogen atmosphere, then reaction mixture was filtered through celite bed, concentrated under vacuum. The residue was recrystalled with ethyl acetate and hexanes to provide compound 62 (A-60) as a pale brown solid (20.0 mg, 50%).

LC-MS (ESI$^+$): m/z 423.8 (M+H)$^+$

1H-NMR (400 MHz, DMSO-d6): δ 9.95 (s, 1H), 7.86 (d, J=8.6 Hz, 2H), 7.77 (d, J=8.6 Hz, 2H), 6.98-6.91 (m, 3H), 5.57 (s, 2H), 2.97-2.88 (m, 1H), 2.07-1.99 (m, 5H), 1.79-1.71 (m, 2H), 1.69-1.63 (m, 1H), 1.49-1.30 (m, 4H), 1.28-1.17 (m, 1H).

146
Synthesis of Compound A-66

Preparation of N-(2-fluoro-4-iodophenyl)-4-methyl-1H-pyrrole-2-carboxamide

SOCl$_2$(5.0 mL) was added to a stirred solution of 4-methyl-1H-pyrrole-2-carboxylic acid (1.50 g, 0.012 mol, 1 equiv) in DCM (30 mL) at 0° C. After the reaction mixture was stirred at ambient temperature for 2 h, the resultant mixture was concentrated under vacuum and azeotroped with toluene. The residue was dissolved in DCM (20 mL) and added to a stirred solution of 2-fluoro-4-iodoaniline (16) (3.41 g, 0.014 mol, 1.2 equiv) and TEA (3.63 g, 0.036 mol, 3 equiv) in DCM (30 mL) at 0° C. The reaction mixture was allowed to warm to ambient temperature and stirred for 16 h. The reaction mixture was diluted with DCM (100 mL) and washed with water (100 mL), brine (100 mL), dried with Na$_2$SO$_4$, filtered and concentrated under vacuum. The crude product was purified by silica gel column chromatography (20% ethyl acetate-hexanes) to provide compound 17 as a pale brown solid (1.50 g, 36%).

LC-MS (ESI$^+$): m/z 345.0 (M+H)$^+$

1H-NMR (400 MHz, DMSO-d6): δ 11.39 (s, 1H), 9.51 (s, 1H), 7.71-7.68 (m, 1H), 7.56-7.54 (m, 1H), 7.48-7.44 (m, 1H), 6.86 (s, 1H), 6.75 (s, 1H), 2.06 (s, 3H).

Preparation of 1-((2-bromothiazol-4-yl)methyl)-N-(2-fluoro-4-iodophenyl)-4-methyl-1H-pyrrole-2-carboxamide

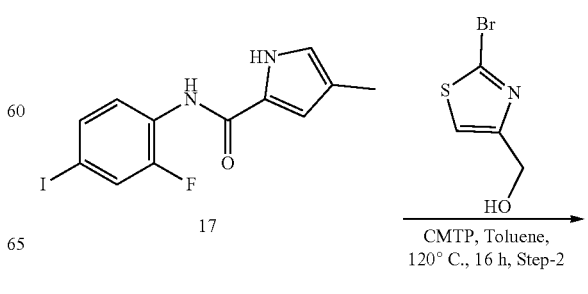

147
-continued

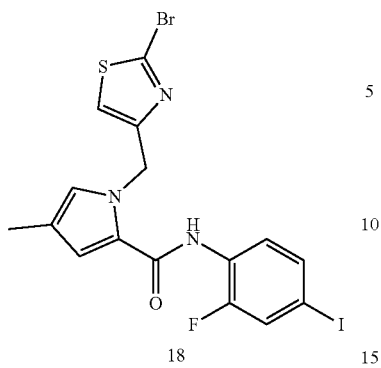

18

148
-continued

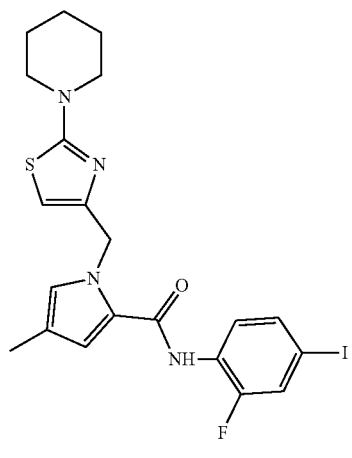

19

(2-Bromothiazol-4-yl)methanol (1.25 g, 6.44 mmol, 1.5 equiv) and CMTP (3.14 g, 0.013 mol, 2 equiv) were added to a stirred solution of N-(2-fluoro-4-iodophenyl)-4-methyl-1H-pyrrole-2-carboxamide (17) (1.50 g, 4.35 mmol, 1 equiv) in Toluene (50 mL) at ambient temperature. The reaction mixture was warmed to 120° C. and stirred for 16 h, and then reaction mixture was cooled to ambient temperature, concentrated under vacuum. The crude product was purified by silica gel column chromatography (20% ethyl acetate-hexanes) to provide compound 18 as a pale brown solid (300 mg, 13%).

LC-MS (ESI$^+$): m/z 521.5 (M+H)$^+$

Preparation of N-(2-fluoro-4-iodophenyl)-4-methyl-1-((2-(piperidin-1-yl)thiazol-4-yl)methyl)-1H-pyrrole-2-carboxamide Piperidine (58.8 mg, 0.692 mmol, 1.2 equiv), K$_2$CO$_3$ (238 mg, 1.73 mmol, 3 equiv) were added to a stirred 1-((2-bromothiazol-4-yl)methyl)-N-(2-fluoro-4-iodophenyl)-4-methyl-1H-pyrrole-2-carboxamide (18) (150 mg, 0.346 mmol, 1 equiv) in dioxane (10 mL) and H$_2$O (3 mL) at ambient temperature. The reaction mixture was heated to 80° C. and stirred for 16 h. The reaction mixture was cooled to ambient temperature and filtered, concentrated under vacuum. The residue was diluted with water and the resulting mixture was extracted with ethyl acetate (2×50 mL). The combined organic layers were washed with water (50 mL), brine (50 mL), dried over Na$_2$SO$_4$, filtered and concentrated under vacuum to provide compound 19 as a pale brown solid (250 mg, crude) without further purification.

LC-MS (ESI$^+$): m/z 524.7 (M+H)$^+$

Preparation of 3-fluoro-4-(4-methyl-1-((2-(piperidin-1-yl)thiazol-4-yl)methyl)-1H-pyrrole-2-carboxamido)benzoic Acid

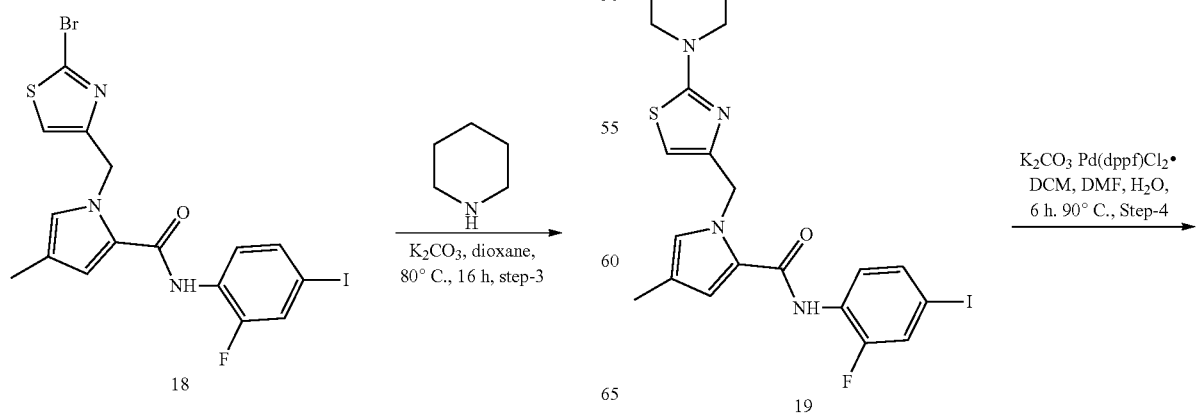

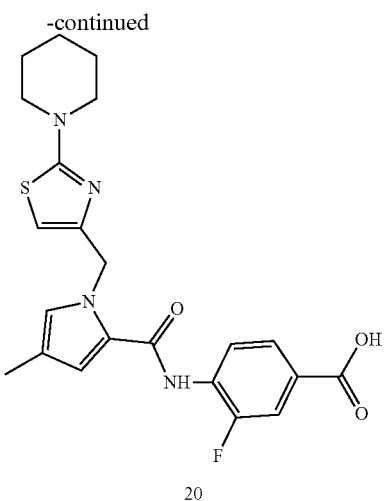

K₂CO₃ (197 mg, 1.43 mmol, 3 equiv) and Pd(dppf)Cl₂.DCM (38.4 mg, 0.047 mmol, 0.1 equiv) were added to a stirred solution N-(2-fluoro-4-iodophenyl)-4-methyl-1-((2-(piperidin-1-yl)thiazol-4-yl)methyl)-1H-pyrrole-2-carboxamide (19) (250 mg, 0.477 mmol, 1 equiv) in DMF (10 mL) and H₂O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered through celite bed and concentrated. The crude product was purified by Prep HPLC (0-60% CH₃CN—H₂O) to provide compound 20 (A-66) as an off-white solid (50.0 mg, 23%).

LC-MS (ESI⁺): m/z 442.8 (M+H)⁺

1H-NMR (400 MHz, DMSO-d6): δ 13.14 (brs, 1H), 9.74 (s, 1H), 7.87-7.80 (m, 1H), 7.79-7.69 (m, 2H), 6.92 (s, 2H), 6.22 (s, 1H), 5.35 (s, 2H), 3.39-3.31 (m, 4H), 2.05 (s, 3H), 1.59-1.51 (m, 6H).

Example 2c: Middle Region Compound Embodiments

Synthesis of Compound A-21

Preparation of Methyl 5-methyl-2-(piperidin-1-yl)thiazole-4-carboxylate

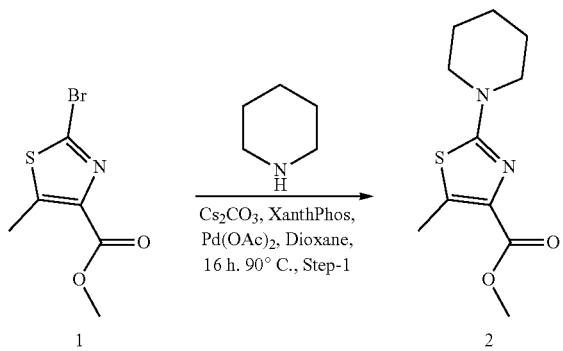 [SMILES: COC(=O)c1nc(Br)sc1C ; C1CCNCC1 ; COC(=O)c1nc(N2CCCCC2)sc1C]

Piperidine (2.01 g, 0.024 mol, 1.2 equiv), Cs₂CO₃ (15.6 g, 0.048 mol, 3 equiv), XanthPhos (0.920 g, 1.58 mmol, 0.1 equiv) and Pd(OAc)₂ (0.180 g, 0.803 mmol, 0.050 equiv) were added to a stirred solution of methyl 2-bromo-5-methylthiazole-4-carboxylate (1) (4.0 g, 0.016 mol, 1 equiv) in dioxane (60 mL) at ambient temperature. The reaction mixture was degassed for 5 min. with N₂ gas and warmed to 90° C. and stirred for 16 h. The reaction mixture was cooled to ambient temperature and then concentrated under vacuum. The residue was diluted with water and the resulting mixture was extracted with ethyl acetate (2×150 mL). The combined organic layers were washed with water (150 mL), brine (150 mL), dried over Na₂SO₄, filtered through celite bed and concentrated. The crude product was purified by silica gel column chromatography (20% ethyl acetate-hexanes) to provide compound 2 as a pale brown solid (2.20 g, 57%).

LC-MS (ESI⁺): m/z 241.0 (M+H)⁺

Preparation of (5-methyl-2-(piperidin-1-yl)thiazol-4-yl)methanol

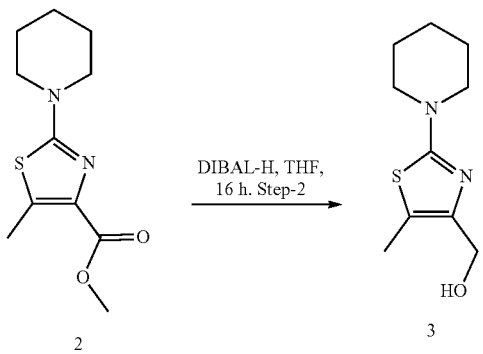 [SMILES: COC(=O)c1nc(N2CCCCC2)sc1C ; Cc1sc(N2CCCCC2)nc1CO]

DIBAL-H (1.0 M in THF) (27 mL, 0.027 mol, 3 equiv) was added to a stirred solution of methyl 5-methyl-2-(piperidin-1-yl)thiazole-4-carboxylate (2) (2.20 g, 9.15 mmol, 1 equiv) in THF (20 mL) at −78° C. The reaction mixture was allowed to warm to ambient temperature and stirred for 16 h. The reaction mixture was quenched with MeOH (27 mL) and 1.5 M hydrochloric acid (27 mL), resultant mixture was concentrated under vacuum. The residue was diluted with water, the resultant mixture was extracted with ethyl acetate (2×75 mL). The combined organic layers were washed with water (2×75 mL), brine (75 mL), dried over Na₂SO₄, filtered and concentrated under vacuum to provide compound 3 as a white solid (1.50 g, 79%).

LC-MS (ESI⁺): m/z 213.0 (M+H)⁺

1H-NMR (400 MHz, DMSO-d6): δ 4.79 (t, J=5.5 Hz, 1H), 4.23 (d, J=5.2 Hz, 2H), 3.34-3.31 (m, 4H), 2.23 (s, 3H), 1.57-1.55 (m, 6H).

151

Preparation of Ethyl 4-methyl-1-((5-methyl-2-(piperidin-1-yl)thiazol-4-yl)methyl)-1H-pyrrole-2-carboxylate

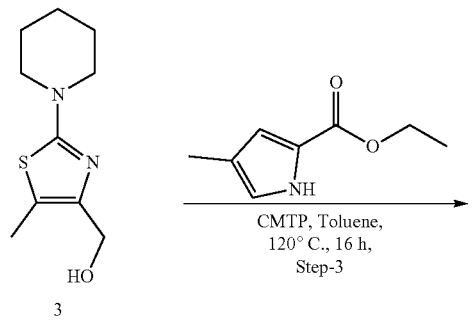

152

Preparation of 4-methyl-1-((5-methyl-2-(piperidin-1-yl)thiazol-4-yl)methyl)-1H-pyrrole-2-carboxylic Acid

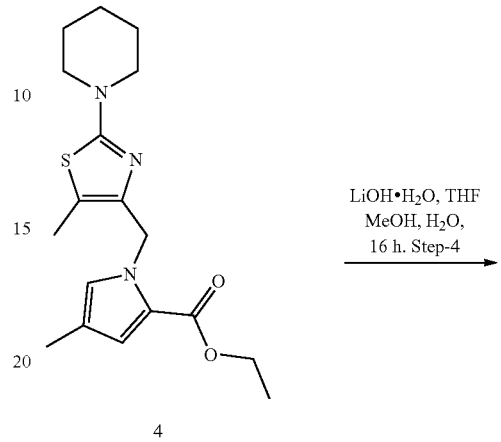

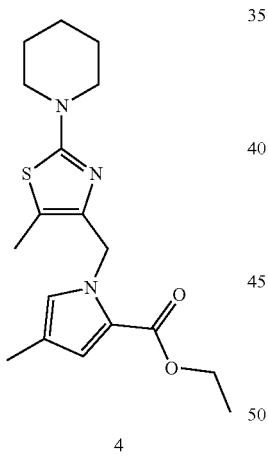

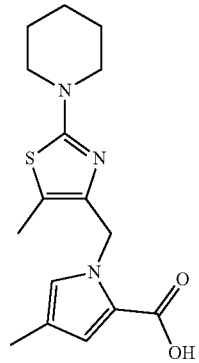

(5-Methyl-2-(piperidin-1-yl)thiazol-4-yl)methanol (3) (1.50 g, 7.06 mmol, 1 equiv) and CMTP (3.38 g, 0.014 mol, 2 equiv) were added to a stirred solution of ethyl 4-methyl-1H-pyrrole-2-carboxylate (1.16 g, 7.06 mmol, 1 equiv) in toluene (30 mL) at ambient temperature. The reaction mixture was warmed to 120° C. and stirred for 16 h, and then reaction mixture was cooled to ambient temperature, concentrated under vacuum. The crude product was purified by silica gel column chromatography (20% ethyl acetate-hexanes) to provide compound 4 as a pale brown solid (1.45 g, 60%).

LC-MS (ESI$^+$): m/z 347.9 (M+H)$^+$

LiOH.H$_2$O (500 mg, 0.012 mol, 3 equiv) was added to a stirred solution of ethyl 4-methyl-1-((5-methyl-2-(piperidin-1-yl)thiazol-4-yl)methyl)-1H-pyrrole-2-carboxylate (4) (1.45 g, 4.17 mmol, 1 equiv) in THF (10 mL), MeOH (10 mL) and H$_2$O (10 mL) at ambient temperature. The reaction mixture was stirred for 16 h, and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered and concentrated under vacuum to provide compound 5 as a pale brown solid (1.0 g, 78%) without further purification.

LC-MS (ESI$^+$): m/z 320.0 (M+H)$^+$

153

Preparation of N-(4-iodophenyl)-4-methyl-1-((5-methyl-2-(piperidin-1-yl)thiazol-4-yl)methyl)-1H-pyrrole-2-carboxamide

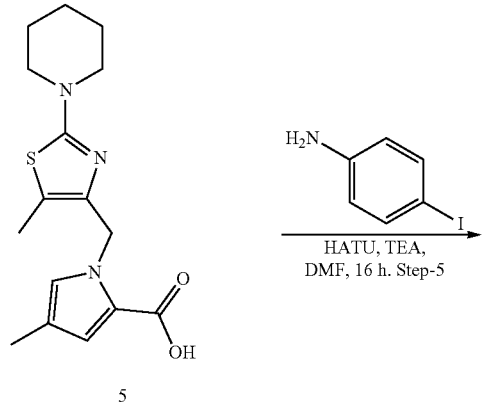

TEA (940 mg, 9.30 mmol, 3 equiv), HATU (1.78 g, 4.68 mmol, 1.5 equiv) and 4-iodoaniline (0.82 g, 3.74 mmol, 1.2 equiv) were added to a stirred solution of 4-methyl-1-((5-methyl-2-(piperidin-1-yl)thiazol-4-yl)methyl)-1H-pyrrole-2-carboxylic acid (5) (1.0 g, 3.13 mmol, 1 equiv) in DMF (20 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 6 as a pale brown solid (800 mg, 49%).

LC-MS (ESI$^+$): m/z 520.7 (M+H)$^+$

154

Preparation of 4-(4-methyl-1-((5-methyl-2-(piperidin-1-yl)thiazol-4-yl)methyl)-1H-pyrrole-2-carboxamido)benzoic Acid

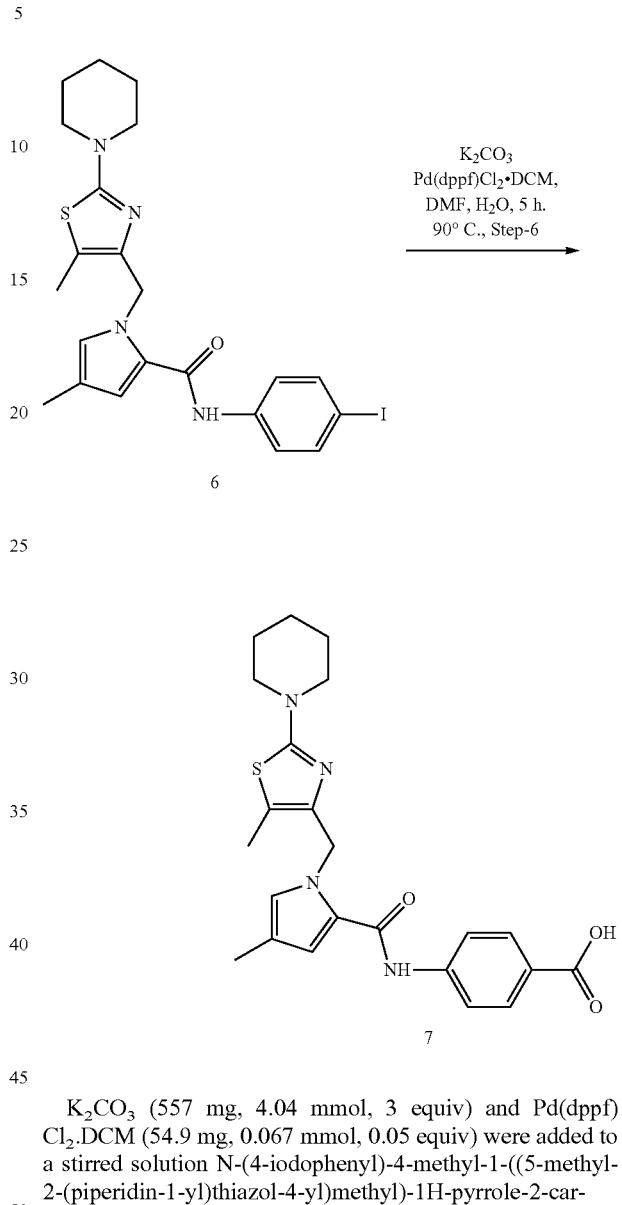

K$_2$CO$_3$ (557 mg, 4.04 mmol, 3 equiv) and Pd(dppf)Cl$_2$·DCM (54.9 mg, 0.067 mmol, 0.05 equiv) were added to a stirred solution N-(4-iodophenyl)-4-methyl-1-((5-methyl-2-(piperidin-1-yl)thiazol-4-yl)methyl)-1H-pyrrole-2-carboxamide (6) (700 mg, 1.35 mmol, 1 equiv) in DMF (20 mL) and H$_2$O (10 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (75 mL), brine (75 mL), dried over Na$_2$SO$_4$, filtered through celite bed and concentrated. The crude product was purified by Prep HPLC (0-50% CH$_3$CN—H$_2$O) to provide compound 7 (A-21) as a pale brown solid (88.0 mg, 15%).

LC-MS (ESI$^+$): m/z 439.3 (M+H)$^+$

1H-NMR (400 MHz, DMSO-d6): δ 12.67 (s, 1H), 10.10 (s, 1H), 7.91-7.82 (m, 4H), 6.84-6.76 (m, 2H), 5.30 (s, 2H), 3.39-3.30 (m, 4H), 2.23 (s, 3H), 2.03 (s, 3H), 1.59-1.51 (m, 6H).

Synthesis of Compound A-39

Preparation of Ethyl 5-methyl-1-((2-(piperidin-1-yl)thiazol-4-yl)methyl)-1H-pyrrole-2-carboxylate

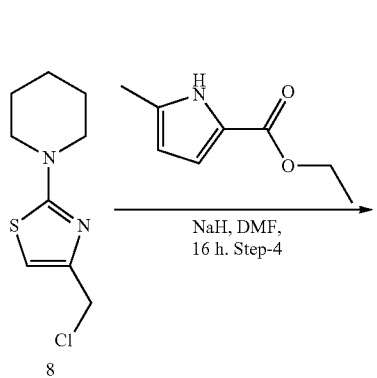

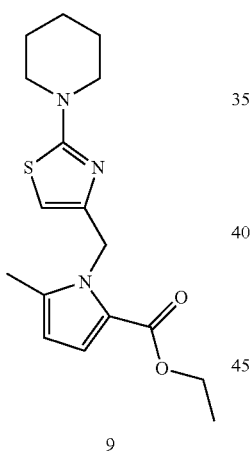

NaH (330 mg, 60% w/w in mineral oil, 6.79 mmol, 1.5 equiv) was added to a stirred solution of ethyl 5-methyl-1H-pyrrole-2-carboxylate (770 mg, 5.02 mmol, 1.1 equiv) in DMF (20 mL) at 0° C. After the reaction mixture was stirred at 0° C. for 30 min, 4-(chloromethyl)-2-(piperidin-1-yl) thiazole (8) (1.0 g, 4.61 mmol, 1 equiv) was added at 0° C. The reaction mixture was allowed to warm to ambient temperature and stirred for 16 h. The reaction mixture was quenched with ice and extracted with ethyl acetate (2×50 mL). The combined organic layers were washed with water (2×50 mL), brine (50 mL), dried over Na$_2$SO$_4$, filtered and concentrated under vacuum. The crude product was purified by silica gel column chromatography (20% ethyl acetate-hexanes) to provide compound 9 as a pale brown solid (900 mg, 58%).

LC-MS (ESI$^+$): m/z 334.2 (M+H)$^+$

Preparation of 5-methyl-1-((2-(piperidin-1-yl)thiazol-4-yl)methyl)-1H-pyrrole-2-carboxylic Acid

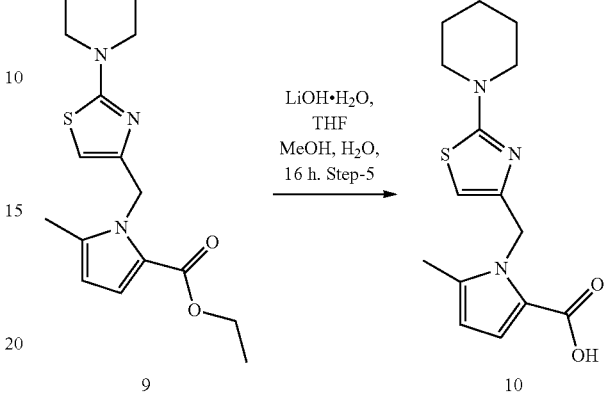

LiOH.H$_2$O (340 g, 8.11 mmol, 3 equiv) was added to a stirred solution of ethyl 5-methyl-1-((2-(piperidin-1-yl)thiazol-4-yl)methyl)-1H-pyrrole-2-carboxylate (9) (900 mg, 2.70 mmol, 1 equiv) in THF (10 mL), MeOH (10 mL) and H$_2$O (10 mL) at ambient temperature. The reaction mixture was heated to 70° C. and stirred for 16 h. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered and concentrated under vacuum to provide compound 10 as a pale brown solid (700 mg, 84%) without further purification.

LC-MS (ESI$^+$): m/z 306.1 (M+H)$^+$

Preparation of 5-methyl-N-phenyl-1-((2-(piperidin-1-yl)thiazol-4-yl)methyl)-1H-pyrrole-2-carboxamide

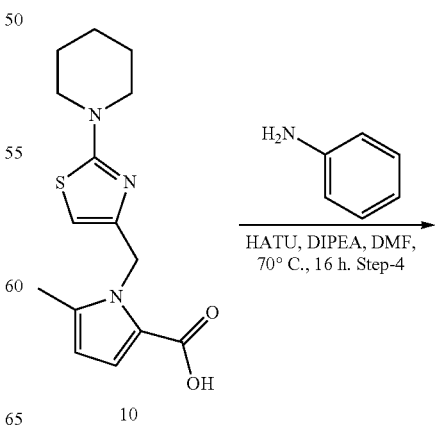

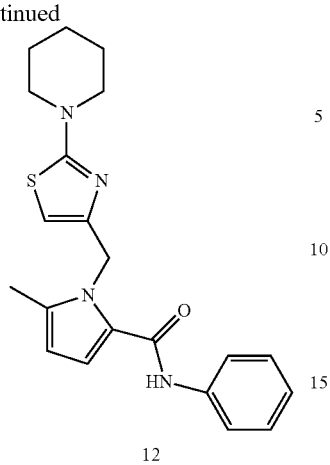

12

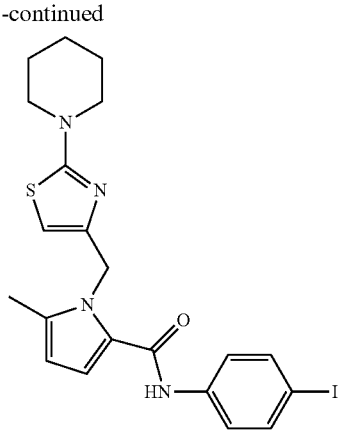

13

DIPEA (190 mg, 1.48 mmol, 3 equiv), HATU (280 mg, 0.736 mmol, 1.5 equiv) and aniline (55.0 mg, 0.589 mmol, 1.2 equiv) were added to a stirred solution of 4-(4-methyl-1-((2-(piperidin-1-yl)thiazol-4-yl)methyl)-1H-pyrrole-2-carboxamido)benzoic acid (11) (150 mg, 0.491 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×30 mL), brine (30 mL), dried over Na$_2$SO$_4$, filtered and concentrated. The crude product was purified by Prep HPLC (0-55% CH$_3$CN—H$_2$O) to provide compound 12 (A-39) as an off-white solid (70.0 mg, 38%).

LC-MS (ESI$^+$): m/z 381.2 (M+H)$^+$

1H-NMR (400 MHz, DMSO-d6): δ 9.74 (s, 1H), 7.68-7.65 (m, 2H), 7.32-7.25 (m, 2H), 7.06-6.96 (m, 2H), 6.02-5.96 (m, 2H), 5.44 (s, 2H), 3.39-3.31 (m, 4H), 2.28 (s, 3H), 1.59-1.51 (m, 6H).

DIPEA (698 mg, 5.41 mmol, 3 equiv), HATU (1.03 g, 2.70 mmol, 1.5 equiv) and 4-iodoaniline (434 mg, 1.98 mmol, 1.1 equiv) were added to a stirred solution of 5-methyl-1-((2-(piperidin-1-yl)thiazol-4-yl)methyl)-1H-pyrrole-2-carboxylic acid (11) (550 mg, 1.80 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×40 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 13 as a pale brown solid (410 mg, 45%).

LC-MS (ESI$^+$): m/z 506.9 (M+H)$^+$

Synthesis of Compound A-42

Step 6: Preparation of N-(4-iodophenyl)-5-methyl-1-((2-(piperidin-1-yl)thiazol-4-yl)methyl)-1H-pyrrole-2-carboxamide Preparation of 4-(5-methyl-1-((2-(piperidin-1-yl)thiazol-4-yl)methyl)-1H-pyrrole-2-carboxamido)benzoic Acid

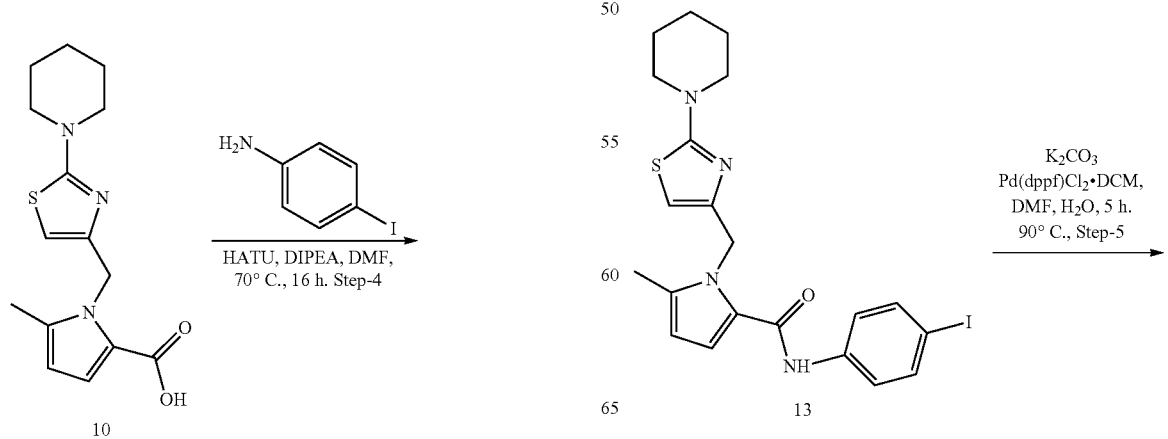

-continued

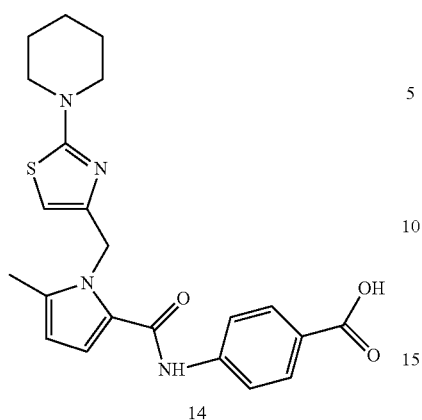

14

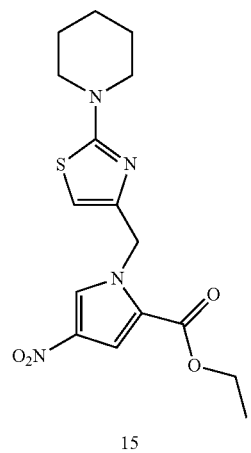

15

K₂CO₃ (327 mg, 2.37 mmol, 3 equiv) and Pd(dppf)Cl₂·DCM (64.5 mg, 0.079 mmol, 0.1 equiv) were added to a stirred solution N-(4-iodophenyl)-5-methyl-1-((2-(piperidin-1-yl)thiazol-4-yl)methyl)-1H-pyrrole-2-carboxamide (13) (400 mg, 0.790 mmol, 1 equiv) in DMF (10 mL) and H₂O (5 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×40 mL). The combined organic layers were washed with water (50 mL), brine (50 mL), dried over Na₂SO₄, filtered through celite bed and concentrated. The crude product was purified by Prep HPLC (0-50% CH₃CN—H₂O) to provide compound 14 (A-42) as a pale brown solid (66.0 mg, 20%).

LC-MS (ESI⁺): m/z 425.2 (M+H)⁺

1H-NMR (400 MHz, DMSO-d6): δ 9.98 (s, 1H), 7.87 (d, J=8.8 Hz, 2H), 7.80 (d, J=8.8 Hz, 2H), 6.99 (d, J=3.6 Hz, 1H), 6.02 (s, 1H), 5.97 (d, J=4.0 Hz, 1H), 5.43 (s, 2H), 3.39-3.30 (m, 4H), 2.30 (s, 3H), 1.59-1.51 (m, 6H).

Synthesis of Compound A-45

Preparation of Ethyl 4-nitro-1-((2-(piperidin-1-yl)thiazol-4-yl)methyl)-1H-pyrrole-2-carboxylate 4-(Chloromethyl)-2-(piperidin-1-yl)thiazole (8) (7.04 g, 0.032 mol, 1.2 equiv) and K₂CO₃ (11.2 g, 0.081 mol, 3 equiv) were added to a stirred solution of ethyl 4-nitro-1H-pyrrole-2-carboxylate (5.0 g, 0.027 mol, 1 equiv) in CH₃CN (100 mL) at ambient temperature. The reaction mixture was heated to 80° C. and stirred for 16 h. The reaction mixture was cooled to ambient temperature, filtered and concentrated under vacuum. The crude product was purified by silica gel column chromatography (20% ethyl acetate-hexanes) to provide compound 15 as a white solid (8.0 g, 81%).

LC-MS (ESI⁺): m/z 364.1 (M+H)⁺

1H-NMR (400 MHz, DMSO-d6): δ 8.28 (s, 1H), 7.34 (s, 1H), 6.40 (s, 1H), 5.44 (s, 2H), 4.24 (q, J=7.2 Hz, 2H), 3.34-3.32 (m, 4H), 1.57-1.55 (m, 6H), 1.29-1.25 (m, 3H).

Preparation of 4-nitro-1-((2-(piperidin-1-yl)thiazol-4-yl)methyl)-1H-pyrrole-2-carboxylic Acid

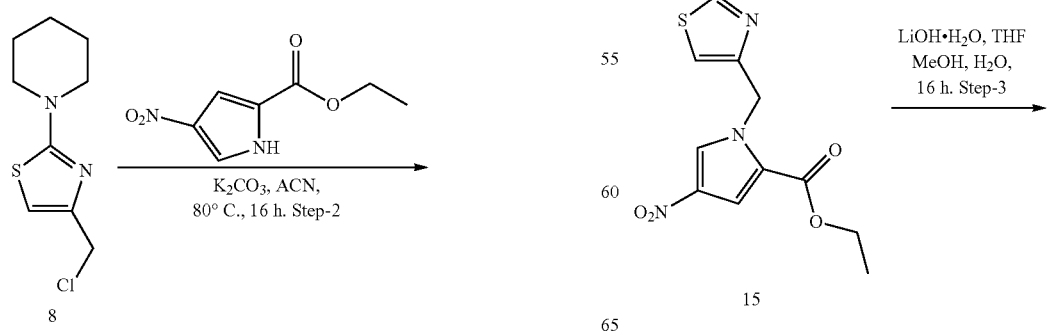

LiOH·H₂O, THF
MeOH, H₂O,
16 h. Step-3

161

-continued

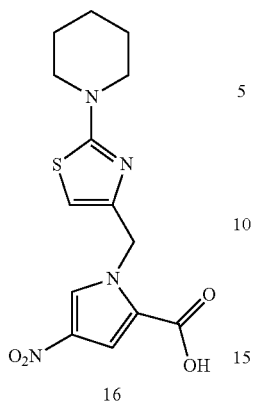

16

LiOH.H$_2$O (2.64 g, 0.063 mol, 3 equiv) was added to a stirred solution of ethyl 4-nitro-1-((2-(piperidin-1-yl)thiazol-4-yl)methyl)-1H-pyrrole-2-carboxylate (15) (8.0 g, 0.021 mol, 1 equiv) in THF (50 mL), MeOH (50 mL) and H$_2$O (50 mL) at ambient temperature. The reaction mixture was stirred for 16 h. then concentrated under vacuum. The residue was acidified with 1.5 M hydrochloric acid, solid was precipitated, and the obtained solid was filtered and dried under vacuum to provide compound 16 as a white solid (6.0 g, 81%) without further purification.

LC-MS (ESI$^+$): m/z 337.0 (M+H)$^+$

1H-NMR (400 MHz, DMSO-d6): δ 8.28 (s, 1H), 7.31 (s, 1H), 6.40 (s, 1H), 5.49 (s, 2H), 3.35-3.33 (m, 4H), 1.59-1.57 (m, 6H).

Preparation of N-(4-iodophenyl)-4-nitro-1-((2-(piperidin-1-yl)thiazol-4-yl)methyl)-1H-pyrrole-2-carboxamide

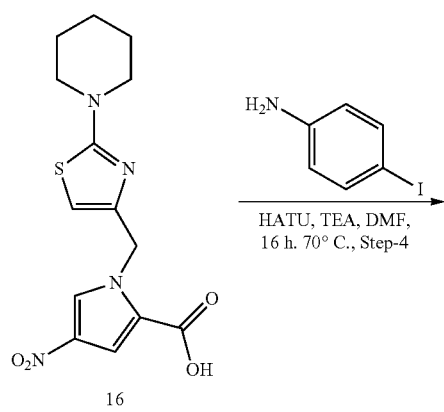

162

-continued

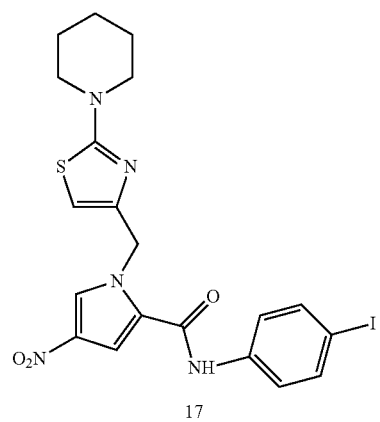

17

TEA (7.28 g, 0.053 mol, 3 equiv), HATU (10.1 g, 0.026 mol, 2 equiv) and 4-iodoaniline (4.69 g, 0.021 mol, 1.2 equiv) were added to a stirred solution of 4-nitro-1-((2-(piperidin-1-yl)thiazol-4-yl)methyl)-1H-pyrrole-2-carboxylic acid (16) (6.0 g, 0.017 mol, 1 equiv) in DMF (100 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×150 mL). The combined organic layers were washed with water (200 mL), brine (200 mL), dried over Na$_2$SO$_4$, filtered and concentrated. The crude product was purified by silica gel column chromatography (30% ethyl acetate-hexanes) to provide compound 17 as a white solid (3.0 g, 32%).

LC-MS (ESI$^+$): m/z 538.0 (M+H)$^+$

1H-NMR (400 MHz, DMSO-d6): δ 10.30 (s, 1H), 8.25 (s, 1H), 7.70-7.68 (m, 2H), 7.60-7.54 (m, 3H), 6.46 (s, 1H), 5.49 (s, 2H), 3.30-3.28 (m, 4H), 1.52-1.50 (m, 6H).

Preparation of 4-(4-nitro-1-((2-(piperidin-1-yl)thiazol-4-yl)methyl)-1H-pyrrole-2-carboxamido)benzoic Acid

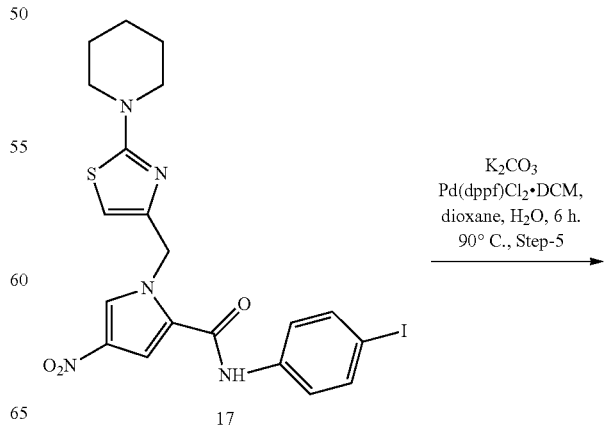

-continued

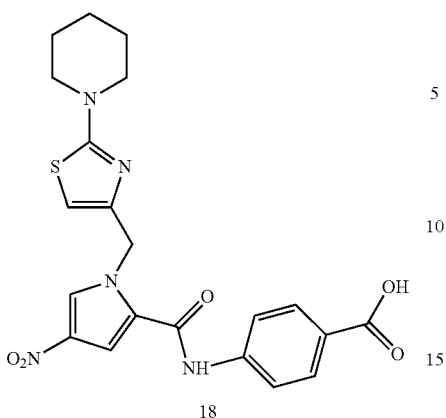

18

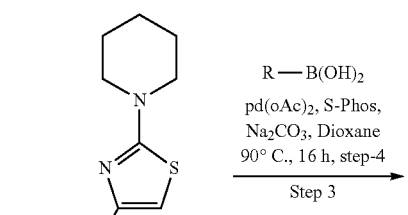

19

K₂CO₃ (385 mg, 2.79 mmol, 3 equiv) and Pd(dppf)Cl₂.DCM (75.9 mg, 0.093 mmol, 0.1 equiv) were added to a stirred solution N-(4-iodophenyl)-4-nitro-1-((2-(piperidin-1-yl)thiazol-4-yl)methyl)-1H-pyrrole-2-carboxamide (17) (500 mg, 0.931 mmol, 1 equiv) in dioxane (20 mL) and H₂O (10 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×40 mL). The combined organic layers were washed with water (50 mL), brine (50 mL), dried over Na₂SO₄, filtered through celite bed and concentrated. The crude product was purified by Prep HPLC (0-50% CH₃CN—H₂O) to provide compound 18 (A-45) as a white solid (42.0 mg, 10%).

LC-MS (ESI⁺): m/z 455.2 (M+H)⁺

1H-NMR (400 MHz, DMSO-d6): δ 12.77 (s, 1H), 10.50 (s, 1H), 8.27 (s, 1H), 7.93 (d, J=8.7 Hz, 2H), 7.83 (d, J=8.4 Hz, 3H), 7.64 (s, 1H), 6.47 (s, 1H), 5.50 (s, 2H), 3.39-3.29 (m, 4H), 1.58-1.48 (m, 6H).

Synthesis of Compound A-52

-continued

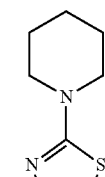

R—B(OH)₂
pd(oAc)₂, S-Phos,
Na₂CO₃, Dioxane
90° C., 16 h, step-4

Step 3

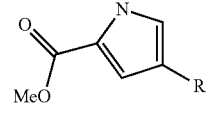

LiOH, MeOH
THF, D, O/N

Step 4

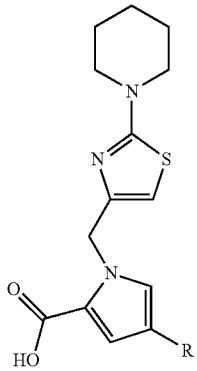

Amines, HATU,
DIPEA, DMF, 80° C.

Step 5

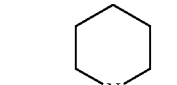

K₂CO₃ Pd(dppf)Cl₂•DCM,
DMF, H₂O, 6 h.
90° C., Step-5

Step 6

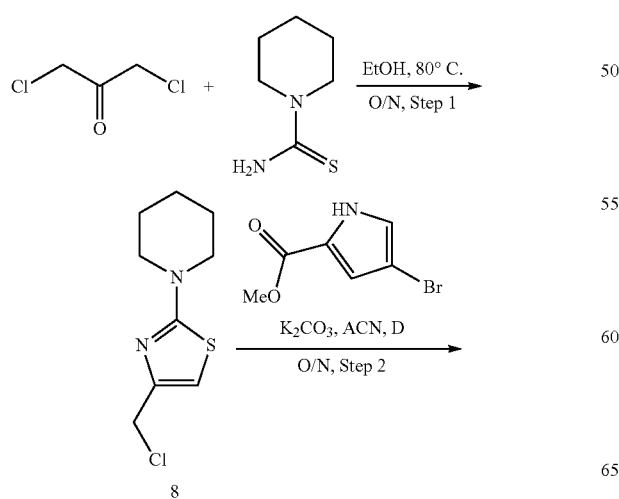

-continued

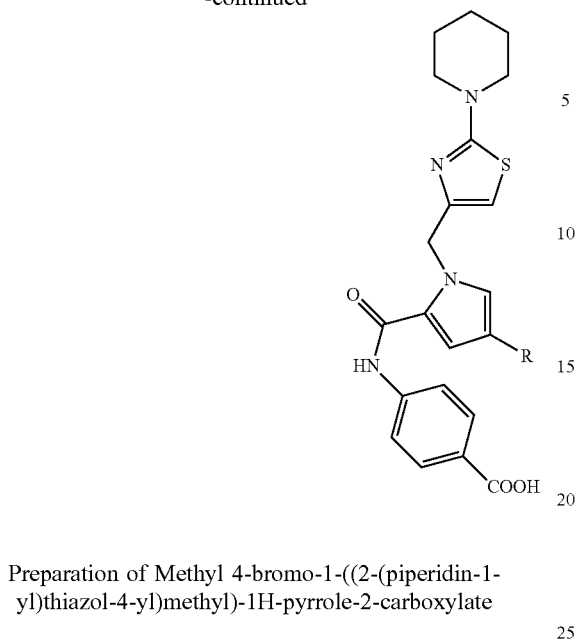

Preparation of Methyl 4-bromo-1-((2-(piperidin-1-yl)thiazol-4-yl)methyl)-1H-pyrrole-2-carboxylate

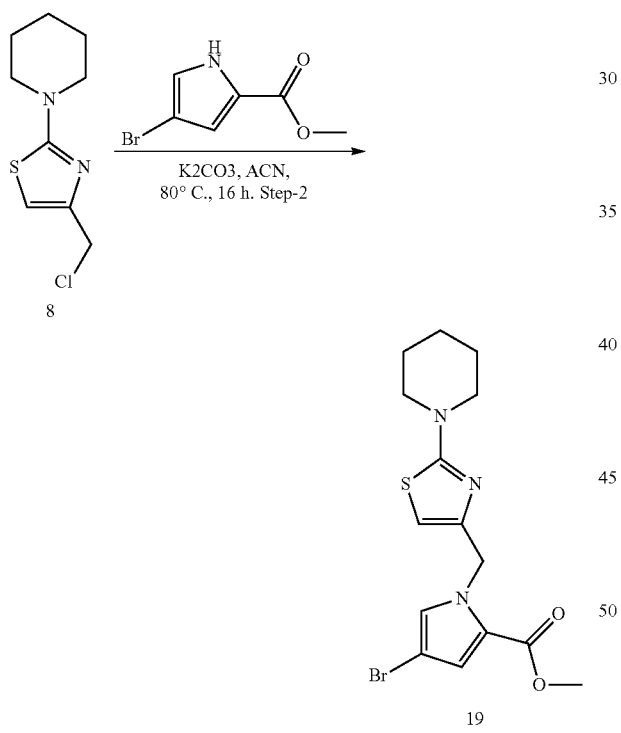

K$_2$CO$_3$ (9.94 g, 0.072 mol, 3 equiv) and 4-(chloromethyl)-2-(piperidin-1-yl)thiazole (8) (6.38 g, 0.029 mol, 1.2 equiv) were added to a stirred solution of methyl 4-bromo-1H-pyrrole-2-carboxylate (5.0 g, 0.024 mol, 1 equiv) in CH$_3$CN (100 mL) at ambient temperature. The reaction mixture was heated to 80° C. and stirred for 16 h. The reaction mixture was cooled to ambient temperature, then filtered and concentrated under vacuum. The crude product was purified by silica gel column chromatography (20% ethyl acetate-hexanes) to provide compound 19 as a pale brown gum (6.0 g, 65%).

LC-MS (ESI$^+$): m/z 384.0 (M+H)$^+$

1H-NMR (400 MHz, DMSO-d6): δ 7.35 (s, 1H), 6.91 (s, 1H), 6.23 (s, 1H), 5.35 (s, 2H), 3.73 (s, 3H), 3.37-3.33 (m, 4H), 1.56-1.54 (m, 6H).

Preparation of Methyl 1-((2-(piperidin-1-yl)thiazol-4-yl)methyl)-4-vinyl-1H-pyrrole-2-carboxylate

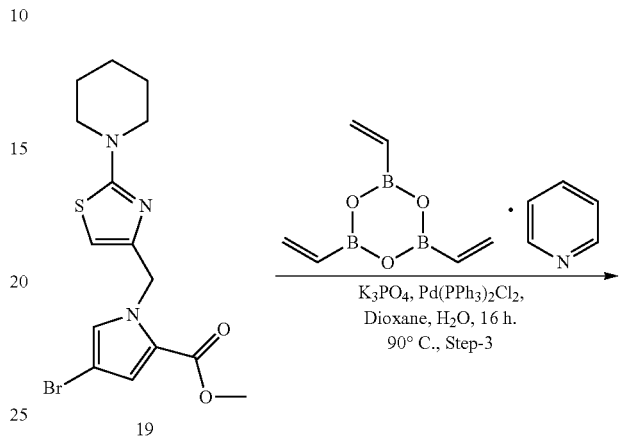

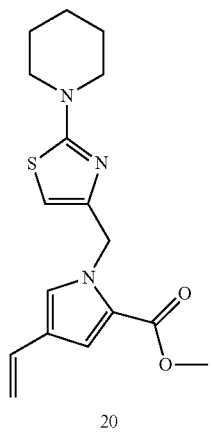

Vinylboronic anhydride pyridine complex (0.620 g, 2.60 mmol, 1 equiv), K$_3$PO$_4$ (1.66 g, 7.82 mmol, 3 equiv) and Pd(PPh$_3$)$_2$Cl$_2$ (180 mg, 0.260 mmol, 0.1 equiv) were added to a stirred solution methyl 4-bromo-1-((2-(piperidin-1-yl)thiazol-4-yl)methyl)-1H-pyrrole-2-carboxylate (19) (1.0 g, 2.60 mmol, 1 equiv) in dioxane (20 mL) and H$_2$O (5 mL) at ambient temperature. The reaction mixture was degassed for 5 min. with N$_2$ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×100 mL). The combined organic layers were washed with water (100 mL), brine (100 mL), dried over Na$_2$SO$_4$, filtered through celite bed and concentrated under vacuum to provide compound 20 as a brown solid (500 mg, 58%) without further purification.

LC-MS (ESI$^+$): m/z 332.3 (M+H)$^+$

Preparation of Methyl 4-ethyl-1-((2-(piperidin-1-yl)thiazol-4-yl)methyl)-1H-pyrrole-2-carboxylate

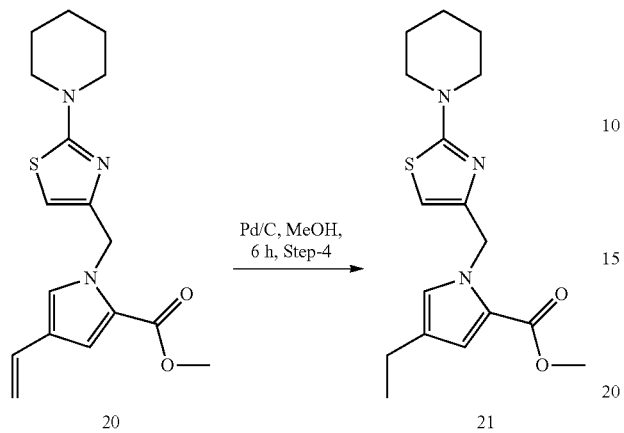

10% Pd/C (50 mg) was added to a stirred solution of methyl 1-((2-(piperidin-1-yl)thiazol-4-yl)methyl)-4-vinyl-1H-pyrrole-2-carboxylate (20) (500 mg, 1.51 mmol, 1 equiv) in MeOH (20 mL) at ambient temperature. The reaction mixture stirred for 6 h under 1 atm hydrogen atmosphere, then reaction mixture was filtered through celite bed, concentrated under vacuum to provide compound 21 as a pale brown solid (450 mg, 89%) without further purification.

LC-MS (ESI+): m/z 334.1 (M+H)+

Preparation of 4-ethyl-1-((2-(piperidin-1-yl)thiazol-4-yl)methyl)-1H-pyrrole-2-carboxylic Acid

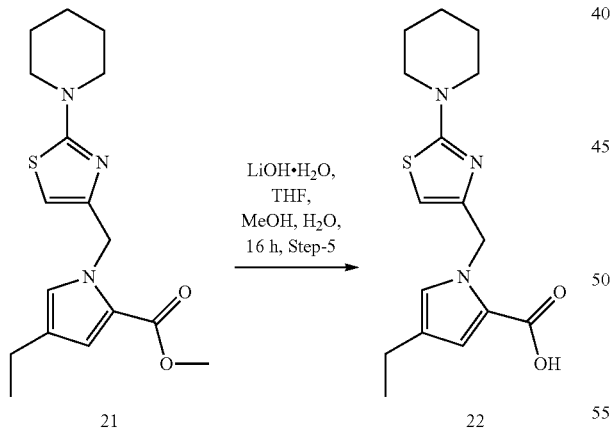

LiOH.H$_2$O (170 mg, 3.44 mmol, 3 equiv) was added to a stirred solution methyl 4-ethyl-1-((2-(piperidin-1-yl)thiazol-4-yl)methyl)-1H-pyrrole-2-carboxylate (21) (450 mg, 1.35 mmol, 1 equiv) in THF (5 mL), MeOH (5 mL) and H$_2$O (5 mL) at ambient temperature. The reaction mixture stirred for 16 h, and then reaction mixture was concentrated under vacuum. The residue was acidified with 1.5 M hydrochloric acid and the resulting mixture was extracted with ethyl acetate (2×50 mL). The combined organic layers were washed with water (40 mL), brine (50 mL), dried over Na$_2$SO$_4$, filtered and concentrated under vacuum. The crude product was purified by silica gel column chromatography (40% ethyl acetate-hexanes) to provide compound 22 as a pale brown solid (400 mg, 93%).

LC-MS (ESI+): m/z 320.1 (M+H)+

Preparation of 4-ethyl-N-(4-iodophenyl)-1-((2-(piperidin-1-yl)thiazol-4-yl)methyl)-1H-pyrrole-2-carboxamide

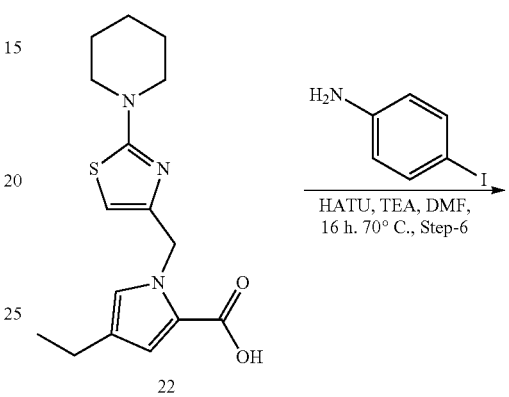

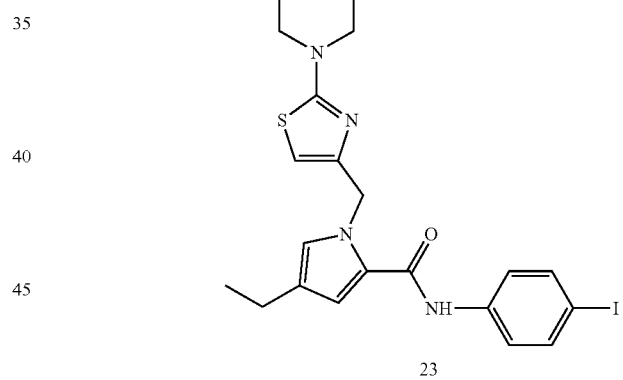

TEA (363 mg, 3.59 mmol, 3 equiv), HATU (683 mg, 1.79 mmol, 1.5 equiv) and 4-iodoaniline (315 mg, 1.44 mmol, 1.2 equiv) were added to a stirred solution of 4-ethyl-1-((2-(piperidin-1-yl)thiazol-4-yl)methyl)-1H-pyrrole-2-carboxylic acid (22) (400 mg, 1.19 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 23 as a pale brown solid (300 mg, 48%).

LC-MS (ESI+): m/z 521.0 (M+H)+

Preparation of 4-(4-ethyl-1-((2-(piperidin-1-yl)thiazol-4-yl)methyl)-1H-pyrrole-2-carboxamido)benzoic Acid

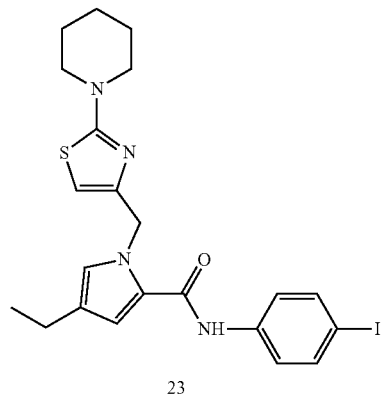

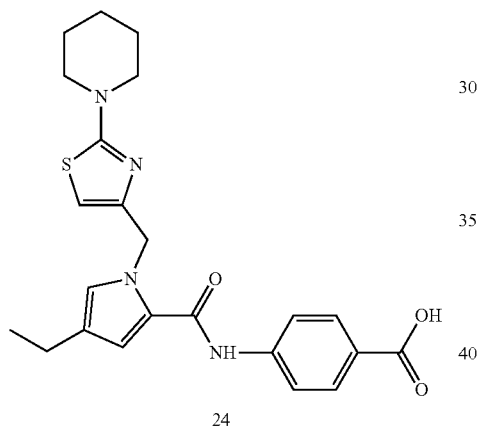

K₂CO₃ (238 mg, 1.73 mmol, 3 equiv) and Pd(dppf)Cl₂.DCM (46.5 mg, 0.057 mmol, 0.1 equiv) were added to a stirred solution 4-ethyl-N-(4-iodophenyl)-1-((2-(piperidin-1-yl)thiazol-4-yl)methyl)-1H-pyrrole-2-carboxamide (23) (300 mg, 0.576 mmol, 1 equiv) in DMF (10 mL) and H₂O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered through celite bed and concentrated. The crude product was purified by Prep HPLC (0-50% CH₃CN—H₂O) to provide compound 24 (A-52) as a pale brown solid (25.0 mg, 10%).

LC-MS (ESI⁺): m/z 439.3 (M+H)⁺

1H-NMR (400 MHz, DMSO-d6): δ 12.66 (s, 1H), 10.02 (s, 1H), 7.89-7.80 (m, 4H), 6.92 (s, 2H), 6.16 (s, 1H), 5.35 (s, 2H), 3.39-3.31 (m, 4H), 2.44 (q, J=7.2 Hz, 2H), 1.58-1.50 (m, 6H), 1.16 (t, J=7.6 Hz, 3H).

Synthesis of Compound A-51

Preparation of Methyl 4-phenyl-1-((2-(piperidin-1-yl)thiazol-4-yl)methyl)-1H-pyrrole-2-carboxylate

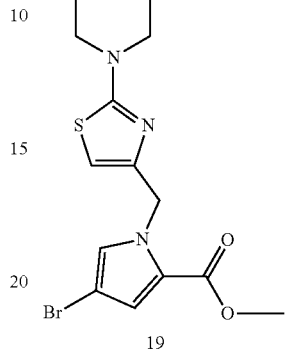 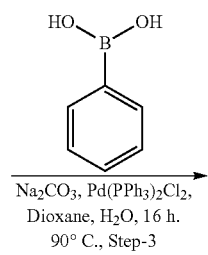

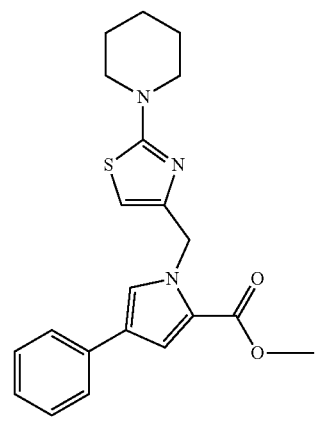

Phenylboronic acid (470 mg, 3.85 mmol, 1.5 equiv), Na₂CO₃ (819 mg, 7.72 mmol, 3 equiv) and Pd(PPh₃)₂Cl₂ (179 mg, 0.269 mmol, 0.1 equiv) were added to a stirred solution methyl 4-bromo-1-((2-(piperidin-1-yl)thiazol-4-yl)methyl)-1H-pyrrole-2-carboxylate (19) (1.0 g, 2.74 mmol, 1 equiv) in dioxane (20 mL) and H₂O (5 mL) at ambient temperature. The reaction mixture was degassed for 5 min. with N₂ gas and heated to 90° C. and stirred for 16 h. The reaction mixture was cooled to ambient temperature and then concentrated under vacuum. The residue was acidified with 1.5 M hydrochloric acid and the resulting mixture was extracted with ethyl acetate (2×75 mL). The combined organic layers were washed with water (100 mL), brine (100 mL), dried over Na₂SO₄, filtered through celite bed and concentrated to provide compound 25 as a pale brown solid (600 mg, 60%) without further purification.

LC-MS (ESI⁺): m/z 382.1 (M+H)⁺

Preparation of 4-phenyl-1-((2-(piperidin-1-yl)thiazol-4-yl)methyl)-1H-pyrrole-2-carboxylic Acid Preparation of N-(4-iodophenyl)-4-phenyl-1-((2-(piperidin-1-yl)thiazol-4-yl)methyl)-1H-pyrrole-2-carboxamide

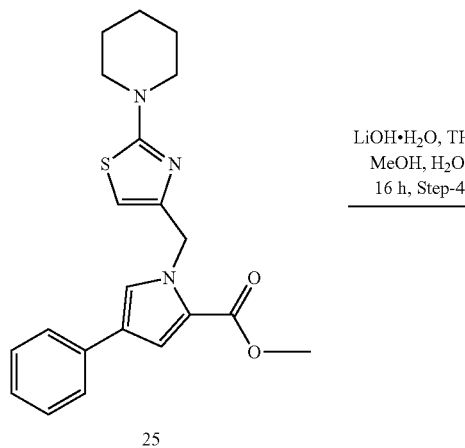

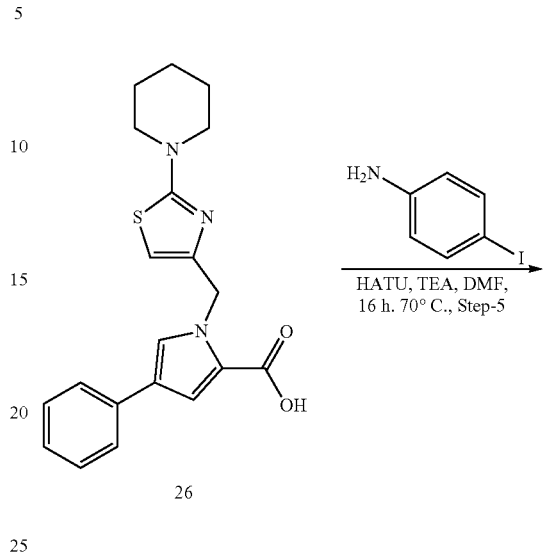

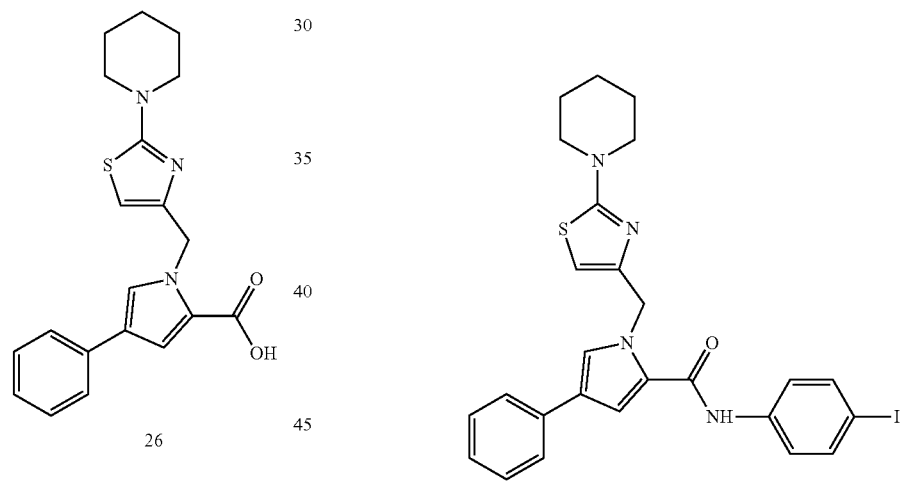

LiOH.H$_2$O (269 mg, 6.41 mmol, 3 equiv) was added to a stirred solution methyl 4-phenyl-1-((2-(piperidin-1-yl)thiazol-4-yl)methyl)-1H-pyrrole-2-carboxylate (25) (600 mg, 2.14 mmol, 1 equiv) in THF (10 mL), MeOH (10 mL) and H$_2$O (10 mL) at ambient temperature. The reaction mixture stirred for 16 h, and then reaction mixture was concentrated under vacuum. The residue was acidified with 1.5 M hydrochloric acid and the resulting mixture was extracted with ethyl acetate (2×50 mL). The combined organic layers were washed with water (50 mL), brine (50 mL), dried over Na$_2$SO$_4$, filtered and concentrated under vacuum. The crude product was purified by silica gel column chromatography (50% ethyl acetate-hexanes) to provide compound 26 as a pale brown solid (500 mg, 86%).

LC-MS (ESI$^+$): m/z 368.1 (M+H)$^+$

1H-NMR (400 MHz, DMSO-d6): δ 7.65-7.57 (m, 4H), 7.36-7.32 (m, 2H), 7.23 (s, 1H), 7.19 (s, 1H), 6.15 (s, 1H), 5.78 (s, 2H), 3.36-3.33 (m, 4H), 1.56-1.53 (m, 6H).

TEA (413 mg, 4.09 mmol, 3 equiv), HATU (776 mg, 2.04 mmol, 1.5 equiv) and 4-iodoaniline (358 mg, 1.63 mmol, 1.2 equiv) were added to a stirred solution of 4-phenyl-1-((2-(piperidin-1-yl)thiazol-4-yl)methyl)-1H-pyrrole-2-carboxylic acid (26) (500 mg, 1.36 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (20% ethyl acetate-hexanes) to provide compound 27 as a pale brown solid (300 mg, 38%).

LC-MS (ESI$^+$): m/z 569.3 (M+H)$^+$

Preparation of 4-(4-phenyl-1-((2-(piperidin-1-yl)thiazol-4-yl)methyl)-1H-pyrrole-2-carboxamido)benzoic Acid

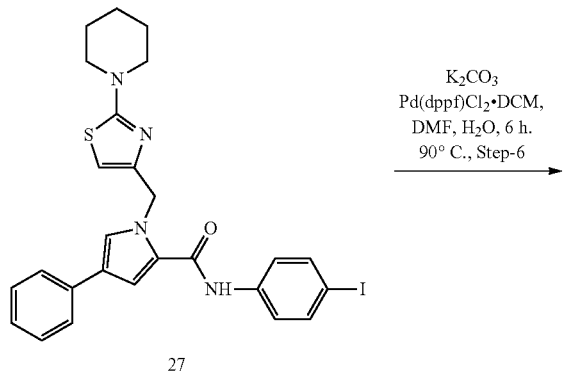

Synthesis of Compound A-58

Preparation of N-(4-(1H-tetrazol-5-yl)phenyl)-4-phenyl-1-((2-(piperidin-1-yl)thiazol-4-yl)methyl)-1H-pyrrole-2-carboxamide

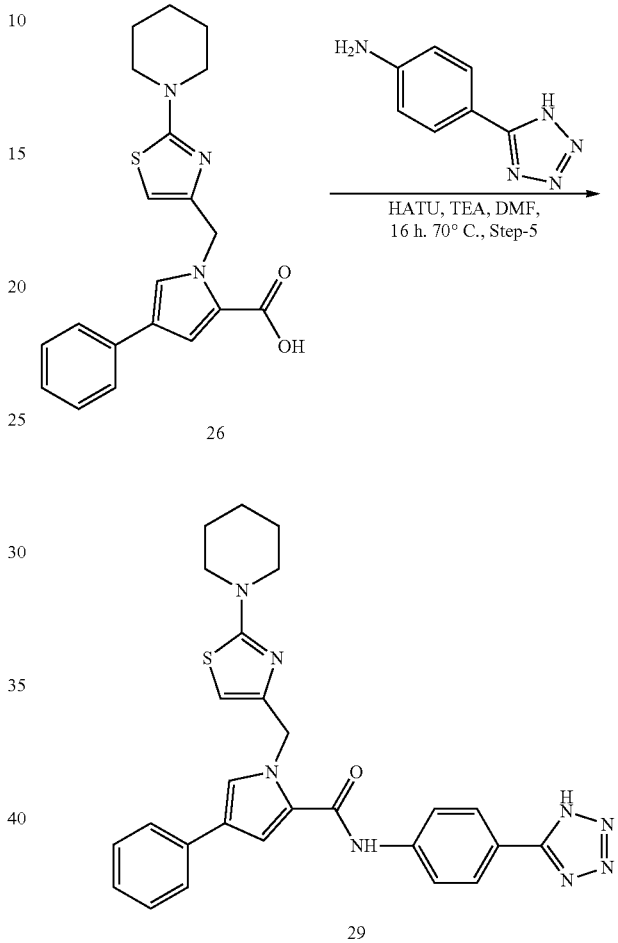

K$_2$CO$_3$ (219 mg, 1.58 mmol, 3 equiv) and Pd(dppf)Cl$_2$.DCM (43.1 mg, 0.052 mmol, 0.1 equiv) were added to a stirred solution N-(4-iodophenyl)-4-phenyl-1-((2-(piperidin-1-yl)thiazol-4-yl)methyl)-1H-pyrrole-2-carboxamide (27) (300 mg, 0.528 mmol, 1 equiv) in DMF (10 mL) and H$_2$O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried (Na$_2$SO$_4$), filtered through celite bed and concentrated. The crude product was purified by Prep HPLC (0-60% CH$_3$CN—H$_2$O) to provide compound 28 (A-51) as a white solid (12.0 mg, 5%).

LC-MS (ESI$^+$): m/z 487.3 (M+H)$^+$

1H-NMR (400 MHz, DMSO-d6): δ 12.72 (s, 1H), 10.21 (s, 1H), 7.94-7.85 (m, 4H), 7.65-7.56 (m, 3H), 7.48-7.35 (m, 3H), 7.22-7.17 (m, 1H), 6.27 (s, 1H), 5.45 (s, 2H), 3.39-3.31 (m, 4H), 1.59-1.51 (m, 6H).

TEA (247 mg, 2.45 mmol, 3 equiv), HATU (621 mg, 1.63 mmol, 2 equiv) and 4-(1H-tetrazol-5-yl)aniline (197 mg, 1.22 mmol, 1.2 equiv) were added to a stirred solution of 4-phenyl-1-((2-(piperidin-1-yl)thiazol-4-yl)methyl)-1H-pyrrole-2-carboxylic acid (26) (300 mg, 0.816 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×40 mL). The combined organic layers were washed with water (2×50 mL), brine (50 mL), dried (Na$_2$SO$_4$), filtered and concentrated. The crude product was purified by Prep HPLC (0-60% CH$_3$CN—H$_2$O) to provide compound 29 (A-58) as off white solid (30.0 mg, 8%).

LC-MS (ESI$^+$): m/z 511.2 (M+H)$^+$

1H-NMR (400 MHz, DMSO-d6): δ 16.74 (s, 1H), 10.25 (s, 1H), 8.05-7.94 (m, 4H), 7.67-7.57 (m, 3H), 7.47 (s, 1H), 7.42-7.35 (m, 2H), 7.23-7.17 (m, 1H), 6.28 (s, 1H), 5.47 (s, 2H), 3.39-3.31 (m, 4H), 1.59-1.51 (m, 6H).

Synthesis of Compound A-63

Preparation of 4-bromo-1-((2-(piperidin-1-yl)thiazol-4-yl)methyl)-1H-pyrrole-2-carboxylic Acid

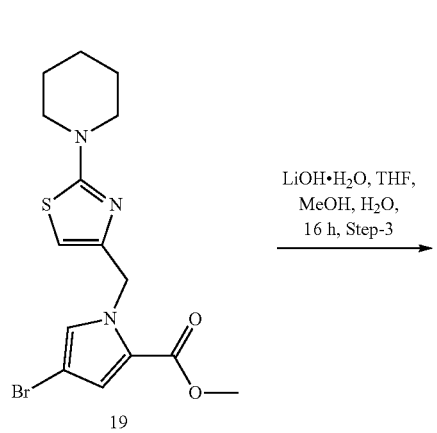

Preparation of 4-bromo-N-(4-(hydroxymethyl)phenyl)-1-((2-(piperidin-1-yl)thiazol-4-yl)methyl)-1H-pyrrole-2-carboxamide

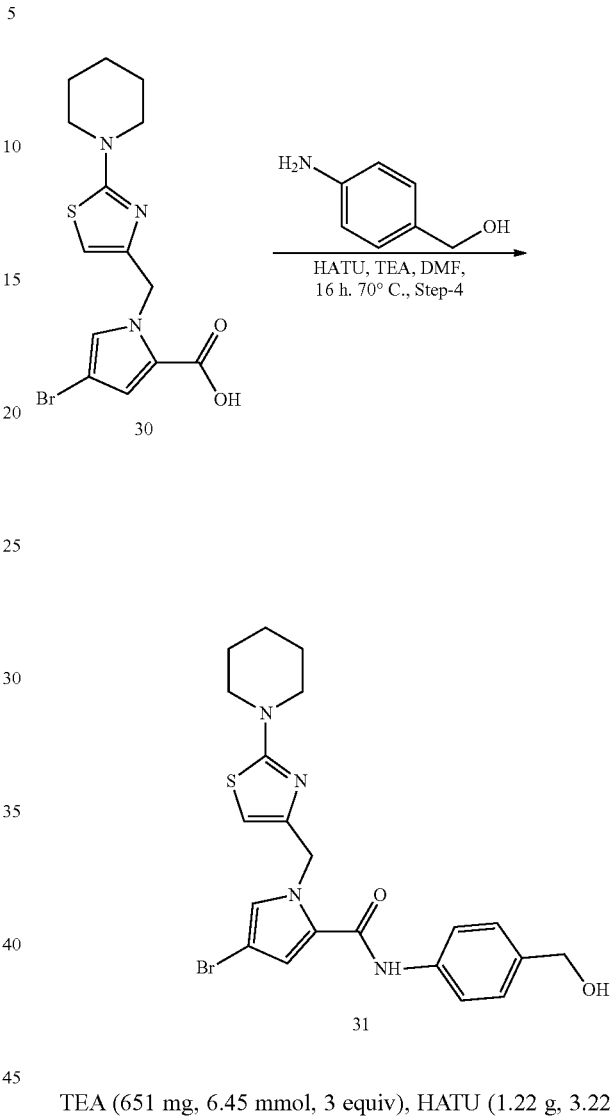

LiOH.H$_2$O (320 mg, 7.62 mmol, 3 equiv) was added to a stirred solution methyl 4-bromo-1-((2-(piperidin-1-yl)thiazol-4-yl)methyl)-1H-pyrrole-2-carboxylate (19) (1.0 g, 2.60 mmol, 1 equiv) in THF (10 mL), MeOH (10 mL) and H$_2$O (10 mL) at ambient temperature. The reaction mixture was stirred for 16 h, and then reaction mixture was concentrated under vacuum. The residue was acidified with 1.5 M hydrochloric acid and the resulting mixture was extracted with ethyl acetate (2×50 mL). The combined organic layers were washed with water (50 mL), brine (50 mL), dried over Na$_2$SO$_4$, filtered and concentrated under vacuum. The crude product was purified by silica gel column chromatography (50% ethyl acetate-hexanes) to provide compound 30 as a pale brown solid (800 mg, 86%).

LC-MS (ESI$^+$): m/z 372.0 (M+H)$^+$

1H-NMR (400 MHz, DMSO-d6): δ 12.56 (brs, 1H), 7.25 (s, 1H), 6.83 (s, 1H), 6.18 (s, 1H), 5.36 (s, 2H), 3.35-3.33 (m, 4H), 1.58-1.53 (m, 6H).

TEA (651 mg, 6.45 mmol, 3 equiv), HATU (1.22 g, 3.22 mmol, 1.5 equiv) and (4-aminophenyl)methanol (312 mg, 2.58 mmol, 1.20 equiv) were added to a stirred solution of 4-bromo-1-((2-(piperidin-1-yl)thiazol-4-yl)methyl)-1H-pyrrole-2-carboxylic acid (30) (800 mg, 2.15 mmol, 1 equiv) in DMF (15 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na$_2$SO$_4$, filtered and concentrated. The crude product was purified by silica gel column chromatography (50% ethyl acetate-hexanes) to provide compound 31 (A-63) as an off-white solid (800 mg, 78%).

LC-MS (ESI$^+$): m/z 474.8 (M+H)$^+$

1H-NMR (400 MHz, DMSO-d6): δ 9.89 (s, 1H), 7.62 (d, J=8.4 Hz, 2H), 7.28-7.21 (m, 3H), 7.04 (s, 1H), 6.28 (s, 1H), 5.40 (s, 2H), 5.12 (t, J=5.6 Hz, 1H), 4.45 (d, J=5.5 Hz, 2H), 3.39-3.31 (m, 4H), 1.59-1.51 (m, 6H).

177

Synthesis of Compound A-64

Preparation of 4-(4-bromo-1-((2-(piperidin-1-yl)thiazol-4-yl)methyl)-1H-pyrrole-2-carboxamido)benzoic Acid

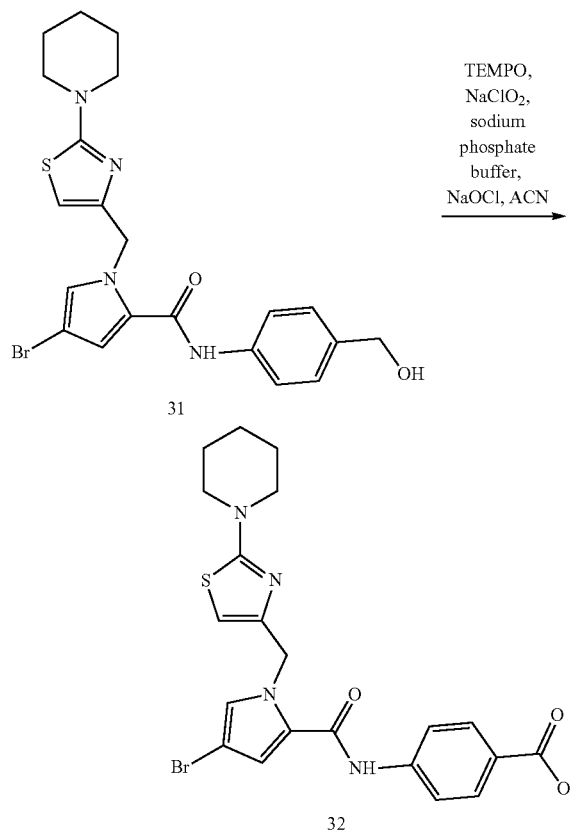

NaClO$_2$ (381 mg, 4.21 mmol, 2 equiv) in water (10 mL) and NaOCl (31.3 mg, 0.421 mmol, 0.2 equiv) in water (5 mL) were added simultaneously to a stirred solution of TEMPO (22.9 mg, 0.147 mmol, 0.07 equiv), sodium phosphate buffer (20 mL, 0.67 M, pH=6.7) and 4-bromo-N-(4-(hydroxymethyl)phenyl)-1-((2-(piperidin-1-yl)thiazol-4-yl)methyl)-1H-pyrrole-2-carboxamide (31) (1.0 g, 2.11 mmol, 1 equiv) in CH$_3$CN (30 mL) at 35° C. over a period of 1 h. The reaction mixture was stirred for 16 h. The reaction mixture was cooled to ambient temperature and then concentrated under vacuum. The residue was acidified with 1.5 M hydrochloric acid and the resulting mixture was extracted with DCM (2×75 mL). The combined organic layers were washed with water (100 mL), brine (100 mL), dried over Na$_2$SO$_4$, filtered and concentrated. The crude product was purified by silica gel column chromatography (50% ethyl acetate-hexanes) followed by Prep HPLC (0-25% CH$_3$CN—H$_2$O) to provide compound 32 (A-64) as a pale brown solid (10.0 mg, 8%).

LC-MS (ESI$^+$): m/z 490.6 (M+H)$^+$

1H-NMR (400 MHz, DMSO-d6): δ 7.25 (s, 1H), 7.23-7.17 (m, 3H), 7.15-7.11 (m, 1H), 7.01 (d, J=7.20 Hz, 1H), 6.72 (s, 1H), 5.69 (s, 2H), 3.33-3.27 (m, 2H), 2.99-2.91 (m, 2H), 1.45-1.32 (m, 2H), 1.21-1.05 (m, 4H).

178

Example 2d: Pyridine Compound Embodiments

Synthesis of Compound A-16

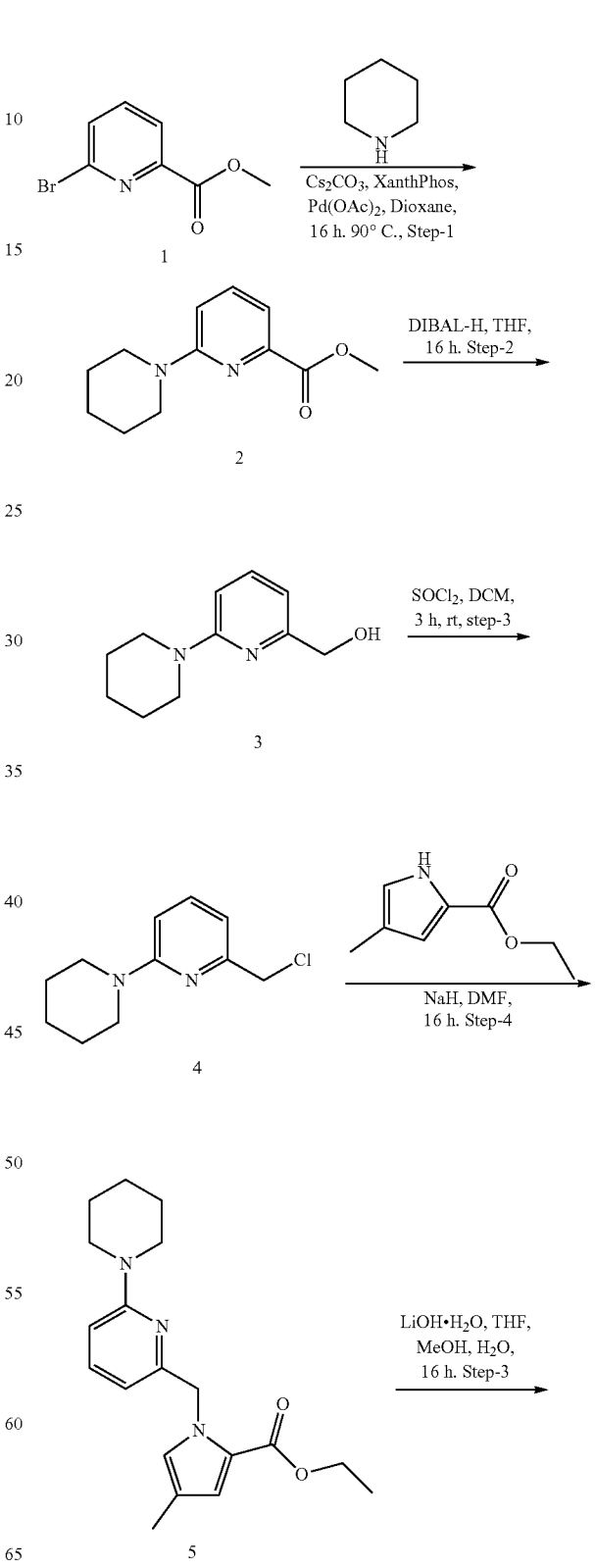

-continued

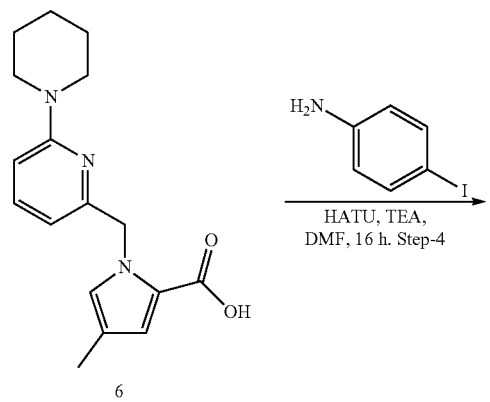

6

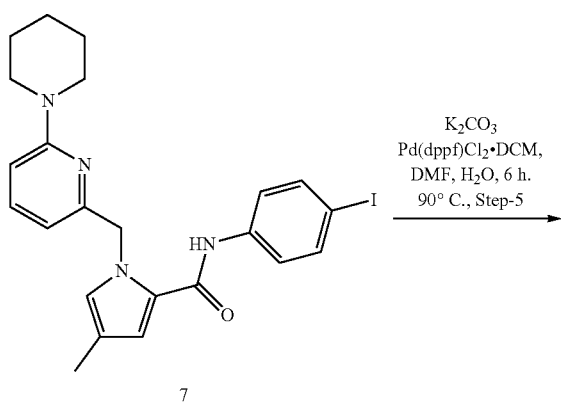

7

Preparation of Methyl 6-(piperidin-1-yl)picolinate

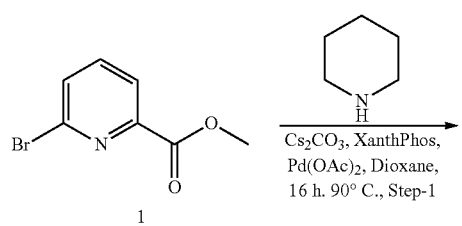

1

-continued

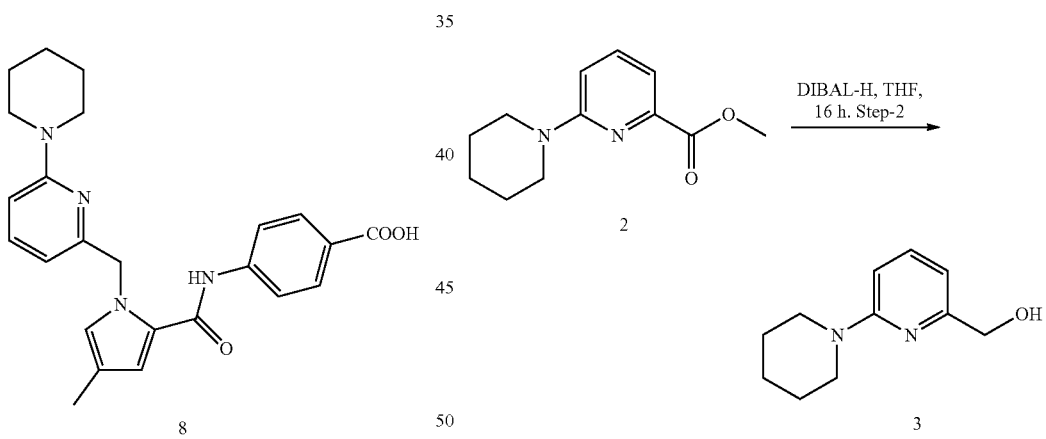

Piperidine (1.10 g, 0.013 mol, 1.5 equiv), $Cs_2CO_3$ (8.79 g, 0.027 mol, 3 equiv), XanthPhos (0.52 g, 0.898 mmol, 0.1 equiv) and $Pd(OAc)_2$ (0.089 g, 0.400 mmol, 0.05 equiv) were added to a stirred methyl 6-bromopicolinate (1) (2.0 g, 9.25 mmol, 1 equiv) in dioxane (30 mL) at ambient temperature. The reaction mixture reaction mixture was degassed for 5 min. with $N_2$ gas and warmed to 90° C. and stirred for 16 h. The reaction mixture was cooled to ambient temperature and then concentrated under vacuum. The residue was diluted with water and the resulting mixture was extracted with ethyl acetate (2×75 mL). The combined organic layers were washed with water (75 mL), brine (75 mL), dried over $Na_2SO_4$, filtered through celite bed and concentrated. The crude product was purified by silica gel column chromatography (20% ethyl acetate-hexanes) to provide compound 2 as a white solid (800 mg, 39%).

LC-MS (ESI$^+$): m/z 221.1 (M+H)$^+$

Preparation of
(6-(piperidin-1-yl)pyridin-2-yl)methanol

DIBAL-H (1.0 M in THF) (10.9 mL, 10.9 mmol, 3 equiv) was added to a stirred solution of methyl 6-(piperidin-1-yl) picolinate (2) (800 mg, 3.64 mmol, 1 equiv) in THF (10 mL) at −78° C. The reaction mixture was allowed to warm to ambient temperature and stirred for 16 h. The reaction mixture was quenched with MeOH (11 mL) and 1.5 M hydrochloric acid (11 mL), resultant mixture was concentrated under vacuum. The residue was diluted with water, the resultant mixture was extracted with ethyl acetate (2×50 mL). The combined organic layers were washed with water (2×50 mL), brine (50 mL), dried over $Na_2SO_4$, filtered and concentrated under vacuum to provide compound 3 as a white solid (500 mg, 71%) without further purification.

LC-MS (ESI$^+$): m/z 193.0 (M+H)$^+$

Preparation of 2-(chloromethyl)-6-(piperidin-1-yl)pyridine

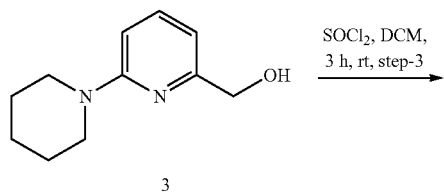

SOCl₂ (0.500 mL) was added to a stirred solution of (6-(piperidin-1-yl)pyridin-2-yl)methanol (3) (500 mg, 2.60 mmol, 1 equiv) in DCM (5.0 mL) at 0° C. The reaction mixture was allowed to warm to ambient temperature and stirred for 3 h. The reaction mixture was concentrated under vacuum and azeotroped with toluene. The residue was basified with 10% NaHCO₃ aqueous solution and the resulting mixture was extracted with DCM (2×40 mL). The combined organic layers were washed with water (40 mL), brine (50 mL), dried over Na₂SO₄, filtered and concentrated under vacuum to provide compound 4 as a white solid (450 mg, 82%) without further purification.

LC-MS (ESI⁺): m/z 211.0 (M+H)⁺

Preparation of Ethyl 4-methyl-1-((6-(piperidin-1-yl)pyridin-2-yl)methyl)-1H-pyrrole-2-carboxylate

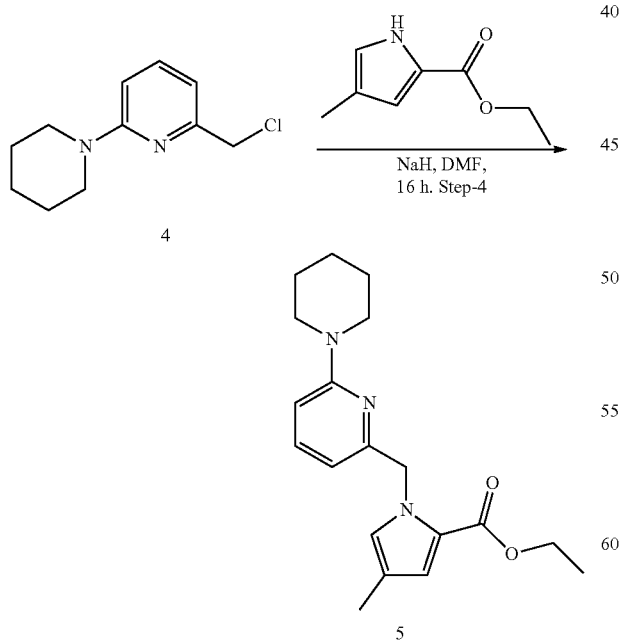

NaH (154 mg, 60% w/w in mineral oil, 3.21 mmol, 1.5 equiv) was added to a stirred solution of ethyl 4-methyl-1H-pyrrole-2-carboxylate (295 mg, 1.93 mmol, 0.9 equiv) in DMF (10 mL) at 0° C. After the reaction mixture was stirred at 0° C. for 30 min, 2-(chloromethyl)-6-(piperidin-1-yl) pyridine (4) (450 mg, 2.14 mmol, 1 equiv) was added at 0° C. The reaction mixture was allowed to warm to ambient temperature and stirred for 16 h. The reaction mixture was quenched with ice and extracted with ethyl acetate (2×50 mL). The combined organic layers were washed with water (2×50 mL), brine (50 mL), dried over Na₂SO₄, filtered and concentrated under vacuum. The crude product was purified by silica gel column chromatography (20% ethyl acetate-hexanes) to provide compound 5 as a pale brown solid (350 mg, 52%).

LC-MS (ESI⁺): m/z 328.0 (M+H)⁺

Preparation of 4-methyl-1-((6-(piperidin-1-yl)pyridin-2-yl)methyl)-1H-pyrrole-2-carboxylic Acid

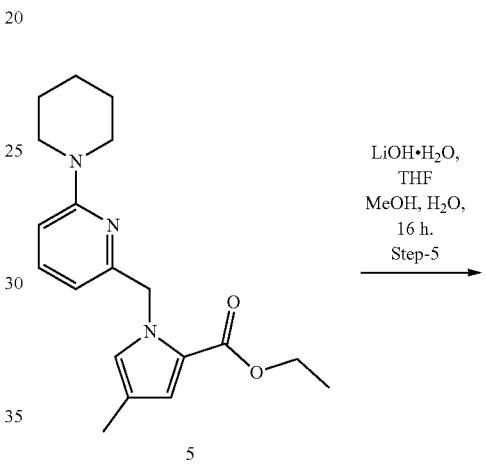

LiOH·H₂O (141 mg, 3.35 mmol, 3 equiv) was added to a stirred solution of ethyl 4-methyl-1-((6-(piperidin-1-yl)pyridin-2-yl)methyl)-1H-pyrrole-2-carboxylate (5) (350 mg, 1.12 mmol, 1 equiv) in THF (2 mL), MeOH (2 mL) and H₂O (2 mL) at ambient temperature. The reaction mixture was stirred for 16 h, and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered and concentrated under vacuum to provide compound 6 as a white solid (300 mg, 89%) without further purification.

LC-MS (ESI⁺): m/z 300.0 (M+H)⁺

Preparation of N-(4-iodophenyl)-4-methyl-1-((6-(piperidin-1-yl)pyridin-2-yl)methyl)-1H-pyrrole-2-carboxamide

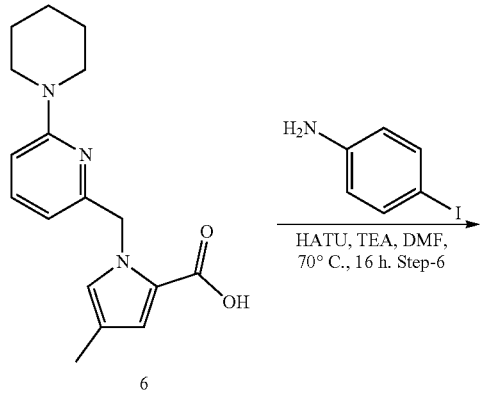

Preparation of 4-(4-methyl-1-((6-(piperidin-1-yl)pyridin-2-yl)methyl)-1H-pyrrole-2-carboxamido)benzoic Acid

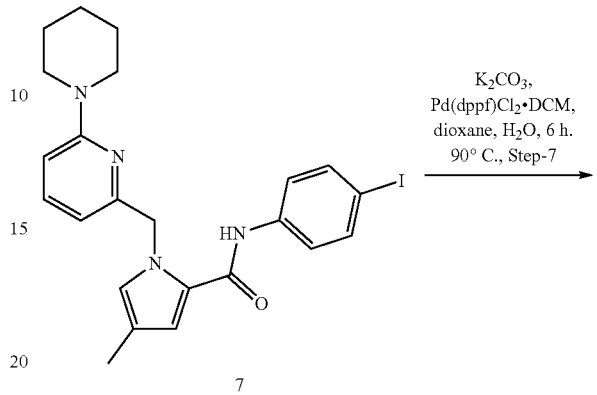

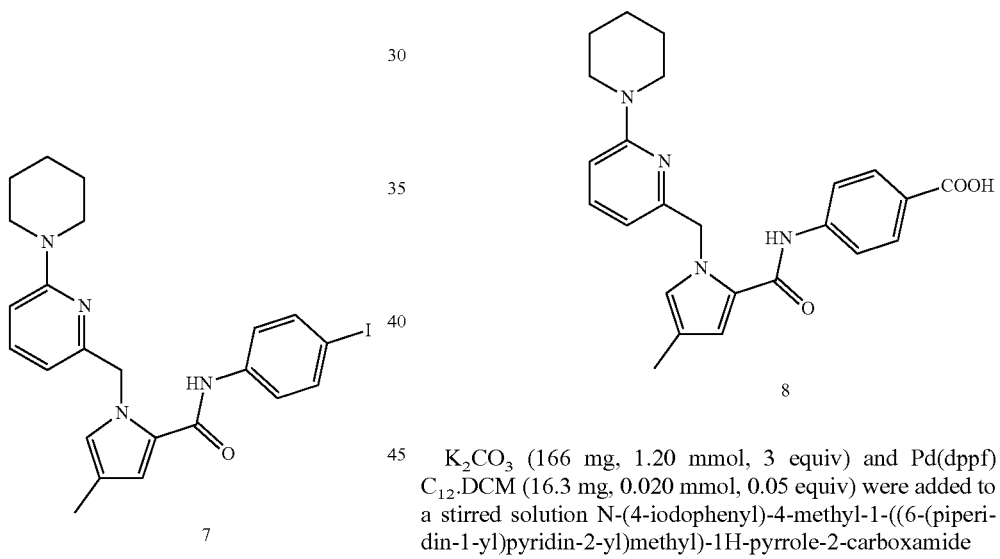

TEA (304 mg, 3.01 mmol, 3 equiv), HATU (572 mg, 1.50 mmol, 1.5 equiv) and 4-iodoaniline (264 mg, 1.20 mmol, 1.2 equiv) were added to a stirred solution of 4-methyl-1-((6-(piperidin-1-yl)pyridin-2-yl)methyl)-1H-pyrrole-2-carboxylic acid (6) (300 mg, 1.0 mmol, 1 equiv) in DMF (5 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×30 mL). The combined organic layers were washed with water (2×40 mL), brine (40 mL), dried over $Na_2SO_4$, filtered and concentrated. The crude product was purified by silica gel column chromatography (20% ethyl acetate-hexanes) to provide compound 7 as a white solid (200 mg, 40%).

LC-MS (ESI$^+$): m/z 501.0 (M+H)$^+$ $K_2CO_3$ (166 mg, 1.20 mmol, 3 equiv) and Pd(dppf)C$_{12}$.DCM (16.3 mg, 0.020 mmol, 0.05 equiv) were added to a stirred solution N-(4-iodophenyl)-4-methyl-1-((6-(piperidin-1-yl)pyridin-2-yl)methyl)-1H-pyrrole-2-carboxamide (7) (200 mg, 0.400 mmol, 1 equiv) in dioxane (5 mL) and $H_2O$ (5 mL) at ambient temperature. The reaction mixture was heated to 90° C. and stirred for 5 h under 3 atm CO. The reaction mixture was cooled to ambient temperature and then concentrated under vacuum. The residue was acidified with 1.5 M hydrochloric acid and the resulting mixture was extracted with DCM (2×40 mL). The combined organic layers were washed with water (40 mL), brine (40 mL), dried over $Na_2SO_4$, filtered through celite bed and concentrated. The crude product was purified by Prep HPLC (0-50% $CH_3CN$—$H_2O$) to provide compound 8 (A-16) as a white solid (10.0 mg, 6%).

LC-MS (ESI$^+$): m/z 419.2 (M+H)$^+$

1H-NMR (400 MHz, DMSO-d6): δ 12.73 (brs, 1H), 9.98 (s, 1H), 7.88-7.83 (m, 2H), 7.81-7.77 (m, 2H), 7.41-7.34 (m, 1H), 6.94 (d, J=5.7 Hz, 2H), 6.62 (d, J=8.5 Hz, 1H), 5.98 (d, J=7.2 Hz, 1H), 5.43 (s, 2H), 3.45-3.42 (m, 4H), 2.07 (s, 3H), 1.59-1.51 (m, 2H), 1.50-1.44 (m, 4H).

Synthesis of Compound A-67

Preparation of N-(4-(1H-tetrazol-5-yl)phenyl)-4-methyl-1-((6-(piperidin-1-yl)pyridin-2-yl)methyl)-1H-pyrrole-2-carboxamide

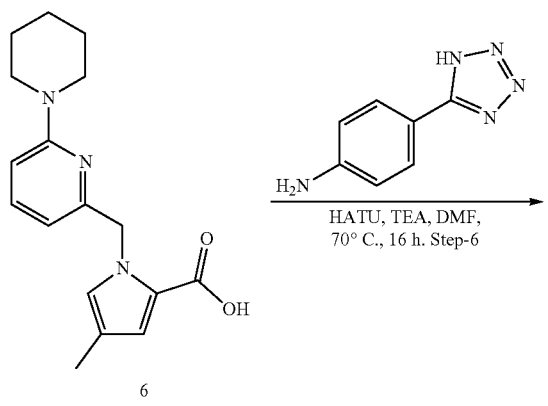

Example 2e: Synthesis of Compound A-11

General Scheme:

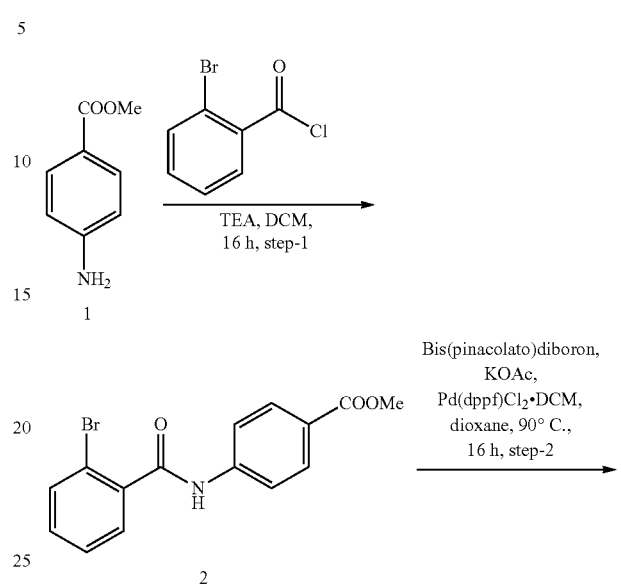

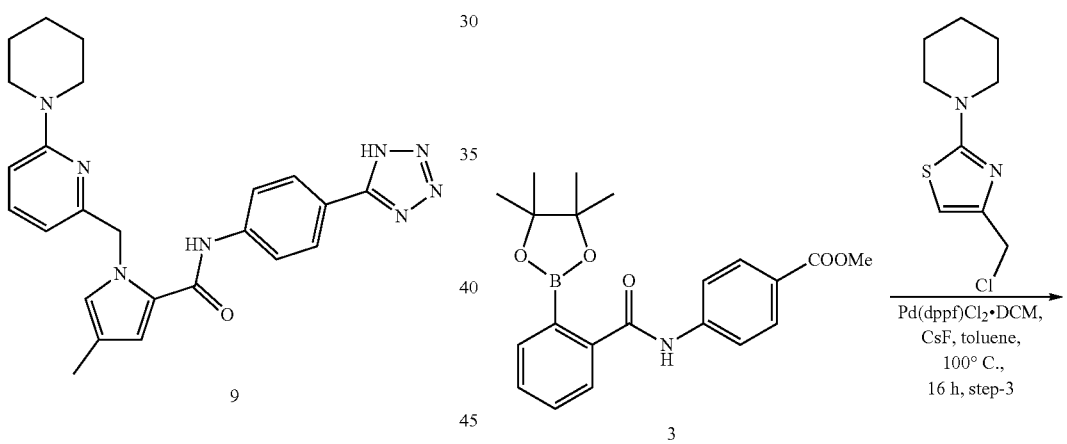

TEA (608 mg, 6.02 mmol, 3 equiv), HATU (1.52 g, 4.01 mmol, 2 equiv) and 4-(1H-tetrazol-5-yl)aniline (484 mg, 3.01 mmol, 1.5 equiv) were added to a stirred solution of 4-methyl-1-((6-(piperidin-1-yl)pyridin-2-yl)methyl)-1H-pyrrole-2-carboxylic acid (6) (600 mg, 2.01 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×40 mL). The combined organic layers were washed with water (2×40 mL), brine (40 mL), dried over $Na_2SO_4$, filtered and concentrated. The crude product was purified by Prep HPLC (0-50% $CH_3CN$—$H_2O$) to provide compound 9 (A-67) as a pale brown solid (40.0 mg, 5%).

LC-MS (ESI+): m/z 442.8 (M+H)+

1H-NMR (400 MHz, DMSO-d6): δ 10.06 (s, 1H), 7.99-7.89 (m, 4H), 7.62 (s, 1H), 6.98 (d, J=7.6 Hz, 2H), 6.73 (s, 1H), 6.04 (s, 1H), 5.47 (s, 2H), 3.53-3.44 (m, 4H), 2.08 (s, 3H), 1.59-1.50 (m, 6H).

-continued

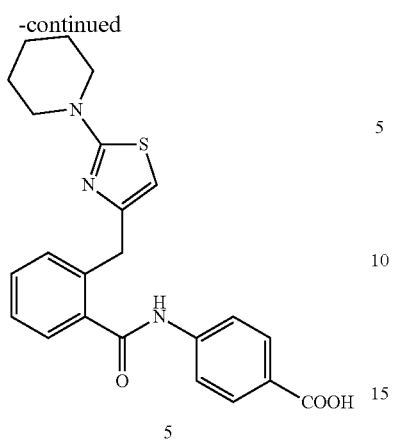

5

Preparation of Methyl 4-(2-bromobenzamido)benzoate

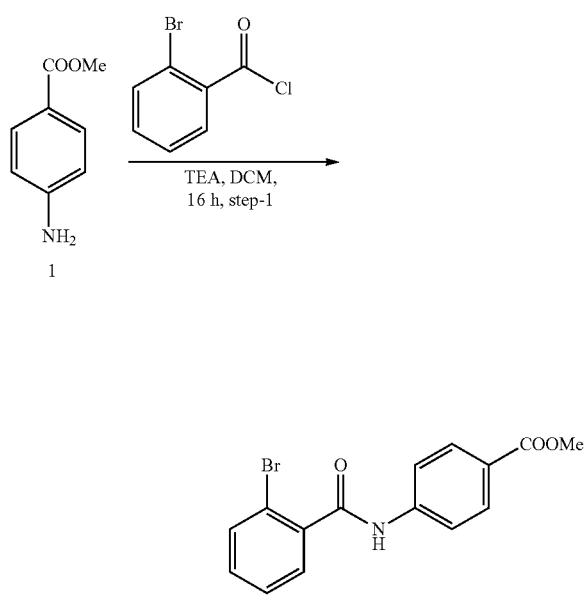

2-Bromobenzoyl chloride (4.14 g, 0.019 mol, 1 equiv) was added to a stirred solution of methyl 4-aminobenzoate (1) (3.0 g, 0.019 mol, 1 equiv) and TEA (5.75 g, 0.057 mol, 3 equiv) in DCM (50 mL) at 0° C. The reaction mixture was allowed to warm to ambient temperature and stirred for 16 h. The reaction mixture was diluted with DCM (150 mL) and washed with water (100 mL), brine (100 mL), dried over Na$_2$SO$_4$, filtered and concentrated under vacuum. The crude product was purified by silica gel column chromatography (20% ethyl acetate-hexanes) to provide compound 2 as a pale brown solid (4.0 g, 63%).

LC-MS (ESI$^+$): m/z 335.8 (M+H)$^+$

1H-NMR (400 MHz, DMSO-d6): δ 10.86 (s, 1H), 7.98 (d, J=8.8 Hz, 2H), 7.87 (d, J=8.8 Hz, 2H), 7.75 (d, J=8.0 Hz, 1H), 7.61-7.59 (m, 1H), 7.54-7.50 (m, 1H), 7.47-7.45 (m, 1H), 3.85 (s, 3H).

Preparation of Methyl 4-(2-(4,4,5,5-tetramethyl-1,3,2-dioxaborolan-2-yl)benzamido)benzoate

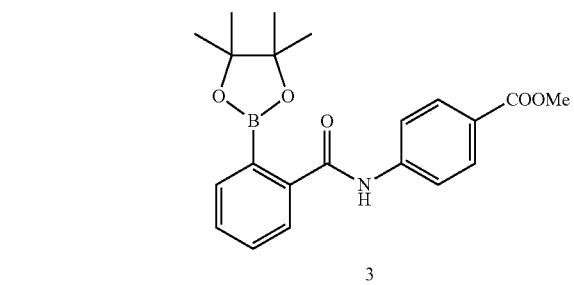

Bis(pinacolato)diboron (3.35 g, 0.013 mol, 1.1 equiv), potassium acetate (2.35 g, 0.024 mol, 2 equiv) and Pd(dppf)Cl$_2$.DCM (0.970 g, 1.18 mmol, 0.1 equiv) were added to a stirred solution methyl 4-(2-bromobenzamido)benzoate (2) (4.0 g, 0.012 mol, 1 equiv) in dioxane (60 mL) at ambient temperature. The reaction mixture was degassed for 5 min. with N$_2$ gas and heated to 90° C. and stirred for 16 h. The reaction mixture was cooled to ambient temperature and then filtered through celite bed and concentrated under vacuum to provide compound 3 as a brown gummy solid (5.0 g) without further purification.

Preparation of Methyl 4-(2-((2-(piperidin-1-yl)thiazol-4-yl)methyl)benzamido) benzoate

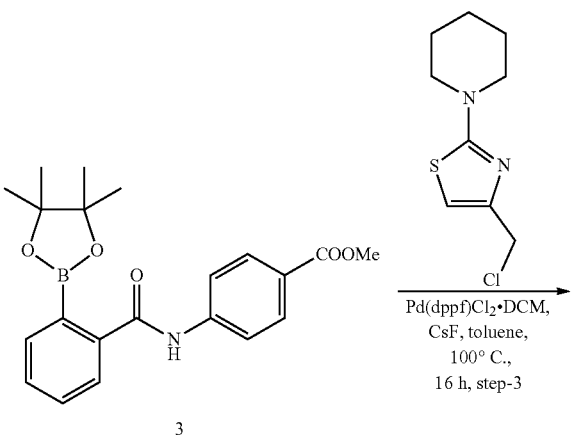

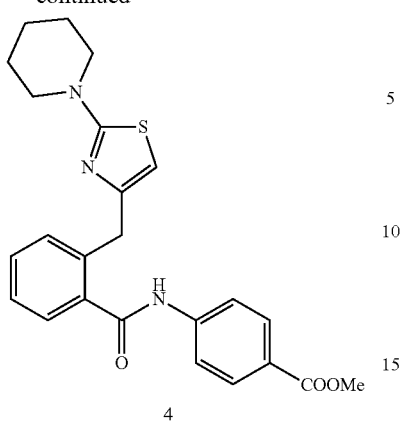

4

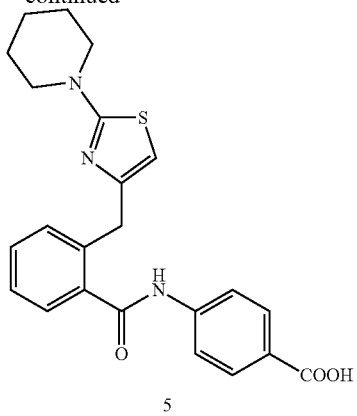

5

Methyl 4-(2-(4,4,5,5-tetramethyl-1,3,2-dioxaborolan-2-yl)benzamido)benzoate (3) (3.50 g, 9.18 mmol, 2 equiv), CsF (2.09 g, 0.013 mol, 3 equiv), Pd(dppf)Cl$_2$.DCM (320 mg, 0.40 mol, 0.1 equiv) were added to a stirred solution 4-(chloromethyl)-2-(piperidin-1-yl)thiazole (1.0 g, 4.61 mmol, 1 equiv) in toluene at ambient temperature. The reaction mixture was degassed for 5 min. with N$_2$ gas and heated to 100° C. and stirred for 16 h. The reaction mixture was cooled to ambient temperature and then concentrated under vacuum. The residue was diluted with water and the resulting mixture was extracted with ethyl acetate (2×75 mL), and the combined organic layers were washed with water (100 mL), brine (100 mL), dried over Na$_2$SO$_4$, filtered and concentrated under vacuum. The crude product was purified by silica gel column chromatography (20% ethyl acetate-hexanes) to provide compound 4 as a pale brown solid (600 mg, 16%).

LC-MS (ESI$^+$): m/z 436.3 (M+H)$^+$

Preparation of 4-(2-((2-(piperidin-1-yl)thiazol-4-yl)methyl)benzamido)benzoic Acid

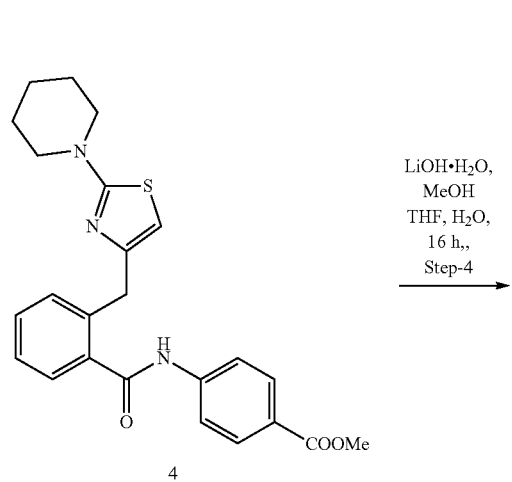

LiOH·H$_2$O (174 mg, 4.13 mmol, 3 equiv) was added to a stirred solution of methyl 4-(2-((2-(piperidin-1-yl)thiazol-4-yl)methyl)benzamido)benzoate (4) (600 mg, 1.38 mmol, 1 equiv) in THF (2 mL), MeOH (2 mL) and H$_2$O (2 mL) at ambient temperature. The reaction mixture was stirred for 16 h, and then concentrated under vacuum. The residue was acidified with 1.5 M hydrochloric acid and the resulting mixture was extracted with DCM (2×50 mL). The combined organic layers were washed with water (50 mL), brine (50 mL), dried over Na$_2$SO$_4$, filtered and concentrated. The crude product was purified by Prep HPLC (0-40% CH$_3$CN—H$_2$O) to provide compound 5 (A-11) as an off-white solid (58.0 mg, 10%).

LC-MS (ESI$^+$): m/z 422.0 (M+H)$^+$

1H-NMR (400 MHz, DMSO-d6): δ 10.82 (s, 1H), 7.93-7.87 (m, 2H), 7.83-7.78 (m, 2H), 7.55-7.50 (m, 1H), 7.44-7.40 (m, 1H), 7.37-7.30 (m, 2H), 6.33 (s, 1H), 4.02 (s, 2H), 3.29-3.23 (m, 4H), 1.53-1.44 (m, 6H).

Example 2f: Synthesis of Compound A-50

Preparation of 4-(chloromethyl)-2-(piperidin-1-yl)thiazole

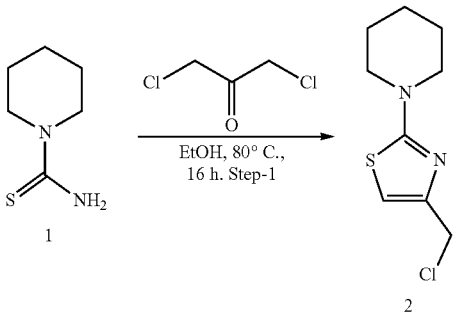 [SMILES: NC(=S)N1CCCCC1 ; O=C(CCl)CCl ; ClCc1csc(N2CCCCC2)n1]

1,3-Dichloroacetone (17.5 g, 0.139 mol, 1 equiv) was added to a stirred solution of piperidine-1-carbothioamide (1) (20.0 g, 0.139 mol, 1 equiv) in EtOH (400 mL) at ambient temperature. The reaction mixture was stirred at 90° C. for 16 h, and then cooled to ambient temperature. The resultant mixture was concentrated under vacuum. The residue was basified with 10% NaHCO$_3$ aqueous solution and extracted with DCM (2×200 mL). The combined organic layer was washed with water (200 mL), brine (200 mL), dried over Na$_2$SO$_4$, filtered and concentrated under vacuum. The crude product was purified by silica gel column chromatography (10% ethyl acetate-hexanes) to provide compound 2 as a colorless liquid (15.0 g, 50%).

LC-MS (ESI$^+$): m/z 217.3 (M+H)$^+$

1H-NMR (400 MHz, DMSO-d6): δ 6.84 (s, 1H), 4.55 (s, 2H), 3.39-3.35 (m, 4H), 1.59-1.53 (m, 6H).

Preparation of 4-(hydrazinylmethyl)-2-(piperidin-1-yl)thiazole

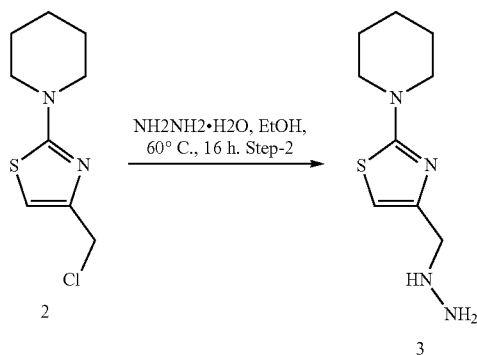 [SMILES: ClCc1csc(N2CCCCC2)n1 ; NNCc1csc(N2CCCCC2)n1]

NH$_2$NH$_2$—H$_2$O (5.78 g, 0.115 mol, 5 equiv) was added to a stirred solution of 4-(chloromethyl)-2-(piperidin-1-yl) thiazole (2) (5.0 g, 0.023 mol, 1 equiv) in EtOH (100 mL) at ambient temperature. The reaction mixture was stirred at 60° C. for 16 h, and then cooled to ambient temperature. The resultant mixture was concentrated under vacuum, azeotroped with toluene to provide compound 3 as a pale brown liquid (6.0 g, crude) without further purification.

LC-MS (ESI$^+$): m/z 213.3 (M+H)$^+$

Preparation of Methyl 3-methyl-1-((2-(piperidin-1-yl)thiazol-4-yl)methyl)-1H-pyrazole-5-carboxylate

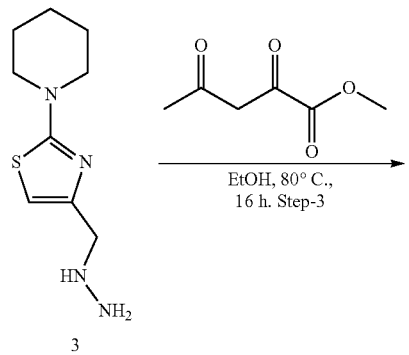

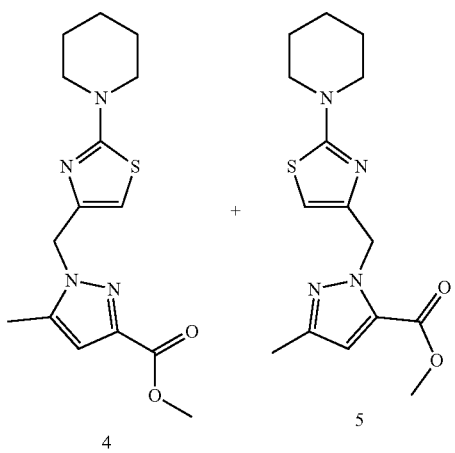

Methyl 2,4-dioxopentanoate (4.48 g, 0.031 mol, 1.1 equiv) was added to a stirred solution of 4-(hydrazinylmethyl)-2-(piperidin-1-yl)thiazole (3) (6.0 g, 0.028 mol, 1 equiv) in EtOH (100 mL) at ambient temperature. The reaction mixture was stirred at 80° C. for 16 h, and then cooled to ambient temperature. The resultant mixture was concentrated under vacuum. The residue was basified with 10% NaHCO$_3$ aqueous solution and the resulting mixture was extracted with DCM (2×150 mL). The combined organic layers were washed with water (150 mL), brine (150 mL), dried over Na$_2$SO$_4$, filtered and concentrated under vacuum. The residue was purified by silica gel column chromatography (40% ethyl acetate-hexanes) to provide compound 5 as a white solid (1.20 g, 13%).

LC-MS (ESI$^+$): m/z 321.1 (M+H)$^+$

1H-NMR (400 MHz, DMSO-d6): δ 6.68 (s, 1H), 6.17 (s, 1H), 5.44 (s, 2H), 3.79 (s, 3H), 3.35-3.33 (m, 4H), 2.18 (s, 3H), 1.56-1.52 (m, 6H).

Preparation of 3-methyl-1-((2-(piperidin-1-yl)thiazol-4-yl)methyl)-1H-pyrazole-5-carboxylic Acid

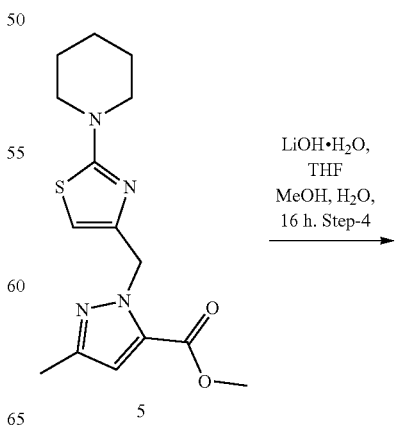

193
-continued

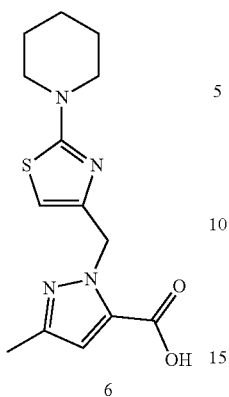

6

LiOH.H₂O (460 mg, 0.011 mol, 3 equiv) was added to a stirred solution of methyl 3-methyl-1-((2-(piperidin-1-yl)thiazol-4-yl)methyl)-1H-pyrazole-5-carboxylate (5) (1.20 g, 3.74 mmol, 1 equiv) in THF (10 mL), MeOH (10 mL) and H₂O (10 mL) at ambient temperature. The reaction mixture was stirred for 16 h, and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered and concentrated under vacuum to provide compound 6 as a white solid (1.0 g, 87%) without further purification.

LC-MS (ESI⁺): m/z 307.1 (M+H)⁺

1H-NMR (300 MHz, DMSO-d6): δ 13.21 (s, 1H), 6.61 (s, 1H), 6.07 (s, 1H), 5.47 (s, 2H), 3.35-3.33 (m, 4H), 2.17 (s, 3H), 1.56-1.52 (m, 6H).

194
-continued

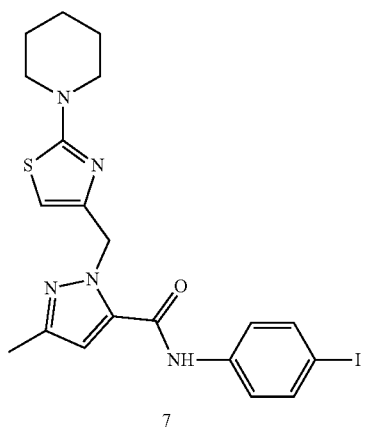

7

TEA (969 mg, 9.58 mmol, 3 equiv), HATU (1.82 g, 4.78 mmol, 1.5 equiv) and 4-iodoaniline (850 mg, 3.88 mmol, 1.2 equiv) were added to a stirred solution of 3-methyl-1-((2-(piperidin-1-yl)thiazol-4-yl)methyl)-1H-pyrazole-5-carboxylic acid (6) (1.0 g, 3.26 mmol, 1 equiv) in DMF (10 mL) at ambient temperature. The reaction mixture was heated to 70° C. and stirred for 16 h. The reaction mixture was cooled to ambient temperature and then concentrated under vacuum. The residue was diluted with water and the resulting mixture was extracted with ethyl acetate (2×50 mL). The combined organic layers were washed with water (2×50 mL), brine (50 mL), dried over Na₂SO₄, filtered and concentrated. The crude product was purified by silica gel column chromatography (40% ethyl acetate-hexanes) to provide compound 7 as a pale brown solid (300 mg, 18%).

LC-MS (ESI⁺): m/z 507.9 (M+H)⁺

Preparation of N-(4-iodophenyl)-3-methyl-1-((2-(piperidin-1-yl)thiazol-4-yl)methyl)-1H-pyrazole-5-carboxamide Preparation of 4-(3-methyl-1-((2-(piperidin-1-yl)thiazol-4-yl)methyl)-1H-pyrazole-5-carboxamido)benzoic Acid

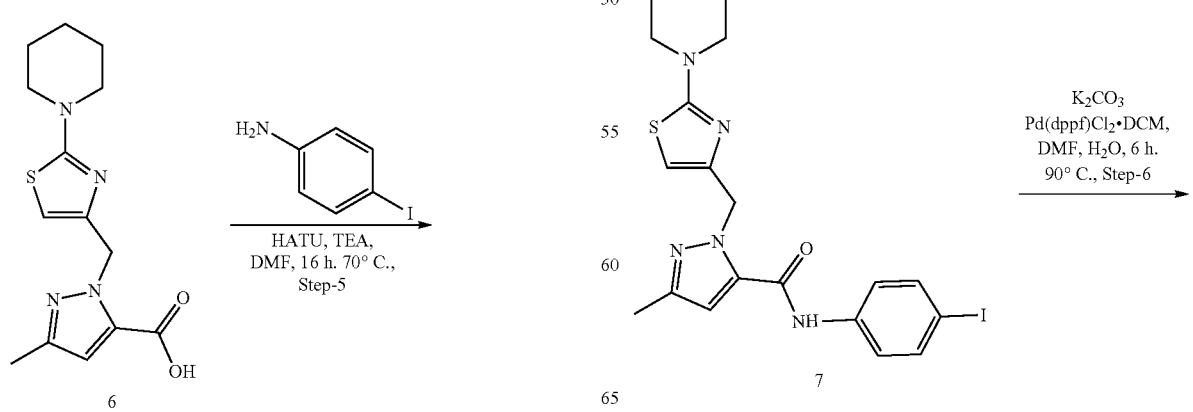

-continued

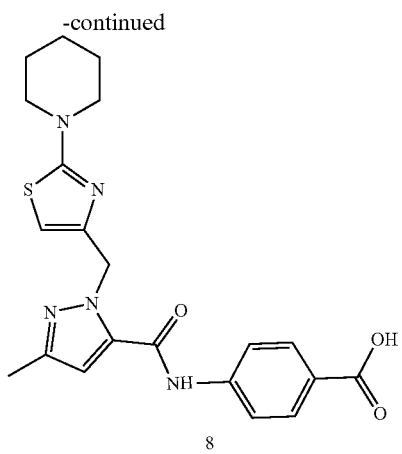

8

K₂CO₃ (245 mg, 1.77 mmol, 3.0 equiv) and Pd(dppf)Cl₂.DCM (48.2 mg, 0.059 mmol, 0.1 equiv) were added to a stirred solution N-(4-iodophenyl)-3-methyl-1-((2-(piperidin-1-yl)thiazol-4-yl)methyl)-1H-pyrazole-5-carboxamide (7) (300 mg, 0.591 mmol, 1 equiv) in DMF (10 mL) and H₂O (3 mL) at ambient temperature. The reaction mixture was heated to 90° C. and stirred for 6 h under 3 atm CO. The reaction mixture was cooled to ambient temperature and then concentrated under vacuum. The residue was acidified with 1.5 M hydrochloric acid and the resulting mixture was extracted with DCM (2×50 mL). The combined organic layers were washed with water (50 mL), brine (50 mL), dried over Na₂SO₄, filtered through celite bed and concentrated. The crude product was purified by Prep HPLC (0-50% CH₃CN—H₂O) to provide compound 8 (A-50) as a white solid (55.0 mg, 36%).

LC-MS (ESI⁺): m/z 426.1 (M+H)⁺

1H-NMR (400 MHz, DMSO-d6): δ 12.78 (s, 1H), 10.56 (s, 1H), 7.93 (d, J=7.3 Hz, 2H), 7.86 (d, J=7.3 Hz, 2H), 6.79 (s, 1H), 6.32 (s, 1H), 5.46 (s, 2H), 3.30-3.21 (m, 4H), 2.22 (s, 3H), 1.55-1.45 (m, 6H).

A-53

4-(4-Amino-1-((2-(piperidin-1-yl)thiazol-4-yl)methyl)-1H-pyrrole-2-carboxamido)benzoic acid This compound was prepared according to methods described above for the other compounds substituting appropriate starting materials.

LC-MS (ESI⁺): m/z 426.2 (M+H)⁺

¹H-NMR (400 MHz, DMSO-d₆, TFA salt): δ 12.77 (brs, 1H), 10.29 (brs, 1H), 9.75 (m, 2H), 7.92 (m, 2H), 7.83 (m, 2H), 7.27 (s, 1H), 7.05 (s, 1H), 6.40 (s, 1H), 5.44 (s, 2H), 3.31 (m, 4H), 1.53 (m, 6H).

A-54

3-Methyl-4-(4-methyl-1-((2-(piperidin-1-yl)thiazol-4-yl)methyl)-1H-pyrrole-2-carboxamido)benzoic acid This compound was prepared according to methods described above for the other compounds substituting appropriate starting materials.

LC-MS (ESI⁺): m/z 439.2 (M+H)⁺

¹H-NMR (400 MHz, DMSO-d6): δ 9.41 (s, 1H), 7.82 (s, 1H), 7.76 (m, 1H), 7.54 (m, 1H), 6.89 (m, 2H), 6.23 (s, 1H), 5.35 (s, 2H), 3.38 (m, 4H), 2.27 (s, 3H), 2.05 (s, 3H), 1.57-1.45 (m, 6H).

A-68

4-(3,4-dimethyl-1-((2-(piperidin-1-yl)thiazol-4-yl)methyl)-1H-pyrrole-2-carboxamido)benzoic acid This compound was prepared according to methods described above for the other compounds substituting appropriate starting materials.

LC-MS (ESI⁺): m/z 439.3 (M+H)⁺

¹H-NMR (400 MHz, DMSO-d6): δ 10.21 (s, 1H), 7.89 (dd, J=8.80 Hz, 2H), 7.79 (dd, J=8.80 Hz, 2H), 6.78 (s, 1H), 6.40 (s, 1H), 5.10 (s, 2H), 3.42-3.36 (m, 4H), 2.10 (s, 3H), 1.93 (s, 3H), 1.57-1.45 (m, 6H).

What is claimed is:

1. A compound represented by the following structural formula:

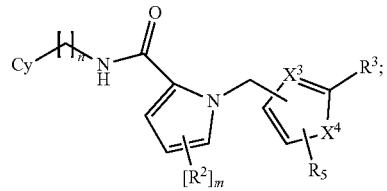

or a pharmaceutically acceptable salt thereof, wherein:
Cy is an optionally substituted ($C_6$-$C_{10}$) carbocyclic aromatic group, optionally substituted ($C_3$-$C_{10}$)cycloaliphatic group, optionally substituted 5-10 membered non-aromatic heterocyclic group, or an optionally substituted 5-10 membered heteroaryl group;
wherein the optionally substituted ($C_6$-$C_{10}$) carbocyclic aromatic group, the optionally substituted ($C_3$-$C_{10}$) cycloaliphatic group, the optionally substituted 5-10 membered non-aromatic heterocyclic group or the optionally substituted 5-10 membered heteroaryl group represented by Cy are each optionally and independently substituted with one or more groups represented by $R^9$, wherein:
i) $R^9$ is selected from halo, —CN, —NO₂, —OR$^a$, —NR$^b$R$^c$, —S(O)$_i$R$^a$, —C(=NR$^a$)NR$^b$R$^c$, —NR$^a$S(O)₂R$^b$, —S(O)₂NR$^b$R$^c$, —S(O)₂(NR$^a$)C(=O)R$^b$, —C(=O)OR$^a$, —OC(=O)OR$^a$, —C(=S)OR$^a$, —O(C=S)R$^a$, —C(=O)NR$^b$R$^c$, —NR$^a$C(=O)R$^b$, —C(=S)NR$^b$R$^c$, —NR$^a$C(=S)R$^b$, —NR$^a$(C=O) OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR$^a$(C=S)NR$^b$R$^c$, —C(=S)R$^a$, —C(=O)R$^a$, ($C_1$-$C_5$) alkyl, ($C_1$-$C_5$)hydroxyalkyl, ($C_1$-$C_5$)methoxyalkyl, phenyl, —CH₂=CH(phenyl), monocyclic heteroaryl group and monocyclic non-aromatic heterocyclic group; or
ii) two $R^9$ groups bonded to adjacent ring carbon atoms of the carbocyclic aromatic group represented by Cy form —OCH₂CH₂—, —OCH₂CH₂CH₂—, —NHCH₂CH₂—, —NHCH₂CH₂CH₂— or —NHC(O)CH₂—; and
wherein the ($C_1$-$C_5$)alkyl, phenyl, monocyclic heteroaryl group and monocyclic non-aromatic heterocyclic groups in the substituents represented by Cy are optionally and independently substituted with one or more groups selected from halo, methoxy, —COOH, halomethoxy, methyl, and =O (for a non-aromatic heterocyclic group);

i is 0, 1, or 2; and $R^{a-c}$ are each independently selected from —H and $(C_1-C_5)$alkyl;

n is 0 or 1;

$R^2$ is —H, $(C_1-C_5)$alkyl, —$NO_2$, —$NH_2$, $(C_2-C_5)$acyl, $(C_1-C_5)$hydroxyalkyl, $(C_1-C_5)$methoxyalkyl, halo, cyano or phenyl wherein the phenyl represented by $R^2$ is optionally substituted by methyl, halo, methoxy, or halomethoxy;

m is 1 or 2;

$X_3$ is N or $CR^5$;

$X_4$ is O, S, or —CH=CH—;

each $R^5$ independently is —H or —$CH_3$;

$R^3$ is —$NR^6R^7$, optionally substituted phenyl, optionally substituted monocyclic nitrogen-containing heteroaryl group, or optionally substituted $(C_3-C_8)$cycloaliphatic group;

$R^6$ and $R^7$ are each independently $(C_1-C_5)$alkyl or —$NR^6R^7$ taken together is a 5-7 membered optionally substituted monocyclic non-aromatic heterocyclic group;

wherein the optionally substituted phenyl, the optionally substituted monocyclic nitrogen-containing heteroaryl group and the optionally substituted cycloaliphatic group represented by $R^3$ and the optionally substituted 5-7 membered monocyclic non-aromatic heterocyclic group represented by —$NR^6R^7$ are each optionally and independently substituted with one or more groups represented by $R^8$, wherein:

i) $R^8$ is selected from -halo, —CN, —$NO_2$, —$OR^a$, —$NR^bR^c$, —$S(O)_iR^a$, —$C(=NR^a)NR^bR^c$, —$NR^aS(O)_2R^b$, —$S(O)_2NR^bR^c$, —$C(=O)OR^a$, —$OC(=O)OR^a$, —$C(=S)OR^a$, —$O(C=S)R^a$, —$C(=O)NR^bR^c$, —$NR^aC(=O)R^b$, —$C(=S)NR^bR^c$, —$NR^aC(=S)R^b$, —$NR^a(C=O)OR^b$, —$O(C=O)NR^bR^c$, —$NR^a(C=S)OR^b$, —$O(C=S)NR^bR^c$, —$NR^a(C=O)NR^bR^c$, —$NR^a(C=S)NR^bR^c$, —$C(=S)R^a$, —$C(=O)R^a$, halo$(C_1-C_5)$alkyl, and $(C_1-C_5)$alkyl, or ii) two $R^8$ groups bonded to adjacent ring carbon atoms of the phenyl group represented by $R^3$ form —$OCH_2CH_2$—, —$OCH_2CH_2CH_2$—, —$NHCH_2CH_2$—, —$NHCH_2CH_2CH_2$— or —$NHC(O)CH_2$—.

2. The compound of claim 1, wherein the compound is represented by the following structural formula:

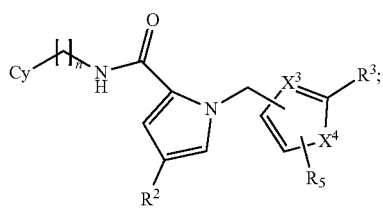

or a pharmaceutically acceptable salt thereof.

3. The compound of claim 1, wherein the compound is represented by a structural formula selected from:

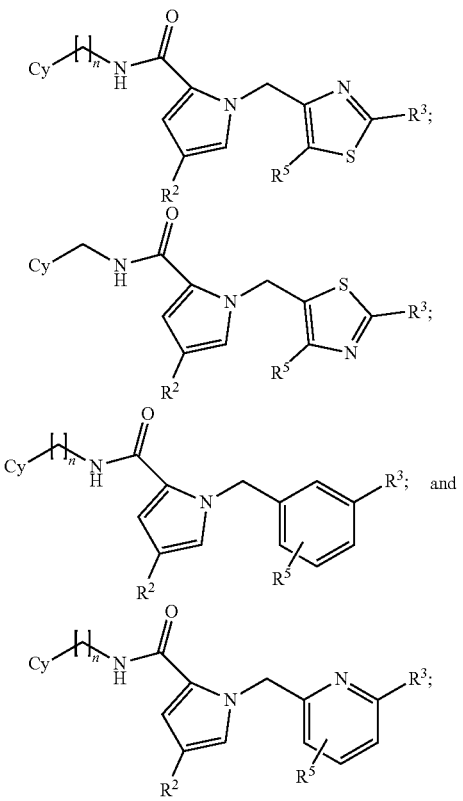

or a pharmaceutically acceptable salt thereof.

4. The compound of claim 1, wherein the compound is represented by a structural formula selected from:

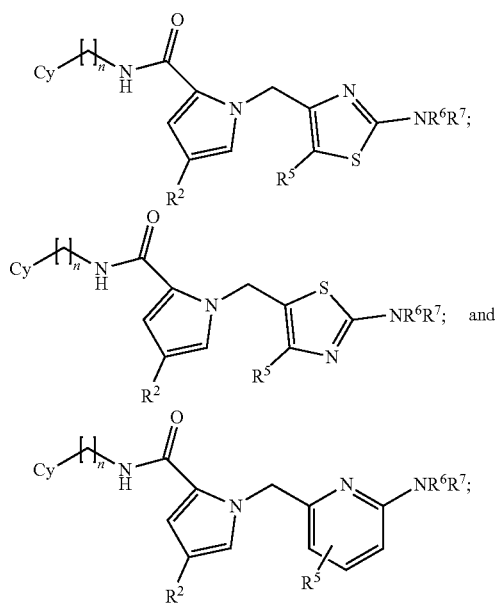

or a pharmaceutically acceptable salt thereof.

5. The compound of claim 1 or a pharmaceutically acceptable salt thereof, wherein:

Cy is

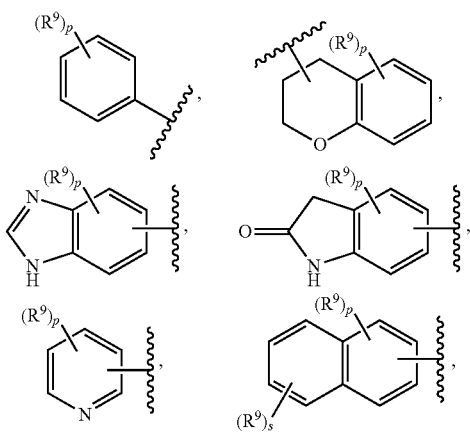

(C$_3$-C$_8$)cycloalkyl or tetrahydropyranyl;
R$^9$ is selected from halo, —CN, —NO$_2$, —OR$^a$, —NR$^b$R$^c$, —S(O)$_j$R$^a$, —C(=NR$^a$)NR$^b$R$^c$, —NR$^a$S(O)$_2$R$^b$, —S(O)$_2$NR$^b$R$^c$, —S(O)$_2$(NR$^a$)C(=O)R$^b$, —C(=O)OR$^a$, —OC(=O)OR$^a$, —C(=S)OR$^a$, —O(C=S)R$^a$, —C(=O)NR$^b$R$^c$, —NR$^a$C(=O)R$^b$, —C(=S)NR$^b$R$^c$, —NR$^a$C(=S)R$^b$, —NR$^a$(C=O)OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR$^a$(C=S)NR$^b$R$^c$, —C(=S)R$^a$, —C(=O)R$^a$, (C$_1$-C$_5$)alkyl, (C$_1$-C$_5$)hydroxyalkyl, (C$_1$-C$_5$)methoxyalkyl, phenyl, —CH$_2$=CH(phenyl), monocyclic heteroaryl group and monocyclic non-aromatic heterocyclic group; and wherein the (C$_1$-C$_5$) alkyl, phenyl, monocyclic heteroaryl group and monocyclic non-aromatic heterocyclic groups in the substituents represented by Cy are optionally and independently substituted with one or more groups selected from halo, methoxy, halomethoxy, methyl, —COOH and =O (for a non-aromatic heterocyclic group);
the (C$_3$-C$_8$)cycloalkyl and tetrahydropyranyl are optionally and independently substituted with methyl or —COOH;
p is 0, 1, 2 or 3; and
s and r are each independently 0, 1, 2 or 3 and s+r are <3.
6. The compound of claim 5, or a pharmaceutically acceptable salt thereof, wherein n is 0.
7. The compound of claim 5, or a pharmaceutically acceptable salt thereof, wherein n is 1.
8. The compound of claim 5, or a pharmaceutically acceptable salt thereof, wherein
—NR$^6$R$^7$ is

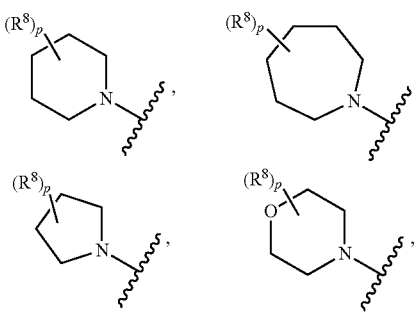

and p is 0, 1, 2 or 3, or wherein R$^6$ and R$^7$ are independently hydrogen or C$_1$-C$_3$ alkyl.
9. The compound of claim 8, or a pharmaceutically acceptable salt thereof, wherein each R$^8$ is independently methyl, or fluoro.
10. The compound of claim 5, or a pharmaceutically acceptable salt thereof, wherein:
R$^3$ is

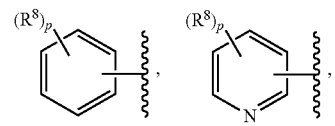

pyrazolyl, or (C$_3$-C$_8$)cycloaliphatic;
each R$^8$ is independently selected from -halo, —CN, —NO$_2$, —OR$^a$, —NR$^b$R$^c$, —S(O)R$^a$, —C(NR$^a$)NR$^b$R$^c$, —NR$^a$S(O)$_2$R$^b$, —S(O)$_2$NR$^b$R$^c$, —C(=O)OR$^a$, —OC(=O)OR$^a$, —C(=S)OR$^a$, —O(C=S)R$^a$, —C(=O)NR$^b$R$^c$, —NR$^a$C(=O)R$^b$, —C(=S)NR$^b$R$^c$, —NR$^a$C(=S)R$^b$, —NR$^a$(C=O)OR$^b$, —O(C=O)NR$^b$R$^c$, —NR$^a$(C=S)OR$^b$, —O(C=S)NR$^b$R$^c$, —NR$^a$(C=O)NR$^b$R$^c$, —NR$^a$(C=S)NR$^b$R$^c$, —C(=S)R$^a$, —C(=O)R$^a$, halo(C$_1$-C$_5$)alkyl and (C$_1$-C$_5$)alkyl;
the pyrazolyl, the (C$_3$-C$_8$)cycloaliphatic are each optionally and independently substituted with methyl; and
p is 0, 1, 2 or 3.
11. The compound of claim 10, or a pharmaceutically acceptable salt thereof, wherein each R$^8$ is independently (C$_1$-C$_5$)alkyl, —OR$^a$, —S(O)$_2$NR$^b$R$^c$, —NR$^a$S(O)$_2$R$^b$, —C(=O)NR$^b$R$^c$, —NR$^a$C(=O)R$^b$, —C(=O)OR$^a$, —C(=S)OR$^a$, —C(=S)NR$^b$R$^c$ or —NR$^a$C(=S)R$^b$.
12. The compound of claim 10, or a pharmaceutically acceptable salt thereof, wherein each R$^8$ is independently methyl, —NHSO$_2$CH$_3$, —OCH$_3$, or —C(=O)NH$_2$.
13. The compound of claim 12, or a pharmaceutically acceptable salt thereof, wherein:
each R$^9$ is independently halo, (C$_1$-C$_3$)alkyl, —OR$^a$, (C$_1$-C$_3$)hydroxyalkyl, —S(O)$_2$NR$^b$R$^c$, —NR$^a$S(O)$_2$R$^b$, —C(=O)NR$^b$R$^c$, —NR$^a$C(=O)R$^b$, —C(=S)NR$^b$R$^c$ or —NR$^a$C(=S)R$^b$, —S(O)$_2$(NR$^a$)C(=O)R$^b$, —C(=O)OH, —C(=S)OH, —CH$_2$=CH(phenyl), phenyl optionally substituted with -methyl, or succinimidyl or 5-6 membered monocyclic heteroaryl group optionally substituted with one or more methyl groups.
14. The compound of claim 12, or a pharmaceutically acceptable salt thereof, wherein:
R$^2$ is —H, —CH$_3$, —CH$_2$CH$_3$, —NO$_2$, —NH$_2$, Cl, Br, —CN, —CH(CH$_3$)OH, —C(=O)CH$_3$, —CH(CH$_3$)OCH$_3$, or phenyl; and
each R$^9$ is independently F, I, —CH$_3$, —OH, —C(=O)OH, —C(O)NHCH$_3$, —CH$_2$OH, —S(O)$_2$NH$_2$, —S(O)$_2$(NH)C(=O)CH$_3$, isoxazolyl optionally substituted with one or two methyl groups, pyridyl, pyrazolyl, furanyl, tetrazolyl, —CH$_2$=CH(phenyl) or phenyl optionally substituted with methyl or —COOH.
15. The compound of claim 12, or a pharmaceutically acceptable salt thereof, wherein:
R$^2$ is Br, Cl, —CH$_3$, —CH$_2$CH$_3$, or phenyl; and
each R$^9$ is independently F, methyl, —C(=O)OH, —C(O)NHCH$_3$, isoxazolyl optionally substituted with one or two methyl groups, pyrazolyl, furanyl, tetrazolyl, or S(O)$_2$(NH)C(=O)CH$_3$.

16. A pharmaceutical composition comprising a pharmaceutically acceptable carrier or excipient and the compound of claim 1, or a pharmaceutically acceptable salt thereof.

17. A method of treating a subject with a disease that can be ameliorated by inhibition of Dynamin-1-like protein (Drp1), comprising administering an effective amount of a compound of claim 1, or a pharmaceutically acceptable salt thereof.

18. A method of treating a subject with acute kidney injury, comprising administering to the subject an effective amount of the compound of claim 1, or a pharmaceutically acceptable salt thereof.

19. The method of claim 17, wherein the disease which can be ameliorated by inhibition of Drp1 is a muscle structure disorder, a neuronal activation disorder, a muscle fatigue disorder, a muscle mass disorder, a beta oxidation disease, a metabolic disease, a cancer, a vascular disease, an ocular vascular disease, a muscular eye disease, or a renal disease.

20. The method of claim 17, wherein the disease which can be ameliorated by inhibition of Drp1 is selected from genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, sarcopenia, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

21. A compound, wherein the compound is

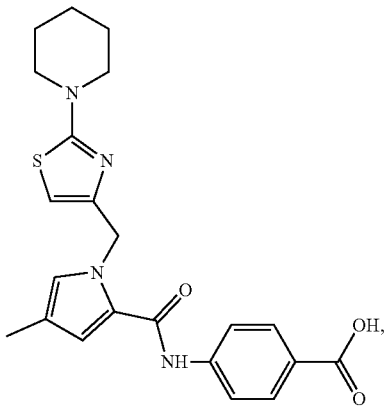 [SMILES: Cc1cc(C(=O)Nc2ccc(C(=O)O)cc2)n(Cc2csc(N3CCCCC3)n2)c1]

or a pharmaceutically acceptable salt thereof.

22. A compound, wherein the compound is

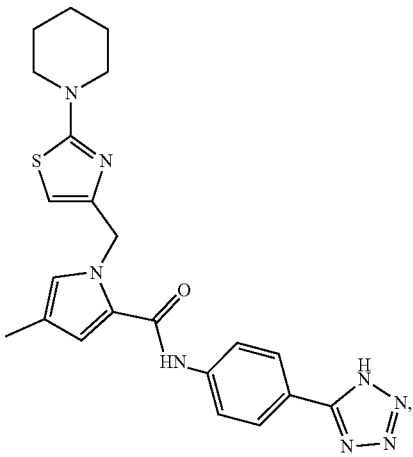 [SMILES: Cc1cc(C(=O)Nc2ccc(-c3nnn[nH]3)cc2)n(Cc2csc(N3CCCCC3)n2)c1]

or a pharmaceutically acceptable salt thereof.

23. A compound, wherein the compound is

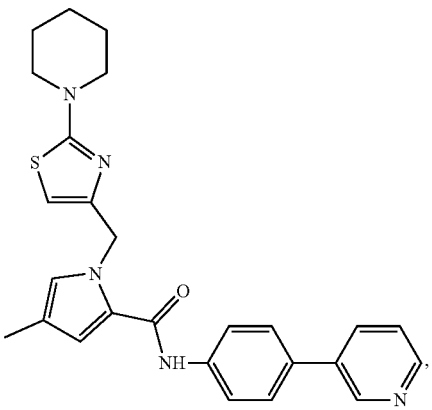 [SMILES: Cc1cc(C(=O)Nc2ccc(-c3cccnc3)cc2)n(Cc2csc(N3CCCCC3)n2)c1]

or a pharmaceutically acceptable salt thereof.

* * * * *